US007538190B2

(12) United States Patent
Robinson et al.

(10) Patent No.: US 7,538,190 B2
(45) Date of Patent: May 26, 2009

(54) METHODS FOR THE SYNTHESIS OF TWO OR MORE DICARBA BRIDGES IN ORGANIC COMPOUNDS

(75) Inventors: Andrea Robinson, St. Kilda (AU); Roy William Jackson, Camberwell (AU); Jim Patel, Parkdale (AU); Jomana Elaridi, Endeavour Hills (AU)

(73) Assignees: Polychip Pharmaceuticals Pty Ltd, Toorak, Victoria (AU); Monash University, Clayton, Victoria (AU)

( * ) Notice: Subject to any disclaimer, the term of this patent is extended or adjusted under 35 U.S.C. 154(b) by 0 days.

(21) Appl. No.: 11/480,114

(22) Filed: Jun. 30, 2006

(65) Prior Publication Data

US 2007/0197771 A1 Aug. 23, 2007

(30) Foreign Application Priority Data

Feb. 17, 2006 (AU) .............................. 2006900800

(51) Int. Cl.
*C07K 1/00* (2006.01)
*C07K 7/50* (2006.01)

(52) U.S. Cl. ........................ 530/333; 530/345; 530/317

(58) Field of Classification Search ................. 530/333, 530/345, 317

See application file for complete search history.

(56) References Cited

U.S. PATENT DOCUMENTS

| | | | | |
|---|---|---|---|---|
| 4,933,402 | A * | 6/1990 | Matlack | 526/189 |
| 5,153,282 | A * | 10/1992 | Datta et al. | 526/75 |
| 6,855,805 | B2 | 2/2005 | Olivera et al. | |
| 7,001,883 | B1 | 2/2006 | Craik et al. | |
| 7,115,708 | B2 | 10/2006 | Jones et al. | |
| 7,183,374 | B2 * | 2/2007 | Brenner et al. | 530/317 |
| 2005/0027105 | A9 | 2/2005 | Arbogast et al. | |
| 2007/0197429 | A1 | 8/2007 | Robinson et al. | |
| 2007/0197771 | A1 | 8/2007 | Robinson et al. | |

FOREIGN PATENT DOCUMENTS

| | | |
|---|---|---|
| WO | WO2005/000873 A1 | 1/2005 |
| WO | WO2007/093012 A1 | 8/2007 |
| WO | WO2007/093013 A1 | 8/2007 |

OTHER PUBLICATIONS

Tezuka (J Am Chem Soc 127, 6266-70, 2005).*
Hamann (Inorg Chem 42, 1877, 2003).*
Oishi (Tetrahedron Letters 44, 7315, 2003).*
Whelan, Amanda N. (Tetrahedron Letters (2004), 45(52), 9545-9547).*
Carotenuto, Alfonso et al., "Synthesis of a dicarba-analog of octreotide keeping the type II' .beta-turn of the pharmacophore in water solution", *Letters in Organic Chemistry*, 2(3), pp. 274-279, (2005).
Munson, Mark C et al., "Solid-phase synthesis of the parallel dimer of deamino-1-carba-oxytocin", Innovation Perspect. Solid Phase Synth. Collect. Pap., Int. Symp., 3rd (1994), Meeting Date 1993, 611-14. Editor(s): Epton, Roger. Publisher: Mayflower Worldwide Ltd., Birmingham, United Kingdom.
Robinson, Andrea J. et al., "A one pot, metathesis-hydrogenation sequence for the selective formation of carbon-carbon bonds", Chem. Commun. (2005), pp. 5544-5545.
Stymiest, Jake L. et al., "Synthesis of biologically active dicarba analogues of the peptide hormone oxytocin using ring-closing metathesis", *Organic Letters*, vol. 5, No. 1, pp. 47-49, (2003).
Undheim, Kjell et al., "Stereocontrolled construction of conformationally constrained and rigid bis(.alpha.-amino acid) derivatives", *Pure and Applied Chemistry*, 75(2-3), pp. 279-292, (2003).
Whelan, Amanda N. et al., "A tandem metathesis-hydrogenation route to dicarba analogues of cystine-containing peptides", *Tetrahedron Letters*, 45(52), pp. 9545-9547, (2004).
Whelan, Amanda N. et al., "Metal-catalysed tandem metathesis-hydrogenation reactions for the synthesis of carba analogues of cyclic peptides", *Canadian Journal of Chemistry*, 83(6-7), pp. 875-881, (2005).

* cited by examiner

*Primary Examiner*—David Lukton
(74) *Attorney, Agent, or Firm*—Marshall, Gerstein & Borun LLP

(57) ABSTRACT

Described herein are methods for forming two or more dicarba bridges, as well as new compounds containing dicarba bridges.

49 Claims, 4 Drawing Sheets

83

19

82

Catecholamine release for dicarba-conotoxins 118 and 119
(Note: In this figure 59=119 and 60=118)

METHODS FOR THE SYNTHESIS OF TWO OR MORE DICARBA BRIDGES IN ORGANIC COMPOUNDS

1.0 RELATED APPLICATIONS

This application claims the benefit of the filing date of Australian Patent Application No. 2006900800, which was filed Feb. 17, 2006. The contents of that application are hereby incorporated by reference in their entirety.

1.1 FIELD OF THE INVENTION

The present application broadly relates to methods for forming two or more dicarba bridges in organic compounds and to compounds such as peptides containing two or more dicarba bridges.

1.2 BACKGROUND

Cysteine (—S—S—) bridges are common structural motifs in naturally occurring cyclic peptides. In some cases, these disulfide bridges act as reactive functional groups. In many other cases however, the cysteine bridge serves a skeletal, structural role, maintaining secondary and tertiary structure. Disulfide bonds in peptides and other compounds are highly reactive under broad-ranging conditions, and therefore useful peptides containing disulfide bonds that have a structural role are at risk of denaturation, resulting in loss of properties.

2.0 SUMMARY

According to the present invention, there is provided a range of methods for forming two or more dicarba bridges, as well as new compounds containing dicarba bridges.

According to one embodiment, there is provided a method for the synthesis of an organic compound with two or more dicarba bridges. The method can be carried out with the steps of: (a) providing one or more reactable organic compounds having within the single compound, or between the multiple compounds, a first pair of complementary metathesisable groups that are unblocked, a second pair of complementary metathesisable groups, which are blocked and can be unblocked by an unblocking reaction or series of reactions specific to that second pair, and optionally further pairs of complementary methathesisable groups, which are blocked and can be unblocked by an unblocking reaction or series of reactions specific to each further pair; (b) subjecting the reactable organic compound or compounds to cross-metathesis to form an organic compound with unsaturated dicarba bridge across the first pair of complementary metathesisable groups, without cross-metathesis between the pair or pairs of blocked complementary metathesisable groups; (c) subjecting the second pair of complementary metathesisable groups to the unblocking reaction or series of reactions specific to the second pair; (d) subjecting the second pair of complementary metathesisable groups to cross-metathesis to form an organic compound with an unsaturated dicarba bridge across the second pair of complementary metathesisable groups, without cross-methathesis between any pair or pairs of complementary methathesisable groups that remain blocked; and (e) if any complementary metathesisable groups remain, subjecting those groups to unblocking reactions specific to those pairs, followed by cross metathesis.

This strategy of providing methods for blocking and unblocking pairs of crossmetathesisable groups enables the stereoselective formation of two or more dicarba bridges in organic compounds, including peptides. In the detailed description below, particular cross-metathesisable group pairs are described, together with the synthetic techniques that enable them to be blocked an unblocked to enable dicarba bond formation between the correct points in the molecule.

In many circumstances, it will be desirable to subject some or all of the unsaturated dicarba bridges formed by cross-metathesis to hydrogenation. This can be completed in stages following each cross-metathesis, or it may be conducted as a single hydrogenation step for converting all unsaturated dicarba bridges present at that point into saturated dicarba bridges (following two or more cross-metathesis reactions). By convenient selection of the appropriate time at which to perform the hydrogenation(s), it is possible for selected dicarba bridges to be saturated and for other dicarba bridges to remain unsaturated. Thus, where all dicarba bridges are desired to be saturated, the process described above may comprise the further steps of: subjecting the unsaturated dicarba bridge formed between the first pair of complementary metathesisable groups to hydrogenation (for instance, homogeneous hydrogenation) and subjecting the unsaturated dicarba bridge formed between the second pair of complementary metathesisable groups to hydrogenation (for instance, homogeneous hydrogenation). Each hydrogenation can be performed either separately or at the same time.

The cross-metathesis is suitably conducted under microwave radiation conditions, particularly for the formation of an intra-molecular dicarba bridge. It is further advantageous to perform each of the cross-metathesis reactions under microwave radiation conditions.

The methods of the present invention are particularly suited to the formation of peptides with dicarba bridges. In this event, the reactable compound, or one of the reactable compounds, is attached to a solid support. Suitable conditions for performing the reaction, taking into account the difficulties that are introduced as a result of conducting the reaction on a solid support, are described in the detailed description. It is noted, however, that compounds other than peptides can also suitably be prepared through a reactable compound which is supported on a solid support, using the microwave cross-metathesis reaction conditions.

According to a second embodiment suited to the synthesis of a peptide with two intramolecular bridges, the method comprises: (a) providing a first peptide comprising a series of amino acids attached to a solid support, wherein two amino acids comprise sidechains with a first pair of complementary metathesisable groups and two amino acids comprise sidechains with a second pair of blocked complementary metathesisable groups; (b) subjecting the peptide to cross-metathesis to form a peptide with an intramolecular dicarba bridge between the amino acids that bore the first pair of complementary metathesisable groups; (c) unblocking the second pair of complementary metathesisable groups; and (d) subjecting the peptide to cross-metathesis to form a peptide with an intramolecular dicarba bridge between the amino acids that bore the second pair of complementary metathesisable groups.

As described previously, one or both unsaturated dicarba bridges formed between the amino acids that bore the first and second pairs of complementary metathesisable groups may be subjected to hydrogenation (suitably homogeneous hydrogenation), separately or at the same time. Each intramolecular cross-metathesis is suitably performed under microwave radiation conditions.

According to a third embodiment suited to the synthesis of a peptide with one intramolecular bridge, and a second bridge which is an intermolecular bridge, the method comprises: providing a first peptide comprising a series of amino acids attached to a solid support, wherein two amino acids comprise sidechains with a first pair of complementary metathesisable groups which may be blocked or unblocked, and one amino acid comprises a sidechain with a second metathesisable group which may be blocked or unblocked, with the proviso that the metathesisable groups out of at least one of the first or the second metathesisable groups are blocked; (b) unblocking the first pair of complementary metathesisable groups, if those groups are blocked and subjecting the peptide to cross-metathesis under microwave radiation conditions to form a peptide with an unsaturated dicarba bridge between the amino acids bearing the first pair of complementary metathesisable groups, to form a peptide with an intramolecular dicarba bridge; and (c) contacting the first peptide with a second peptide comprising one amino acid with a metathesisable group complementary to the second metathesisable group on the first peptide, unblocking the second complementary metathesisable groups, if the second metathesisable groups are blocked, and subjecting the peptide to cross-metathesis to form a peptide with an unsaturated dicarba bridge between the amino acids bearing the second pair of complementary metathesisable groups, to form a dicarba bridge between the amino acids that bore the second metathesisable groups. Steps (b) and (c) can be performed in either order so as to form a peptide with an intermolecular bridge and an intramolecular bridge.

The methods may further comprise the step or steps of subjecting one or both of the products of step (b) and step (c) to hydrogenation (e.g., suitably homogeneous hydrogenation) to form a peptide with a saturated intramolecular dicarba bridge and/or a saturated intermolecular dicarba bridge.

These methods may be combined with a third stage of bridge-formation to form a peptide with three bridges, one two or three of which are intramolecular. This is achieved by providing a third pair of metathesisable groups in the first peptide, or one in the first peptide and one in the second or in a third peptide to be coupled to the first peptide through an intermolecular bridge, and then subjecting the third pair of metathesisable groups to unblocking to form the compound. In another alternative, a complimentary metathesisable group can be “added” to the first or second peptide through the addition of an amino acid or peptide fragment bearing the metathesisable group. This is illustrated in FIG. 1.

According to a fourth embodiment suited to the formation of a peptide with three intramolecular bridges, the method comprises: (a) providing a first peptide comprising a series of amino acids attached to a solid support, wherein two amino acids comprise sidechains with a first pair of complementary metathesisable groups, two amino acids comprise sidechains with a second pair of blocked complementary metathesisable groups and two amino acids comprise sidechains with a third pair of blocked complementary metathesisable groups; (b) subjecting the peptide to cross-metathesis under microwave radiation conditions to form a peptide with an unsaturated dicarba bridge between the amino acids bearing the first pair of complementary metathesisable groups; (c) optionally subjecting the unsaturated dicarba bridge to hydrogenation (suitably homogeneous hydrogenation); (d) unblocking the second pair of complementary metathesisable groups; (e) subjecting the peptide to cross-metathesis to form a peptide with an unsaturated dicarba bridge between the amino acids that bore the second pair of complementary metathesisable groups; (f) optionally subjecting the unsaturated dicarba bridge to hydrogenation (suitably homogeneous hydrogenation); (g) unblocking the third pair of complementary metathesisable groups; (h) subjecting the peptide to cross-metathesis to form a peptide with an unsaturated dicarba bridge between the amino acids that bore the third pair of complementary metathesisable groups, and (i) optionally subjecting the unsaturated dicarba bridge to hydrogenation (suitably homogeneous hydrogenation).

Each of these techniques for the synthesis of peptides with one or more intramolecular bridges may be combined with additional steps for the formation of one or more intramolecular disulfide bridges.

The present invention also provides for a compound produced by the method of the invention. The compound may be a peptide with at least two dicarba bridges, or may be any other organic compound with at least two dicarba bridges.

2.1 BRIEF DESCRIPTION OF THE DRAWINGS

3.0 DETAILED DESCRIPTION

Figure 1:
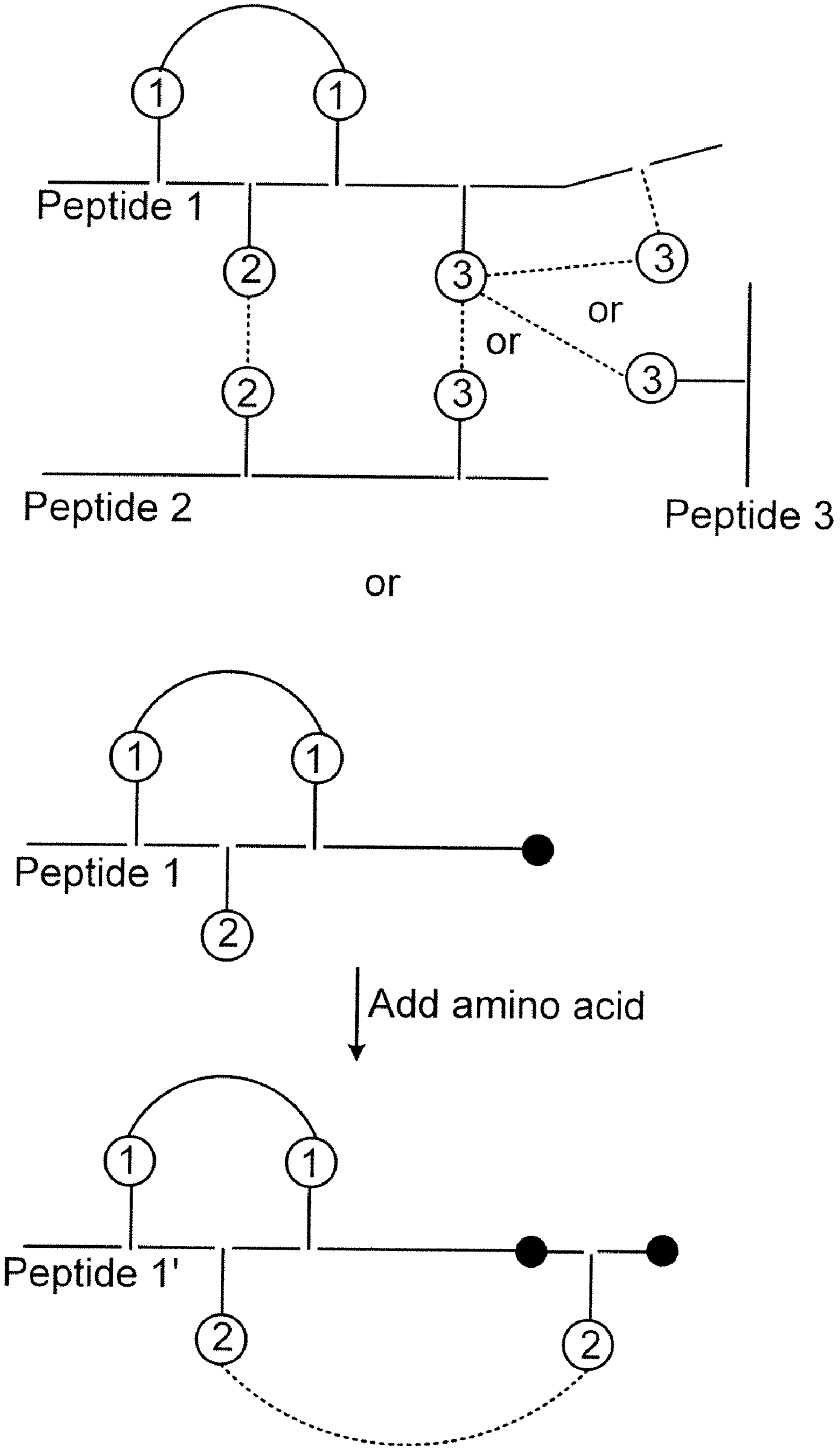
FIG. 1 is a schematic exemplifying bridge formation.

Conotoxins are the active peptide components present in the venom of cone snails of the genus *Conus* (*Conidae*). Conotoxins are usually fairly small peptides (12-30 amino acid residues in length, although lengths of as little as 9 and as great as 47 are also known) and are rich in disulfide bonds. They are potent and highly specific antagonists for different receptor targets. The conotoxins that have been the focus of recent investigation are the α-, ω- and μ-conotoxins. All of these conotoxins act by preventing neuronal communication, but each targets a different aspect of the process to achieve this. Currently, it is unclear what influence the disulfide bonds of the conotoxins have on their activity, and studies of derivatives in which disulfide bonds are replaced with structural equivalents will help elucidate this. The derivatives are also anticipated to have interesting pharmaceutical properties of their own.

Accordingly, there is interest in developing methods for creating intramolecular dicarba (—C—C—) containing bridges in conotoxins, and for creating other peptides with combinations of intramolecular dicarba- and disulfide-bridges. There is also interest in forming analogues of known peptides that naturally have multiple disulfide bridges, the analogues having selected disulfide bridges replaced with dicarba bridges. A peptide possessing four cysteine residues, and two cysteine bridges, has three topoisomers: the [1,3],[2,4]-isomer (globule); the [1,4],[2,3]-isomer (ribbon); and the [1,2],[3,4]-isomer (bead). It would be useful to be able to selectively form one of these isomers with dicarba bridges in place of the cysteine bridges, without any of the other two topoisomers. It would also be useful to replace one of the disulfide bridges with dicarba bridges, between the correct amino acids, so that no undesired mixed pairings are created. It is therefore important for the dicarba bridge forming method to be capable of taking place despite the presence of sulphur-containing groups, such as cysteine and disulfides, which could otherwise interfere with dicarba bridge-forming reactions. It is also of interest to be able to form a dicarba bridge using chemistry that does not destroy any disulfide bridges that are present, so that dicarba-disulfide containing compounds can additionally be formed.

Once this is achievable, it is of interest to be able to form intramolecular dicarba-containing analogues of a range of disulfide-containing peptides, such as conotoxins. It will also be of interest to form peptides containing two or more intramolecular dicarba bridges.

As described above, this application relates to the formation of organic compounds containing two or more dicarba bridges.

3.1 Types of Compounds and Groups

The term organic compound is used in its broadest sense to refer to organic, carbon-containing compounds, as opposed to inorganic compounds that are not based on carbon. To the extent that the method can be used to prepare organic ligands for organometallic compounds, this is also encompassed. Specific examples of organic compounds that the invention is particularly suited to are peptides.

The term "peptide" is used in this specification in its broadest sense to refer to oligomers of two or more amino acids. The term "side chain" is used in the usual sense to refer to the side chain on the amino acid, and the backbone to the $H_2N$—$(C)_x$—$CO_2H$ (where x=1, 2 or 3) component, in which the carbon in bold text bears the side chain (the side chain being possibly linked to the amino nitrogen, as in the case of proline).

One class of peptides of interest are the peptidomimetics—that is, a peptide that has a series of amino acids that mimics identically or closely a naturally-occurring peptide, but with at least one dicarba bridge, and optionally one or more further differences, such as the removal of a cysteine bridge, a change by up to 20% of the amino acids in the sequence, as non-limiting examples. Of particular interest are dicarba analogues of naturally occurring disulfide-containing peptides, in which one or more of the disulfide bonds are replaced with dicarba bridges. These may also be classed as pseudo-peptides.

The term "amino acid" is used in its broadest sense and refers to L- and D-amino acids including the 20 common amino acids such as alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine (illustrated in the Appendix); and the less common amino acid derivatives such as homo-amino acids, N-alkyl amino acids, dehydroamino acids, aromatic amino acids and α,α-disubstituted amino acids, for example, cysteine, 5-hydroxylysine, 4-hydroxyproline, α-aminoadipic acid, α-amino-n-butyric acid, 3,4-dihydroxyphenylalanine, homoserine, α-methylserine, ornithine, pipecolic acid, ortho, meta or para-aminobenzoic acid, citrulline, canavanine, norleucine, δ-glutamic acid, aminobutyric acid, L-fluorenylalanine, L-3-benzothienylalanine and thyroxine; β-amino acids (as compared with the typical α-amino acids) and any amino acid having a molecular weight less than about 500. The term also encompasses amino acids in which the side chain of the amino acid comprises a metathesisable group, as described herein.

The amino acids may be optionally protected. The term "optionally protected" is used herein in its broadest sense and refers to an introduced functionality which renders a particular functional group, such as a hydroxy, amino, carbonyl or carboxy group, unreactive under selected conditions and which may later be optionally removed to unmask the functional group. A protected amino acid is one in which the reactive substituents of the amino acid, or the amino group or carboxyl group of the amino acid are protected. Suitable protecting groups are known in the art and include those disclosed in Greene, T. W., "Protective Groups in Organic Synthesis" John Wiley & Sons, New York 1999, (the contents of which are incorporated herein by reference) as are methods for their installation and removal.

Preferably the N-protecting group is a carbamate such as, 9-fluorenylmethyl carbamate (Fmoc), 2,2,2-trichloroethyl carbamate (Troc), t-butyl carbamate (Boc), allyl carbamate (Alloc), 2-trimethylsilylethyl (Teoc) and benzyl carbamate (Cbz), more preferably Fmoc.

The carbonxl protecting group is preferably an ester such as an alkyl ester, for example, methyl ester, ethyl ester, t-Bu ester or a benzyl ester.

The amino acids may be protected, for example, the carboxyl groups of aspartic acid, glutamic acid and α-aminoadipic acid may be esterified (for example as a $C_1$-$C_6$ alkyl ester), the amino groups of lysine, ornithine and 5-hydroxylysine, may be converted to carbamates (for example as a $C(=O)OC_1$-$C_6$ alkyl or $C(=O)OCH_2Ph$ carbamate) or imides such as thalimide or succinimide, the hydroxyl groups of 5-hydroxylysine, 4-hydroxyproline, serine, threonine, tyrosine, 3,4-dihydroxyphenylalanine, homoserine, α-methylserine and thyroxine may be converted to ethers (for example a $C_1$-$C_6$ alkyl or a ($C_1$-$C_6$ alkyl)phenyl ether) or esters (for example a $C{=}OC_1$-$C_6$ alkyl ester) and the thiol group of cysteine may be converted to thioethers (for example a C1-C6 alkyl thioether) or thioesters (for example a $C(=O)$ $C_1$-$C_6$ alkyl thioester).

The term "dicarba bridge" is used broadly, unless the context indicates otherwise, to refer to a bridging group that includes the sequence —C—C—. This encompasses both the unsaturated (—C=C—) and saturated (—C—C—) dicarba sequence. The atoms directly attached to the carbon atoms of the dicarba sequence (—C—C—) are typically H, although further or alternative reactions can be performed to introduce substituents other than hydrogen onto the carbon atoms of the dicarba sequence of the dicarba bridge. Hydrogenated dicarba bridge refers to the specific case where the dicarba bridge is —$CH_2$—$CH_2$—. The term unsaturated hydrogen dicarba bridge is used to refer to —CH=CH—. This may be cis- or trans- in geometry.

In addition to the dicarba sequence, the dicarba bridge may include any other series of atoms, typically selected from C, N, O, and P, although the atoms to either side of the dicarba sequence are preferably carbon, and with the proviso that the nitrogen atoms present in the compound during metathsis are not free amines (protected amines, such as carbamates, are acceptable). Thus, the dicarba bridge encompasses the following possible bridges, as illustrative examples:

(I)

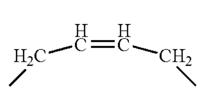

(II)

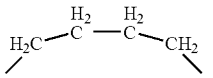

(III)

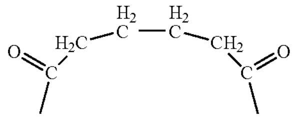

-continued (IV)

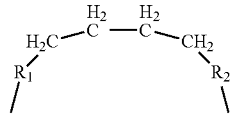

In IV, $R_1$ and $R_2$ are each independently selected from any divalent linking group. Such divalent linking groups should not be groups that poison the metathesis catalyst. Most free amines poison metathesis catalysts and therefore are preferably protected or avoided during methathesis.

The dicarba bridge may form a bridge between two separate reactable organic compounds, to form an intermolecular bridge, or it may form a bridge between two points in a single reactable organic compound, so as to form an intramolecular bridge, otherwise known as a ring. It is particularly difficult to form intramolecular bridges, due to steric hindrance, and the need to bring the reactable (metathesisable) groups together. The use of microwave radiation in the cross-metathesis step has enabled this to occur, or occur more efficiently.

"Reactable organic compound" is a term used to refer to the organic compound that is subjected to the reaction, as distinct from the target organic compound, to facilitate understanding of which "organic compound" is being referred to in the process. The "reactable" organic compound is therefore any compound that can be subjected to the reaction described, and using other terminology may be considered to be a starting material, an intermediate, a reagent or otherwise.

In this specification, including the claims which follow, except where the context requires otherwise due to express language or necessary implication, the word "comprising" or variations such as "comprise" or "comprises" is used in the inclusive sense, to specify the presence of the stated features or steps but not to preclude the presence or addition of further features or steps.

As used in the specification, the words "a", "an" and "the" include the plural equivalents, unless the context clearly indicates otherwise. Thus, for example, reference to "an amino acid" includes one or more amino acids.

The method for the formation of dicarba bridges involves the use of complementary pairs of metathesisable groups on a compound.

3.2 Cross-Metathesis

Cross-metathesis is a type of metathesis reaction involving the formation of a single olefin bond across two unblocked, or reactive olefins, to form a new olefinic bridge spanning across the two reactive olefins. In a general sense, metathesis can be described as the mutual intermolecular exchange of alkylidene (or carbene) fragments between two olefins promoted by metal-carbene complexes. The cross-metathesis is conducted with a metathesis catalyst. There are many metathesis catalysts known in the art. Examples of suitable catalysts are the ruthenium catalysts, such as Grubbs' catalyst—first and second generation. For details of other suitable cross-metathesis catalysts, reference is made to Grubbs, R. H. *Handbook of Metathesis*; Wiley-VCH: New York, 2003; 1204 pages, 3 volumes, the entirety of which is incorporated by reference. New catalysts are being developed all the time, and any of these new cross-metathesis catalysts can be used. For additional information on this reaction, and appropriate conditions and catalysts for the performance of the reaction, reference is also made to Chatterjee et al, *J. Am, Chem, Soc,* 2003, 125, 11360-11370, the entirety of which is incorporated herein by reference.

Ring-closing metathesis is a particular example of cross-metathesis where the two reactive olefins are on the one compound, so as to form an intra-molecular bridge, or ring.

3.3 Hydrogenation

The product of the cross-metathesis reaction is a compound with an unsaturated dicarba bridge. If the target organic compound is to contain a saturated dicarba bridge, the process further comprises the step of subjecting the unsaturated dicarba bridge to hydrogenation (suitably homogeneous hydrogenation).

Hydrogenation of the dicarba bridge is performed with a catalyst that is chemoselective for unblocked non-conjugated carbon-carbon double bonds, as distinct from other double bonds (such as carbon-oxygen double bonds in carbonyl groups and carboxylic acids, and blocked conjugated double bonds). One notable example of a suitable catalyst is Wilkinson's catalyst. Wilkinson's catalyst and catalysts like it are not asymmetric hydrogenation catalysts but however as this type of hydrogenation does not form a new chiral centre this is acceptable for this form of hydrogenation reaction. Although the use of asymmetric hydrogenation catalyst is not necessary in the hydrogenation of the dicarba bridge, asymmetric hydrogenation catalysts can nevertheless be used. Suitable catalysts are well known in the art, and include the range of catalysts described for this purpose in Ojima, I. *Catalytic Asymmetric Synthesis*; Wiley-VCH: New York, 2000; Second Edition, Chapter 1, 1-110, the entirety of which is incorporated by reference. New catalysts having such properties are developed from time to time, and these may also be used. Further examples of suitable asymmetric hydrogenation catalysts are the chiral phosphine catalysts, including chiral phospholane Rh(I) catalysts. Catalysts in this class are described in U.S. Pat. No. 5,856,525. Such homogenous hydrogenation catalysts are tolerant of sulfide, and disulfide bonds, so that the presence of disulfide bonds and the like will not interfere with the synthetic strategy. The hydrogenation can be conducted at any temperature, such as room temperature or at elevated temperature. The reaction is typically conduced at elevated pressure, although if slower reaction times can be tolerated, the reaction can be performed at atmospheric pressure.

In other stages of the process in which hydrogenation is used as a strategy for unblocking complimentary methasisable groups, it may be beneficial for the hydrogenation catalyst used in those reactions to be asymmetric to stereoselectively form a new chiral centre. Nevertheless, if a racemic mixture can be tolerated, a catalyst such as Wilkinson's catalyst could be used.

Homogeneous hydrogenation is used in its broadest sense to refer to catalytic hydrogenations conducted in one phase such as a liquid phase, where the liquid phase contains the substrate molecule/s and solvent. More than one solvent, such as organic/aqueous solvent combinations, or fluorous solvent combinations, non-aqueous ionic pairs, supercritical fluids, or systems with soluble polymers may also be employed. This is distinct from heterogeneous reactions, which involve more than one phase—as in the case of hydrogenations performed with solid-supported catalysts in a liquid reaction medium.

3.4 Blocking and Activation

For metathesis to occur between two alkylidenes (olefins), the alkylidenes must not be blocked by any steric or electronic blocking groups. A steric blocking group is any bulky group that sterically prevents the metathesis from taking place in the presence of a cross-metathesis catalyst. Examples of steric blocking groups on an olefin are alkyl. Prenylglycine is an example of an amino acid containing a dialkyl-blocked olefin side chain (specifically, dimethyl-blocked). Removal of one or both of the blocking groups unblocks the olefin, and enables the cross-metathesis to take place. It is noted that the pair of metathesisable groups that remain after unblocking need not be identical—a mono-substituted olefin (such as a mono-methylated olefin) and an unsubstituted olefin (being unsubstituted at the open olefinic end) can form a suitable pair of crossmetathesisable groups. The term "complementary" is used to indicate that the pair of unblocked metathesisable groups are not necessarily identical, but are merely complementary in the sense that cross-metathesis can take place across the two olefinic groups.

Electronic blocking refers to the presence of a group on the reactable organic compound or compounds that modifies the electronic nature of the olefin group of the reactable organic compound (which would otherwise undergo cross-metathesis), so as to prevent that olefin group from undergoing cross-metathesis. An example of an electronic blocking group is a conjugated double bond—that is, a double bond located in an α-β relationship to the olefinic group that would otherwise undergo cross-metathesis. The α-β-unsaturation withdraws electrons away from the olefinic cross-metathesisable group, to cause electronic blocking preventing cross-metathesis from taking place.

By using a combination of blocking mechanisms, a series of pairs of cross-metathesisable olefinic groups in the reactable organic compound or compounds can be designed, with different reaction conditions to effect selective unblocking of particular pairs. In this way, it becomes possible to regioselectively synthesise multiple dicarba bridges (inter and/or intramolecular) in compounds.

3.5 Regioselective Formation of Multiple Dicarba Bridges

The strategy for the formation of a dicarba bridge described above can be combined with other reaction steps for the formation of an organic compound with a dicarba bridge and a disulfide bridge, or for the formation of organic compounds with multiple dicarba bridges, optionally with disulfide bridges.

To form a plurality of (i.e. two or more (e.g., 2, 3, or 4) dicarba bridges, it is necessary to include at appropriate locations in the reactive organic compound or compounds pairs of complementary metathesisable groups which are blocked or deactivated for the times when different pairs of metathesisable groups are being linked together, and unblocked or "activated" to enable reaction to occur between those pairs. Accordingly, for each bridge-forming pair, there needs to be an unblocking reaction available that will selectively unblock the required pairs.

The first pair to be subjected to the cross metathesis and hydrogenation to form a saturated dicarba bridge need not be blocked during synthesis of the reactive organic compound or compounds. The compound with this pair of unblocked complementary metathesisable groups is then subjected to the reactions described above to form a dicarba bridge (saturated or unsaturated). Suitable groups for forming the first pair of complementary methathesisable groups which are not blocked are $—CH{=}CH_2$—containing organic moieties, and $—CH{=}CH—CH_3$—containing moieties. In the case of peptide synthesis, this may be provided by any amino acid containing the side chain $—CH{=}CH_2$, optionally with any divalent linking group linking the carbon at the "open" end (the —CH=carbon atom) to the amino acid backbone, such as an -alkylene-, -alkylene-carbonyl-, and so forth. Examples of $—CH{=}CH_2—$ containing amino acids and $—CH{=}CH—CH_3—$ containing amino acids are allyl glycine and crotyl glycine, respectively. Each of these amino acids contains the divalent linking group $—CH_2—$ between the alkylene and the amino acid (peptide) backbone.

At the completion of that reaction, (and optionally after hydrogenation of the first dicarba bridge) the blocked second pair of complementary metathesisable groups, can be subjected to an unblocking reaction.

Suitable functional groups for forming the second pair of complementary metathesisable groups are di-blocked alkylenes, such as the group $—CH{=}CR_3R_4$, in which $R_3$ and $R_4$ are each independently selected from any blocking groups, such as alkyl, for example methyl. Again, there may be a divalent linking group between the —CH=carbon atom, and the amino acid backbone, such as an alkylene group, for instance $—CH_2—$. An example of an amino acid containing this group is prenyl glycine, or protected prenyl glycine.

The unblocking reaction, or activation reaction, to convert the pair of di-blocked alkylenes into an unblocked alkylenes involves subjecting the blocked second pair of complementary metathesisable groups to cross-metathesis with a disposable olefin, to effect removal of the blocking groups (such as $R_3$ and $R_4$ in the example shown above).

It will be understood that in this case, cross metathesis is used to replace the portion ${=}CR_3R_4$ with another unblocked portion $={CH_2}$ or $={CHR_5}$, (in which $R_5$ may be alkyl for instance) which is then "activated" or "unblocked" and ready for being subjected to cross-methathesis for the formation of a dicarba bridge, using the same techniques described above.

The conditions for this activation-type of cross-metathesis are the same as described above for the dicarba bridge forming methathesis. It can be performed under microwave conditions, although it need not be, as the disposable olefin is a smaller molecule and less subject to the spatial constraints as larger reactable organic compounds and single reactable organic compounds in which intramolecular bridges are to be formed.

The "disposable olefin" is suitably a mono-substituted ethylene (such as monoalkylated ethylene—such as propene, which is a mono-methylated ethylene), or a 1,2-disubstituted ethylene. The substituents of the substituted ethylene are substituents that do not participate in the reaction. Examples are alkyl or a functionalised alkyl. The functional group of the alkyl is suitably a polar functional group, to assist with swelling of the solid support, and solubility. Examples are hydroxy, alkoxy, halo, nitrile and carboxylic acids/esters. One specific example is the di-ester functionalised disposable olefin 1,4-diacetoxy-2-butene.

After this second group has been activated or unblocked, it is subjected to the same series of cross-metathesis optionally followed by homogeneous hydrogenation described in detail above.

For the creation of a third dicarba bridge, another activation or unblocking mechanism is required that will not be activated under the conditions of the activation technique for the second pair of cross-metathesisable groups (or any fourth or following pair of cross-metathesisable groups).

Suitable functional groups for forming the third pair of complementary metathesisable groups are diblocked, conjugated dienes, such as the group $={CH}—CH{=}CR_3R_4$, in which $R_3$ and $R_4$ are each independently selected from any blocking groups, such as alkyl, for example methyl. The open-ended, double-bonded carbon atom (in bold above) may be attached directly to the amino acid backbone, for the synthesis of a peptide. Otherwise, there may be a divalent linking group such as an alkylene group between the double bonded carbon and the amino acid backbone. An example of an amino acid containing this group is (2Z)-methyl 2-N-benzoylamino-5-methylhexa-2,4-dienoate.

To assist in distinguishing between the two double bonds of the diene, the double bond at the "closed end"——

$CH{=}CR_3R_4$— will be referred to as the first double bond, and the double bond at the "open end" will be referred to as the second double bond.

The unblocking reaction, or activation reaction, to convert the pair of di-blocked conjugated dienes into unblocked alkylenes involves subjecting the blocked third pair of complementary metathesisable groups to asymmetric hydrogenation, to regioselectively, stereoselectively and chemoselectively hydrogenate the second double bond. This removes the electronic blocking of the first double bond, leaving just the steric blocking groups. Consequently, the electronically unblocked group can be subjected to cross-metathesis with a disposable olefin (in the manner described above for the second pair), to effect removal of the blocking groups (such as $R_3$ and $R_4$ in the example shown above) and consequently complete the series of unblocking or activation reactions for the third pair of cross-metathesisable groups.

Any further complementary metathesisable groups for the formation of further bridges require another level of unblocking mechanism. Such suitable combinations of blocking can be devised by a person skilled in the art, utilising the theory presented above.

3.6 Peptide Synthesis

For the synthesis of a peptide with an intramolecular dicarba bridge, the method may comprise:

- providing a peptide comprising a series of amino acids attached to a solid support, wherein two amino acids comprise sidechains with a first pair of complementary metathesisable groups which may be blocked or unblocked;
- unblocking the first pair of complementary metathesisable groups, if said groups are blocked;
- subjecting the peptide to cross-metathesis (suitably under microwave radiation conditions) to form a peptide with an unsaturated dicarba bridge between the amino acids bearing the metathesisable groups, and
- optionally subjecting the unsaturated dicarba bridge to homogeneous hydrogenation, to form a peptide with an intramolecular dicarba bridge.

Generally, the peptide will be a protected peptide (such as Fmoc protected). The amino acids can be any of the amino acids described earlier, but it is convenient for the synthesis of peptidomimetics for the amino acids to be selected from the 20 naturally-occurring amino acids, γ- and β-amino acids, and from allyl glycine-allyl glycine being an unblocked metathesisable group-bearing amino acid.

Each of the techniques for the synthesis of peptides with one or more intramolecular bridges may be combined with additional steps for the formation of one or more intramolecular or intermolecular disulfide bridges.

According to this embodiment, the peptide or peptides comprise between them two protected cysteine residues, and the method comprises deprotecting the cysteine residues and oxidising the cysteine residues to form a disulfide bridge. This may be performed at any stage, such as before the formation of the dicarba bridge(s) or after.

It will be appreciated that if a peptide sequence is added later through an intermolecular bridge, the corresponding metathesisable groups on that peptide need not be blocked—as they can be added to the reaction at the time of cross-metathesis, after the unblocking of the groups on the solid-supported peptide.

3.7 Microwave Reaction Conditions

It has been found that when the cross-metathesis reaction is performed under microwave reaction conditions, the reaction takes place in situations where the reaction would not otherwise take place—for instance, when the metathesisable groups are unblocked, but the arrangement, length or spatial orientation of the reactable organic compound prevents the metathesisable groups from being close enough to one another to enable the reaction to proceed.

The microwave reaction conditions involve applying microwave radiation to the reactable organic compounds in the presence of the cross-metathesis catalyst for at least part of the reaction, usually for the duration of the reaction. The microwave or microwave reactor may be of any type known in the art, operated at any suitable frequency. Typical frequencies in commercially available microwave reactors are 2.45 GHz, at a power of up to 500 W, usually of up to 300 W. The temperature of the reaction is preferably at elevated temperature, as a consequence of the microwave radiation, preferably at reflux, or around 100° C., as is appropriate in the case. The reaction is preferably performed in a period of not more than 5 hours, suitably for up to about 2 hours.

The present application also details a method for the synthesis of an organic compound with an unsaturated dicarba bridge, comprising:

- providing a reactable organic compound having a pair of unblocked complementary metathesisable groups, or two or more reactable organic compounds having between them a pair of unblocked complementary metathesisable groups, and
- subjecting the reactable organic compound or compounds to cross-metathesis under microwave radiation conditions to form an organic compound with an unsaturated dicarba bridge. This method can be followed by a step of subjecting the unsaturated dicarba bridge to homogeneous hydrogenation, to form a the saturated dicarba bridge.

3.8 Solvents

Particularly for reactions conducted with the (or one of the) reactable organic compound(s) attached to a solid support such as a resin, the cross-metathesis is preferably performed in a solvent combination of a resin-swelling solvent, with a coordinating solvent for the catalyst. In resin-supported reactions, swelling of the resin is required to avoid "clumping", but such solvents are not generally compatible with cross-metathesis catalysts. For example, polystyrene-based resins show optimal swelling in chlorinated solvents such as dichloromethane, however these solvents are not compatible with hydrogenation catalysts. The solvents react with such catalysts to compromise catalyst function—which in turn reduces the catalytic cycle (or turn-over number—TON), resulting in incomplete conversion. It was found that the addition of a small amount of a coordinating solvent for the catalyst, such as an alcohol (methanol, isopropanol, etc) which can coordinate into a vacant site of the catalyst to facilitate stability, overcame this problem. The coordinating solvent is suitably used in an amount of about 1-30%, for example constituting 10% of the solvent, by volume. The resin swelling agent may be any polar solvent known to swell the resin, such as dichloromethane. Other suitable solvents for a range of resins are as set out in Santini, R., Griffith, M. C. and Qi, M., *Tet. Lett.*, 1998, 39, 8951-8954, the entirety of which is incorporated herein by reference.

3.9 Solid Supports

The (or one of the) reactable organic compound(s) is preferably attached to a solid support—especially in the case of peptide reactable organic compound(s). A plethora of solid supports are known and available in the art, and include pins, crowns, lanterns and resins. Examples are polystyrene-based resins (sometimes referred to as solid supports), including cross-linked polystyrene containing some divinylbenzene (e.g. 1%), functionalised with linkers (or handles) to provide a reversible linkage between the reactable organic compound (which may be a peptide sequence containing side-chains with cross-metathesisable groups) and the resin. Examples are the Wang resin, Rink amide resin, BHA-Gly-Gly-HMBA resin and 2-chlorotrityl chloride resin, which are all polystyrene-based. Other forms of solid supports that may not necessarily be characterised as resins can also be used.

It has been surprisingly found that using the microwave reaction conditions, it is possible to have a higher solid support loading than is conventionally used in peptide synthesis on solid supports. Typical solid support loadings are at the 0.1 mmol/g level, but microwave radiation (optionally combined with solvent choice, as described above) overcomes the aggregation problems at higher solid support loadings, so that solid support loading at around 0.9 mmol/g (nine times higher) is achievable. As a consequence, one embodiment of the invention relates to the performance of the reaction at high solid support loadings—that is, at loadings of 0.2 mmol/g and above, such as 0.5 mmol/g and above.

3.10 Products of Methods

The present invention also provides for a compound produced by the method of the invention. The compound may be a peptide with at least one dicarba bridge, or may be any other organic compound with a dicarba bridge. Salts, solvates, derivatives, isomers and tautomers are encompassed in this context.

Possible products include the dicarba analogues of cysteine-containing peptides. Dicarba analogues refers to peptides which contain the same amino acid sequence as the natural or native peptide, but with one or more of the bridged cysteine-amino acid residue pairs substituted with amino acids bearing a dicarba bridge. Native conotoxin refers to conotoxins that are not naturally occurring, but are nevertheless recognised peptides within the conotoxin class. Native conotoxins are to be distinguished from the dicarba analogue being synthesised, but it includes dimerised conotoxins, which are based on two joined conotoxins, and higher multiples of coupled conotoxins. Bis- and higher dicarba analogues are also of particular interest, in view of the difficulty in synthesising such compounds. Examples are the dicarba analogues of Conotoxin ImI which are presented in FIG. 6.4. These include the fully dicarba-substituted analogues (the final three compounds in that figure) and the partial dicarba analogues (identified as "hybrids" in FIG. 6.4). Other suitable terminology is the mono-dicarba analogues (containing one dicarba bridge), and the bis-dicarba analogues (two bridges). Thus, the present application also relates to dicarba analogues of Conotoxin, including the bis-dicarba and higher-dicarba analogues.

In FIG. 6.4, the residue between the bridges is represented as "Hag"—based on its synthesis via this amino acid, although the double bond of Hag is no longer present. In some cases the new bridge is unsaturated and bears a new double bond; in other cases the bridge is saturated. If the peptide was synthesised via another amino acid, such as crotyl glycine (Crt), Crt would appear in place of Hag. In fact, the peptides are identical irrespective of whether they were synthesised via one of these amino acids or the other, as the dicarba bridge is all that remains from those starting amino acids. Accordingly, the amino acid indicated in the formula for the peptide should not be read as limiting the peptide to one made specifically through that amino acid. Sub (representing the amino acid suberic acid, which has the cyclised side chain $-(CH_2)_4-$) could also have been used to represent the same peptide.

"Conotoxin" is used in its broadest sense, and encompasses the peptides or peptide fragments that are present in the venom of cone snails of the genus *Conus* (*Conidae*). The term conotoxin also extends to analogues or derivatives of naturally-occuring conotoxins, including native conotoxins, which are recognised to be of the conotoxin type. All species which are encompassed within this genus [class] are contemplated, including the species *Conus imperialis, Conus geographus, Conus textile, Conus amadis, Conus tulipa, Conus marmoreus, Conus lynceus, Conus armadillo, Conus geographus* and so forth. The peptides within this class include natural and synthetic peptides, and derivatives of the naturally occurring peptides and peptide fragments. Conotoxins are classified according to their receptor subtype specificity and the arrangement of disulfide bonds and resultant loop sizes. The paralytic components of the venom (the conotoxins) that have been the focus of recent investigation are the alpha, omega- and mu-conotoxins. All of these conotoxins act by preventing neuronal communication, but each targets a different aspect of the process to achieve this. The α-conotoxins target nicotinic ligand gated channels, and the μ-conotoxins target the voltage-gated sodium channels and the omega-conotoxins target the voltage-gated calcium channels. Of particular interest here are the α-, χ- and ω-conotoxins, which contain two or three disulfide bridges, although μ-conotoxins, δ-conotoxins, κ-conotoxins π-conotoxins and conatokins are also relevant.

The (undimerised) naturally occuring conotoxins are generally between 9 and 47 amino acid residues in length, although the most commonly studied ones are between 12 and 30 amino acid residues in length. It is also noted that it is possible to remove or add amino acids in native conotoxins, so that the number of amino acids in the simple conotoxin analogues contemplated here may be between 8 and 50, preferably 10-35, and usually 12-30. In the case of dimerised conotoxins, themselves considered to be within the broad conotoxin class, the number of amino acids is double this, and therefore the conotoxin analogues that may be prepared according to the present application may be between 8 and 100 amino acids in length, commonly between 10-70, and most usually between 10-60.

The salts of compounds are preferably pharmaceutically acceptable, but it will be appreciated that non-pharmaceutically acceptable salts also fall within the scope of the present invention, since these are useful as intermediates in the preparation of pharmaceutically acceptable salts. Examples of pharmaceutically acceptable salts include salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulphuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulphonic, trihalomethanesulphonic, toluenesulphonic, benzenesulphonic, salicylic, sulphanilic, aspartic, glutamic, edetic, stearic, palmitic, oleic, lauric, pantothenic, tannic, ascorbic and valeric acids.

In addition, some of the compounds may form solvates with water or common organic solvents. Such solvates are encompassed within the scope of the invention.

By "derivative" is meant any salt, hydrate, protected form, ester, amide, active metabolite, analogue, residue or any other compound which is not biologically or otherwise undesirable and induces the desired pharmacological and/or physiological effect. Preferably the derivative is pharmaceutically acceptable.

The term "tautomer" is used in its broadest sense to include compounds which are capable of existing in a state of equilibrium between two isomeric forms. Such compounds may differ in the bond connecting two atoms or groups and the position of these atoms or groups in the compound.

The term "isomer" is used in its broadest sense and includes structural, geometric and stereo isomers. As the compounds that may be synthesised by these techniques may have one or more chiral centres, it is capable of existing in enantiomeric forms.

4.0 Controlled Synthesis of (S,S)-2.7-Diaminosuberic Acid: A Method for the Regioselective Construction of Dicarba Analogues of Dicysteine-containing Peptides This section describes a solution phase model study for the development of a methodology that enables the regioselective formation of dicarba isosteres of cysteine bonds. We investigated a sequence of ruthenium-catalysed metathesis and rhodium-catalysed hydrogenation reactions of non-proteinaceous allylglycine derivatives to achieve high yielding and unambiguous formation of two dicarba bridges. This theory can also be applied to the synthesis of non-peptide compounds with 2 or 3 dicarba bridges.

4.1 Initial Strategy

Our initial strategy planned to capitalise on the use of α-N-acyl-dienamide 57, a masked precursor to allylglycine derivatives.[118,119] We devised a strategy involving a double metathesis-hydrogenation sequence (Scheme 4.1). This required a selective ring closing metathesis of allylglycine units in the presence of dienamide functionalities. Grubbs et al. have previously reported that selective cross metathesis can be accomplished with olefins of varying reactivity.[130,182] Terminal olefins such as allylglycine undergo rapid homodimerisation with both Grubbs' catalyst[120] and second generation Grubbs' catalyst,[121] whereas the electron-deficient α-N-acyl-dienamide 57 should be considerably less reactive. Subsequent asymmetric hydrogenation of the dienamide moieties would lead to reactive allylglycine units which could undergo ring closing metathesis to produce the second carbocycle. The final step in this catalytic sequence involves hydrogenation of the unsaturated carbocycles, if required, to afford the saturated cysteine isosteres.

Scheme 4.1

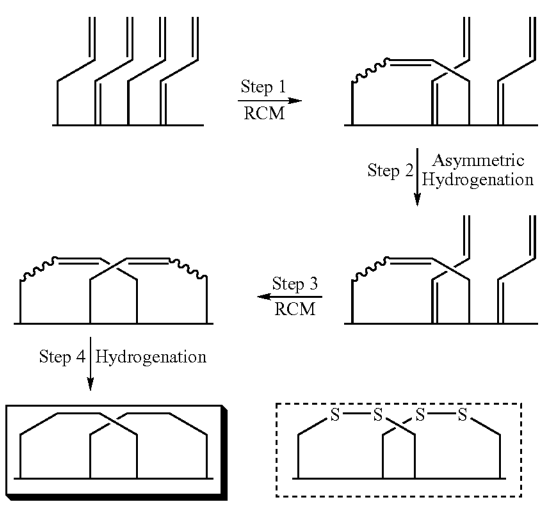

In order to validate the proposed strategy, we needed to show that: i) the dienamide 57 would not react under conditions required for the ring closing metathesis of allylglycine residues, ii) asymmetric hydrogenation of the dienamide 57 would proceed in a highly regioselective and stereoselective manner, iii) ring closing metathesis of the resulting allylglycine units would proceed in the presence of an unsaturated carbocycle (without resulting in mixed cross metathesis products), and iv) the unsaturated carbocycles could be reduced to afford saturated dicarba bridges. We therefore conducted a series of independent experiments that would serve as a model to the peptide system.

4.1.1 Synthesis of Olefinic Moieties

The dienamide 57 was synthesised according to a literature procedure reported by Teoh et al.[119] from a Horner-Emmons olefination of a phosphonate ester 39 and an α,β-unsaturated aldehyde 58 (Scheme 4.2).

Scheme 4.2

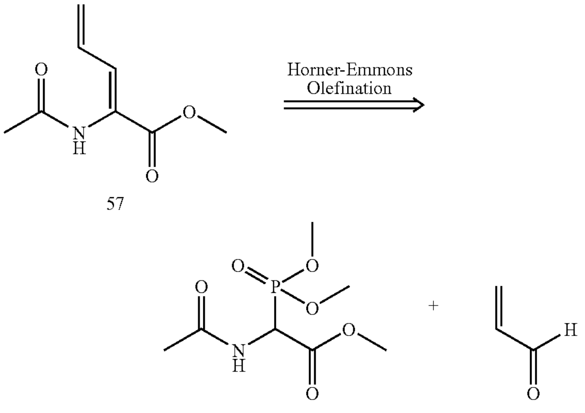

57

39 58

The phosphonate, methyl 2-N-acetylamino-2-(dimethoxyphosphinyl)acetate 39, was prepared in three steps from commercially available acetamide 34 and glyoxylic acid 41.

Scheme 4.3

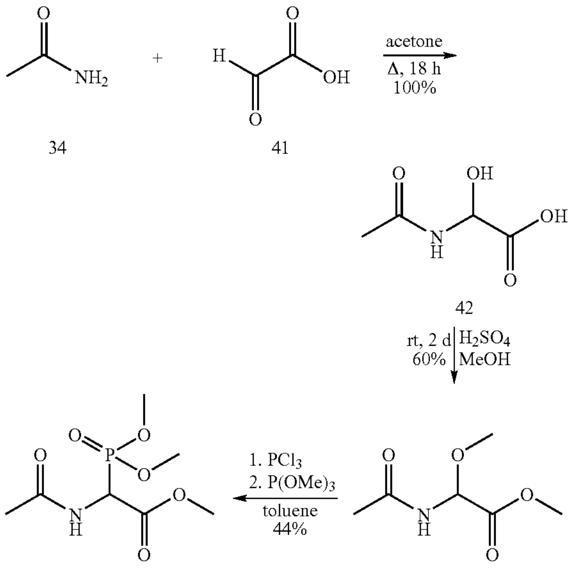

34 41

42

39 43

A mixture of commercially available acetamide 34 and glyoxylic acid 41 was heated at reflux in acetone to give pure N-acetyl-2-hydroxyglycine 42 as a viscous yellow oil in quantitative yield. The $^1$H n.m.r. spectrum supported formation of the α-hydroxyglycine derivative 42 with the appearance of a methine (H2) doublet and broad amide (NH) doublet at δ 5.39 and δ 8.65 respectively. Spectroscopic data were in agreement with those reported in the literature.[195]

Treatment of N-acetyl-2-hydroxyglycine 42 with a catalytic amount of concentrated sulfuric acid in methanol furnished methyl N-acetyl-2-hydroxyglycinate 43 in 60% yield. These reaction conditions converted the carboxylic acid to the methyl ester and the hydroxyl functional group to methyl ether.

Modification of the reported work-up procedure led to a significantly improved yield to that reported in the literature (32%).[196] The presence of two new methoxyl peaks in the $^{13}$C n.m.r. spectrum at δ 53.0 and δ 56.8 and the corresponding methyl singlets in the $^1$H n.m.r. spectrum at δ 3.47 and δ 3.82 supported formation of the desired product 43. Spectroscopic data were also in agreement with those reported in the literature.[196]

The final step in the synthesis of methyl 2-N-acetylamino-2-(dimethoxyphosphinyl)-acetate 39 involved reaction of methyl N-acetyl-2-hydroxyglycinate 43 with phosphorous trichloride to produce the intermediate α-chloro ester. Nucleophilic attack of the newly introduced chlorine substituent with trimethyl phosphite gave phosphonate ester 39 as a colourless solid in low yield (14%). The high solubility of the ester in water initially led to poor mass recovery. The use of continuous extraction partially overcame this problem and led to isolation of the product in satisfactory yield (44%).

The $^1$H n.m.r. spectrum confirmed formation of the target compound 39 with the appearance of a doublet of doublets attributed to the methine (H2) proton coupling to the phosphorous (J=22.2 Hz) and amide proton (J=8.8 Hz). The $^{13}$C n.m.r. spectrum displayed similar behaviour with the methine (C2) peak appearing as a doublet with large coupling to the vicinal phosphorous atom (J=146.8 Hz). The melting point of the isolated solid (89-91° C.) was consistent with that reported in the literature (88-89° C.).[197]

(2Z)-Methyl 2-N-acetylaminopenta-2,4-dienoate 57 was synthesised by Horner-Emmons olefination of methyl 2-N-acetylamino-2-(dimethoxyphosphinyl)acetate 39 with commercially available acrolein 58 in the presence of tetramethylguanidine (TMG) (Scheme 4.4). Hydroquinone was added to prevent polymerisation of acrolein 58 and was found to be critical to the success of this reaction. The reaction requires the addition of base to a solution of phosphonate 39 in tetrahydrofuran to generate the carbanion 45, which was then reacted with aldehyde 58 to afford the dienoate 57 as an off-white solid in 85% yield (Scheme 4.4).

Scheme 4.4

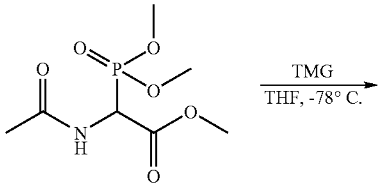

39

-continued

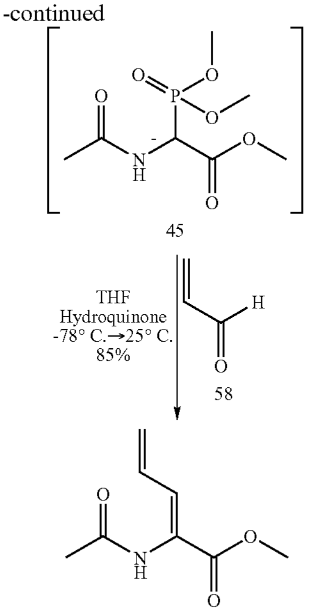

45

58

57

The $^1$H n.m.r. spectrum of the product supported formation of the dienamide 57 with the appearance of signals corresponding to a new terminal olefin. Doublets at δ 5.49 and δ 5.61 for H5-E and H5-Z respectively, and an olefinic methine (H4) multiplet at δ 6.47 were consistent with formation of dienamide 57. The melting point of the isolated solid (60-62° C.) was also in agreement with that reported in the literature (61-63° C.).[119]

Our group have demonstrated that high regioselectivity and enantioselectivity can be achieved in the asymmetric hydrogenation of dienamide esters. In this case, hydrogenation of dienamide 57 was effected with Rh(I)-(S,S)-Et-DuPHOS under 30 psi of hydrogen in benzene for 3 hours (Scheme 4.5). Over-reduction of the terminal olefinic bond was minimal (<3% 59) under these mild conditions (Scheme 4.5). The (S)-configuration was determined based on literature assignment for the same transformation[118] and a comparative optical rotation sign to that reported in the literature for (2S)-methyl 2-N-acetylaminopent-4-enoate 21a.[208]

Scheme 4.5

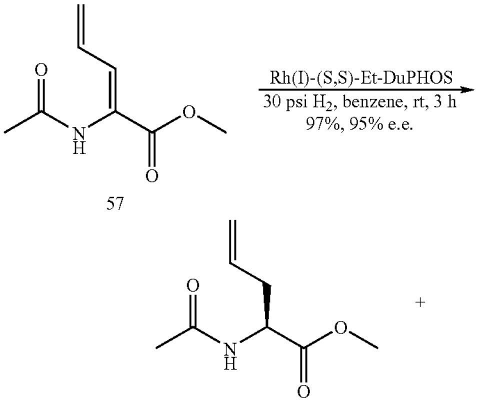

57

21a

+

-continued

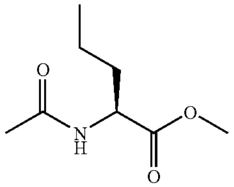

59 <3%

Asymmetric hydrogenation of dienamide 57 was also performed with Rh(I)—(R,R-Et-DuPHOS to facilitate enantiomeric excess assessment. The reaction proceeded in quantitative conversion and <5% over-reduced product was detected. Chiral GC indicated the reactions proceeded with excellent enantioselectivity (95% e.e.).

$^{1}$H n.m.r. spectroscopy showed the replacement of an olefinic methine (H3) doublet at δ 7.05 with a methylene (H3) multiplet at δ 2.43-2.62. The $^{13}$C n.m.r. spectrum also displayed new methine (C2) and methylene (C3) peaks at δ 51.8 and δ 36.5 respectively. Spectroscopic data were in agreement with those reported in the literature.[119]

4.1.2 Cross Metathesis: Homodimerisation

Homodimerisation is a type of cross metathesis in which an olefin self-couples. Conveniently, the only byproduct is a low molecular weight volatile olefin which is most commonly ethylene (Scheme 4.6).

Scheme 4.6

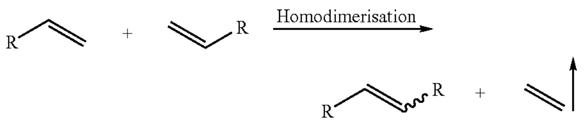

The mechanism involves an intermolecular exchange of alkylidene fragments between the metal-carbene catalyst and the reacting olefin. An unstable metallocyclobutane intermediate then decomposes to release the homodimer and a volatile olefinic byproduct (Scheme 4.7).

Scheme 4.7

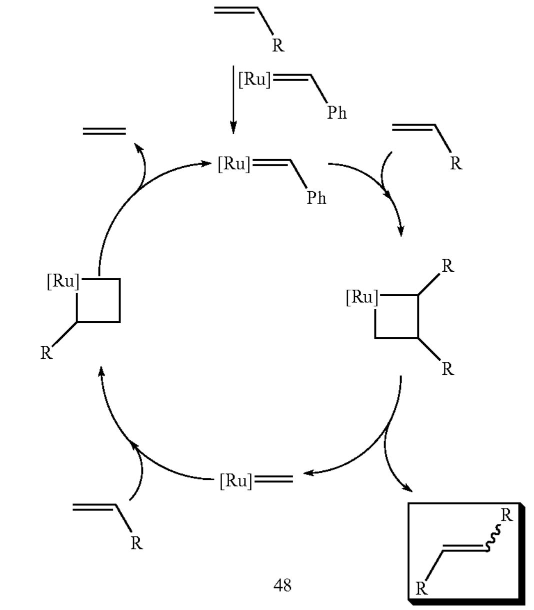

48

R = alkyl (substrate)

Quantitative homodimerisation of allylglycine derivative 21a was achieved using Grubbs' catalyst in dichloromethane heated at reflux (Scheme 4.8). Purification of the crude product by flash chromatography gave the target compound, (2S, 7S)-dimethyl 2,7-N,N'-diacetylaminooct-4-enedioate 60, as a brown oil in 88% yield.

Scheme 4.8

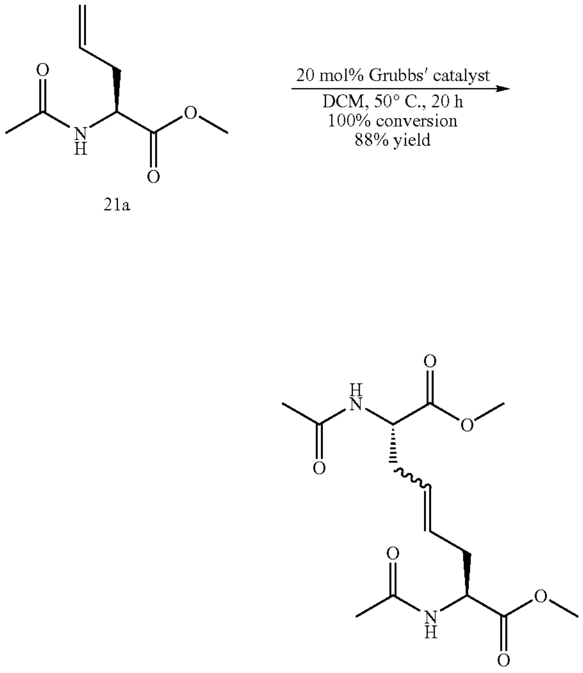

21a

60

High resolution mass spectrometry confirmed formation of the desired product 60 with the appearance of a molecular ion plus sodium peak at m/z 337.1375 for the expected molecular formula ($C_{14}H_{22}N_2NaO_6$). In addition, the $^{13}$C n.m.r. spectrum displayed a new olefinic methine (C4, 5) peak at δ 128.8, whilst the terminal and methine olefinic (C5 and C4) peaks of the starting material 21a were absent.

The solution phase dimerisation of the allylglycine unit 21a is analogous to ring closing metathesis of allylglycine sidechains in a peptide (Step 1, Scheme 4.1). In order to regioselectively construct multiple dicarba bonds within a peptide, via the strategy shown in Scheme 4.1, the dienamide 57 must not react under the conditions used for cross metathesis of allylglycine units 21a (Scheme 4.8).

The dienamide 57 was therefore subjected to analogous dimerisation conditions to those described above for allylglycine 21a. $^{1}$H n.m.r. spectroscopy confirmed complete recovery of the starting olefin 57 with no evidence of the dimerised dienoate 61 (Scheme 4.9). These results were very encouraging and supported our postulate that the dienamide 57 would be electronically compromised and therefore inert to metathesis (Step 1, Scheme 4.1).

Scheme 4.9

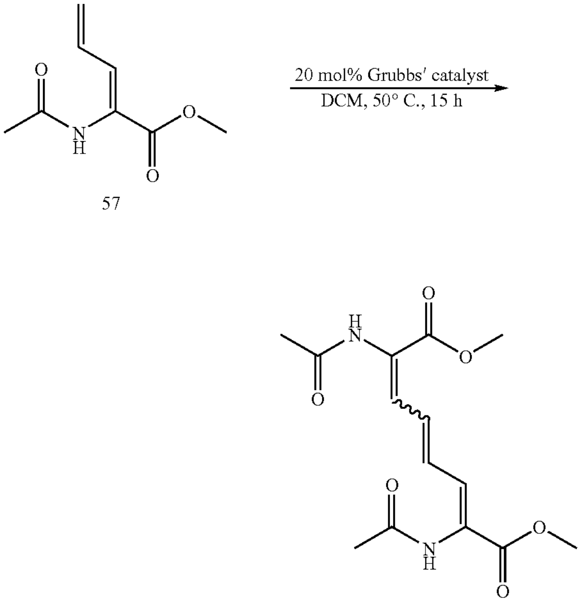

57

61

Subsequent asymmetric hydrogenation of the dienoate 57 would activate the olefin to metathesis by producing a reactive allylglycine unit 21a (Step 2, Scheme 4.1). This hydrogenation proceeds with excellent stereoselectivity (>95% e.e.) and regioselectivity (<3% over-reduction) (Section 4.1.1) as it relies on chelation of the asymmetric Rh(I)-catalyst to the enamide olefin and amide carbonyl group. The terminal C═C bond does not chelate to the catalyst and is therefore not reduced under these conditions. Similarly, the newly formed C═C bond, generated via cross metathesis in Step 1, would be inert to this catalyst.

4.1.3 Dimerisation of an Allylglycine Unit in the Presence of an Unsaturated Dimer In our strategy, the next step involved ring closing metathesis of allylglycine units in the presence of an unsaturated carbocycle (Step 3, Scheme 4.1).The solution phase model study therefore required the dimerisation of allylglycine in the presence of an unsaturated dimer (Scheme 4.10). A differentially protected allylglycine derivative 62 was synthesised to facilitate unambiguous assessment of cross metathesis selectivity.

Scheme 4.10

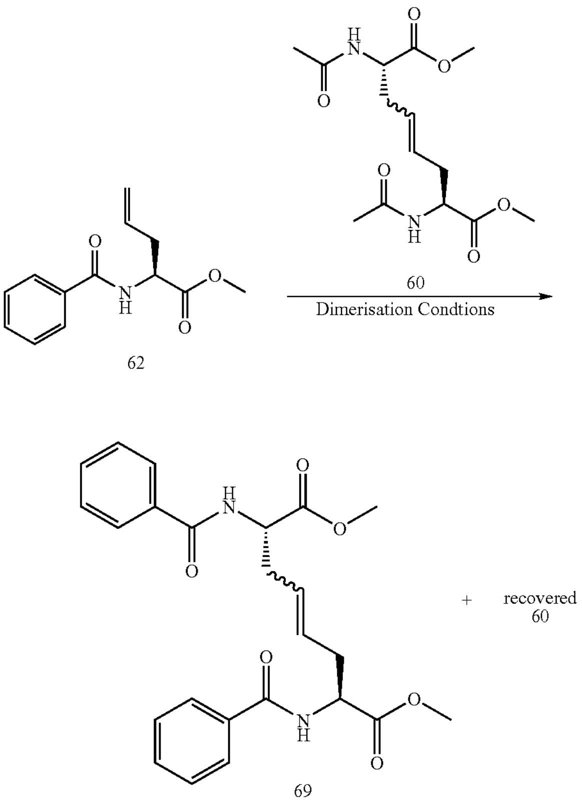

62

60

69

4.1.3.1 Synthesis of (2S)-Methyl 2-N-Benzoylaminopent-4-enoate 62

The benzoyl-protected allylglycine derivative 62 was prepared via catalytic asymmetric hydrogenation of the dienamide 63. The hydrogenation precursor 63 was synthesised by Horner-Emmons olefination of the phosphonate ester 64 which was isolated in three steps from commercially available benzamide 35 and glyoxylic acid 41 (Scheme 4.11).

Scheme 4.11

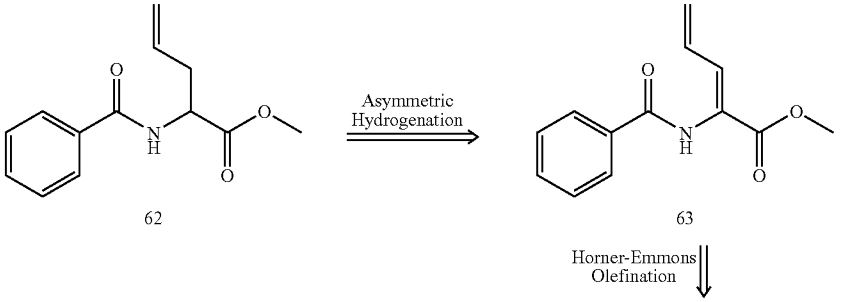

62

63

-continued

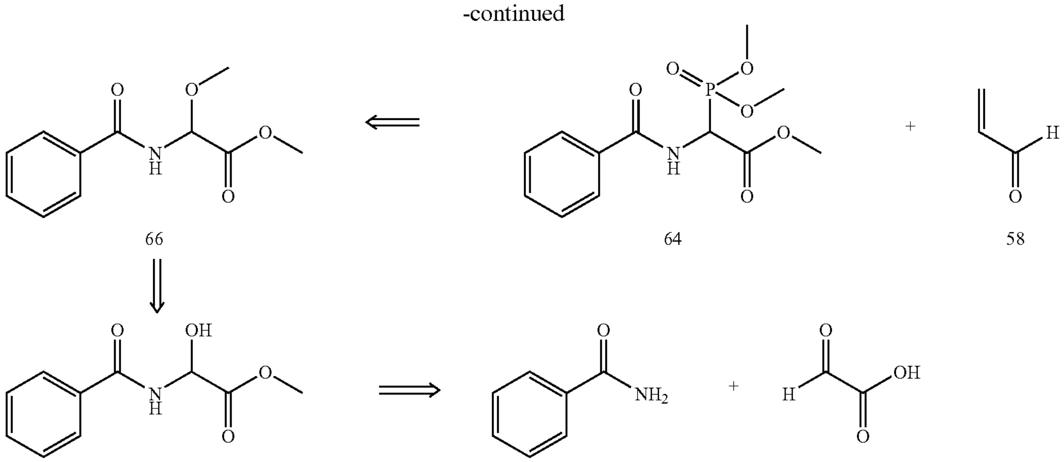

66 64 58

65 35 41

A mixture of commercially available benzamide 35 and glyoxylic acid 41 was heated at reflux in acetone to give pure N-benzoyl-2-hydroxyglycine 65 as a colourless solid in quantitative yield (Scheme 4.12). The $^{1}H$ n.m.r. spectrum supported formation of the α-hydroxyglycine derivative 65 with the appearance of a methine (H2) doublet and broad amide (NH) doublet at δ 5.60 and δ 9.26 respectively. Spectroscopic data were in agreement with those reported in the literature.[209]

Scheme 4.12

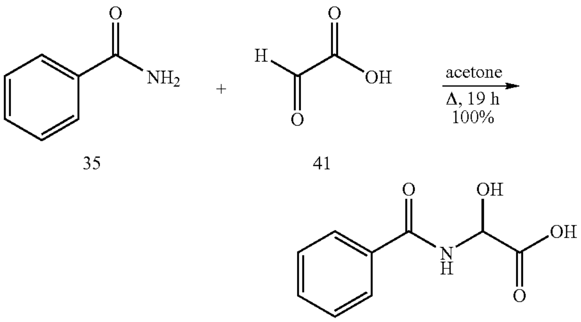

35 41

65

Treatment of N-benzoyl-2-hydroxyglycine 65 with a catalytic amount of concentrated sulfuric acid in methanol furnished methyl N-benzoyl-2-methoxyglycinate 66 in 87% yield (Scheme 4.13). These reaction conditions converted the carboxylic acid to the methyl ester and the hydroxyl functional group to the methyl ether.

Scheme 4.13

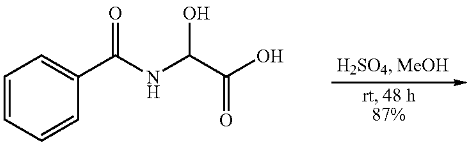

65

-continued

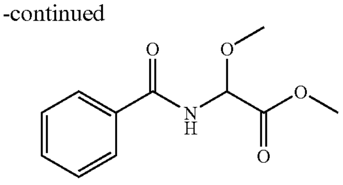

66

The presence of two new methoxyl peaks in the $^{13}C$ n.m.r. spectrum at δ 53.2 and δ 57.0 and the corresponding methyl singlets in the $^{1}H$ n.m.r. spectrum at δ 3.54 and δ 3.85 supported formation of the desired product 66. Spectroscopic data were in agreement with those reported in the literature.[209] Reaction of methyl N-benzoyl-2-methoxyglycinate 66 with phosphorous trichloride and trimethyl phosphite in toluene at 70° C. gave the phosphonate ester 64 in 76% yield (Scheme 4.14). The appearance of a methine doublet of doublets (H2) at δ 5.47 was consistent with vicinal phosphorous coupling and was in agreement with data reported in the literature.[210]

Scheme 4.14

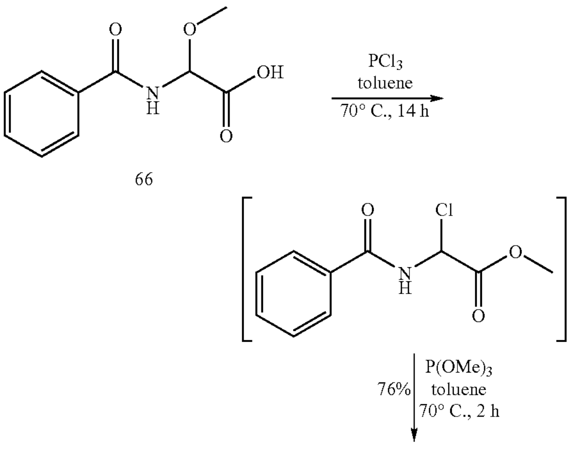

66

-continued

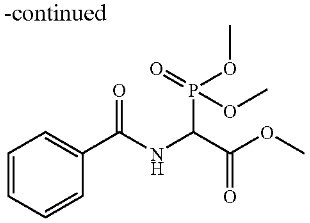

64

(2Z)-Methyl 2-N-benzoylaminopenta-2,4-dienoate 63 was synthesised by Horner-Emmons olefination of methyl 2-N-benzoylamino-2-(dimethoxyphosphinyl)acetate 64 with commercially available acrolein 58 in the presence of tetramethylguanidine (TMG) (Scheme 4.15). The reaction proceeded through a nucleophilic intermediate 67 which reacted with acrolein 58 to afford the dienoate 63 as colourless needles in 80% yield.

The $^{1}H$ n.m.r. spectrum displayed a new terminal olefin doublet of doublets at δ 5.50 and δ 5.64 corresponding to H5-E and H5-Z respectively in addition to a well-defined methine (H4) doublet of doublet of doublets at δ 6.56. Spectroscopic data were in agreement with those reported in the literature.[211]

Scheme 4.15

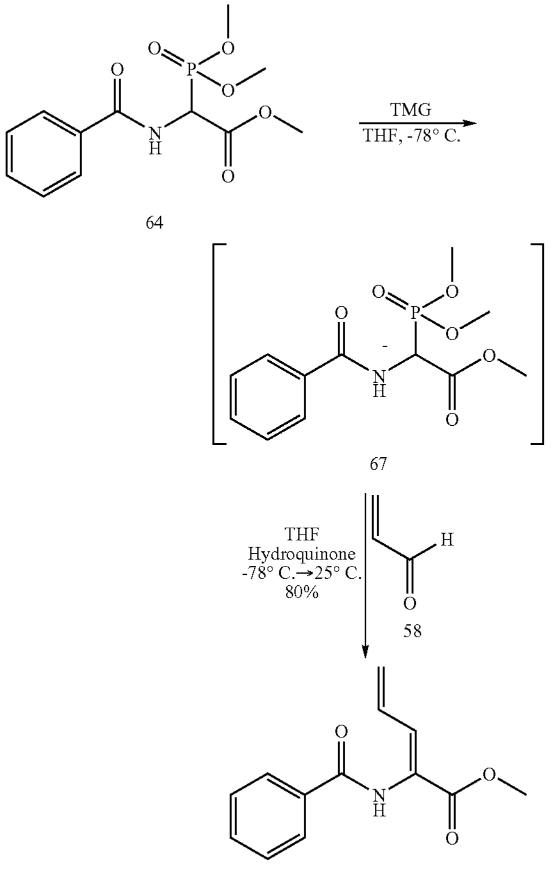

The final step in the synthesis of (2S)-methyl 2-N-benzoylaminopent-4-enoate 62 involved asymmetric hydrogenation of the dienamide 63.[†] Use of Rh(I)-(S,S)-Et-DuPHOS under 30 psi $H_2$ in benzene gave the allylglycine derivative 62 with excellent enantioselectivity[‡] (100% e.e., Scheme 4.16). Approximately 7% of the over-reduced product 68 was obtained under these conditions and attempts to separate allylglycine 62 from 68 were unsuccessful. The contaminated sample of allylglycine 62 was used in subsequent reactions as the presence of the inert impurity 68 would not interfere in the catalytic strategy.

† The benzoyl-protected olefin 62 can also be prepared in two steps from commercially available L-allylglycine ((2S)-2-aminopent-4-enoic acid).

‡ Asymmetric hydrogenation of the dienamide 63 with Rh(I)-(R,R)-Et-DuPHOS was performed in order to facilitate enantiomeric excess determination. Chiral GC confirmed that the (R)- and (S)-allylglycine derivatives 62 were produced in 100% e.e.

Formation of allylglycine 62 was supported by $^{13}C$ n.m.r. spectroscopy which showed the replacement of an olefinic methine (C3) peak with a new methylene signal at δ 36.8 and a methine (C2) peak at δ 52.1. Spectroscopic data were in agreement with those reported in the literature.[212]

Scheme 4.16

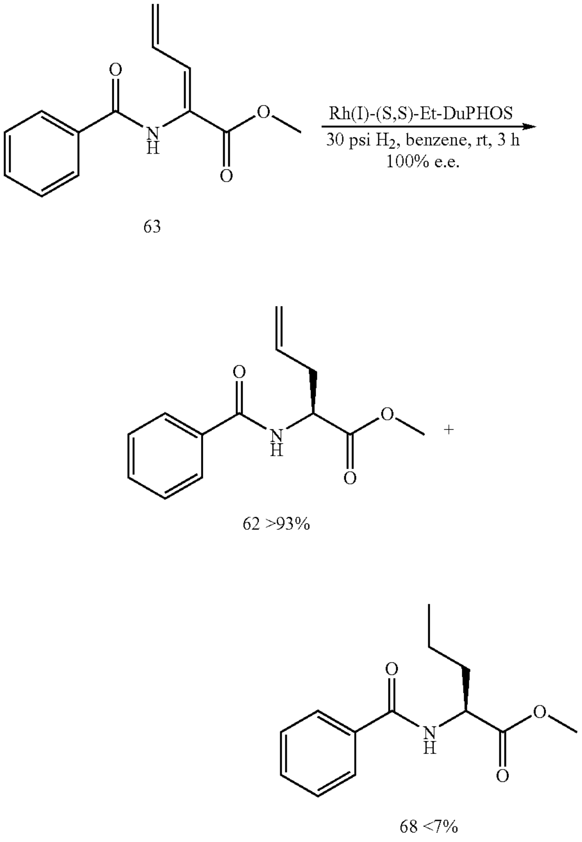

4.1.3.2 Dimerisation of (2S)-Methyl 2-N-Benzoylaminopent-4-enoate 62

The benzoyl-protected allylglycine unit 62 was quantitatively homodimerised under general cross metathesis conditions using Grubbs' catalyst (Scheme 4.17). The loss of ethylene drives the metathesis reaction to completion.

Scheme 4.17

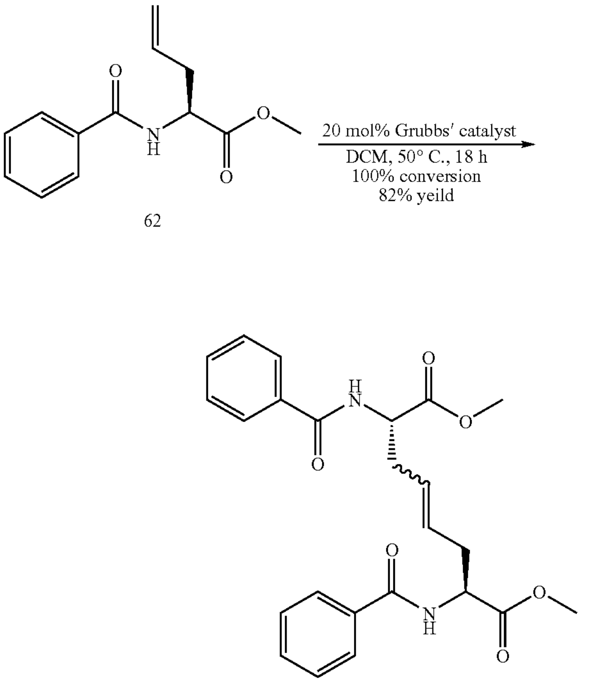

62

69

Purification by flash chromatography furnished (2S,7S)-dimethyl 2,7-N,N'-dibenzoylaminooct-4-enedioate 69 as a pale brown solid in 82% yield. [1]H n.m.r. spectroscopy supported synthesis of the dimer 69 with the replacement of terminal olefin peaks by a new methine (H4, 5) triplet at δ 5.49. The accurate mass spectrum also displayed a molecular ion plus sodium peak at m/z 461.1695 which is consistent with that expected for the molecular formula $C_{24}H_{26}N_2NaO_6$.

With the benzoyl-protected allylglycine 62 in hand and characterisation of its dimer 69 complete, we attempted the cross metathesis of allylglycine 62 in the presence of the unsaturated N-acetyl-protected allylgycine dimer 60 (Step 3, Scheme 4.4).

4.1.3.3 Dimerisation of (2S)-Methyl 2-N-Benzoylamino-pent-4-enoate 62 in the presence of (2S,7S)-Dimethyl 2,7-N, N'-Diacetylaminooct-4-enedioate 60

Cross metathesis of allylglycine derivative 62 in the presence of unsaturated dimer 60 proceeded with Grubbs' catalyst to afford dimer 69 (Scheme 4.18). No mixed cross metathesis product 70 was observed. However, use of the more reactive metathesis catalyst, second generation Grubbs' catalyst, did lead to a mixture of cross metathesis products, 69, 70 and recovered dimer 60. The complicated [1]H n.m.r. spectrum did not allow the distribution of products to be quantified but mass spectrometry confirmed the presence of homodimers 60 and 69 and the mixed cross metathesis product 70.

Scheme 4.18

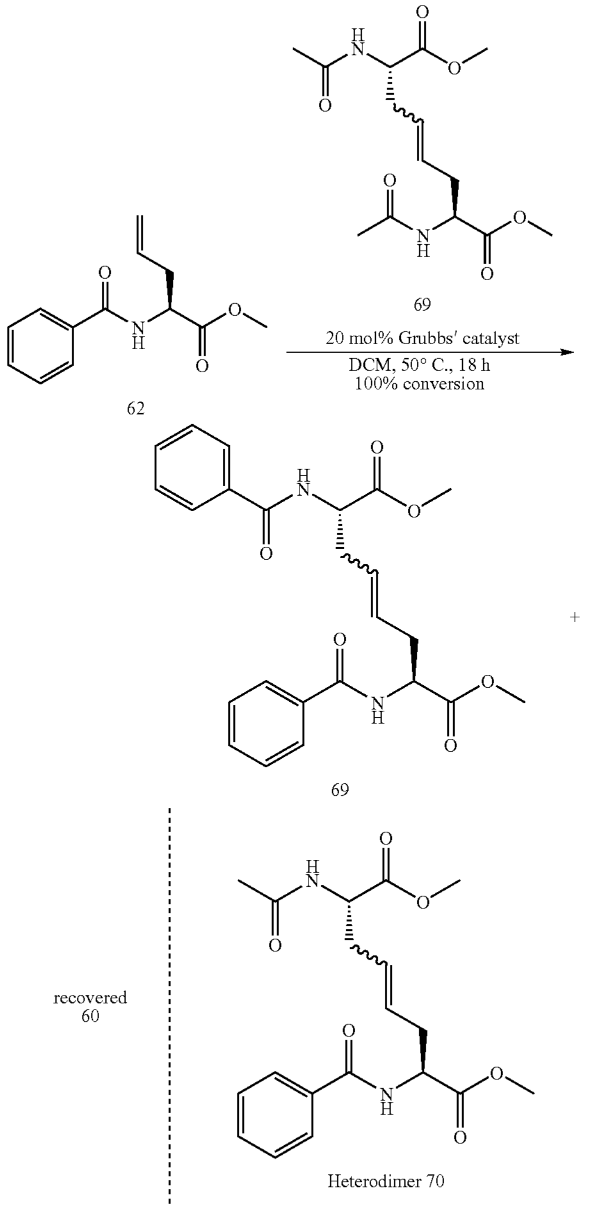

69

62

69 recovered 60

Heterodimer 70

These results indicated that in a peptide application of this strategy (Step 3, Scheme 4.1), selective cyclisation of the allylglycine units will only be successful in the presence of Grubbs' catalyst and the use of the more reactive second generation Grubbs' catalyst must be avoided. With successful completion of Step 3, we moved to the last step of the strategy (Step 4, Scheme 4.1).

4.1.4 Wilkinson's Hydrogenation of Unsaturated Dimers

The final step in the model sequence involved reduction of the unsaturated dimers 60 and 69 to give the corresponding saturated dicarba bridges 71 and 72. Homogeneous hydrogenation of dimers 60 and 69 with Wilkinson's catalyst, Rh(I) $(PPh_3)_3Cl$, under mild experimental conditions, gave the saturated diaminosuberic acid derivatives 71 and 72 in excellent yields (>99%) (Scheme 4.19). We employed a homogeneous catalyst in order to facilitate the on-resin application of this hydrogenation which would otherwise be complicated by the more commonly employed heterogeneous systems such as palladium on charcoal.

Scheme 4.19

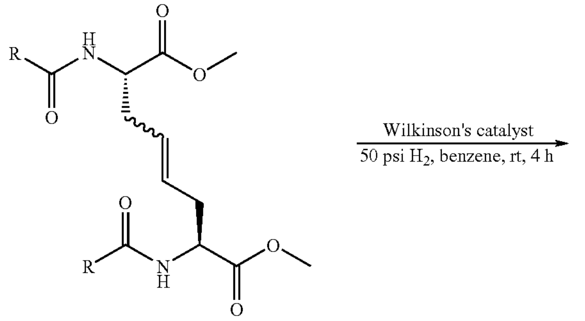

60 R = Me
69 R = Ph

100% conversion, 99% yield
100% conversion, 100% yield

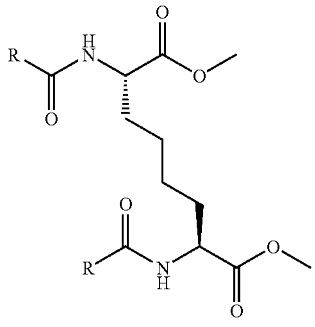

71 R = Me
72 R = Ph

Formation of the saturated dimers 71 and 72 was supported by spectroscopic analysis which displayed new methylene proton (H3, 4) and carbon (C3, 4) signals in the $^1H$ and $^{13}C$ n.m.r. spectra respectively.

4.1.5 Dimerisation of Allylglycine 21a in the presence of (2Z)-Methyl 2-N-Acetylaminopenta-2,4-dienoate 57

These results looked very promising: We had successfully completed all four steps in our devised synthesis (Scheme 4.1). However, our attempts to dimerise allylglycine 21a in the presence of dienamide 57 were unsuccessful with both first and second generation Grubbs' catalysts (Scheme 4.20). The inclusion of dienamide 57 also hampered dimerisation of benzoyl-protected allylglycine 62 and led to complete recovery of the starting dienoate 57 and allylglycine unit 62.

Scheme 4.20

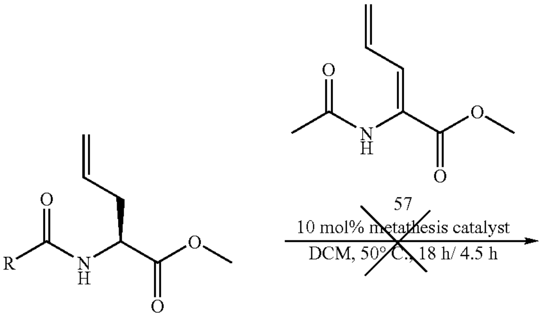

21a R = Me
62 R = Ph

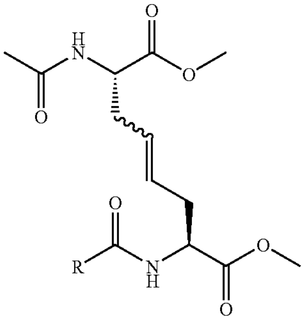

+ recovered 57

Figure 2:
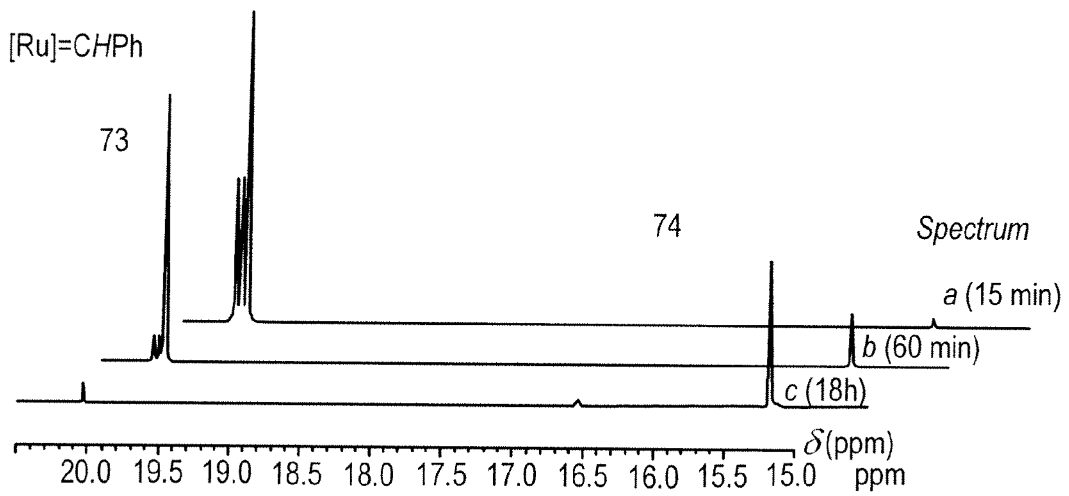
FIG. 2 shows nmr tracings (the spectra are described at 4.1.5).

60 R = Me
69 R = Ph $^1H$ n.m.r. binding studies between the catalyst and dienamide 57 (ratio of 1:1) showed that the dienamide 57 rapidly coordinated to the ruthenium centre forming a ruthenium-vinylalkylidene complex 73 (spectrum a in FIG. 2). Within 60 minutes, complex 73 had diminished and a new ruthenium species 74 was generated (spectrum b in FIG. 2). The second species is postulated to involve coordination of the ester carbonyl group to the ruthenium centre and liberation of a tricyclohexylphosphine ligand 75. Formation of complex 74 was complete within 2 hours and was stable and unreactive over 18 hours (spectrum c in FIG. 2).[213] Unfortunately, attempts to isolate this complex 74 were unsuccessful.

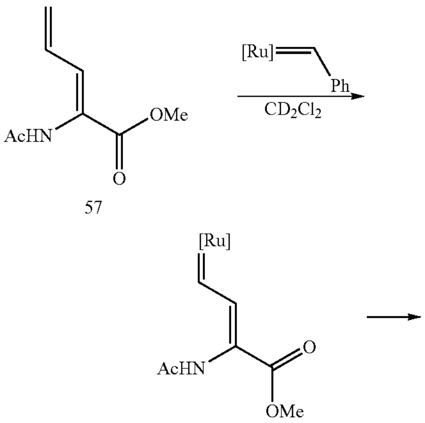

57

73

-continued

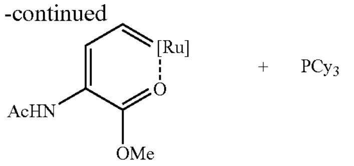

74 75

Furthermore, attempts to regenerate the dienamide 57 from the ruthenium-carbonyl chelate 74 via reaction with ethyl vinyl ether and formation of the Fischer-type carbene complex,[214] failed due to conjugate addition of liberated tricyclohexylphosphine 75 to the dienamide substrate 57. This highlighted the sensitivity of acrylate 57 to N- and P-based nucleophiles and potential problems that could arise during peptide synthesis, where piperidine is routinely used to facilitate Fmoc-cleavage from residues prior to coupling.

a (15 min)

b (60 min)

Although the dienamide 57 was unexpectedly reactive to Grubbs' catalyst, the proposed strategy showed potential. Solution phase experiments with Steps 2-4 (Scheme 4.21) were not problematic and indicated that multiple dicarba bond formation was indeed feasible via a modified strategy. The first step, however, required revision. We postulated that the presence of a substituent at the olefinic terminus of the dienamide substrate might impede binding to the metathesis catalyst and therefore allow the ring closing metathesis of the more reactive allylglycine sidechains to proceed.

Scheme 4.21

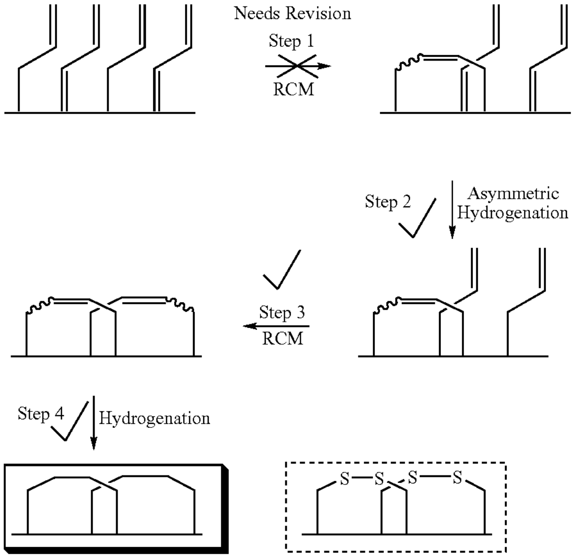

4.2 Revised Strategy

A revised strategy was investigated centering on the use of non-proteinaceous, terminally functionalised allylglycine units. This modified route involved: i) metathesis of allylglycine units in the presence of a terminal-phenyl substituted dienamide 76, and ii) subsequent hydrogenation of the dienamide 76 to yield a more reactive olefin 77 for the second ring closing metathesis (Scheme 4.22). We postulated that the presence of a phenyl substituent at the olefin terminus might impede binding of the metathesis catalyst and circumvent the problems experienced in the first strategy. The solution phase model studies of this revised strategy therefore commenced with the synthesis of the phenyl-substituted dienamide 76.

Scheme 4.22

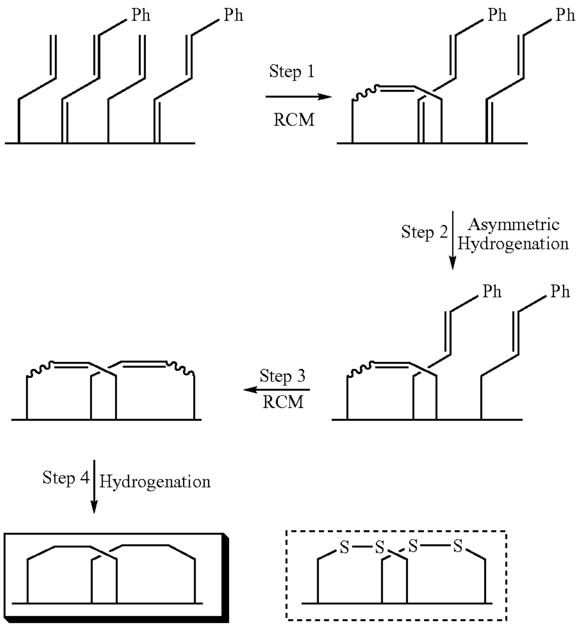

4.2.1 Synthesis of (2Z)-Methyl 2-N-Acetylamino-5-phenylpenta-2,4-dienoate

The dienamide 76 was prepared according to a procedure by Burk et al.[117] from a Horner-Emmons olefination of methyl 2-N-acetylamino-2-(dimethoxyphosphinyl)acetate 39 and commercially available trans-cinnamaldehyde 78 (Scheme 4.23). The phosphonate 39 was prepared in three steps from commercially available acetamide 34 and glyoxylic acid 41.

The dienamide 76 was isolated as an off-white solid in 74% yield. Mass spectrometry supported formation of the dienoate 76 with a molecular ion plus proton peak at m/z 246.2 which is consistent with that expected for molecular formula $C_{14}H_{16}NO_3$. Spectroscopic data were in agreement with those reported in the literature.[117]

Scheme 4.23

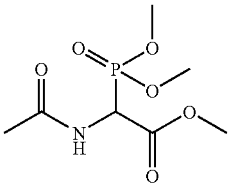

39

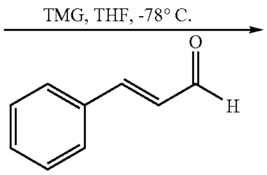

78

-78° C.→25° C.

74%

-continued

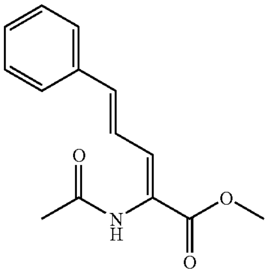

76

4.2.2 Solution Phase Reactions with Dienamide 76

[1]H n.m.r. binding studies of a 1:1 mixture of Grubbs' catalyst and dienamide 76 showed no ruthenium-vinylalkylidene formation. Hence, this suggested that the poor chelating properties of the modified dienamide 76 to Grubbs' catalyst should now facilitate high yielding homodimerisation of allylglycine 21a into its dimer 60 (Scheme 4.24).

Surprisingly, homodimerisation of 21a to 60 was found to proceed but with poor conversion (28%). This suggested that the dienamide 76 was still capable of influencing the metathesis cycle. Hopeful that this would later be rectified through modification of metathesis conditions, we continued to investigate subsequent steps of the proposed strategy.

Scheme 4.24

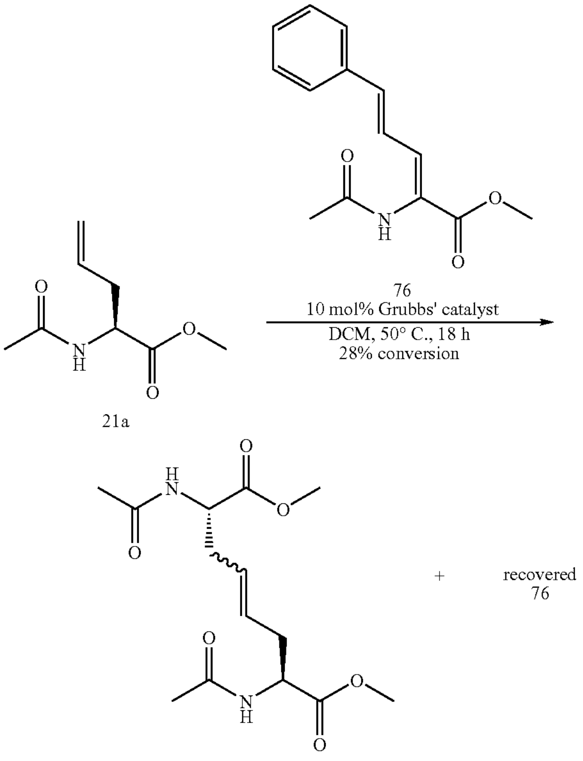

60

Rh(I)-DuPHOS-catalysed asymmetric hydrogenation of dienamide 76 under mild conditions (75 psi $H_2$) gave (2S)-methyl 2-N-acetylamino-5-phenylpent-4-enoate 77 in 99% e.e. (Scheme 4.25). Formation of the desired phenyl-substituted enamide 77 was confirmed by spectroscopic analysis which was in agreement with literature data.[117]

Scheme 4.25

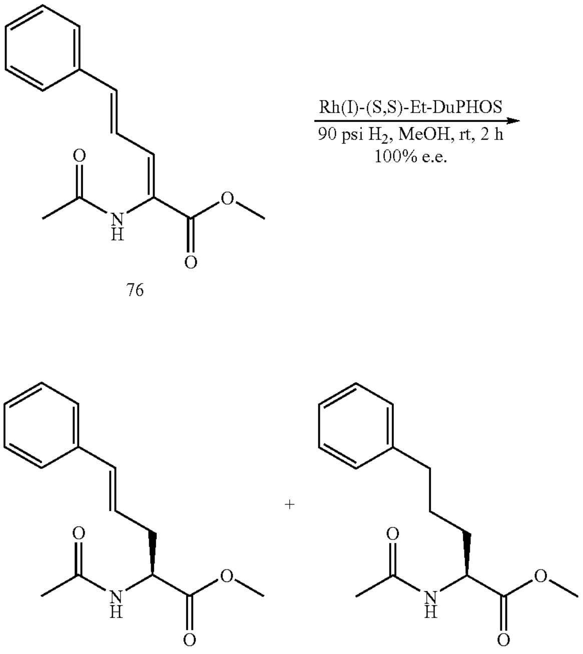

77 >90%

79 <10%

Cross metathesis of 77 using Grubbs' catalyst was unsuccessful. After 13 hours, [1]H n.m.r. spectroscopy showed no conversion to the desired homodimer 60. Conditions to facilitate the required cross metathesis were found, however, using a 5 mol % solution of second generation Grubbs' catalyst in dichloromethane (Scheme 4.26). A modest conversion (44%) to the expected homodimer 60 was achieved. In spite of this promising result, this chemistry was not investigated further since the requirement for the more reactive second generation Grubbs' catalyst would render the previously formed unsaturated carbocycle vulnerable to further cross metathesis. Mixed cross metathesis products would therefore result (Section 4.1.3.3).

Scheme 4.26

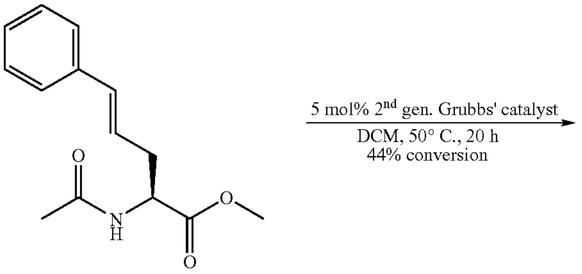

77

-continued

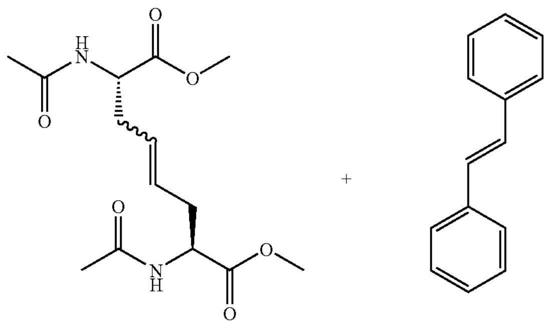

60

Selective reduction of the first-formed unsaturated carbocycle prior to the second metathesis reaction would, however, eliminate the chance of mixed cross metathesis (Step 2, Scheme 4.27). We therefore subjected the phenyl substituted diene 76 to the hydrogenation conditions previously developed for the hydrogenation of the unsaturated dimer 60. Unfortunately, these conditions resulted in a 1:4 mixture of olefin 77: saturated derivative 79 (Scheme 4.28).

Scheme 4.27

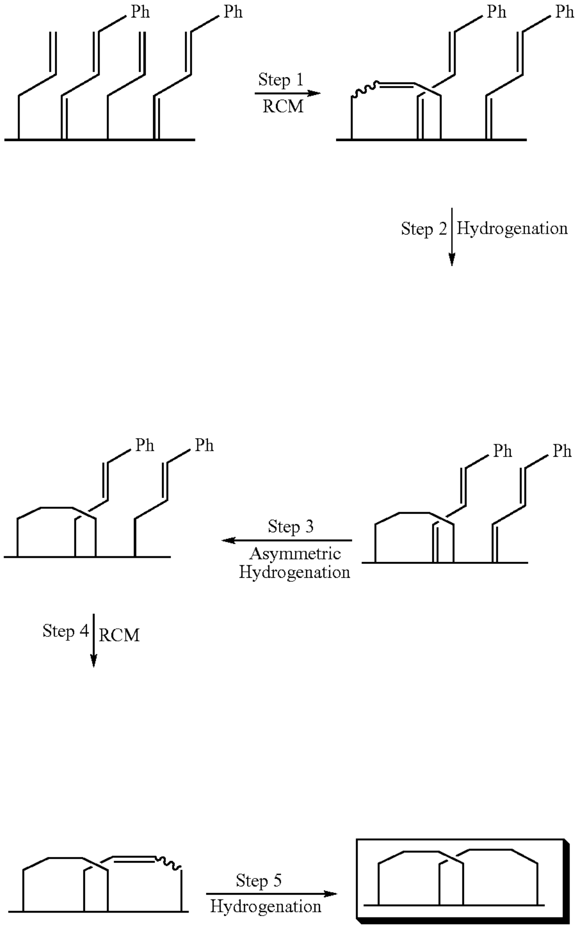

Scheme 4.28

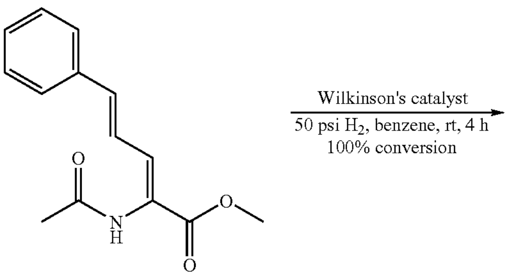

76

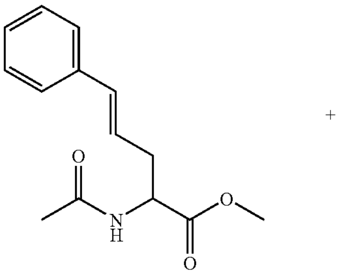

77 20%

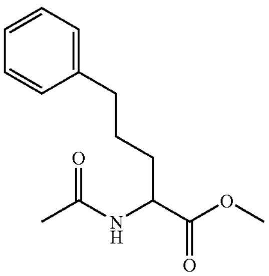

79 80%

This result is not without literature precedent. The rate of olefin reduction by Wilkinson's catalyst is profoundly influenced by steric hindrance about the C=C double bond, but related reductions involving styrene have previously shown that electronic effects override these steric effects and that the aromatic substituent enhances the rate of reduction.[215,216]

4.3 Final Strategy

The failure of this second strategy led to a final revision and the discovery of a strategy which would enable the selective hydrogenation of an unsaturated carbocycle in the presence of a deactivated but potentially metathesis-active olefin. We decided to capitalise on the slow reactivity of trisubstituted olefins to Wilkinson's hydrogenation and their reduced reactivity to metathesis. 1,1-Disubstituted olefins, for example, do not undergo homodimerisation and only react with more reactive olefins.[130,182] This differential reactivity would therefore facilitate the cross metathesis of allylglycine units and subsequent hydrogenation without interference from the 1,1-disubstituted olefin residues. A simple transformation then renders the trisubstituted olefin more reactive to metathesis and facilitates the formation of the second carbocycle (Scheme 4.29).

Scheme 4.29

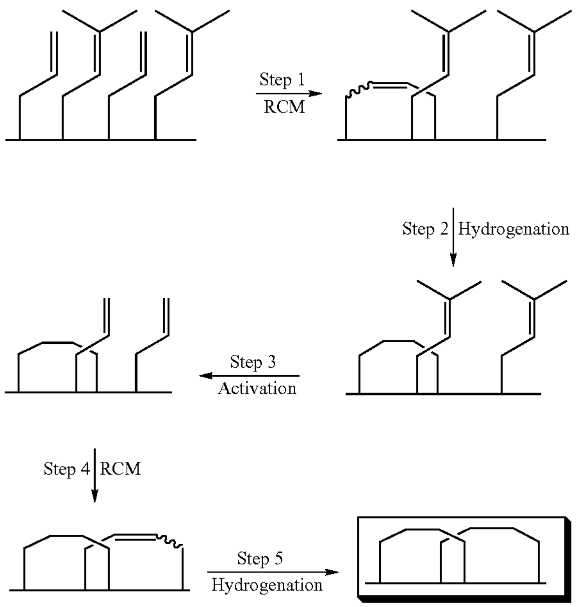

4.3.1 Synthesis of (2S)-Methyl 2-N-Acetylamino-5-methylhex-4-enoate 19

The prenyl olefin 19 was prepared via asymmetric hydrogenation of the corresponding dienamide 20. The prenylglycine derivative 19 was isolated in quantitative yield and excellent enantioselectivity (Scheme 4.30).

Scheme 4.30

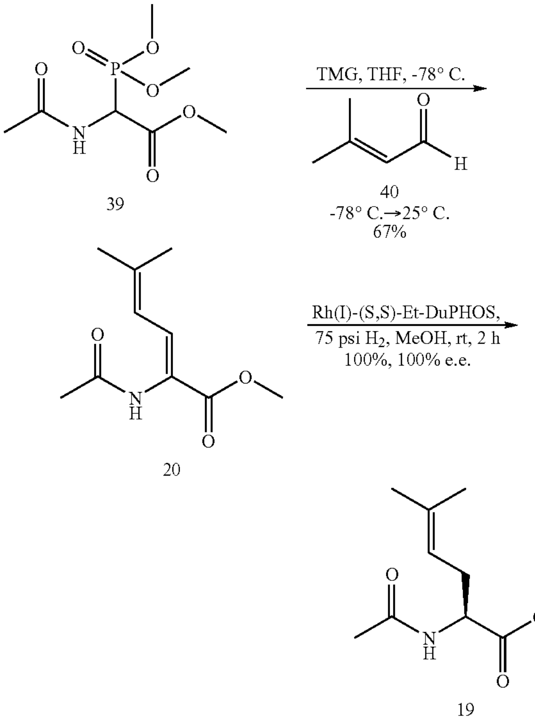

39

40

20

19

4.3.2 Reactions with (2S)-Methyl 2-N-Acetylamino-5-methylhex-4-enoate 19

This prenylglycine unit 19 was subjected to the hydrogenation conditions that quantitatively reduce the dimer 60 to the saturated analogue 71 (Scheme 4.19) and encouragingly, 94% of the starting enamide 19 was recovered (Scheme 4.31). This was a very promising result which prompted us to further investigate cross metathesis reactions involving this substrate 19. Furthermore, we envisaged that incorporation of this unit 19 into a peptide via solid phase peptide synthesis (SPPS) would be straightforward.

Scheme 4.31

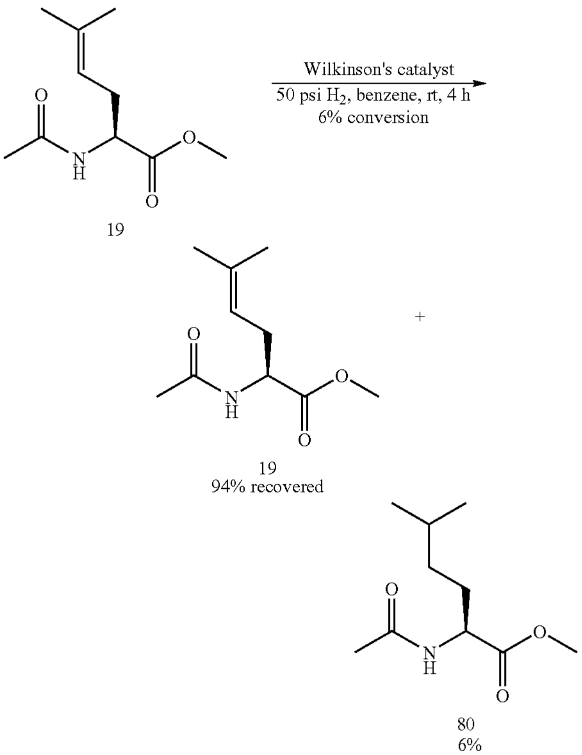

19

+

19
94% recovered 80
6%

Cross metathesis of allylglycine unit 21a into dimer 60 in the presence of the prenyl enamide 19 proceeded smoothly with quantitative conversion (Scheme 4.32); the starting prenyl enamide 19 was recovered unchanged.

Scheme 4.32

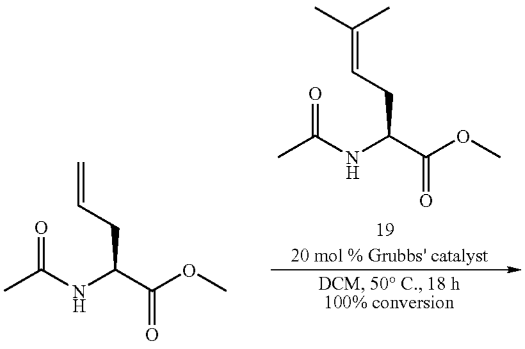

19

21a

-continued

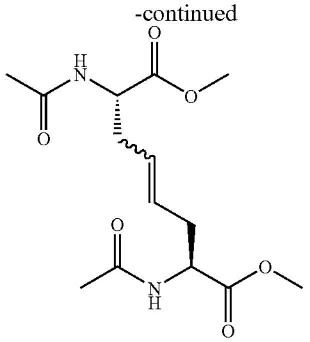

60

+

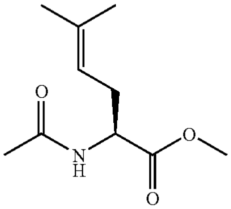

19

The reduced reactivity of prenylglycine 19 enabled the dimerisation of allylglycine 21a and the selective hydrogenation of the resultant homodimer 60. The next step in the strategy involves activation of the dormant olefin 19 (Step 3, Scheme 4.29). This can be achieved by cross metathesis with ethylene via a more active ruthenium alkylidene.

The prenyl compound 19 was subjected to ethenolysis to convert it to the more reactive allylglycine derivative 21a (Scheme 4.33). Exposure of 19 to 20 mol % of Grubbs' catalyst under an atmosphere of ethylene resulted in the recovery of the starting olefin 19. Use of the more reactive 2$^{nd}$ generation Grubbs' catalyst at higher reaction temperature (50° C.) and ethylene pressure (60 psi) still led to only poor conversions to 21a (<32%).

Scheme 4.33

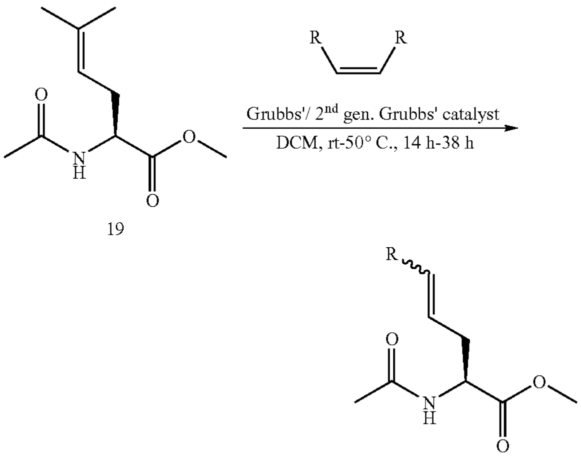

19

21a R = H
81 R = $CH_3$

R = H, 0-32% conversion
R = $CH_3$, 100% conversion
(84% yield)

We postulated that this result may be due to the unstable nature of the in situ generated ruthenium-methylidene intermediate 48 at elevated temperature (50° C.),[202-204] or unfavourable competition between the rising concentration of terminal olefins and 21a for binding to the ruthenium catalyst.[217]

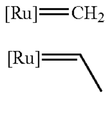

48

49

In order to circumvent this problem, the prenyl enamide 19 was instead exposed to an atmosphere of cis-2-butene (15 psi) thereby facilitating the catalysis via the more stable ruthenium-ethylidene complex 49. Butenolysis of 19 in the presence of 5 mol % second generation Grubbs' catalyst gave the expected crotylglycine derivative 81 with quantitative conversion (Scheme 4.33).

(2S)-Methyl 2-N-acetylaminohex-4-enoate 81 was isolated as a brown oil in 84% yield after flash chromatography. The $^1$H n.m.r. spectrum showed the replacement of the olefinic methine (H4) triplet in the starting prenyl compound 19 with new olefinic methine (H4, 5) multiplets at δ 5.49 and δ 5.24 respectively. Spectroscopic data were also in agreement with those reported in the literature.[117,119]

Interestingly, the purity of the 2-butene was found to be critical to the success of the cross metathesis reaction. When butenolysis reactions were conducted with a less expensive, commercially available mixture of cis- and trans-2-butene, only a trace of the butenolysis product was detected. Gas chromatographic analysis of the isomeric butene mixture showed that it was contaminated with 2.6% butadiene while none was detected in the pure cis-2-butene.[218] The addition of butadiene (2%) to cis-2-butene inhibited formation of the butenolysis product while a cis+trans mixture (30:70) of 2-butene, free of butadiene,† led to quantitative conversion to the expected cross metathesis product. These results strongly suggested that butadiene was poisoning the metathesis catalyst. Grubbs et al. have previously reported that butadiene can react with the rutheniumbenzylidene catalyst to produce a vinyl alkylidene which is inactive for acyclic metathesis reactions.[219]

† The cis+trans-2-butene mixture (30:70) free of butadiene was obtained by isomerisation of cis-2-butene with benzylidene[1,3-bis(2,4,6-trimethylphenyl)-2-imidazolidinylidene]dichloro[bis(3-bromopyridine)]ruthenium at −5° C.[218]

This activated crotylglycine derivative 81 was readily cross metathesised to the expected homodimer 60 with 5 mol % of second generation Grubbs' catalyst in dichloromethane (Scheme 4.34). Spectroscopic data were in agreement with those previously reported (Section 4.1.2).

Scheme 4.34

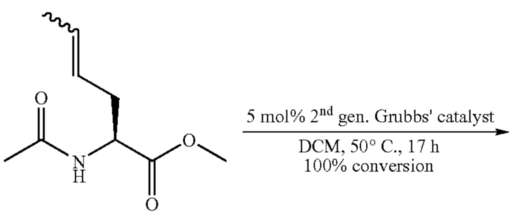

81

-continued

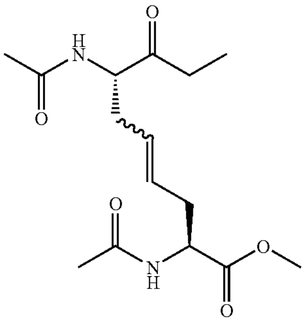

60

4.3.3 Reaction Sequence

Finally, an equimolar mixture of olefins 62 and 19 was exposed to a tandem sequence of the previously described five homogeneous catalytic reactions: i) dimerisation of allylglycine 62, ii) hydrogenation of the resultant homodimer 69, iii) activation of prenylglycine 19, iv) dimerisation of the activated crotylglycine derivative 81 and v) hydrogenation of the resultant homodimer 60. Solvent removal and subsequent [1]H n.m.r. analysis was performed on the crude product mixture after each transformation. The catalytic sequence resulted in quantitative conversion of the reactive substrate in each step and ultimately yielded diaminosuberic acid derivatives 71 and 72 as the only isolated products in 84 and 70% yield respectively (Scheme 4.35).

Scheme 4.35

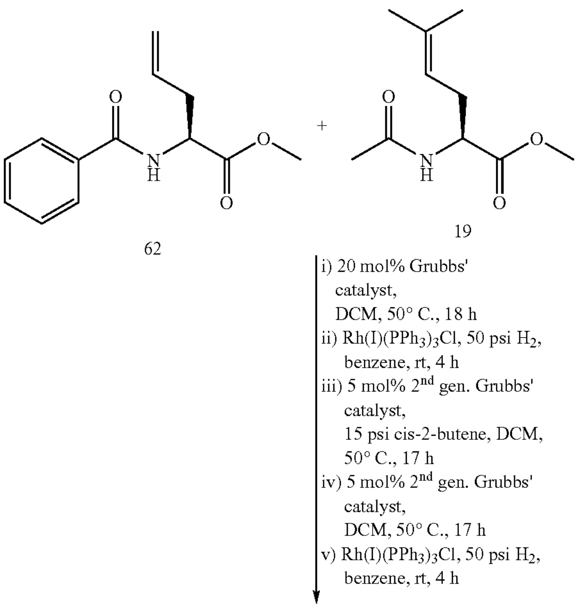

-continued

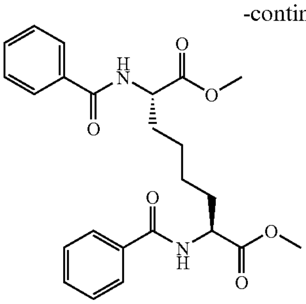

+

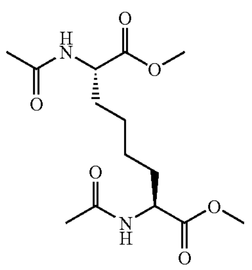

72 70%

71 84%

4.4 Summary

In conclusion, these model studies demonstrate that through the combination of homogeneous catalysis and judicious selection of non-proteinaceous allylglycine residues of varying reactivity, a highly efficient, unambiguous and regioselective synthesis of dicarba analogues of multi-cysteine containing peptides may be achievable. The methodology is also amenable to natural product and polymer synthesis or wherever selective carbon-carbon bond formation is required. Section 6 investigates the application of this methodology to synthetic and naturally occurring peptides.

5.0 A Tandem Metathesis-hydrogenation Strategy for the Selective Formation fo Three Carbon-carbon Bonds The selective formation of multiple dicarba bonds in complex molecules is a significant synthetic challenge. In section 4, we devised a strategy for a solution phase regioselective synthesis of two dicarba bridges. This chapter describes a catalytic strategy for the regioselective construction of three dicarba bridges in solution by selective and successive metathesis-hydrogenation transformations.

5.1 Proposed Strategy

In the preceding chapter we achieved regioselective C—C bond formation through the use of olefinic substrates possessing tuneable reactivity and highly chemo- and stereoselective catalysts. The varying reactivity of allylglycine and prenylglycine units towards metathesis and hydrogenation has been previously described (Chapter 4). We postulated that the steric and particularly electronic effects of a prenylglycine dienoate 82 would render it inert to metathesis and Wilkinson's hydrogenation. Two dicarba bridges can therefore be constructed in the presence of this inert olefin (Scheme 5.1). The diene can then be activated in two simple steps, the first of which involves a catalytic asymmetric hydrogenation to give optically pure prenylglycine. We have already demonstrated the facile activation of the prenyl sidechain by cross metathesis with either ethylene or cis-2-butene to give the corresponding allyl- or crotylglycine derivative respectively. The resultant activated olefin can readily undergo homodimerisation to give an unsaturated dimer which can be reduced to afford the saturated dicarba bridge. The final product mixture would ultimately contain three different diaminosuberic acid derivatives where the selective C—C bond formation would represent the formation of a dicarba analogue of a tricysteine-containing peptide (Scheme 5.1). In order to validate the proposed strategy we conducted a series of solution phase reactions.

Scheme 5.1
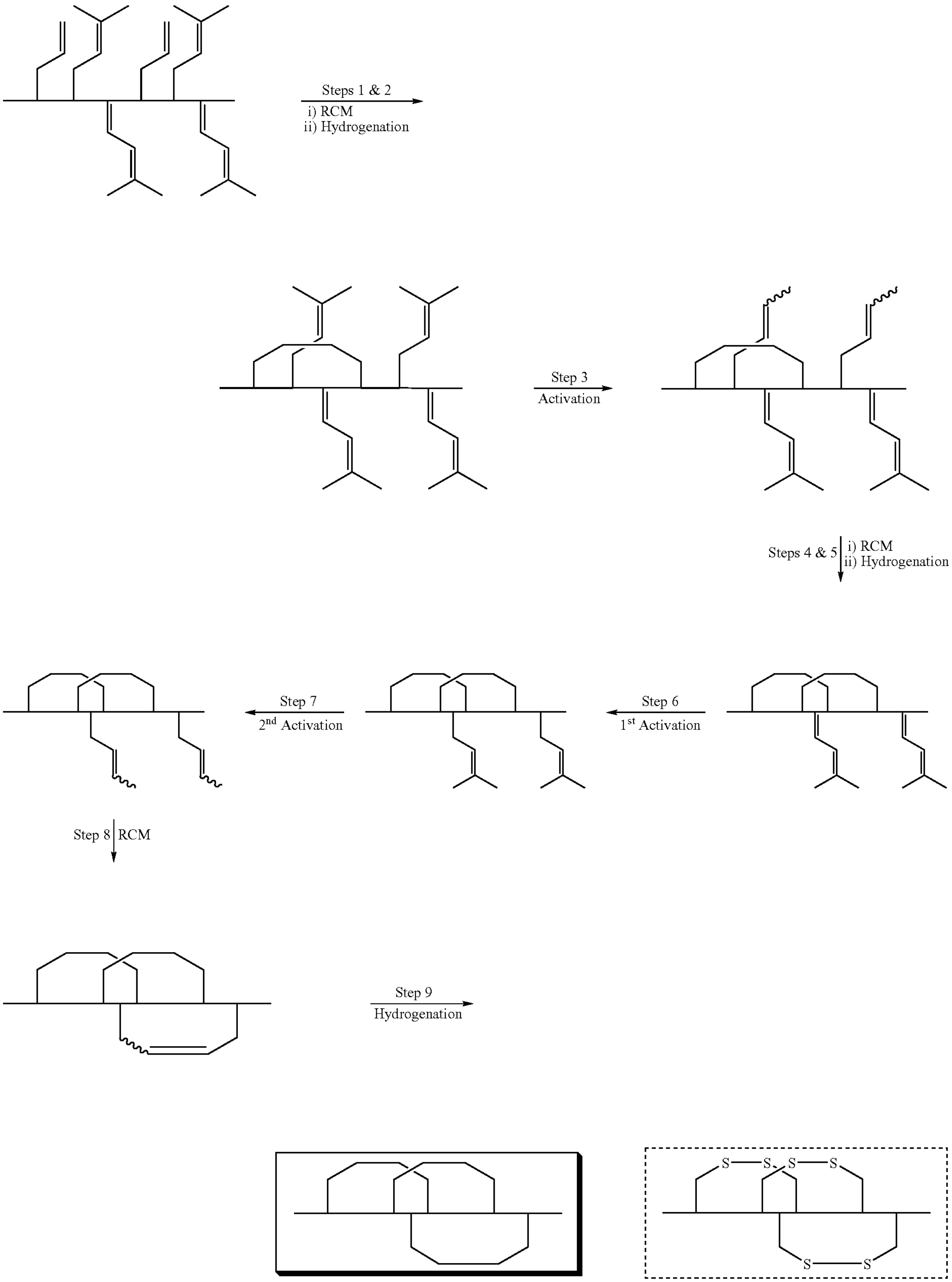

5.2 Solution Phase Model Study

A metathesis triplet 83, 19 and 82 was developed to facilitate the controlled formation of three diaminosuberic acid derivatives (Table 5.1). The differing olefin substitution in the molecules provides tuneable reactivity towards homogeneous metathesis[120,121] and hydrogenation catalysts.[33,215]

TABLE 5.1

Reaction Sequence for the Construction of Three Dicarba Bridges[a]

| Sidechain | | | | | | | | | | Summary of Activity |
|---|---|---|---|---|---|---|---|---|---|---|
| 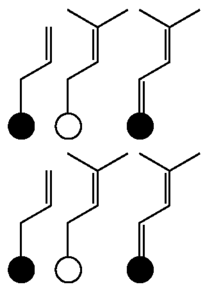 | Step 1: CM-H Grubbs' catalyst | Step 2: Wilkinson's Hydrogenation | Step 3: CM $2^{nd}$ gen. Grubbs' catalyst | Step 4: CM-H $2^{nd}$ gen. Grubbs' catalyst | Step 5: Wilkinson's Hydrogenation | Step 6: Rh(I)-DuPHOS Hydrogenation | Step 7: CM $2^{nd}$ gen. Grubbs' catalyst | Step 8: CM-H $2^{nd}$ gen. Grubbs' catalyst | Step 9: Wilkinson's Hydrogenation | 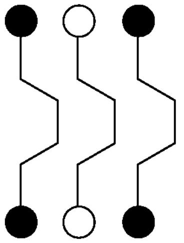 |
| Substrates | C═C | C—C | Act | C═C | C—C → | Act | Act | C═C | C—C | Products |
| Sidechain | | | | | Reactivity | | | | | Summary of Activity |
| 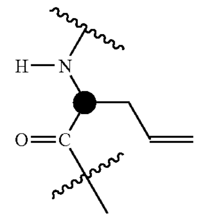 83 | ✓ | ✓ | — | — | — | — | — | — | — | Terminal allylic olefin. No activation required. |
| 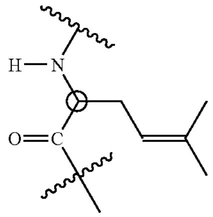 19 | x | x | ✓ | ✓ | ✓ | — | — | — | — | Trisubstituted olefin. Activated via CM with 2-butene. |
| 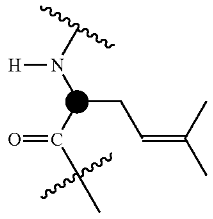 82 | x | x | x | x | x | ✓ | ✓ | ✓ | ✓ | Hindered extended acrylamide olefin. Activated via i) asymmetric hydrogenation and ii) CM with 2-butene. |

Figure 3:
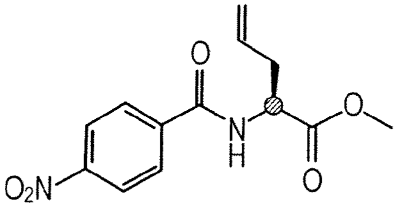
FIG. 3 illustrates a metathesis triplet and a related nmr tracing (see 5.2).
Figure 3:
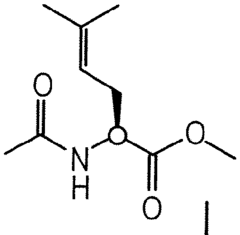
Figure 3:
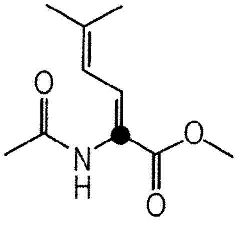
Figure 3:
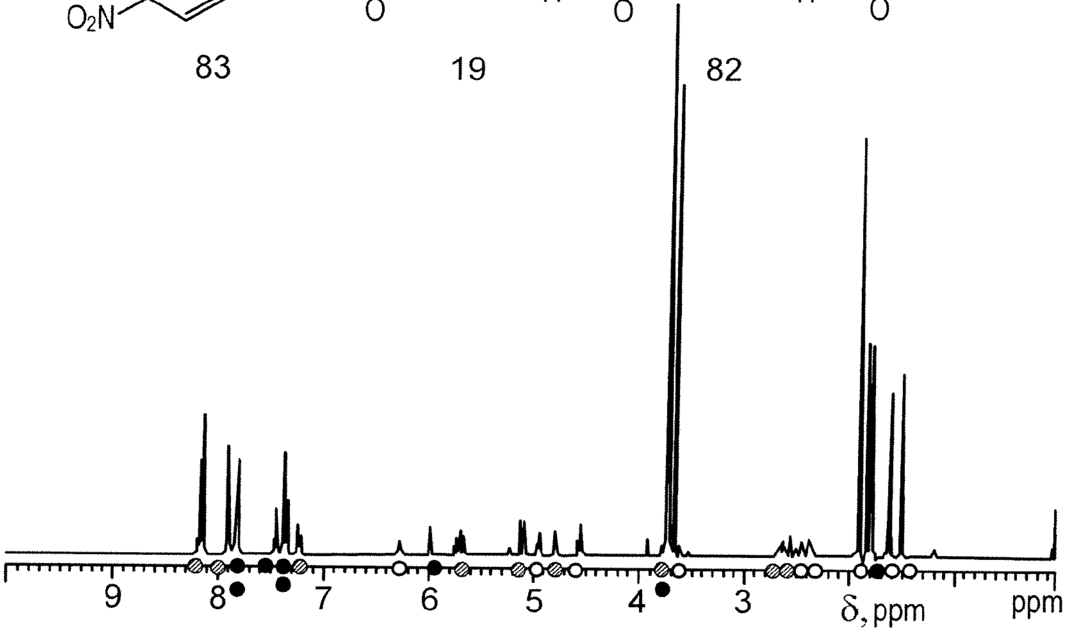

[a] ✓ = Reactive olefin. x = Unreactive olefin. — = Unreactive dicarba bridge. Act = Olefin activation step. CM-H = Cross metathesis-homodimerisation. CM = Cross metathesis Three different N-acyl protecting groups were employed to facilitate unambiguous assessment of cross metathesis selectivity. A mixture of a p-nitrobenzoyl-protected allylglycine derivative 83, an acetyl-protected prenylglycine unit 19 and a benzoyl-protected prenylglycine dienamide 82 gave adequate separation of characteristic peaks in the $^1H$ n.m.r. spectrum (FIG. 3) to enable reaction monitoring of Steps 1-9. Importantly, the protecting groups on the amino group do not affect the mechanistic course of the reaction sequence.

The solution phase studies therefore commenced with preliminary experiments on the diene 82 to ensure it was inert to metathesis and Wilkinson's hydrogenation.

5.2.1 Synthesis of (2Z)-Methyl 2-N-Benzoylamino-5-methylhexa-2,4-dienoate

The dienamide 82 was synthesised by Horner-Emmons olefination of methyl 2-N-benzoylamino-2-(dimethoxyphosphinyl)acetate 64 with commercially available 3-methyl-2-butenal 40 and tetramethylguanidine (TMG) (Scheme 5.2), as described for several dienamides in this application.

Scheme 5.2

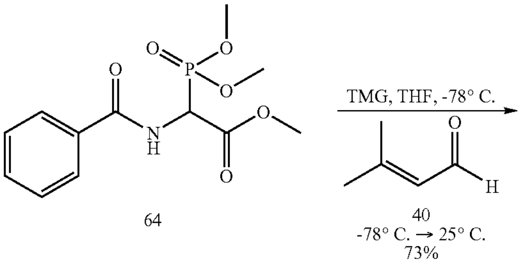

64

-continued

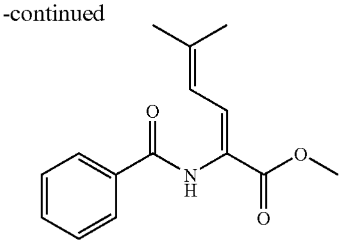

82

Methyl 2-N-benzoylamino-5-methylhexa-2,4-dienoate 82 was isolated as an off-white solid in 73% yield. Formation of the prenylglycine dienamide 82 was supported by $^{13}C$ n.m.r. spectroscopy which displayed new olefinic methyl peaks at δ 19.3 and δ 27.1 respectively, in addition to characteristic olefinic methine (C3, 4) and quaternary (C2, 5) peaks. A molecular ion plus proton peak at m/z 260.1282 in the accurate mass spectrum was consistent with the molecular formula $C_{15}H_{18}NO_3$ and also supported formation of the dienamide 82.

5.2.2 Reactivity of (2Z)-Methyl 2-N-Benzoylamino-5-methylhexa-2,4-dienoate 82 toward Metathesis and Hydrogenation The dienamide 82 was subjected to homodimerisation conditions with second generation Grubbs' catalyst (Scheme 5.3). $^1H$ n.m.r. spectroscopy confirmed complete recovery of the starting olefin 82 with no evidence of the dimerised dienoate 84. This result supported our postulate that diene 82 is electronically and sterically compromised and therefore inert to metathesis.

Scheme 5.3

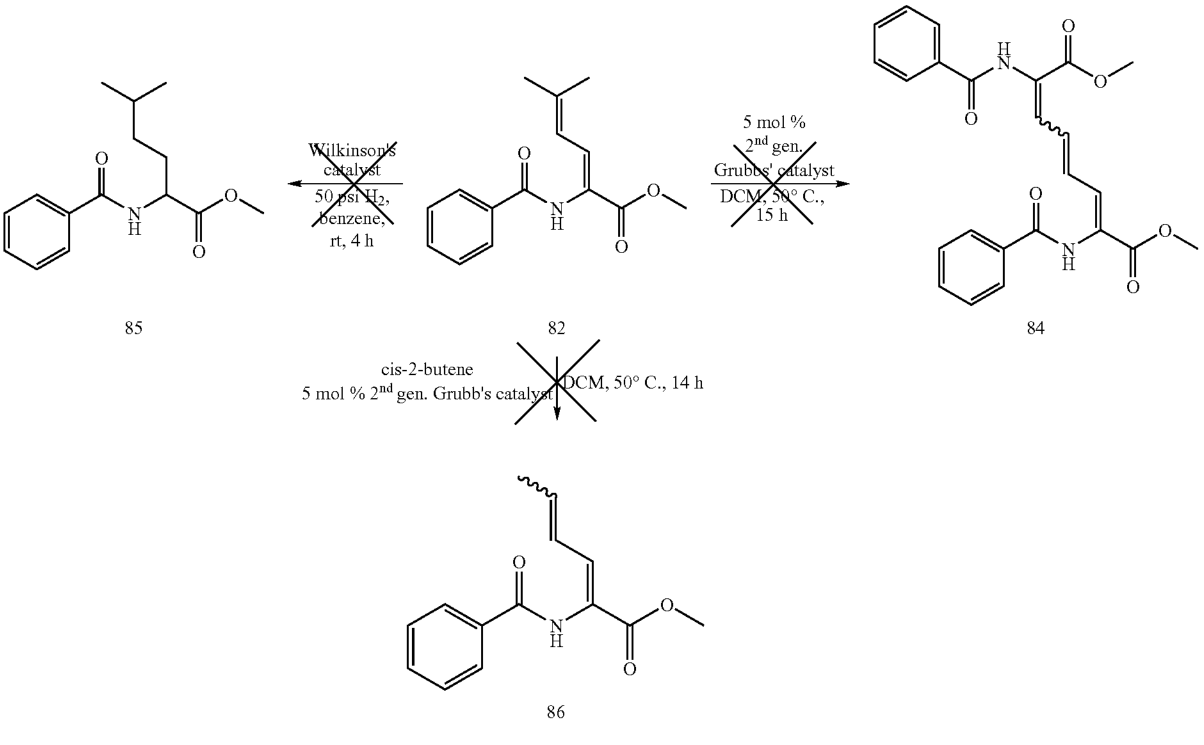

85

82

84

86

Our proposed reaction sequence then required the reduction of an unsaturated dicarba bridge in the presence of a diene moiety (Step 2, Scheme 5.1). The dienamide 82 was therefore subjected to the hydrogenation conditions that quantitatively reduce unsaturated dimers to their saturated analogues (Wilkinson's catalyst, 50 psi $H_2$). Encouragingly, the reduced prenyl compound 85 was not observed and the starting olefin 82 was recovered unchanged (Scheme 5.3).

Finally, the diene 82 was exposed to metathesis conditions used to activate prenylglycine 19 by conversion to the crotyl derivative 81 (cis-2-butene, second generation Grubbs' catalyst, Scheme 5.3). Again $^1$H n.m.r. spectroscopy indicated that the dienamide 82 was inert to these conditions. The starting olefin 82 was recovered unchanged with no evidence of the potential cross metathesis product 86.

5.2.3 Activation of (2Z)-Methyl 2-N-Benzoylamino-5-methylhexa-2,4-dienoate

Activation of the dienamide 82 was initiated with a Rh(I)-Et-DuPHOS-catalysed asymmetric hydrogenation to give the prenylglycine derivative 87 in excellent yield and enantioselectivity (100% e.e.) (Scheme 5.4).

The replacement of olefinic methine (H3, 4) proton peaks in the $^1$H n.m.r. spectrum with new methylene (H3) and olefinic (H4) multiplets at δ 2.52-2.76 and δ 5.08 confirmed formation of the prenylglycine residue 87. Over-reduction of the terminal double bond was not observed under these conditions.

Scheme 5.4

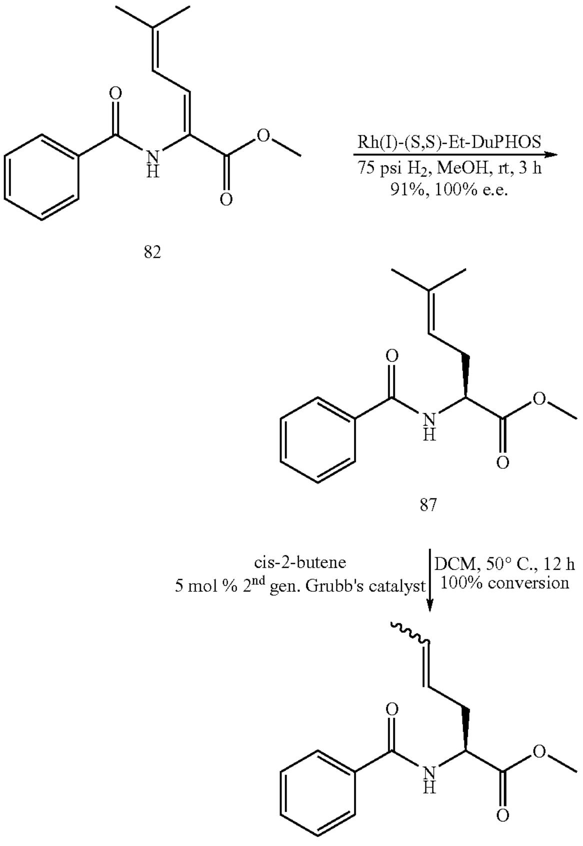

82

87

88

The second activation step involved treatment of the prenyl olefin 87 with 5 mol % second generation Grubbs' catalyst and cis-2-butene (15 psi) to yield the crotylglycine derivative 88 (Scheme 5.4). The reaction proceeded with quantitative conversion as indicated by $^1$H n.m.r. and $^{13}$C n.m.r. spectroscopic analysis. The accurate mass spectrum also displayed a molecular ion plus proton peak at m/z 248.1284 which is consistent with that expected for the molecular formula $C_{14}H_{18}NO_3$.

5.2.4 Reactions with (2S)-Methyl 2-N-(p-Nitrobenzoyl) aminopent-4-enoate 83

The third olefin in the metathesis triplet is the allylglycine derivative 83. Reaction of the hydrochloride salt of allylglycine methyl ester 51 with p-nitrobenzoyl chloride 89 and triethylamine in a mixture of dichloromethane: diethyl ether gave the protected allylglycine residue 83 in 99% yield (Scheme 5.5).

The $^1$H n.m.r. and $^{13}$C n.m.r. spectra supported formation of the protected allylglycine 83 with the downfield shift of the methine (H2) doublet of triplets at δ 4.90 and the introduction of aromatic resonances at δ 7.95 (H2',6') and δ 8.30 (H3',5').

Scheme 5.5

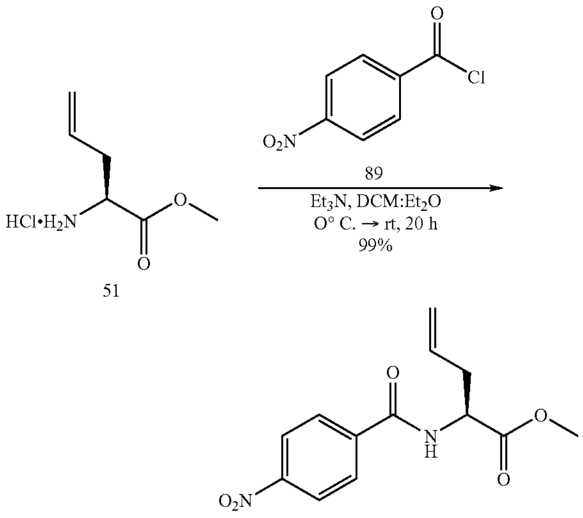

51

89

83

The allylglycine derivative 83 was quantitatively dimerised with Grubbs' catalyst in dichloromethane heated at reflux (Scheme 5.6). Formation of the dimer 90 was supported by $^1$H and $^{13}$C n.m.r. spectroscopic analysis which displayed signals due to the new olefinic methine proton (H4, δ 5.49-5.53) and carbon (C4, 128.8) respectively.

The unsaturated dimer 90 was subjected to the previously described Wilkinson's hydrogenation conditions (50 psi $H_2$, benzene, 4 hours). Unfortunately, under these conditions, the aromatic nitro substituents were reduced, thus providing a potential mechanism for poisoning of the metathesis catalyst. Fortunately, Jourdant et al. recently reported the selective reduction of an olefin in the presence of an aromatic nitro group.[220] Homogeneous hydrogenation under 15 psi $H_2$ in a mixture of tetrahydrofuran: tert-butanol (1:1) led to the selective reduction of the unsaturated dimer 90 without concomitant reduction of pendant aromatic nitro groups (Scheme 5.6).

Scheme 5.6

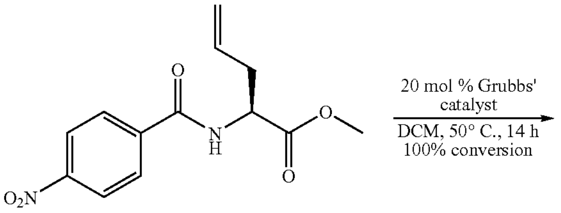

83

-continued

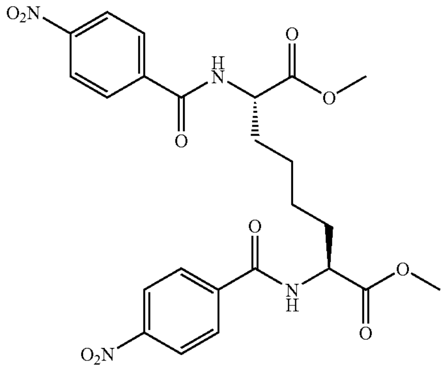

91

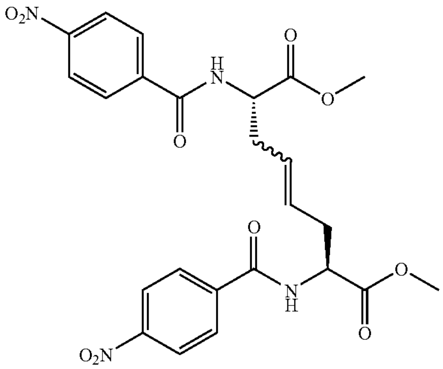

90

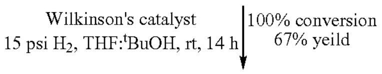

(2S,7S)-Dimethyl 2,7-N,N'-di(p-nitrobenzoyl)aminooctanedioate 91 was isolated as an off-white solid in 67% yield. The replacement of olefinic peaks in the $^1H$ n.m.r. spectrum with new methylene (H4, 6 and H3, 5) multiplets at δ 1.39-1.54 and δ 1.74-2.04 respectively confirmed formation of the saturated dimer 91.

5.2.5 Reaction Sequence

An equimolar mixture of olefins 83, 19 and 82 was subjected to the catalytic sequence outlined in Scheme 5.7. Solvent removal and subsequent $^1H$ n.m.r. and mass spectral analysis was performed on the crude product mixture after each transformation. Exposure of the olefinic mixture 83, 19 and 82 to Grubbs' catalyst in dichloromethane led to homodimerisation of allylglycine 83 to form an unsaturated dicarba bridge 90. Predictably, the more sterically hindered olefin 19 and the electronically compromised olefin 82 were unreactive under these reaction conditions. The resultant alkene 90 was then selectively hydrogenated in a mixture of tert-butanol:tetrahydrofuran (1:1) with Wilkinson's catalyst to afford the saturated dicarba bridge 91. Again, olefins 19 and 82 were inert to these conditions. Both the metathesis and hydrogenation reactions proceeded under mild experimental conditions with quantitative, unambiguous conversion to give the first suberic acid derivative 91 as shown by n.m.r. and MS analysis.

Scheme 5.7

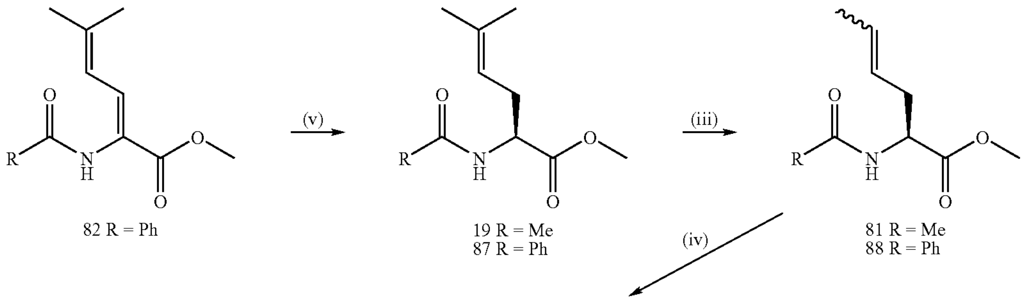

82 R = Ph

19 R = Me
87 R = Ph

81 R = Me
88 R = Ph

-continued

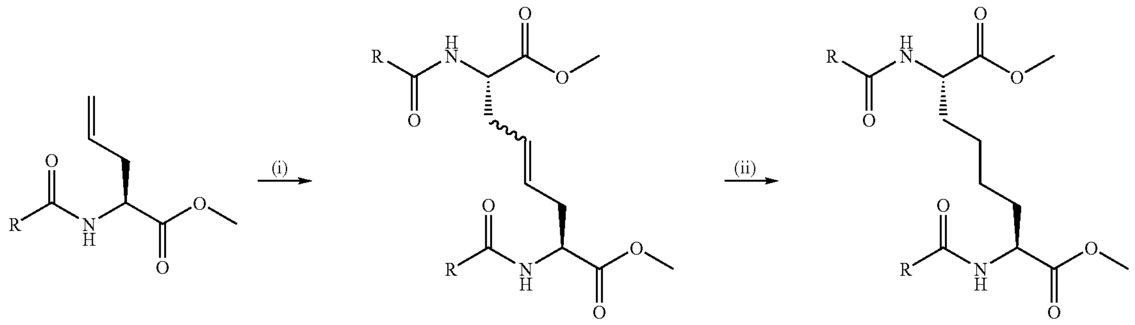

83 R = p-$NO_2$-Ph

90 R = p-$NO_2$—Ph
60 R = Me
69 R = Ph

91 R = p-$NO_2$-Ph
71 R = Me
72 R = Ph

Reagents and conditions: (i) 20 mol % Grubbs' catalyst, DCM, 50° C., 18 h; (ii) Rh(I)$(PPh_3)_3Cl$, 15 psi $H_2$, THF:$^t$BuOH (1:1), rt, 14 h; (iii) 5 mol % 2nd generation Grubbs' catalyst, 15 psi cis-2-butene, DCM, 50° C., 17 h; (iv) 5 mol % 2nd generation Grubbs' catalyst, DCM, 50° C., 17 h; (v) Rh(I)-(S,S)-Et-DuPHOS, 75 psi $H_2$, MeOH, rt, 2 h 100% e.e..

The next reaction in this catalytic sequence involved the activation of the dormant prenyl olefin 19 via cross metathesis with cis-2-butene (butenolysis) to generate a more reactive crotylglycine derivative (Section 4.3.2). The mixture of 91, 19 and 82 was exposed to an atmosphere of cis-2-butene (15 psi) in the presence of 5 mol % second generation Grubbs' catalyst to afford the expected crotylglycine derivative 81 and a trace of the corresponding homodimer 60. The activated olefin 81 was then quantitatively homodimerised to the expected unsaturated dimer 60 with 5 mol % of second generation Grubbs' catalyst. Exposure of the newly formed olefin 60 to a hydrogen atmosphere and Wilkinson's catalyst resulted in quantitative conversion to the saturated dicarba bridge 71 (Section 4.1.4). Once again, the sterically and electronically compromised olefin 82 remained a spectator over the three reactions used to form the second diaminosuberic acid derivative 71.

The remaining acrylate-type olefin 82 was then used to form the final dicarba bridge. A double activation sequence was employed to render this remaining olefin reactive to homodimerisation. Homogeneous hydrogenation of dienamide 82 using chiral Rh(I)-(S,S)-Et-DuPHOS catalyst gave (S)-configured prenylglycine derivative 87 in excellent enantioselectivity (100% e.e.), chemoselectivity and conversion. No evidence of over-reduction of the C4 carbon-carbon double bond was observed. The resulting prenyl olefin 87 was then converted to the crotylglycine analogue 88 via butenolysis. Exposure of this olefin to the previously described cross-metathesis and hydrogenation conditions then led to the formation of the final dicarba bond and the third diaminosuberic acid derivative 72 via alkene intermediate 69. The metathesis-hydrogenation sequence led to generation of three diamidosuberic acid esters 91, 71 and 72 in 67, 81 and 70% yields respectively. Significantly, residual catalyst and/or decomposition products did not compromise subsequent transformations and no other byproducts were isolated. This demonstrates the high chemoselectivity exhibited by each catalytic step.

5.3 Summary

A combination of homogeneous hydrogenation and metathesis reactions has enabled the highly efficient, stepwise chemo- and stereoselective formation of three identical dicarba C—C bonds in three different 2,7-diaminosuberic acid derivatives without purification of intermediates. This homogeneous catalytic methodology can be used widely in peptidomimetics and total product synthesis where multiple (preferably 3) C—C bonds and/or rings need to be selectively constructed.

6.0 Synthesis of Dicarba Cyclic Peptides via Regioselective Cross Metathesis METATHESIS This section describes the application of the regioselective strategy developed in section 4 to a series of peptides. A model synthetic pentapeptide was initially investigated. The results from this substrate led to the production of dicarba analogues of conotoxin ImI.

6.1 Solid Phase Peptide Synthesis (SPPS)

Linear peptides were synthesised via standard solid phase peptide synthesis (SPPS) methodology.[221] This procedure involves the attachment of an N-Fmoc-protected amino acid to a solid support and the construction of the sequence from the C— to N-terminus Scheme 6.1. Peptide construction requires: i) Fmoc-deprotection of the resin-tethered amino acid under basic conditions, ii) activation of the incoming Fmoc-protected amino acid and iii) its subsequent coupling to the resin-tethered amino acid. The process is repeated until the desired peptide sequence is constructed. Conveniently, the use of orthogonally protected amino acids enables sequential Fmoc-deprotection and coupling without loss of acid-sensitive sidechain protecting groups.

Scheme 6.1

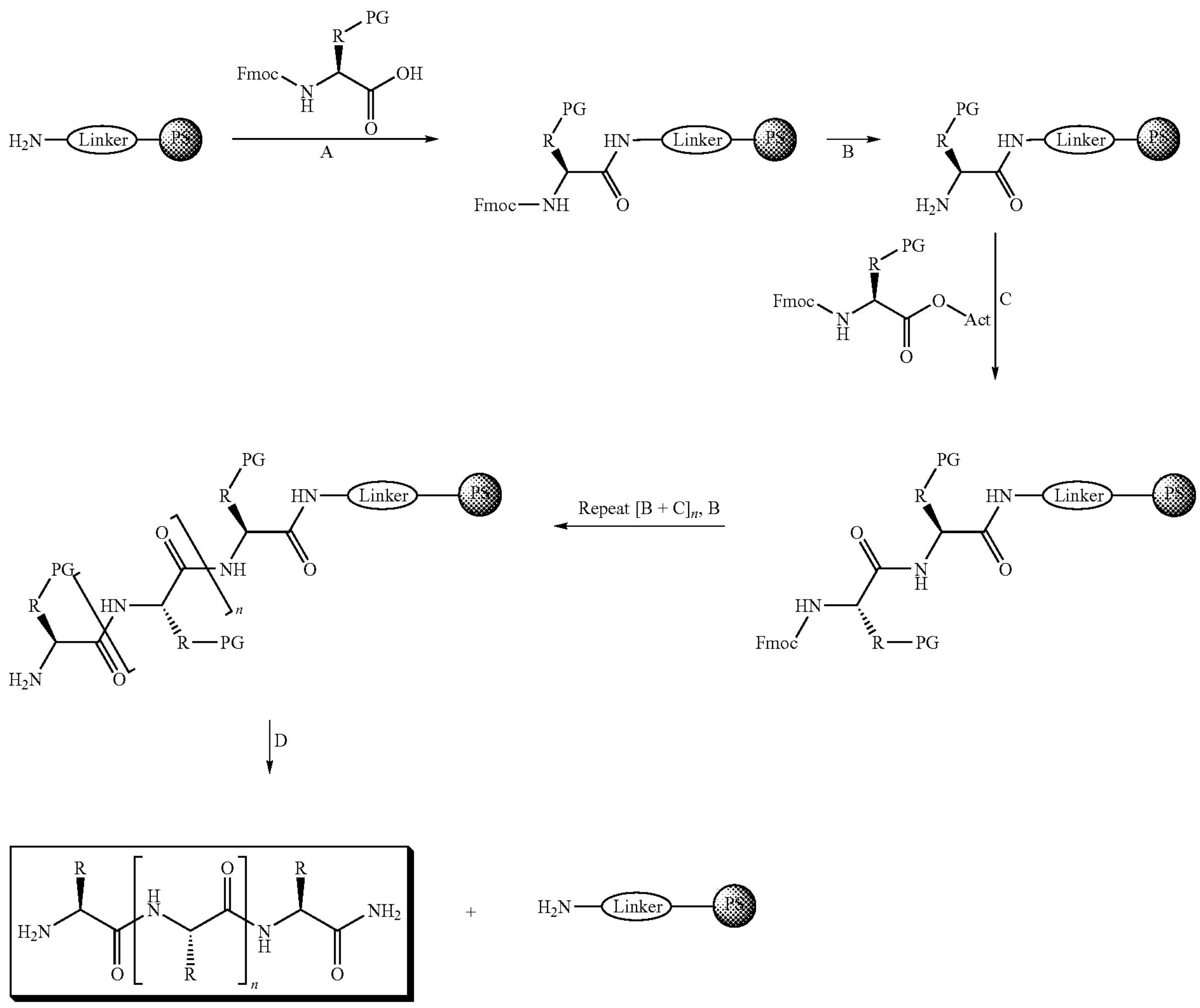

A = Resin attachment
B = Fmoc-deprotection
C = Coupling of activated amino acid
D = Peptide clevage from resin The choice of resin plays an important role in peptide synthesis. A plethora of polystyrene-based supports are commercially available. These resins are typically cross-linked polystyrene (PS) containing 1% divinylbenzene and are functionalised with linkers (or handles) to provide a reversible linkage between the synthetic peptide chain and the solid support.[221] Several linkers commonly utilised in Fmoc-SPPS are presented in. Diagram 6.1. With the target peptide in mind, the appropriate resin-linker can be chosen to functionalise the C-terminus as a carboxylic acid, carboxamide, ester or alcohol. In addition, peptides can be cleaved under acidic or basic conditions where acid sensitive sidechain protecting groups can be retained or simultaneously deprotected during peptide cleavage. Importantly, the resin-linkers must be inert to metathesis and hydrogenation catalysis conditions.

Diagram 6.1

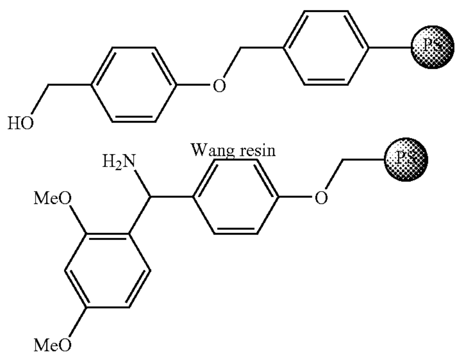

Wang resin

Rink amide resin

-continued

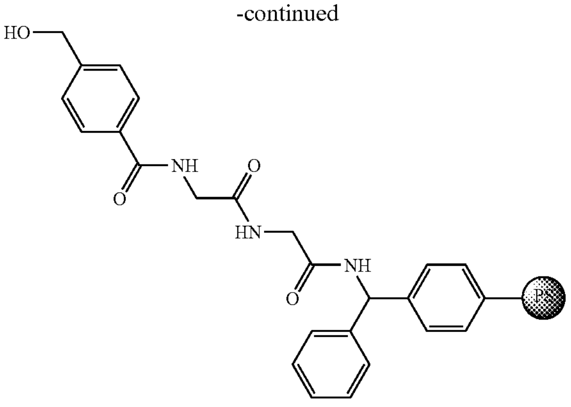

BHA-Gly-Gly-HMBA resin

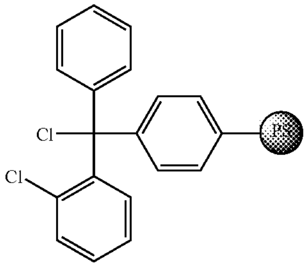

2-Chlorotrityl chloride resin

Construction of the linear peptides via solid phase methodology provides two options for the construction of dicarba bridges: The complete linear sequence can be cleaved from the resin and then subjected to metathesis and hydrogenation in solution. Alternatively, the regioselective catalytic sequence can be performed entirely on the resin-bound peptides.

We have conducted an on-resin metathesis-hydrogenation sequence for the preparation of carbocyclic analogues of cysteine-containing peptides. This strategy involves conventional solid phase peptide synthesis followed by on-resin ruthenium-catalysed ring closing metathesis and on-resin homogeneous rhodium-catalysed hydrogenation of the resultant unsaturated bridge (Scheme 6.2).

Scheme 6.2

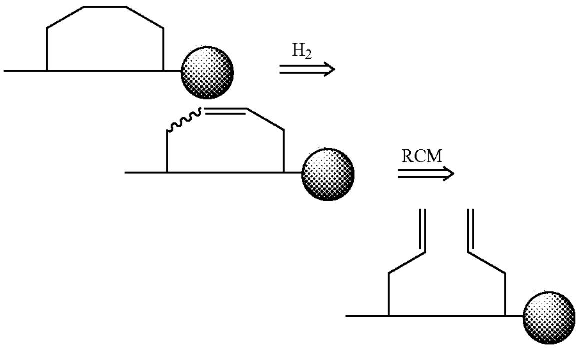

The on-resin strategy, however, is compromised by decreased activity of the metathesis and hydrogenation catalysts in the heterogeneous system. Previous studies have shown that higher catalyst loadings and longer reaction times are required to achieve quantitative conversion on resin-bound substrates.[141,142] In addition, ring closing metathesis of peptidic substrates is highly sequence dependent due to the involvement of aggregation phenomena. We have found that peptide aggregation, resulting from interchain secondary structures, can lead to poor solvation of the peptidyl-resin, reduced reagent penetration and ultimately low reaction yields. Strategies had to be developed to address these problems.

6.2 Ring Closing Metathesis Reactions of Synthetic Pentapeptides

We have investigated the synthesis of bis-dicarba analogues of bicyclic peptides possessing two disulfide bonds. To achieve this aim we required the use of complimentary pairs of both allyl- and prenylglycine residues (although variations described above can be used). In order to transfer the solution phase methodology across to the solid phase, we needed to demonstrate that Fmoc-protected prenylglycine 92 could be i) synthesised and incorporated into a peptide sequence using standard SPPS protocol; ii) that it was stable to peptide coupling and deprotection conditions, and iii) that it possessed analogous reactivity to its solution phase congener in the catalysis steps. We therefore decided to synthesise model peptides based on naturally occurring conotoxin peptides.[171,172,225] Conotoxin ImI 93 (Ctx ImI) is a small dodecapeptide possessing two cysteine bonds.[173,174,226] A truncated sequence 94 of the Cys8-Ala9-Trp10-Arg11-Cys12 Ctx ImI domain was initially investigated. This sequence possesses two allylglycine residues which undergo ring closing metathesis to yield an unsaturated carbocycle 95. After establishing optimum conditions for the formation of the first dicarba bond, the sequence was modified to include a prenylglycine residue to facilitate the formation of a second dicarba linkage.

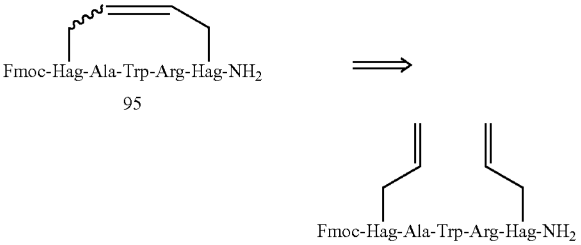

94

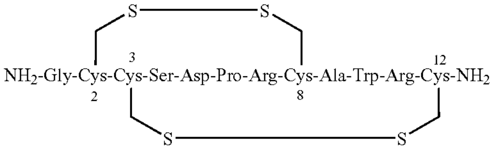

93

The pentapeptide 94 was synthesised on Rink amide resin, a polystyrene-based solid support bearing an amine linker that generates a C-terminal carboxamide upon resin cleavage. (FIG. 6.1). Prior to attachment of the first amino acid, the resin was swollen in dichloromethane to increase surface availability of resin active sites towards the incoming C-terminal Fmoc-protected amino acid. Peptide construction began with attachment of non-proteinaceous Fmoc-L-allylglycine (Fmoc-Hag-OH) 96 to Rink amide resin (A, FIG. 6.1) and remaining resin active sites were capped with acetic anhydride. Fmoc-deprotection of resin-tethered allylglycine followed by coupling of the successive amino acid and repetition of these steps (B and C, FIG. 6.1) enabled chain elongation. After coupling the last amino acid, a small aliquot of peptidyl-resin was exposed to trifluoroacetic acid cleavage solution (D, FIG. 6.1) to liberate the peptide 94 as a colourless solid. The mass spectrum displayed a molecular ion peak at m/z 847.1 $(M+H)^+$ which was consistent with the formation of the pentapeptide 94.

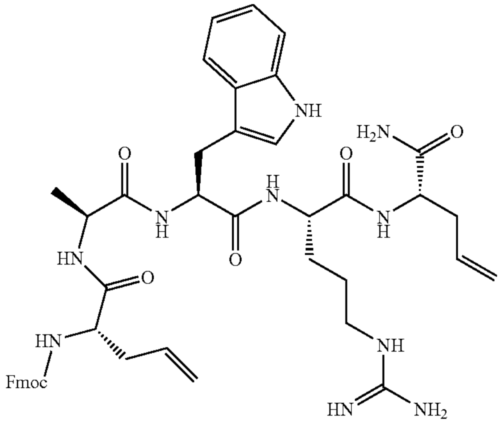

After confirming that pentapeptide synthesis had been successful, ring closing metathesis of the fully-protected resin-tethered sample 94a was performed with 20 mol % Grubbs' catalyst in dichloromethane and 10% lithium chloride in dimethylformamide. Mass spectral analysis of a cleaved aliquot of peptide indicated that these conditions resulted in complete recovery of the linear peptide 94. Use of the more active second generation Grubbs' catalyst did, however, lead to unsaturated carbocycle 95 but cyclisation failed to go to completion (Scheme 6.3). The presence of molecular ion peaks at m/z 819.2 $(M+H)^+$ and m/z 847.2 $(M+Na)^+$ were consistent with the presence of the unsaturated carbocycle 95 and the linear peptide 94 respectively.

Scheme 6.3

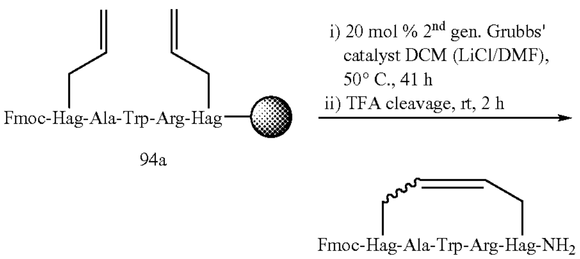

94a

95

We postulated that the peptide sequence itself may be responsible for the reduced ring closing metathesis yield. Pentapeptide 94 lacks a proline residue between the two allylglycine sidechains and hence the predominance of transoid peptide bonds would disfavour a close arrangement of the reacting terminal olefins. The inclusion of turn inducers in a peptide sequence can reduce peptide aggregation via the formation of cisoidal amide bonds.[227-229] In addition, the resultant turn can position the reactive allylglycine sidechains in close proximity to each other and thus facilitate cyclisation. The peptide was therefore reconstructed to incorporate proline, a naturally occurring turn-inducing amino acid.

The pentapeptide 97 was synthesised on Rink amide resin via the general SPPS methodology previously described. The peptide possessed an Ala-Pro replacement adjacent to the N-terminal allylglycine residue. Formation of the pentapeptide 97 was confirmed by mass spectrometry with the appearance of a molecular ion peak at m/z 873.2 $(M+H)^+$.

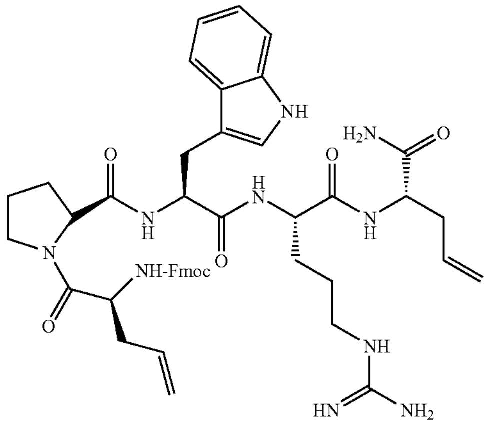

Ring closing metathesis of the fully protected resin-bound peptide 97a with Grubbs' catalyst (20 mol %) in dichloromethane and 10% lithium chloride in dimethylformamide led to recovery of the starting peptide 97 with only a trace of product 98 evident in the mass spectrum. Use of second generation Grubbs' catalyst (20 mol %), however, led to complete cyclisation (Scheme 6.4). The appearance of molecular ion peaks at m/z 845.1 $(M+H)^+$ and m/z 867.1 $(M+Na)^+$ in the mass spectrum confirmed formation of the unsaturated carbocycle 98. This result clearly demonstrates the influence of the turn-inducing proline residue on peptide conformation and reactivity.

Scheme 6.4

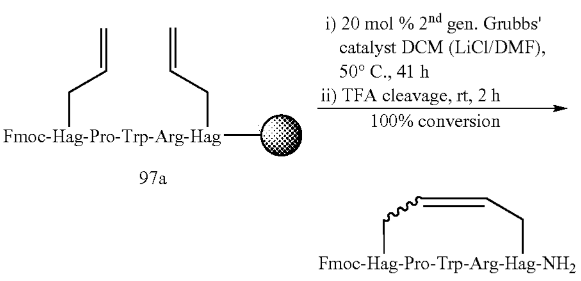

97a

98

In conjunction with this study, we simultaneously assessed the role of the catalytic cycle in affecting ring closing metathesis yield. We postulated that the incomplete cyclisation of linear sequence 94 could be due to thermal decomposition of the ruthenium-methylidene intermediate 48. We therefore investigated synthesis of the crotylglycine-containing peptide, Fmoc-Crt-Ala-Trp-Arg-Crt-$NH_2$ 99, for which metathesis proceeds through the more stable ruthenium-ethylidene species 49.

This initially required the synthesis of the crotylglycine derivative 100. Acid-promoted hydrolysis of (2S)-methyl 2-N-acetylaminohex-4-enoate 81 gave (2S)-2-aminohex-4-enoic acid hydrochloride salt 101. Fmoc-protection of amino acid 101 was performed according to the procedure described by Paquet et al. using N-fluorenylmethoxycarbonylamino-succinimide (Fmoc-OSu) in aqueous sodium carbonate and acetone (Scheme 6.5).230

Scheme 6.5

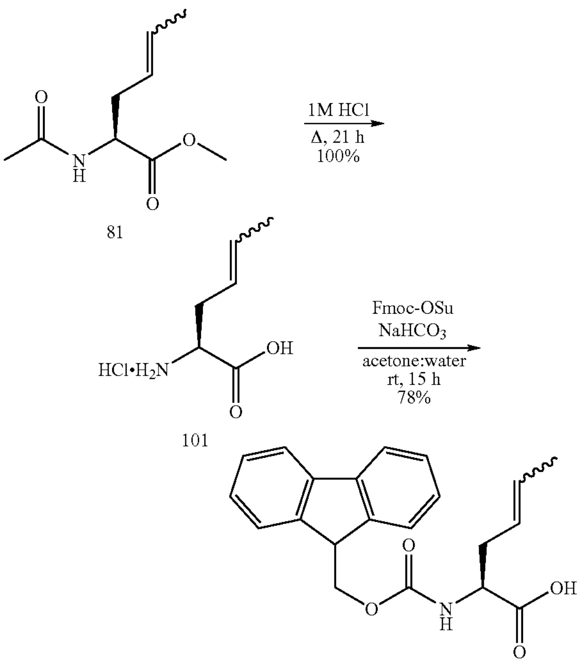

81

101

100

$^1H$ n.m.r. and $^{13}C$ n.m.r. spectral analysis of the product confirmed the formation of (2S)-2-N-fluorenylmethoxycarbonylaminohex-4-enoic acid (Fmoc-Crt-OH) 100 with the downfield shift of the methine proton (H2) peak (δ 4.55) and the corresponding carbon signal (δ 52.3). In addition, the appearance of aromatic signals characteristic of the Fmoc-group supported product formation. Spectroscopic data were also in agreement with those reported in the literature.[146]

With the Fmoc-protected crotylglycine derivative 100 in hand, we synthesised the linear peptide, Fmoc-Crt-Ala-Trp-Arg-Crt-$NH_2$ 99, on Rink amide resin using the SPPS methodology previously described. The mass spectrum displayed a molecular ion peak at m/z 875.2 $(M+H)^+$ corresponding to the linear peptide 99.

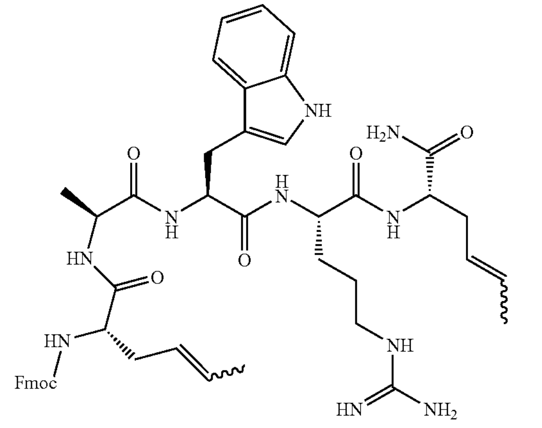

Ring closing metathesis of the linear resin-tethered peptide 99a with second generation Grubbs' catalyst (20 mol %) in dichloromethane and 10% lithium chloride in dimethylformamide led to quantitative formation of the unsaturated carbocycle 95[†] (Scheme 6.6). Note: RCM of the crotylglycine-containing peptide 99 leads to the same unsaturated carbocycle 95 resulting from cyclisation of the allylglycine-containing sequence 94, i.e. Fmoc-c[Hag-Ala-Trp-Arg-Hag]—OH is identical to Fmoc-c[Crt-Ala-Trp-Arg-Crt]—OH.

Scheme 6.6

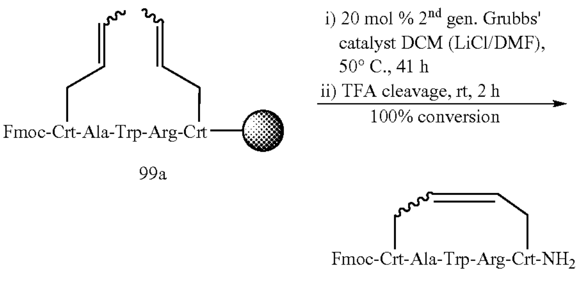

99a

95

These studies revealed two successful strategies for the synthesis of a dicarba cyclic peptide: i) the inclusion of proline residues to induce a turn in the peptide backbone and ii) the use of crotylglycine to avoid a ruthenium-methylidene intermediate in the catalytic cycle. Many naturally occurring cyclic peptides possess proline residues in their primary sequences and this could be used to advantage in RCM reactions. On the other hand, if the target peptide does not possess a proline residue (or a residue which can temporarily act as a pseudo-proline), incorporation of a non-native proline residue to enhance RCM yield is likely to have significant structural and biological impact on the final peptide. In this case, the use of crotylglycine residues would be beneficial.

6.3 Regioselective Synthesis of an Intra- and Intermolecular Dicarba Bridge in a Synthetic Pentapeptide Capitalising on the findings of the previous study (Section 6.2) we constructed another model peptide, Fmoc-Hag-Pro-Pre-Arg-Hag-OH 102, with a strategically placed proline residue. The synthetic pentapeptide 102 contains two types of metathesis active groups: Two allylglycine (Hag) residues and a less reactive prenylglycine unit (Pre). This linear sequence facilitates the regioselective construction of two dicarba bonds: An intramolecular metathesis reaction (RCM) of the allylglycine residues generates a carbocyclic ring and the remaining prenylglycine can be used to form an intermolecular dicarba bridge via cross metathesis (CM) with a second unsaturated molecule (Scheme 6.7).

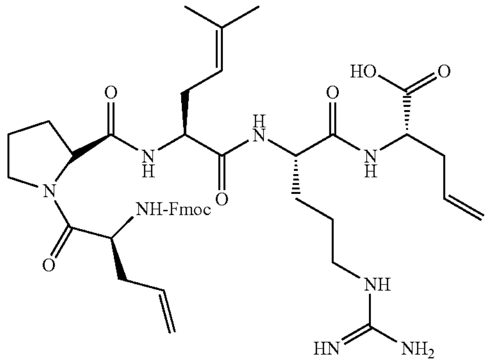

This second dicarba linkage could be used to attach the carbocyclic peptide to another peptide chain, a drug molecule, a solid support or a chelating heterocycle for the generation of radiopharmaceuticals.

Scheme 6.7

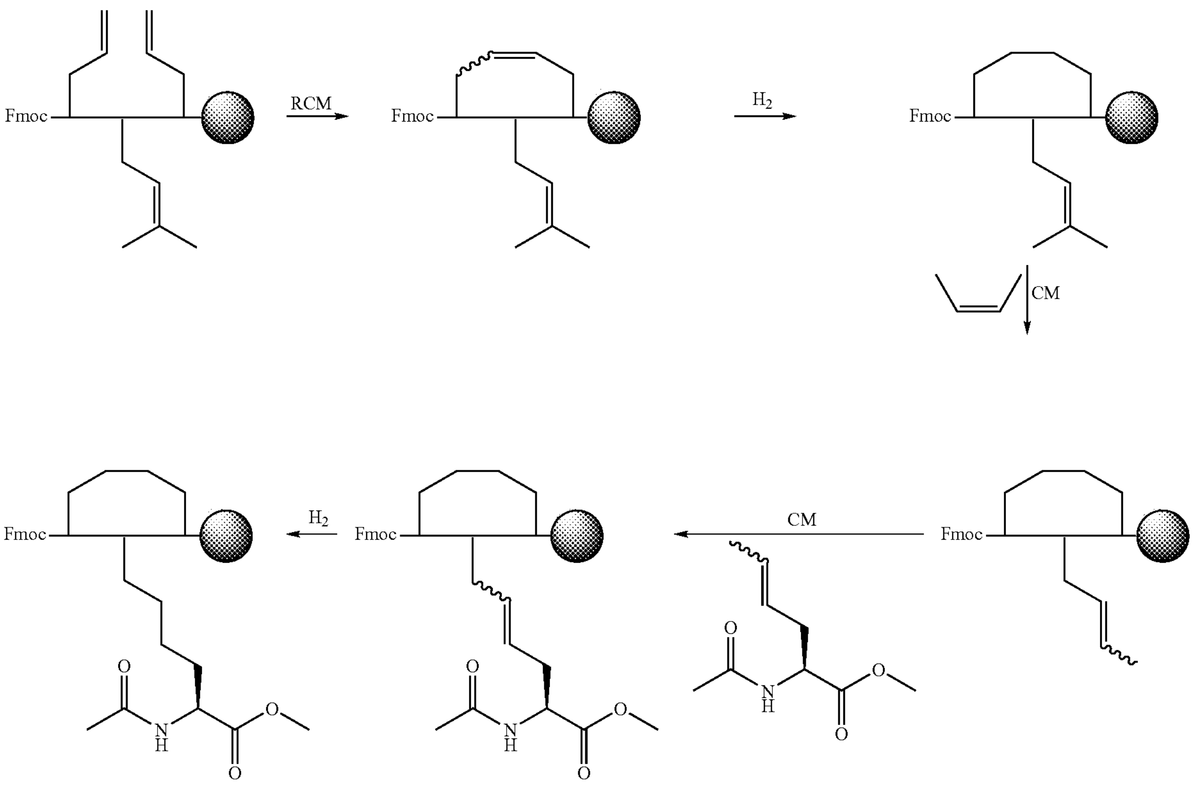

Synthesis of the peptide 102 firstly required the preparation of the Fmoc-protected prenylglycine derivative (Fmoc-Pre-OH) 92. Cross metathesis of Fmoc-protected allylglycine 96 with 2-methyl-2-butene in the presence of 5 mol % second generation Grubbs' catalyst gave the target (2S)-2-N-fluorenylmethoxycarbonylamino-5-methylhex-4-enoic acid 92 with quantitative conversion (Scheme 6.8).

Scheme 6.8

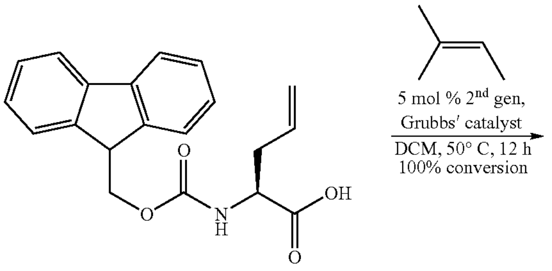

96

-continued

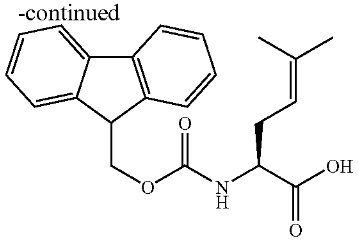

92

$^1H$ n.m.r. spectroscopy confirmed formation of the trisubstituted olefinic amino acid 92 by the replacement of terminal olefinic peaks with a new methine multiplet (H4) at δ 5.11 and two methyl singlets at δ 1.63 and δ 1.73. These signals are consistent with the generation of a prenyl group. The accurate mass spectrum also displayed a molecular ion peak at m/z 388.1525 $(M+Na)^+$ which was consistent with that required for 92. Unfortunately, purification of the product 92 from residual catalyst was difficult. We later found, however, that the crude amino acid 92 could be used without affecting subsequent SPPS procedures.

The peptide 102 was synthesised on inexpensive, readily available Wang resin, a polystyrene-based solid support bearing a benzylic alcohol linker (FIG. 6.1). The non-proteinaceous prenylglycine residue 92 was incorporated into the peptide sequence without complication. Formation of the pentapeptide 102 was confirmed by mass spectral analysis with the appearance of a molecular ion peak at m/z 813.5 $(M+H)^+$ and an additional peak at m/z 831.5 $(M+H_2O+H)^+$. The latter peak was due to the acid-promoted hydration of the prenyl sidechain during peptide cleavage, leading to the alcohol 103. The hydration of the prenyl group under acidic conditions was not unexpected. During the acid-catalysed cyclisation of the simple prenylglycine derivative 19 to pseudo-proline 18, acid-mediated hydration yielded alcohol 47 as a minor byproduct.

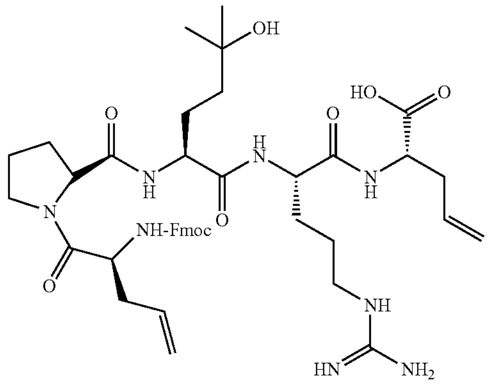

After confirming the synthesis of the pentapeptide 102, the peptidyl-resin was subjected to the regioselective catalytic strategy outlined in section 4. This is presented in Scheme 6.7.

The first step involved selective RCM of the allylglycine residues in the presence of the less reactive prenyl sidechain. RCM of the resin-tethered pentapeptide 102a was performed with 40 mol % second generation Grubbs' catalyst in dichloromethane and 10% lithium chloride in dimethylformamide and, as expected, incorporation of prenylglycine did not hinder cyclisation (Scheme 6.9). Mass spectral analysis of a cleaved aliquot of peptide confirmed formation of the unsaturated carbocycle 104 with the appearance of a molecular ion peak at m/z 785.4 $(M+H)^+$. A peak at m/z 803.4 $(M+H_2O+H)^+$, corresponding to a hydrated prenyl sidechain in the cyclic product, was also evident. Importantly, prenylglycine remained inert to the metathesis conditions and no mixed cross metathesis products were observed.

Scheme 6.9

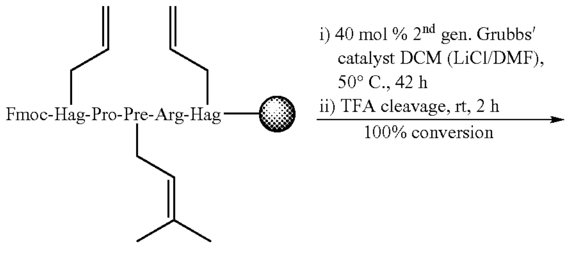

102a

-continued

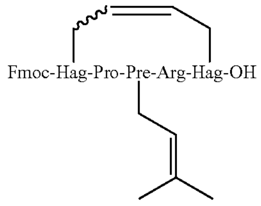

104

Attempts to decrease reaction time and catalyst loading led to incomplete reaction. We therefore decided that the high catalyst loading and extended reaction times could be tolerated in order to avoid the time consuming and poor yielding HPLC purification of mixtures resulting from non-quantitative cyclisation reactions. Decreasing peptide loading on the resin (from 0.9 to 0.3 $mmolg^{-1}$) did, however, enable complete RCM with 10 mol % of second generation Grubbs' catalyst. This is probably due to the fact that the use of low substitution resins decreases the density of peptide chains on the solid phase and minimises aggregation. The reduced loading enhances resin solvation and reagent access and ultimately leads to improved reaction yields.

Selective hydrogenation of the resin-bound unsaturated carbocycle 104a was performed under 80 psi of hydrogen with homogeneous Wilkinson's catalyst, $Rh(I)(PPh_3)_3Cl$, in a mixture of dichloromethane:methanol (9:1) (Scheme 6.10). This solvent system served a dual function in maintaining a swollen resin (dichloromethane) and participating in the catalytic cycle (methanol). After 22 hours, a small aliquot of peptide was cleaved and analysed by mass spectrometry. The appearance of peaks at m/z 787.3 $(M+H)^+$ and m/z 805.4 $(M+H_2O+H)^+$ were consistent with formation of the saturated carbocycle 105. Importantly, the prenyl group remained stable to these reducing conditions which was consistent with the observed reactivity of prenylglycine in the solution phase model studies.

Scheme 6.10

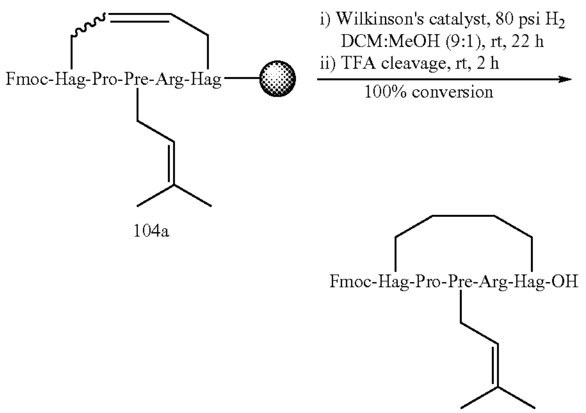

104a

105

So far, the application of the solution phase methodology to resin-bound peptide substrates was proceeding as expected. A need for longer reaction times and catalyst loadings was apparent, however, and highlighted the subtle differences between the two approaches. After selective ring closing metathesis, the remaining prenylglycine residue was employed for the formation of the second dicarba bond.

Activation of the prenyl group was achieved via butenolysis of the resin-bound pentapeptide 105a. The peptide was exposed to an atmosphere of cis-2-butene (15 psi) and 40 mol % second generation Grubbs' catalyst in dichloromethane for 42 hours. This led to a mixture of the desired product 106 and the starting peptide 105. The reaction was unexpectedly and inexplicably slow compared to the analogous solution phase activation step. The recovered resin-peptide was therefore re-subjected to analogous butenolysis conditions which led to the formation of the target crotylglycine-containing peptide 106 (Scheme 6.11). Mass spectral analysis of the cleaved peptide displayed the product molecular ion peak at m/z 773.2 $(M+H)^+$ and no evidence of the starting prenylglycine-containing peptide 105 was observed.

Scheme 6.11

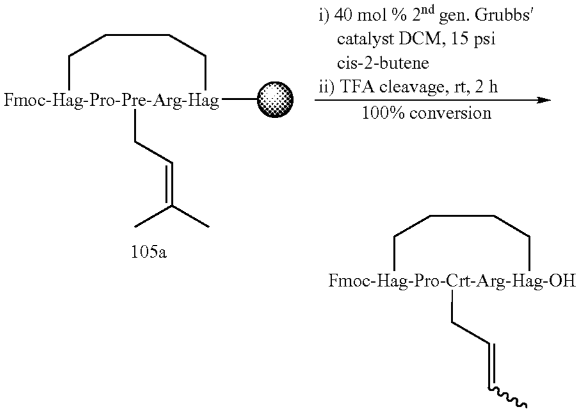

105a

106

A cross metathesis reaction between the activated-resin bound peptide 106a and crotylglycine derivative 81 was then performed. We decided to investigate microwave technology as a means of decreasing reaction time in the solid-phase approach. Microwave irradiation of a mixture of resin-tethered peptide 106a with 40 mol % second generation Grubbs' catalyst, excess crotylglycine 81 (~50 equiv) in dichloromethane and 10% lithium chloride in dimethylformamide resulted in formation of the desired intermolecular dicarba linkage (Scheme 6.12). Mass spectrometry confirmed product formation 107 with the appearance of a molecular ion peak at m/z 902.3 $(M+H)^+$.

Scheme 6.12

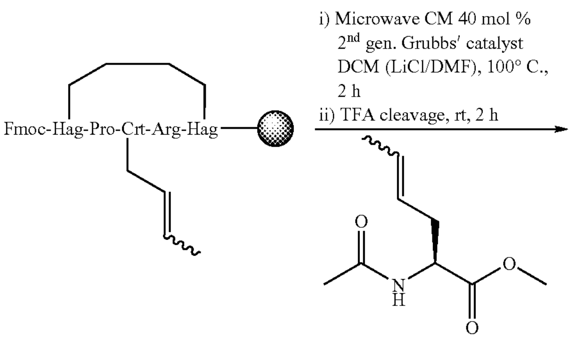

106a 81

-continued

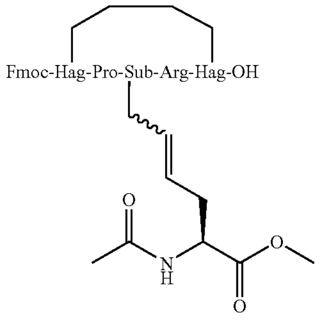

107

Wilkinson's hydrogenation of the unsaturated intermolecular bridge was achieved under conditions previously established (80 psi $H_2$, dichloromethane:methanol (9:1), room temperature, 22 hours) to give the target peptide 108 containing two regioselectively constructed dicarba bridges (Scheme 6.13).

Scheme 6.13

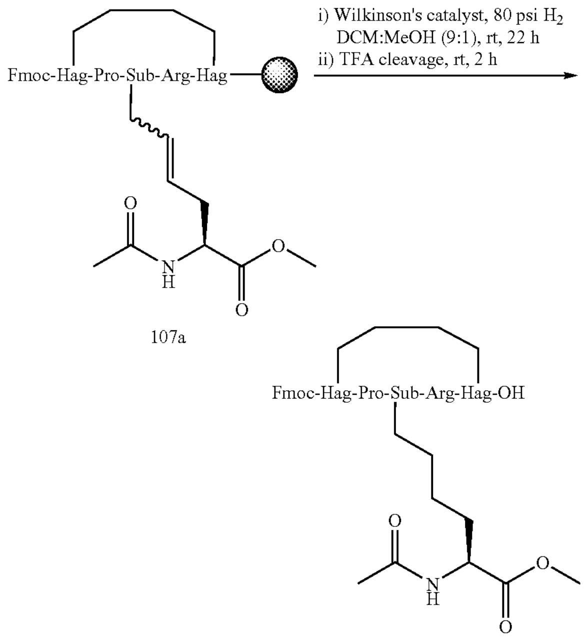

107a

108

The successful application of the solution phase methodology (section 4) to a resin-bound pentapeptide 102a led to selective construction of an intramolecular and an intermolecular dicarba bridge. Several important biologically active peptides, such as those within the insulin superfamily (insulin and relaxin), possess metabolically unstable inter- and intramolecular cysteine bonds. This methodology can be applied to the regioselective construction of stable dicarba analogues of these peptides. We next examined the extension of this strategy to the construction of bicyclic peptides—as cystino-dicarba analogues and bis-dicarba analogues. The latter analogues require the formation of two intramolecular dicarba bridges via sequential ring closing metathesis reactions.

Liskamp et al. recently reported the synthesis of a crossed alkene-bridge of the complex DE-bisthioether ring system of nisin, a lantibiotic that possesses five thioether bridges (as distinct to disulfide bridges—which are less stable) (Diagram 6.2).[157]

Diagram 6.2

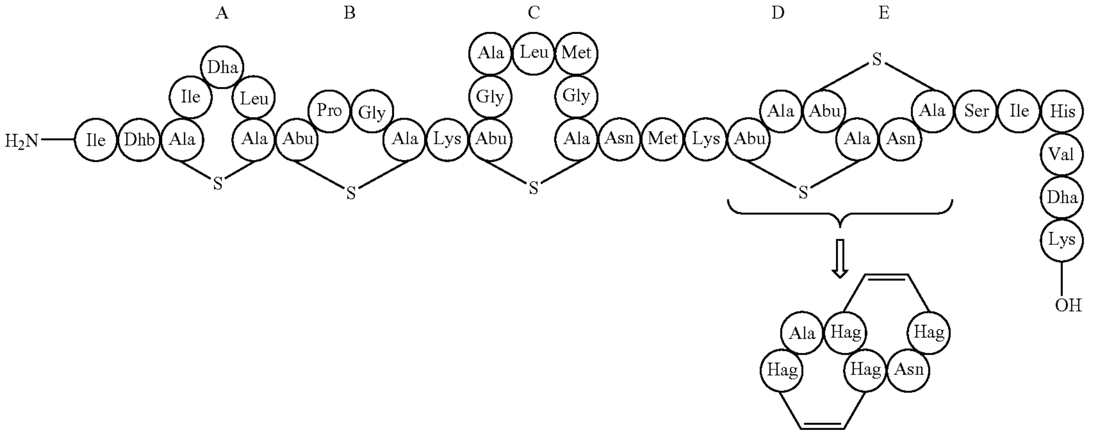

A linear precursor 109 containing four identical allylglycine residues was subjected to a solution phase double ring closing metathesis reaction. The first cyclisation reaction yielded four out of a possible six mono-cyclic peptides. Successive ring closing metathesis under similar conditions ultimately yielded the target 1-4, 3-6-carbocyclic peptide 110 (72%) and a contaminating 1-3, 4-6-bicycle 111 (19%) (Scheme 6.14).

Scheme 6.14

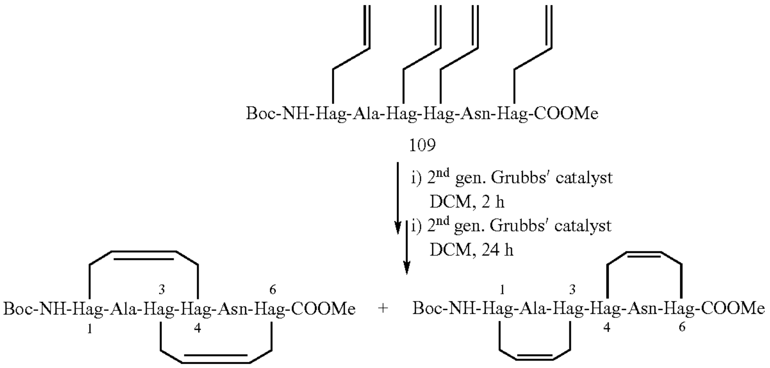

109

110 72%

111 19%

These results suggest favourable pre-organisation of the linear peptide for generation of the target regioisomer.[157] The selective synthesis of multiple bridges, however, is rarely so fortuitous.[129,225,231,232] Indeed, in the synthesis of native conotoxin sequences, several topoisomers (ribbon, globule and beads) are obtained after oxidative folding.[225,231,233] Multiple cysteine formation usually requires an orthogonal protection strategy and sequential oxidation of cysteine residues.[225] For this reason, we investigated the regioselective methodology developed in section 4 for the synthesis of dicarba analogues of a native conotoxin sequence, Ctx ImI 93.

6.4 Synthesis of Dicarba Analogues of Conotoxin ImI

Conotoxins are venom components of cone snails (Conidae) and represent a group of small disulfide-rich peptides that act as potent and highly specific antagonists for different receptor targets.[171-174] Conotoxins derive their receptor subtype specificity from the arrangement of their disulfide bonds and resultant loop sizes. For example, α-conotoxins, which contain two disulfide bonds in a 1-3, 2-4 arrangement (Diagram 6.3), target nicotinic acetylcholine receptors of vertebrates.[234] χ-Conotoxins, on the other hand, possess a 1-4, 2-3 disulfide bond arrangement and are selective for noradrenaline transporters.

Diagram 6.3

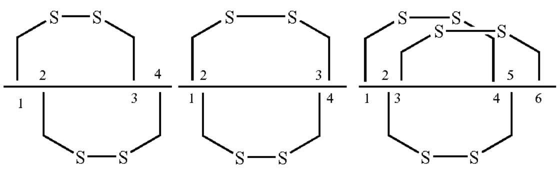

α-conotoxins χ-conotoxins ω-conotoxins

The small size (typically between 10-40 amino acids), selectivity and potency of conotoxins make them ideal therapeutic candidates for clinical conditions such as pain, epilepsy, stroke and cancer.[171,234] Recently Ziconotide, an ω-conotoxin, completed Phase III clinical trials for neuropathic pain whilst two new conotoxin analogues (ω-Ctx CVID and χ-Ctx MrIA) are in clinical trials for chronic pain.

Conotoxins possess a rich diversity of amino acid residues and this, coupled with their potential as pharmaceutical agents, makes them challenging and interesting targets. We chose to examine α-conotoxin ImI 93 (Ctx ImI), a small cysteine rich dodecapeptide isolated from the vermivorous conus species *Conus imperialis*.[173,174,226] Its two intramolecular disulfide bonds form the hydrophobic core of the molecule and generate a constrained two loop structure which, together with a central proline residue, arrange three essential residues (Asp5, Arg7, Trp10) for selective interaction with complementary residues within the α7 neuronal nicotinic acetylcholine receptor.

-continued

Dicarba-Cystino Ctx Hybrids

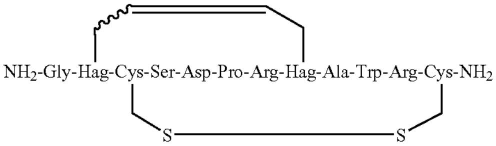
$NH_2$-Gly-Hag-Cys-Ser-Asp-Pro-Arg-Hag-Ala-Trp-Arg-Cys-$NH_2$

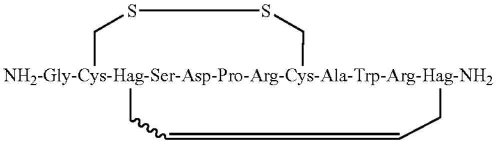
$NH_2$-Gly-Cys-Hag-Ser-Asp-Pro-Arg-Cys-Ala-Trp-Arg-Hag-$NH_2$

93

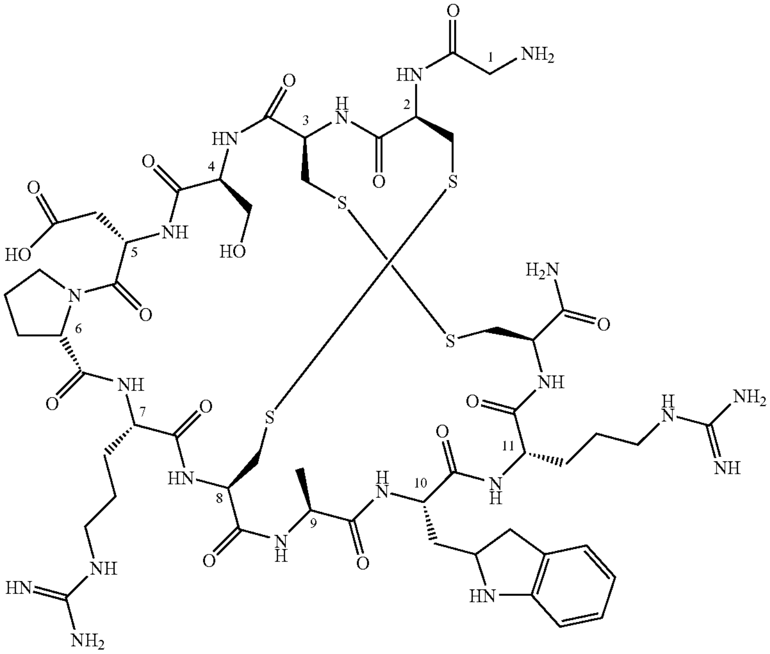

Interestingly, the structural and functional role of the disulfide bonds in these natural products is yet to be elucidated. Generation of dicarba-cystino hybrids of conotoxin ImI and ultimately bis-dicarba analogues allows the importance of the constituent bridges on the structure and activity of the peptide to be elucidated. We therefore investigated the application of the on-resin metathesis-hydrogenation sequence to generate a library of dicarba analogues of conotoxin ImI (Diagram 6.4).

Diagram 6.4

Native α-Conotoxin ImI (Ctx)

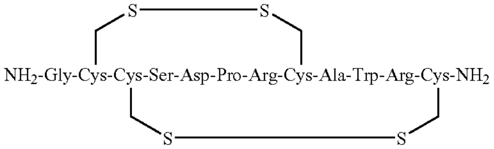
$NH_2$-Gly-Cys-Cys-Ser-Asp-Pro-Arg-Cys-Ala-Trp-Arg-Cys-$NH_2$

-continued

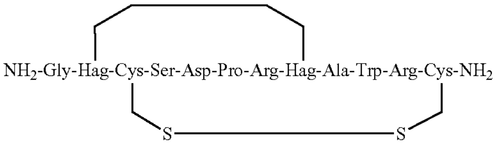
$NH_2$-Gly-Hag-Cys-Ser-Asp-Pro-Arg-Hag-Ala-Trp-Arg-Cys-$NH_2$

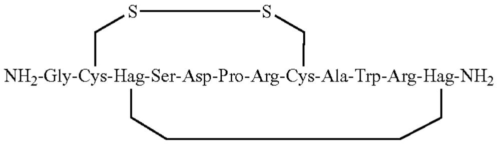
$NH_2$-Gly-Cys-Hag-Ser-Asp-Pro-Arg-Cys-Ala-Trp-Arg-Hag-$NH_2$

-continued

Bis-Dicarba Ctx Analogues

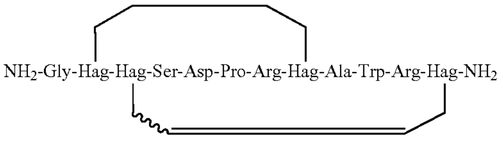

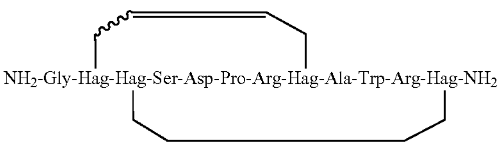

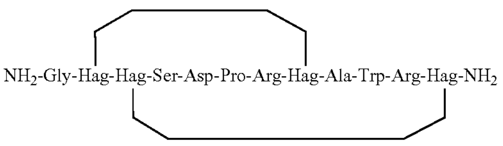

Metathesis catalysts display high functional group tolerance and homogeneous rhodium-based catalysts, unlike their heterogeneous counterparts, are not poisoned by sulfur-containing functionality. We decided to initiate our study with the synthesis of dicarba-cystino hybrids of Ctx ImI.

6.4.1 Cystino-Dicarba Hybrids of Conotoxin ImI

Native α-conotoxins are amidated at their C-termini. Rink amide resin was therefore chosen to facilitate linear peptide construction and generate the required C-terminal carboxamide upon resin cleavage. The low loading (0.52 $mmolg^{-1}$) of the Rink amide linker helps to reduce crowding and aggregation of peptide chains and reduces the likelihood of homodimerisation in the subsequent metathesis reaction. Standard SPPS using HATU-NMM activation and Fmoc-protected amino acids was used to construct the two linear peptides: [2,8]-Hag-[3,12]-Cys conotoxin ImI 112 and [2,8]-Cys-[3,12]-Hag conotoxin ImI 113. Both of these sequences possess two strategically placed non-proteinaceous L-allylglycine (Hag) residues to facilitate construction of the dicarba bridge. Intermediates were carried through without purification or characterisation up to the dodecapeptides 112 and 113. A sample of each linear peptide was obtained by cleavage from the resin and determined to be of >95% purity by reverse-phase-HPLC. Mass spectral analysis gave the molecular ion peak at m/z 1565.7 $(M+H)^+$ and the corresponding doubly charged ion peak at m/z 783.5 $[\frac{1}{2}(M+2H)]^+$. Both ions are consistent with the structures of the isomeric sidechain deprotected linear peptides 112 and 113.

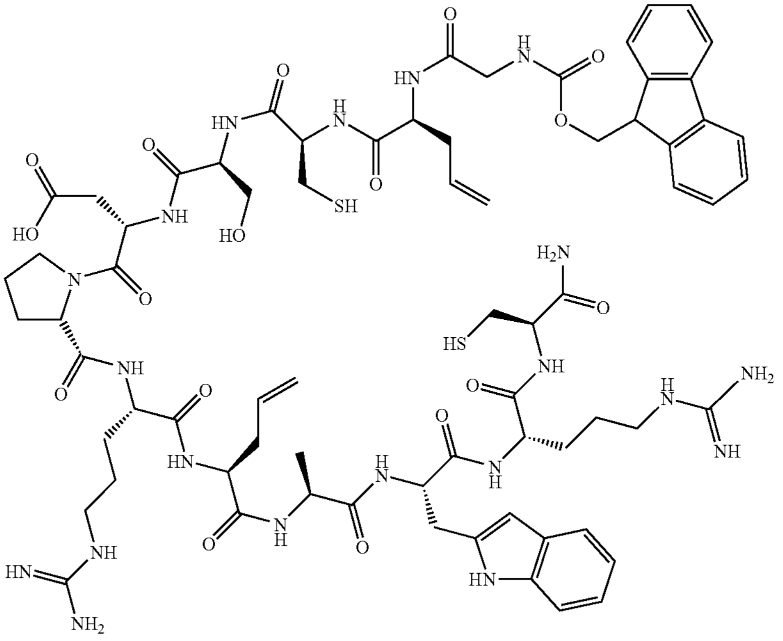

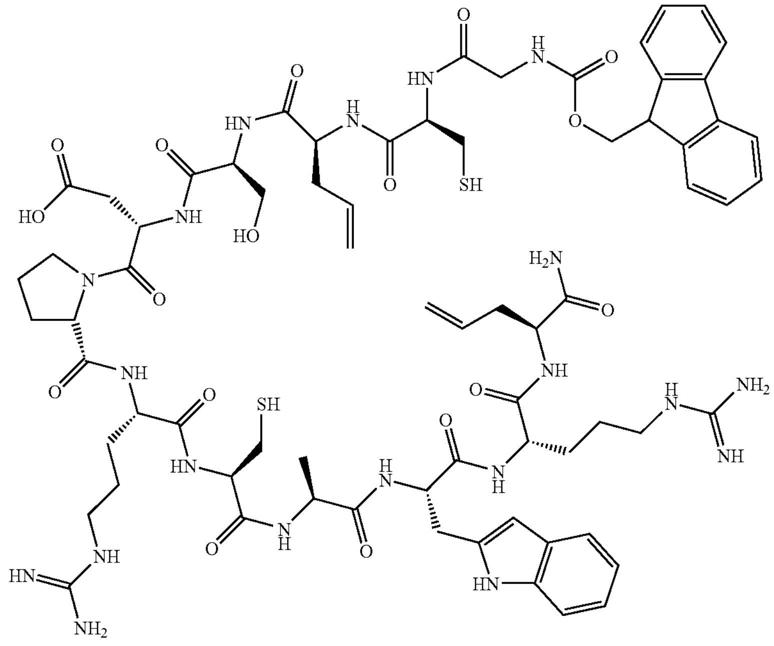

Ring closing metathesis was performed on resin-attached linear peptides to eliminate any potential problems arising from dimerisation and/or poor peptide solubility. Exposure of [2,8]-Hag Ctx ImI 112a to first generation Grubbs' catalyst (50 mol %) in dichloromethane at 50° C. for 72 hours gave only trace amounts (<10%) of cyclised product 114. The more reactive second generation Grubbs' catalyst was then used to improve the cyclisation yield (Scheme 6.15). While RCM progressed further (~70%) with this catalyst, conditions could not be found to effect full cyclisation to 114. Change in solvent, concentration, catalyst loading, and reaction time had no positive effect on conversion. The addition of a chaotropic salt (lithium chloride in dimethylformamide) to the reaction mixture also had no effect on RCM yield. Similarly, RCM of a dicrotylglycine analogue of the primary sequence of 112, which avoids catalytic cycling through an unstable ruthenium-methylidene species, also failed to achieve complete conversion to the cyclic target 114.

Scheme 6.15

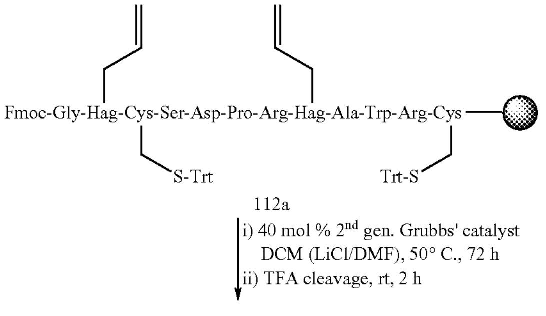

-continued

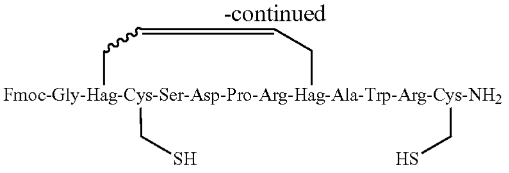

114

Construction of the isomeric [3,12]-unsaturated carbocyclic Ctx ImI 115 was found to be even more problematic. Exposure of the resin-bound peptide 113a to both first and second generation Grubbs' catalysts under a variety of experimental conditions failed to yield the unsaturated carbocycle 115. Possible reasons for the poor reactivity of this isomer 113 included the dimished influence of the proline residue in assisting formation of the larger carbocycle (28-membered ring) and the close proximity of the C-terminal allylglycine residue to the bulky Rink amide linker. The sequence was therefore reconstructed on BHA resin bearing a linear HMBA-Gly-Gly-linker. Cyclisation of the BHA resin-bound peptide was attempted in the presence of 20 mol % second generation Grubbs' catalyst and chaotropic salts. Unfortunately, mass spectral analysis of the product mixture again showed only the starting peptide 113.

Microwave-assisted ring closing metathesis of isomeric linear peptides 112a and 113a provided both of the target carbocycles 114 and 115. In our study, a microwave reactor emitting a focused irradiation at 2.45 GHz with a maximum power of 300 W was used. Irradiation of a mixture of Rink amide-bound [2,8]-Hag-[3,12]-Cys Ctx ImI 112a and second generation Grubbs' catalyst (10 mol %) in dichloromethane containing 10% lithium chloride in dimethylformamide resulted in complete ring closure in only one hour (Scheme 6.16). Decreasing the catalyst loading (5 mol %) also led to quantitative conversion to the unsaturated carbocycle 114 after just two hours of microwave irradiation. Mass spectral analysis of the product mixture showed the required molecular ion peak at m/z 1537.7 $(M+H)^+$ and the corresponding doubly charged ion at m/z 769.5 $[½(M+2H)]^+$ for the unsaturated carbocyclic peptide 114 and no starting linear peptide 112.

Scheme 6.16

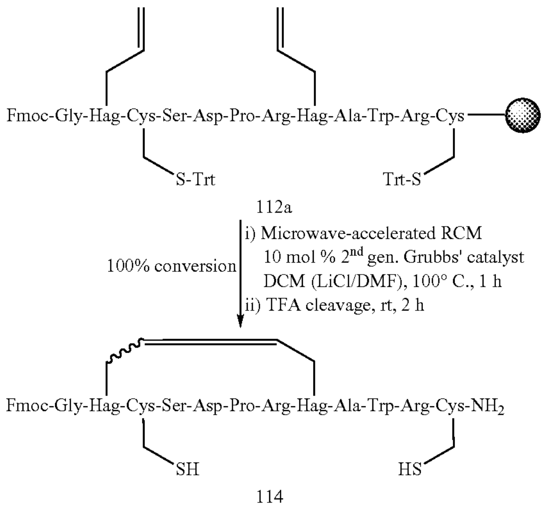

Similar reaction conditions also resulted in complete cyclisation of 113a to the isomeric [3,12]-dicarba analogue 115 (Scheme 6.17). Although a higher catalyst loading (20 mol %) was required, the reaction went to completion in one hour. The enhancement in RCM yield via this microwave-assisted approach is remarkable in light of the poor results obtained using conventional heating methods. It is considered that the results must be attributed to something beyond just more efficient heating. It has been postulated that another possible factor is that microwave radiation causes highly efficient disruption of peptide aggregation on the solid support. It is noted that the reaction of scheme 6.17 does not proceed without microwave.

Scheme 6.17

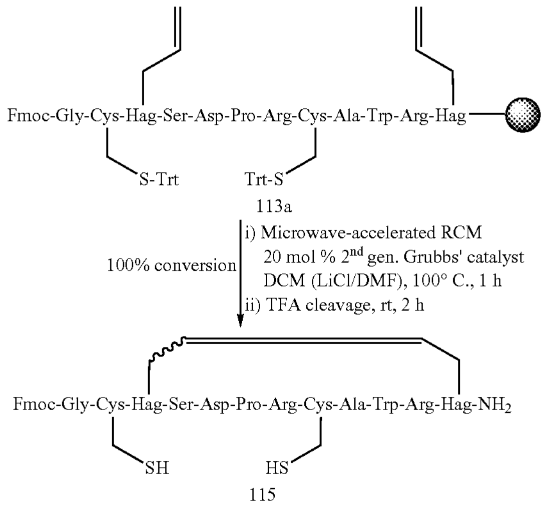

On-resin Fmoc-deprotection of the unsaturated carbocycles 114a and 115a followed by acid-mediated cleavage yielded the fully deprotected peptides 116 and 117. Aerial oxidation of 116 and 117 in 5% dimethylsulfoxide/aqueous ammonium carbonate (0.1 M, pH 8) then afforded the unsaturated cystino-dicarba Ctx ImI analogues 118 and 119 respectively (Scheme 6.18, Scheme 6.19). Each peptide was purified by reverse-phase HPLC (>99% purity) and isolated in 5% yield. These analogues are currently being assessed for biological activity and in vivo stability.

It is important to note that the isolation and purification of native conotoxin sequences from cone snail venom is a low yielding and tedious process.[247] Recently, 200 mg of venom extract from five cone snails (Conus textile) was purified to yield 1.1 mg (560 nmol) of conotoxin ϵ-TxIX.[248] Most references detailing the isolation of conotoxin molecules from venom, however, do not cite isolation yields. Synthesis of conotoxin molecules can also be low yielding where oxidative folding leads to several topoisomers.[225,231,233,249-251] Extensive chromatography must be employed to isolate pure samples of the target peptide. Although the final purified yields of our dicarba-cystino conotoxin analogues 118 and 119 were low, separation conditions were not optimised and the scale of the reactions could be easily increased to afford larger quantities of pure peptide.

Scheme 6.18

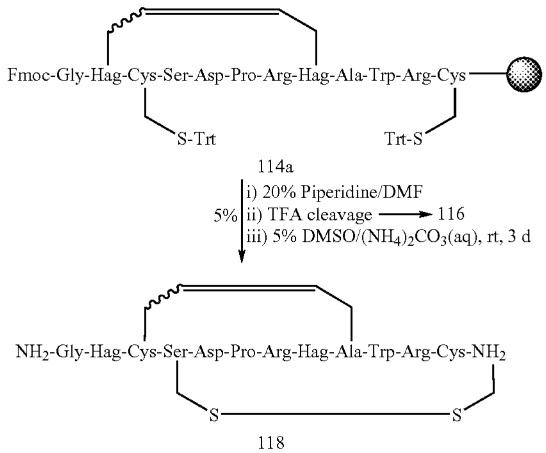

Scheme 6.19

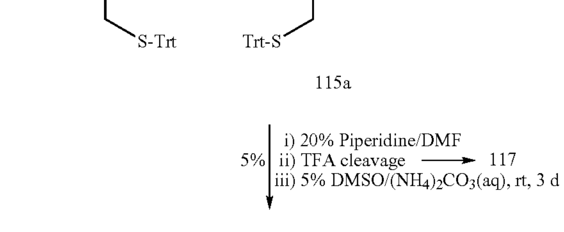

-continued

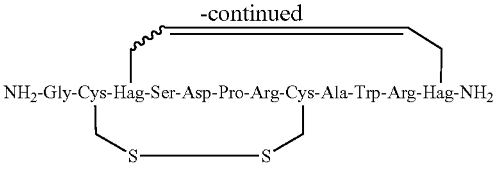

119

Hydrogenation of resin-bound unsaturated carbocyclic peptides 114a and 115a was performed with Wilkinson's catalyst. This homogeneous catalyst is ideal for this transformation as it allows reduction to be performed on the resin, operates under mild reaction conditions and is highly tolerant of sulfur-containing functionality. Hence, rhodium-catalysed hydrogenation of resin-bound carbocycles 114a and 115a in dichloromethane:methanol (9:1) effected quantitative reduction of the olefin at room temperature and low hydrogen pressure (80 psi) (Scheme 6.20). Interestingly, the crude product from each of these reactions was obtained as a mixture of the cysteine reduced (120, 121) and oxidised (122, 123) forms. It is important to note that the final targets 122 and 123 are isomeric with the unsaturated deprotected precursor peptides, 116 and 117 respectively. An analogous hydrogenation experiment spiked with linear diallyl conotoxin sequence 112, the precursor to the unsaturated carbocycle 114, showed a molecular ion consistent with the formation of the dipropyl sidechain-containing peptide 124.[235] This mass spectral data strongly suggests that the catalyst is not poisoned by the trityl-protected cysteine residues and that the hydrogenation conditions needed for olefin reduction are uncompromised. Hence, the species contributing to the peak at m/z 769.5 [½(M+2H)]$^+$ are likely to be the final isomeric cystino-dicarba Ctx ImI peptides 122 and 123.

124

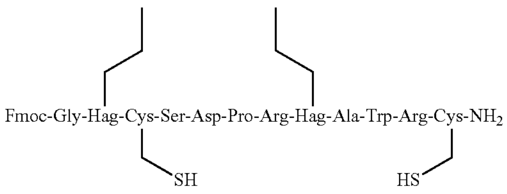

Further support for this hypothesis comes from the LC-MS traces of the product mixtures. In each case, a signal at $t_R$=6.01 min (122) and $t_R$=7.02 min (123) was observed. In comparison, the retention times for the isomeric unsaturated carbocycles 116 and 117, under identical chromatographic conditions, are 5.66 min and 6.64 min respectively. The saturated cystino-dicarba α-conotoxin analogues 122 and 123 are currently undergoing chromatographic purification and are being assessed for biological activity and in vivo stability. NMR spectroscopy will also be used to further confirm the structures of the isomeric conotoxin analogues 122 and 123.

Scheme 6.20

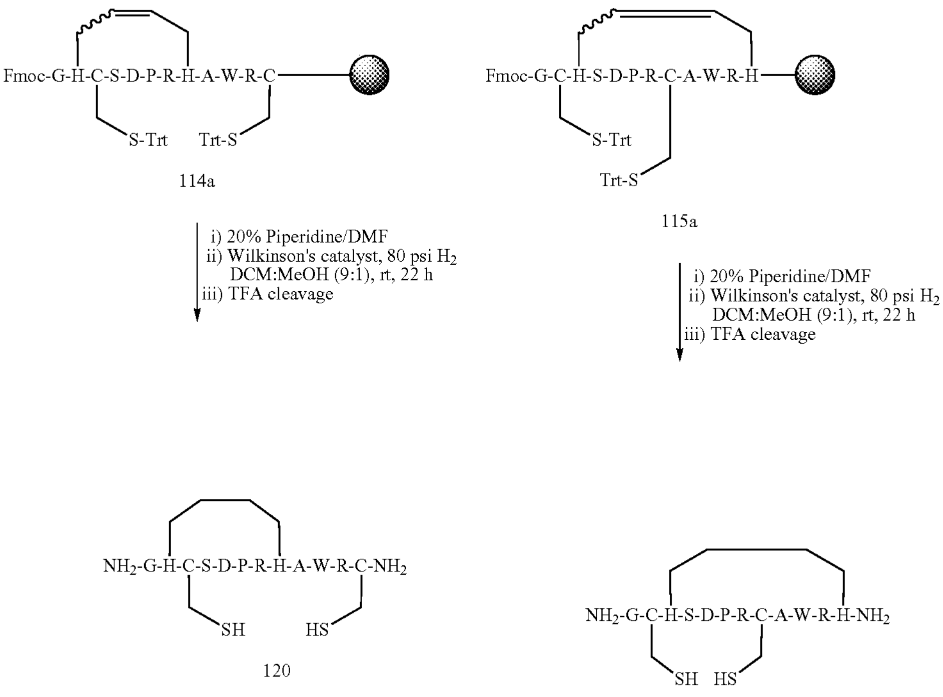

114a

115a

120

121

+

-continued

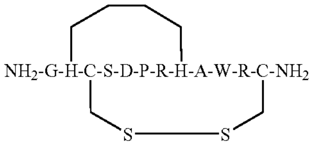

122

+

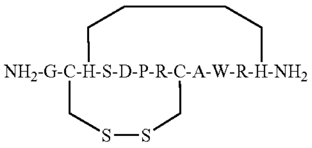

123

6.4.2 Bis-Dicarba Conotoxin Analogues

The regioselective on-resin methodology described in section 4 was also applied to the synthesis of fully carbocyclic conotoxin ImI analogues. The catalytic sequence involves the selective RCM of reactive allylglycine units in the presence of dormant prenylglycine residues followed by selective hydrogenation of the resultant unsaturated carbocycle. Activation of the prenyl groups via butenolysis gives the active crotyl sidechains which can undergo the RCM-hydrogenation process to afford the target bicycles 125 and 126 (Scheme 6.21).

This study commenced with the construction of the linear isomeric conotoxin analogues, [2,8]-Hag-[3,12]-Pre conotoxin ImI 127 and [2,8]-Pre-[3,12]-Hag conotoxin ImI 128. Standard SPPS techniques employing Rink amide resin, HATU-NMM activation and Fmoc-protected amino acids facilitated synthesis of the peptides 127 and 128. Both of these sequences possess two strategically placed non-proteinaceous L-allylglycine (Hag) residues to facilitate the selective construction of the first carbocycle. The incorporation of two less reactive prenylglycine residues later enables Scheme 6.21

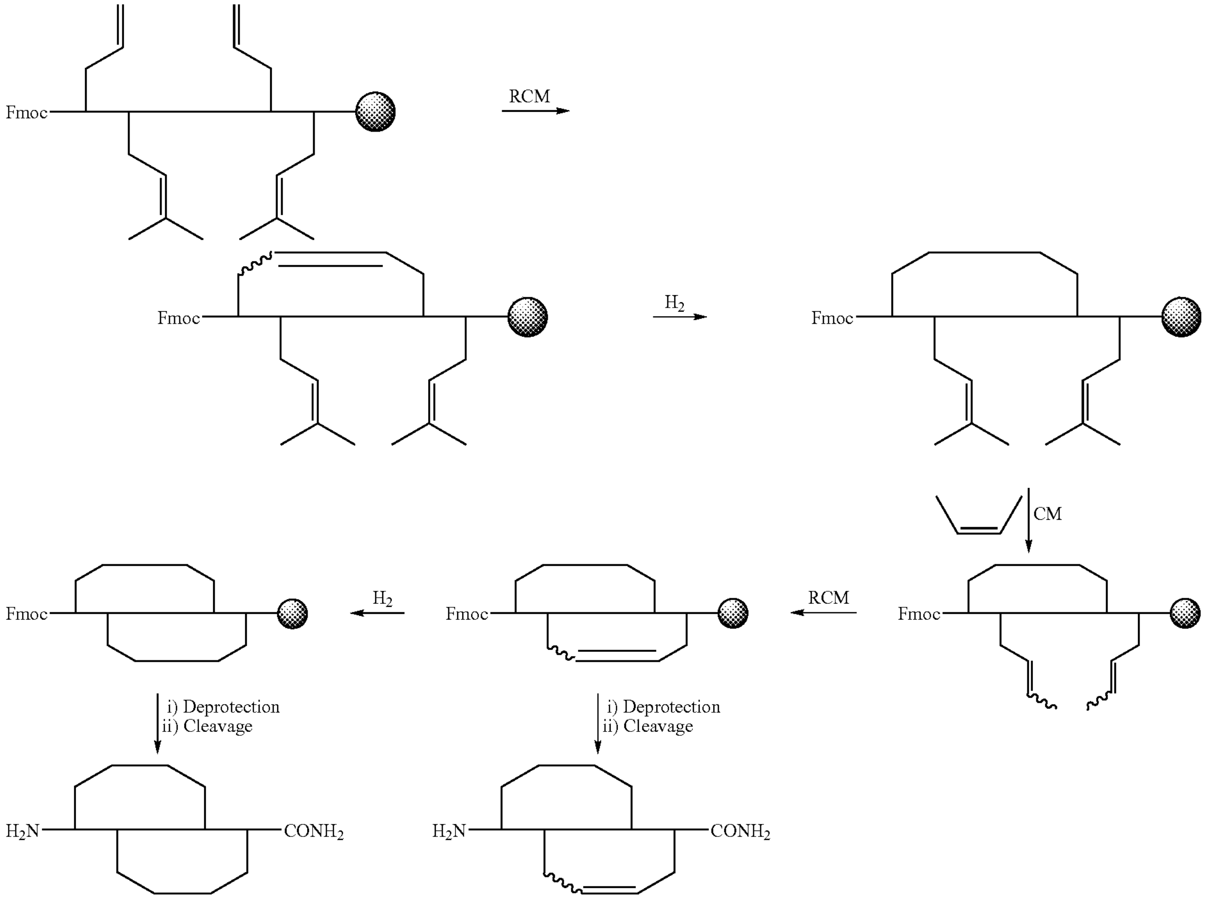

125 126 the selective formation of the second carbocycle. During construction of the linear peptides, intermediates were carried through without purification or characterisation up to the dodecapeptides 127 and 128. As expected, the prenylglycine residues were incorporated without complication and mass spectral analysis gave doubly charged molecular ion peaks at m/z 805.6 [½(M+2H)]$^+$ and 816.6 [½(M+Na$^+$ H)]$^+$ which are consistent with the structures of the isomeric sidechain deprotected linear peptides 127 and 128. An additional peak at m/z 814.6 [½(M+$H_2O$+2H)]$^+$, corresponding to the acid-promoted hydration of a prenyl group, was also apparent in the spectrum.

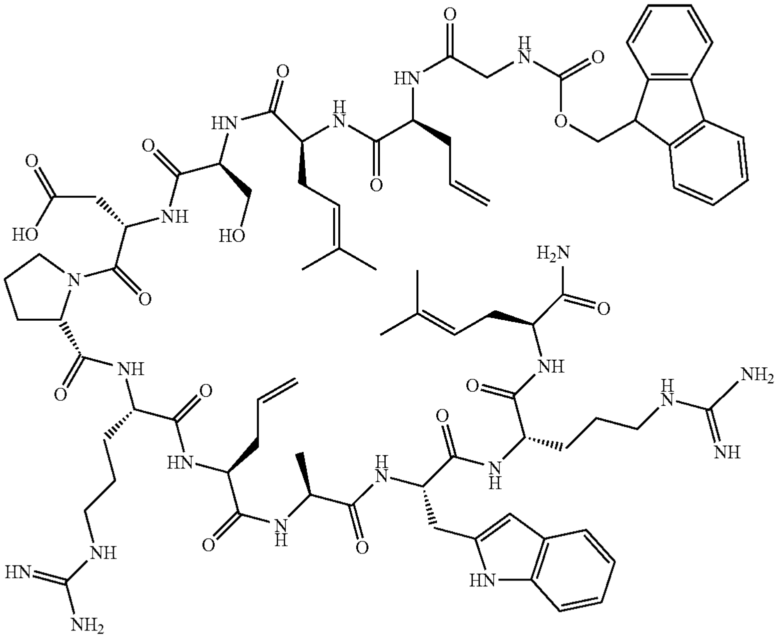

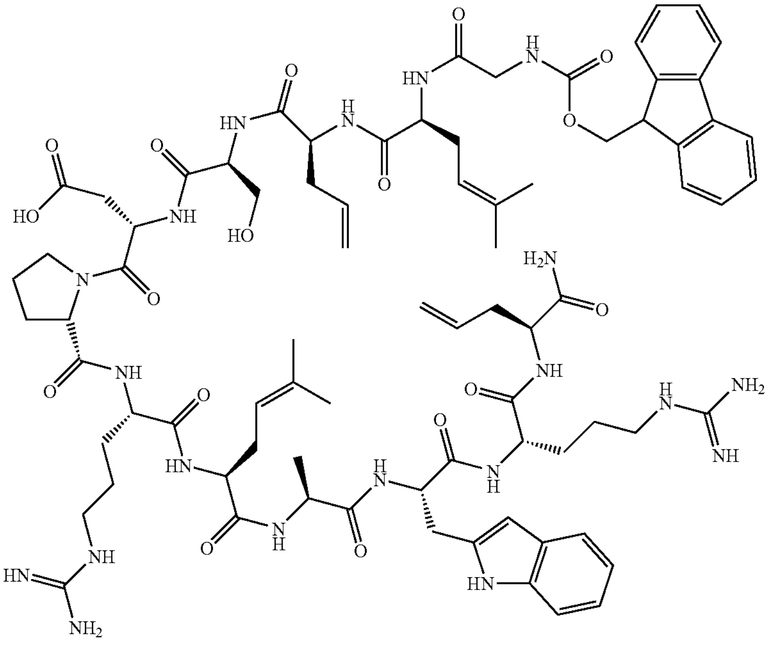

After confirming the successful synthesis of the linear peptides 127 and 128, ring closing metathesis of the resin-tethered peptides was performed using conventional heating methods. Exposure of peptide 127a to second generation Grubbs' catalyst (40 mol %) in dichloromethane and 10% lithium chloride in dimethylformamide at 50° C. for 40 hours gave the unsaturated carbocycle 129 (Scheme 6.22).

Scheme 6.22

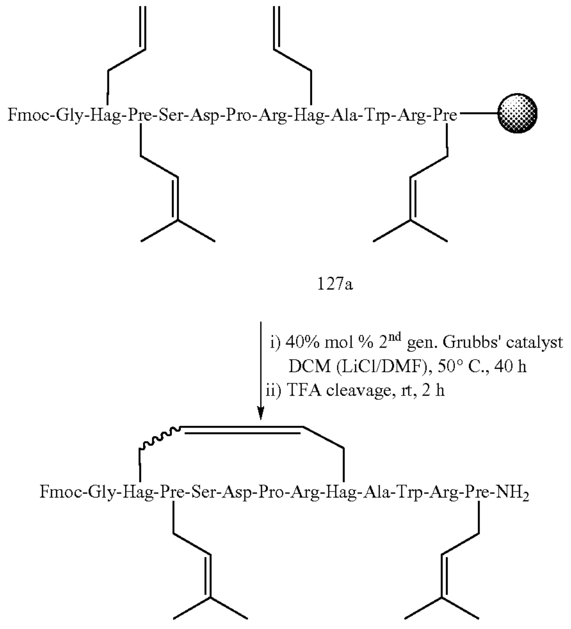

127a

129

Analogous RCM conditions for 128a, however, led to complete recovery of the linear peptide. These results highlight the influence of the peptide sequence on RCM success when microwave is not used. A derivative of the problematic sequence 128 was therefore constructed to elucidate the effect of a turn-inducer. A new peptide sequence 130 was synthesised possessing a Pro9 residue rather than the native Ala9 residue. Interestingly, the resultant solid-supported peptide 130a cyclised under the previously unsuccessful metathesis conditions (without microwave radiation) to give 131, but the RCM did not go to completion (Scheme 6.23). Unfortunately, LC-MS analysis did not enable separation of the linear 130 and cyclic 131 peptide and hence an estimation of reaction conversion could not be made.

Scheme 6.23

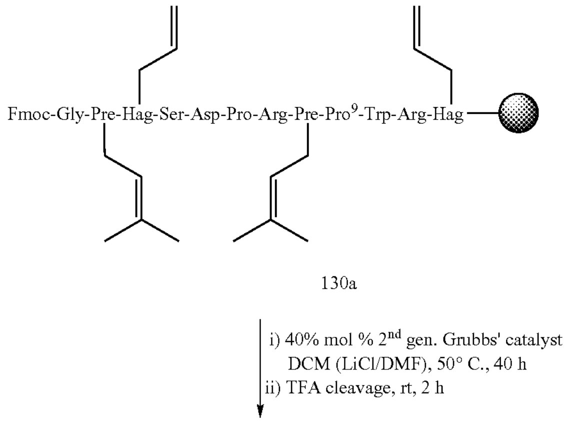

130a

-continued

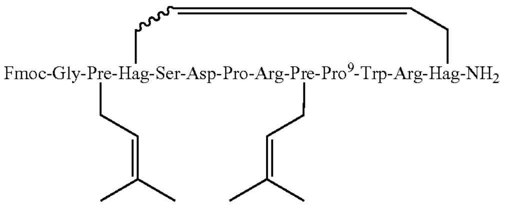

131

Microwave-assisted ring closing metathesis, however, provided expedient syntheses for both the target carbocycles 129 and 132. Microwave irradiation of a solution of Rink amide bound-peptide 127a and second generation Grubbs' catalyst (10 mol %) in dichloromethane containing 10% lithium chloride in dimethylformamide at 100° C. resulted in complete ring closure in only one hour (Scheme 6.24). Mass spectral analysis of the product mixture showed the required molecular ion with m/z 791.4 [½(M+2H)]$^+$ for the unsaturated dicarba peptide 129 and no starting linear peptide 127.

The resin-bound isomeric dicarba analogue 128a also completely cyclised in one hour with 20 mol % second generation Grubbs' catalyst using the same solvent system at 100° C. (Scheme 6.25).

Scheme 6.24

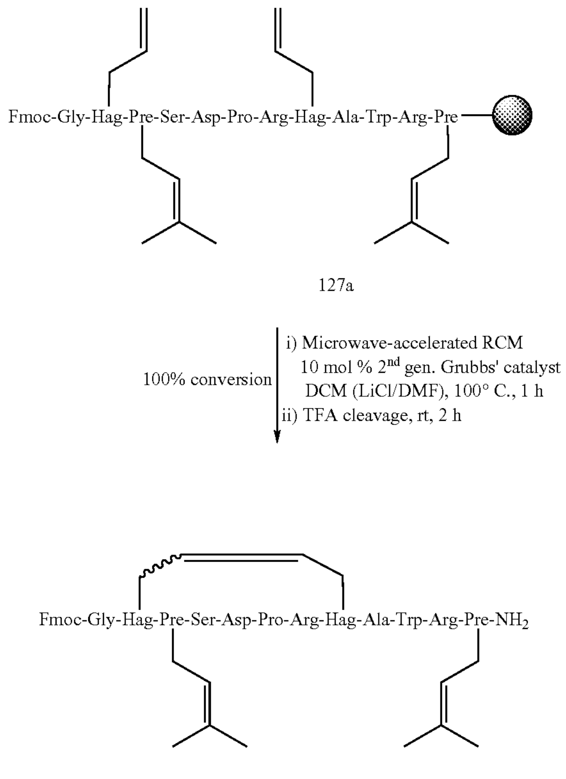

127a

129

Scheme 6.25

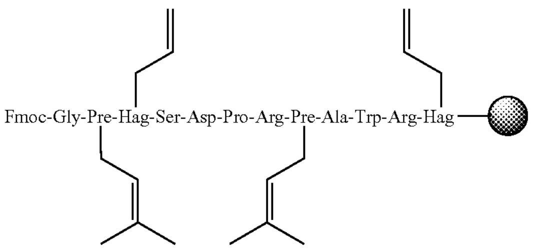

128a

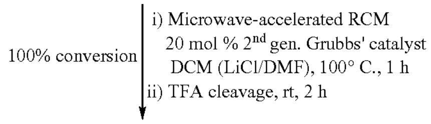

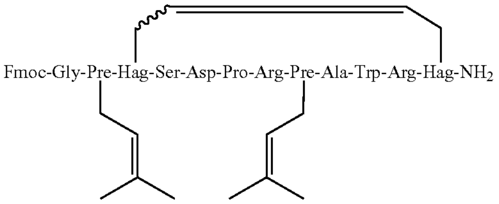

132

These results were very exciting and demonstrated the power of microwave energy to yield carbocycles that were unattainable by conventional heating methods. In addition, the prenyl sidechains remained inert to the microwave-accelerated metathesis conditions and no cross metathesis products were observed.

Rhodium-catalysed hydrogenation of the resin-bound carbocycles 129a and 132a in dichloromethane:methanol (9:1) effected quantitative reduction of the unsaturated carbocycle at room temperature and low hydrogen pressure (80 psi) (Scheme 6.26 and Scheme 6.27). The mass spectra of cleaved peptides from both reactions displayed doubly charged molecular ion peaks at m/z 792.5 [½(M+2H)]$^+$ and m/z 801.5 [½(M+$H_2O$+2H)]$^+$ confirming formation of the isomeric products 133 and 134. Importantly, the prenyl groups resisted hydrogenation and were now available for activation to facilitate construction of the second carbocycle.

Scheme 6.26

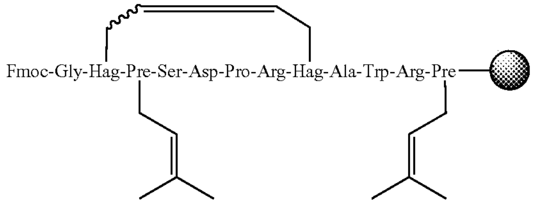

129a

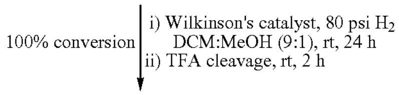

-continued

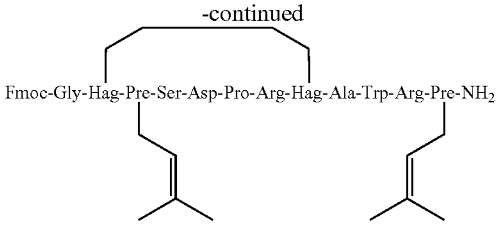

133

Scheme 6.27

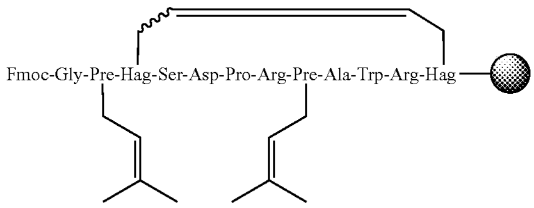

132a

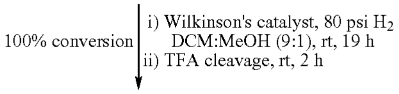

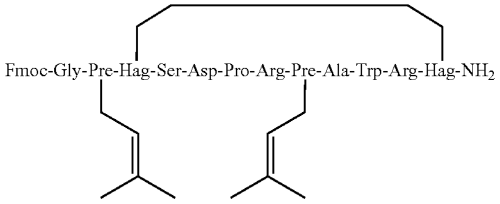

134

Activation of the prenyl sidechains involved butenolysis of the solid-supported peptides 133a and 134a. The peptide 133a was exposed to an atmosphere of cis-2-butene (15 psi) and a mixture of 40 mol % second generation Grubbs' catalyst and benzoquinone in dichloromethane for 38 hours (Scheme 6.28). Benzoquinone was added to the reaction mixture to reduce or eliminate the potential for olefin isomerisation. Mass spectral analysis of a cleaved aliquot of peptide confirmed formation of the target dicrotylglycine-containing peptide 135 with the appearance of a peak at m/z 778.4 [½(M+2H)]$^+$. No starting prenyl-containing peptide 133 was observed, however, mass spectral data revealed low intensity, doubly charged higher homologue species separated by m/z+7 units. Under the above described metathesis conditions, the generated crotyl sidechain can isomerise to a terminal butenyl chain and then undergo secondary cross metathesis with cis-2-butene (Scheme 6.29). The products arising from this process of isomerisation-cross metathesis are consistent with the observed mass spectral data.

Scheme 6.28
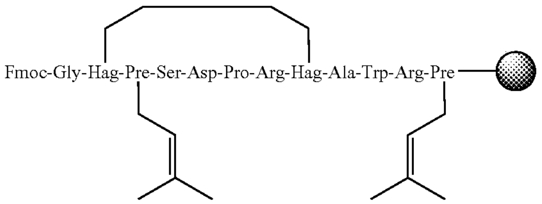
133a
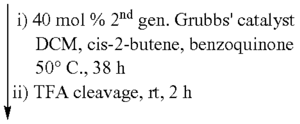
-continued
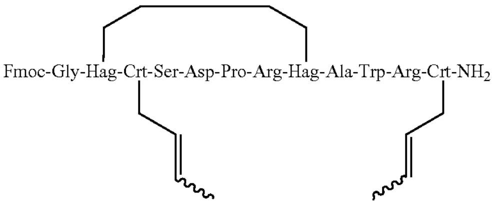
135
Scheme 6.29
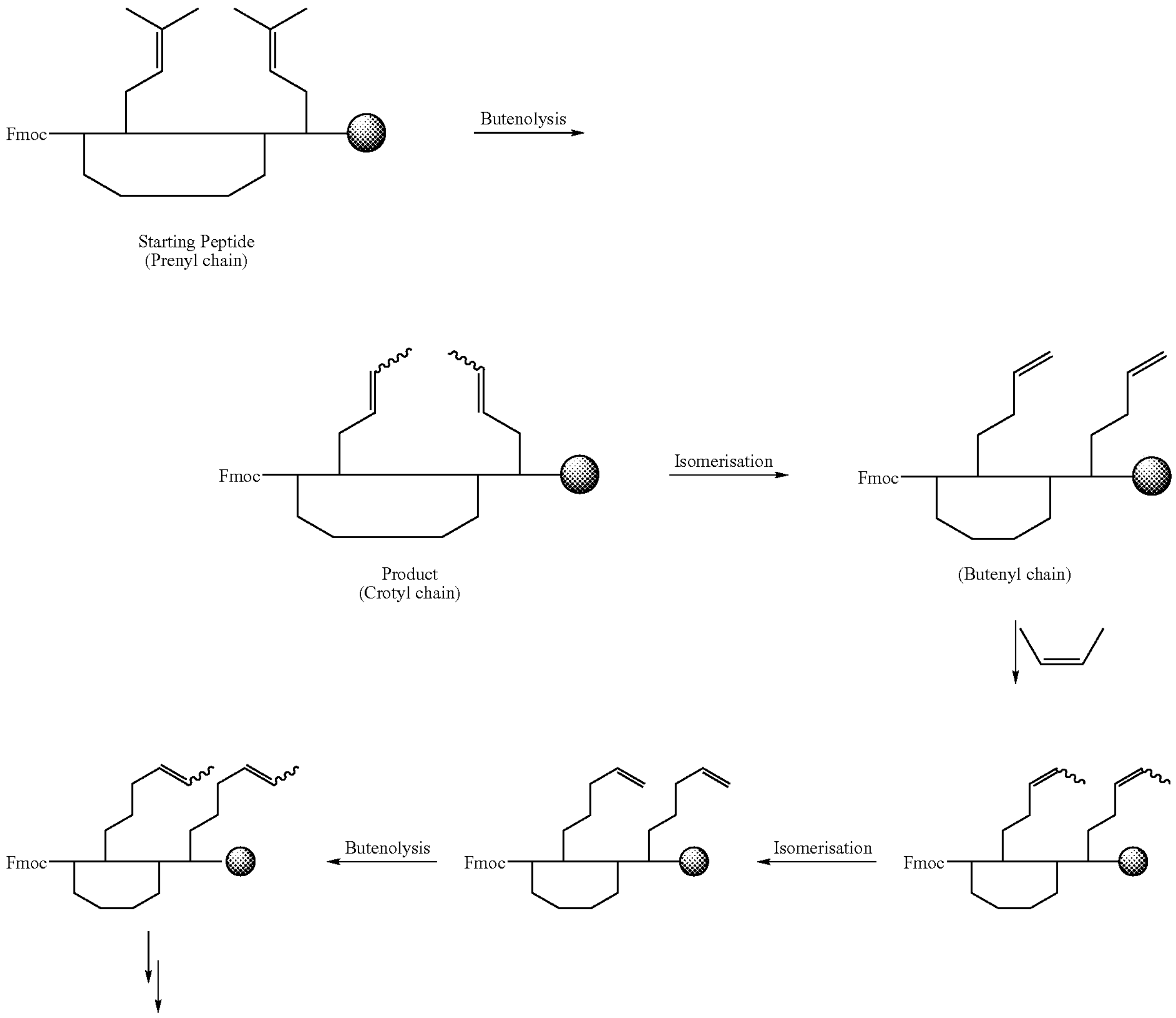

Reaction conditions were modified to minimise this competing isomerisation reaction. These changes involved the addition of chaotropic salts and variation of catalyst loading and reaction time. This aim was realised, although to a small extend this was still accompanied by partially metathesised peptide 136 and starting material 133.

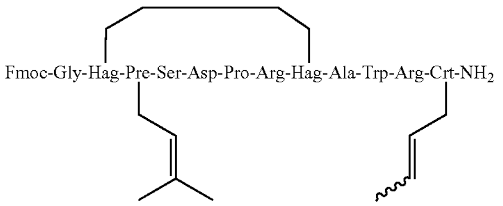

136

Microwave-accelerated ring closing metathesis of the resin-tethered peptide 135a using second generation Grubbs' catalyst (20 mol %) in dichloromethane and 10% lithium chloride in dimethylformamide afforded the target peptide 140 in only one hour (Scheme 6.30). Preliminary LC-MS analysis was encouraging with the appearance of the required doubly charged molecular ion peak at m/z 750.4 $[(M+2H)]^+$, corresponding to the bicyclic peptide 140. Interestingly, a very low intensity peak at m/z 764.4 was also evident which corresponded to the cyclic product of a contaminating isomerisation-butenolysis adduct. The Fmoc-deprotected product 125 is being purified and submitted for biological testing.

Scheme 6.30

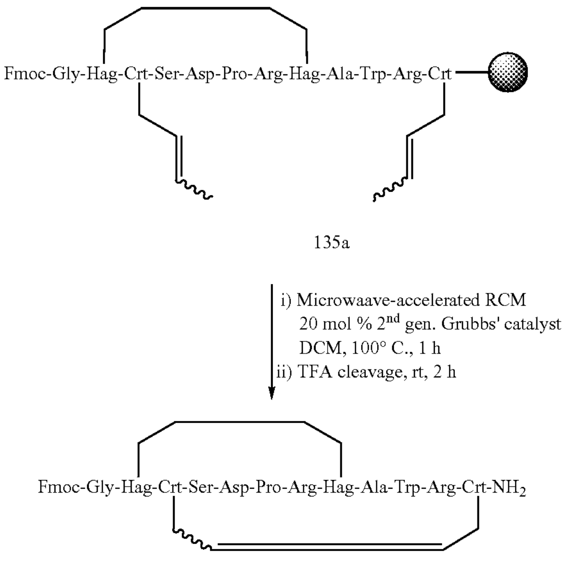

135a

140

Rhodium-catalysed hydrogenation of the resin-bound bicycle 140a was performed in dichloromethane:methanol (9:1) at room temperature under low hydrogen pressure (80 psi) (Scheme 6.31). Preliminary mass spectral and LC-MS data of the isolated residue confirmed the formation of the saturated bicycle 126.

Scheme 6.31

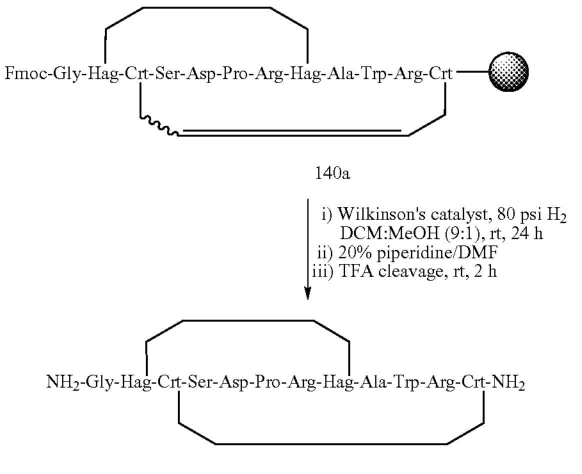

140a

126

The lower than expected butenolysis yields of resin-bound substrates was not consistent with the higher reaction yields and rates of analogous solution phase reactions. It was hypothesised that accessibility of the resin-bound peptide chain to the reagents, ie catalysts, may have been compromised. To maximise this accessibility, we considered the relationship between solvent properties and peptide-resin solvation. The use of polar solvents in SPPS provides optimum solvation and accessibility; towards this end, our examples show that dichloromethane is a suitable solvent for effective resin-swelling and metathesis. We postulated, however, that the introduction of a pressurised 2-butene atmosphere during the activation cross-metathesis phase could generate a two-solvent system with considerably altered polarity and hence resin-swelling capability. We considered that the introduction of a non-polar solvent (i.e. 2-butene) could decrease solvation of the peptide backbone and promote aggregation and could therefore account for the slower butenolysis rate for peptide-bound substrates. Alternative alkene sources to 2-butene were therefore examined to enable more effective activation of dormant prenyl sidechains within resin-bound peptide sequences. Towards this end, 1,4-diacetoxy-2-butene 141, a 1,2-disubstituted ethylene containing polar functional groups, was found to be a more suitable 'disposable' alkene for achieving activation of resin-bound prenyl-substituted peptides.

Scheme 6.32

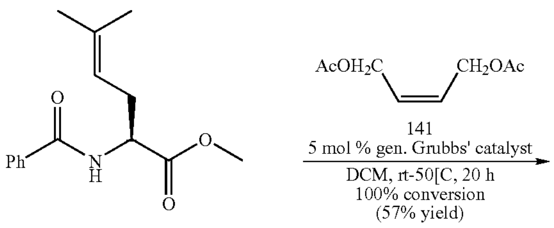

87

-continued

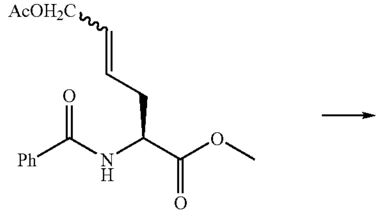

142

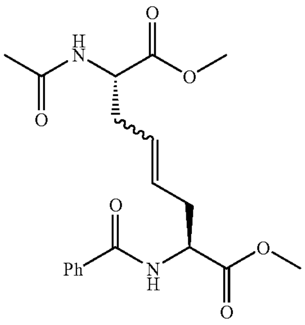

143

Solution phase studies were firstly performed as previously described in Scheme 4.33 and are summarised above (Scheme 6.32). The prenyl compound 87 was subjected to the modified 'ethenolysis' reaction with cis-1,4-diacetoxy-2-butene to convert it to the more reactive olefin 142 (Scheme 6.32). Exposure of a mixture of 87 and 141 to 5 mol % of $2^{nd}$ generation Grubbs' catalyst Grubbs' catalyst in DCM at 50° C. resulted in quantitative conversion to 142. The activated crotylglycine derivative 142 was then readily cross metathesised with allyl glycine derivative 21a to afford the expected heteroodimer 143 with 5 mol % of second generation Grubbs' catalyst in dichloromethane (Scheme 6.32). This process is equivalent to the formation of an intermolecular dicarba peptide bond. Similarly, homodimerisation of 142 to 69 was readily achieved after exposure to a 5 mol % solution of second generation Grubbs' catalyst. This process is equivalent to the formation of an intramolecular dicarba peptide bond.

This chemistry was then applied to peptide substrates bound to a solid phase support and is illustrated by the dipeptide example shown below (Scheme 6.33). Microwave irradiation of the peptide-resin 144 to 20 mol % of second generation Grubbs' catalyst in a solution of 1,4-diacetoxy-2-butene 141 and DCM produced the expected dipeptide 145 with quantitative conversion in just one hour. This represents a significant enhancement of reactivity compared to the afore-described butenolysis method and strongly supports the postulate that more polar disposable olefins can improve the reaction rate and resin swelling.

Scheme 6.33

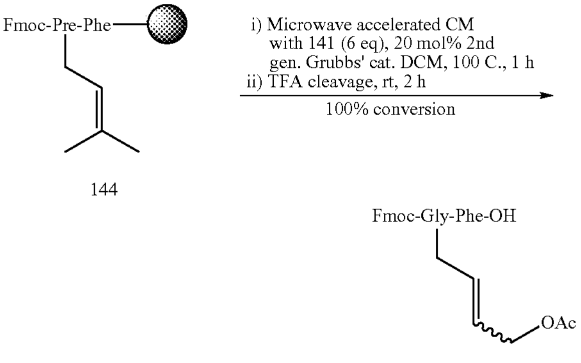

144

145

6.5 Stability

Despite the known activity of conotoxins as therapeutics, their multiple disulfide bond frameworks are known to be unstable under reducing conditions. Reduction or framework scrambling by thiol containing molecules such as glutathione or serum albumin in intracellular or extracellular environments such as blood plasma can decrease their effectiveness as drugs.

Incubation of native-Ctx ImI in human blood plasma has been shown to produce significant rearrangement of the disulfide framework (i.e. scrambling). Similarly, treatment of Ctx-IMI with glutathione, a reducing enzyme commonly found in blood plasma, results in complete scrambling of the disulfide framework in ~6 hours. See for instance Armishaw, C. J., Daly, N. L., Nevin, S. T., Adams, D. J., Craik, D. J., Alewood, P. F., J. Biol. Chem., 2006, in press. Such scrambling or reduction is not possible with dicarba-Ctx IMI analogues; the dicarba linkage is completely inert to such reductants.

6.6 Summary

In conclusion, the above described strategy can be used for the regioselective construction of multi-dicarba bond-containing peptides. The methodology was successfully applied to a model synthetic pentapeptide 102 and led to the regioselective construction of an intramolecular and intermolecular dicarba bridge. Similarly, a tandem metathesis-hydrogenation sequence provided dicarba-cystino analogues of naturally occurring conotoxin ImI 93. Here, a microwave accelerated ring closing metathesis provided cyclic peptides that were unattainable via conventional heating methods. A fully carbocyclic analogue of conotoxin ImI 140 was also synthesised. Although activation of the prenylglycine units via butenolysis was slow on the resin-bound peptide 133a, butenolysis did lead to the desired activated crotyl sidechains; alternatively, 1,4-diacetoxy-2-butene was found to be more compatible with the polystyrene-based solid support and provided quantitative activation of prenyl olefins over short reaction times. The selectivity of the methodology was maintained when investigated in the heterogeneous system. An intramolecular dicarba bridge was selectively constructed from allylglycine units in the presence of two prenyl olefins. A microwave-promoted RCM of the resin-bound crotyl-containing peptide ultimately afforded the desired bicycle 140, and reduction lead to conotoxin 126.

7.0 EXAMPLES 7.1 Instrumentation

Microwave reactions were carried out on a Personal Chemistry (now Biotage) Smith Synthesiser. The instrument produces a continuous focussed beam of microwave irradiation at 2.45 GHz with a maximum power delivery of 300W, which reaches and maintains a selected temperature (100° C.). Reactions were performed in high pressure quartz microwave vessels fitted with self-sealing Teflon septa as a pressure relief device, that were crimped in place. The vessels contained magnetic stirrer beads and the pressure and temperature of each reaction was monitored continuously with an in built pressure transducer (located in the lid) and infrared pyrometer respectively. Reaction times were measured from the time the microwave began heating until the reaction period had elapsed (cooling periods were not inclusive).

7.2 Intentionally Left Blank 7.3 Peptide Procedures 7.3.1 Materials and Reagents Peptides were synthesised in polypropylene Terumo syringes (10 mL) fitted with a polyethylene porous (20 μm) filter. Solid phase peptide synthesis (SPPS) was performed using a Visprep™ SPE DL 24-port model vacuum manifold supplied by Supelco. Coupling reactions and cleavage mixtures were shaken on a KS125 basic KA elliptical shaker supplied by Labortechnik at 400 motions per minute. Cleaved peptides were centrifuged on a HermLe Z200A centrifuge supplied by Medos at a speed of 4500 cycles per minute.

N,N'-Dimethylformamide (DMF) was supplied by Auspep and stored over 4 Å molecular sieves. Dichloromethane (DCM) was supplied by BDH and stored over 4 Å molecular sieves. Wang resin, Rink amide resin, piperidine and trifluoroacetic acid (TFA) were used as supplied by Auspep. Phenol was used as supplied by BDH. Diisopropylcarbodiimide (DIC), diisopropylethylamine (DIPEA), 4-(N,N'-dimethylamino)pyridine (DMAP), ethanedithiol (EDT), Ellman's reagent (5,5'-dithiobis(2-nitrobenzoic acid), N-methylmorpholine (NMM), and thioanisole were used as supplied by Aldrich. (2S)-2-Aminopent-4-enoic acid (L-allylglycine, Hag) was used as supplied by Peptech. N-Fluorenylmethoxycarbonylaminosuccinimide (Fmoc-OSu), O-(7-azabenzotriazol-1-yl)-N,N,N',N'-tetramethyluronium hexafluorophosphate (HATU) and sidechain-protected Fmoc-amino acids were used as supplied by GL Biochem unless otherwise specified.

7.3.2 Peptide Synthesis Procedure

Peptides were prepared using general Fmoc-SPPS methodology.[142,221] Manual SPPS was carried out using fritted plastic syringes, allowing filtration of solution without the loss of resin. The tap fitted syringes were attached to a vacuum tank and all washings were removed in vacuo. This involved washing (or swelling) the resin in the required solvent for a reported period of time, followed by evacuation which allowed the removal of excess reagents before subsequent coupling reactions.

7.3.2.1 Wang Resin

In a fritted syringe, Wang resin was swollen with DCM (7 mL, 3×1 min, 1×60 min) and DMF (7 mL, 3×1 min, 1×30 min). DIC (3 equiv.) was added to a solution of protected amino acid, Fmoc-L-Xaa-OH, (3 equiv.) in DMF (3 mL). The activated amino acid solution was added to the swelled resin and shaken gently for 1 min. A solution of DMAP (0.3 equiv.) in DMF (1 mL) was added to the resin and the reaction mixture was shaken gently for the reported period of time. The mixture was then filtered and the resin-tethered amino acid was washed with DMF (7 mL, 3×1 min) to ensure excess reagents were removed. In order to prevent formation of deletion products, remaining resin active sites were capped with an anhydride solution (5% acetic anhydride, 1% NMM, 94% DMF) for 1 h. The mixture was filtered and the resin was washed with DMF (7 mL, 3×1 min) and deprotected with 20% piperidine in DMF (7 mL, 1×1 min, 2×10 min). After this deprotection step, the resin was washed with DMF (7 mL, 5×1 min) to remove traces of base prior to coupling the next amino acid.

Subsequent amino acids were coupled using the following procedure:

NMM (6 equiv.) was added to a solution of protected amino acid, Fmoc-L-Xaa-OH (3 equiv.) and HATU (2 equiv.) in DMF (3 mL) and shaken gently for 1 min. The activated amino acid solution was added to the resin-tethered amino acid and shaken gently for the reported period of time. The peptidyl-resin was then washed with DMF (7 mL, 3×1 min) and the Kaiser test[255] was performed to monitor coupling success. Any incomplete reactions were repeated with extended reaction times (indicated in brackets). Upon negative test results for the presence of free amine, the resin-peptide was deprotected with 20% piperidine in DMF (7 mL, 1×1 min, 2×10 min) and washed again with DMF (7 mL, 5×1 min) to remove traces of base prior to coupling the next amino acid.

The above procedure was repeated until the desired peptide sequence was constructed. Once complete, the resin was washed with DMF (7 mL, 3×1 min), DCM (7 mL, 3×1 min), MeOH (7 mL, 3×1 min), DCM (7 mL, 3×1 min), MeOH (7 mL, 3×1 min) and dried in vacuo for 1 h. A small aliquot of resin-tethered peptide was then exposed to a TFA cleavage solution (Section 7.3.3).

7.3.2.2 Rink Amide Resin

In a fritted syringe, Rink amide resin was swollen with DCM (7 mL, 3×1 min, 1×60 min) and DMF (7 mL, 3×1 min, 1×30 min) and deprotected with 20% piperidine in DMF (7 mL, 1×1 min, 2×10 min) and washed again with DMF (7 mL, 5×1 min). NMM (6 equiv.) was added to a solution of a protected amino acid, Fmoc-L-Xaa-OH (3 equiv.) and HATU (2 equiv.) in DMF (3 mL) and shaken gently for 1 min. The activated amino acid solution was added to the resin and shaken gently for the reported period of time. The peptidyl-resin was washed with DMF (7 mL, 3×1 min) to ensure excess reagents were removed. Kaiser tests were performed to monitor coupling success and any incomplete reactions were repeated with extended reaction times (indicated in brackets). Upon negative test results for the presence of free amine, the resin-peptide was deprotected with 20% piperidine in DMF (7 mL, 1×1 min, 2×10 min) and washed again with DMF (7 mL, 5×1 min). This coupling procedure was repeated until the desired peptide sequence was constructed.

The above procedure was repeated until the desired peptide sequence was constructed. Once complete, the resin was washed with DMF (7 mL, 3×1 min), DCM (7 mL, 3×1 min), MeOH (7 mL, 3×1 min), DCM (7 mL, 3×1 min), MeOH (7 mL, 3×1 min) and dried in vacuo for 1 h. A small aliquot of resin-tethered peptide was then exposed to a TFA cleavage solution (Section 7.3.3).

Kaiser Test

The Kaiser test was performed in order to monitor coupling success by detecting the presence of resin-bound free amines.[221,255] Two drops of 5% ninhydrin in EtOH, 80% phenol in EtOH and 2% v/v 0.001 M potassium cyanide in pyridine were added to prewashed (EtOH) resin beads in a tube and the mixture was subsequently heated at 120° C. for 3-5 min. Blue colouration of the beads indicate the presence of free amines and provide evidence for an incomplete coupling reaction. It should be noted that this test cannot be performed after coupling asparagine, aspartic acid, serine and proline.[221,256]

7.3.3 Peptide Cleavage: TFA-Mediated Cleavage Procedure

A small aliquot of the resin-peptide (~1 mg) was suspended in a cleavage solution 2 mL): 90% TFA: 5% thioanisole: 2.5% EDT: 2.5% water and phenol (1.6 g/5 mL of cleavage solution) and shaken gently for 1.5 h. The mixture was then filtered and the resin beads were rinsed with TFA (2×0.5 mL). The filtrate was concentrated with a constant stream of air to yield an oil. The peptide was precipitated with ice-cold $Et_2O$ (2 mL) and collected by centrifugation (3×10 min). The supernatant liquid was decanted and the resultant residue was collected and analysed by mass spectrometry.

7.3.4 Ellman's Test

The Ellman's test was performed in order to monitor reaction progress during thiol oxidation (cysteine formation) by detecting the presence of free sulfhydryl groups.[257] 200 μL of a solution of Ellman's reagent in aqueous $(NH_4)_2CO_3$ buffer (4 mg $mL^{-1}$ in 0.1 M buffer) was added to 200 μL of the reacting peptide solution. An intense yellow colouration of the solution indicates the presence of free thiol groups and provides evidence for an incomplete oxidation reaction.

7.4 Hydrogenation Procedures 7.4.1 Catalysts and Materials

Catalysts: Palladium on charcoal (Pd/C) with 10% Pd concentration was used as supplied by Aldrich and stored in a desiccator. Tris(triphenylphosphine)rhodium(I) chloride (Wilkinson's catalyst, $Rh(I)(PPh_3)_3Cl]$) was used as supplied by Aldrich and stored under argon in a dry box. Asymmetric catalysts: (+)-1,2-Bis[(2S,5S)-2,5-diethylphospholano]benzene(1,5-cyclooctadiene)rhodium(I) trifluoromethane-sulfonate ([(COD)Rh(I)-(S,S)-Et-DuPHOS]OTf, Rh(I)-(S,S)-Et-DuPHOS), (−)-1,2-bis[(2R,5R)-2,5-diethylphospholano] benzene(1,5-cyclooctadiene)rhodium(I) tetra-fluoroborate ($[(COD)Rh(I)-(R,R)-Et-DuPHOS]BF_4$, Rh(I)-(R,R)-Et-DuPHOS), (+)-1,2-bis[(2S,5S)-2,5-dimethylphospholano]benzene(1,5-cyclooctadiene)rhodium(I) trifluoromethane-sulfonate ([(COD)Rh(I)-(S,S)-Me-DuPHOS]OTf, Rh(I)-(S, S)-Me-DuPHOS), (−)-1,2-bis[(2R,5R)-2,5-dimethylphospholano]benzene(1,5-cyclooctadiene)rhodium (I) tetrafluoroborate ($[(COD)Rh(I)-(R,R)-Me-DuPHOS]BF_4$, Rh(I)-(R,R)Me-DuPHOS), and (+)-1,2-bis[(2R,5R)-2,5-dimethylphospholano]ethane(1,5-cyclooctadiene) rhodium(I) trifluoromethanesulfonate ([(COD)Rh(I)-(R,R)-Me-BPE]OTf, Rh(I)-(R,R)-Me-BPE) and bis(carboxylato) [2,2'-bis(diphenylphosphino)-(R)-1,1-binapthyl]ruthenium (II) ((S)-Ru-BINAP) were used as supplied by Strem Chemicals and stored under argon.

Gases: Argon and hydrogen were supplied by BOC gases and were of high purity (<10 ppm oxygen). Additional purification was achieved by passage of the gases through water, oxygen and hydrocarbon traps.

Solvents: Benzene, MeOH, DCM, $^tBuOH$ and THF used in metal-catalysed hydrogenation reactions were degassed with high purity argon prior to use.

Reaction Vessels: Fischer-Porter shielded aerosol pressure reactors (100 mL) fitted with pressure gauge heads and stirrer beads were employed for hydrogenation reactions.

7.4.2 Pd/C Hydrogenation Procedure[36,37]

A Fischer-Porter tube was charged with substrate, catalyst (substrate:catalyst, 50:1) and solvent (5-10 mL). The reaction vessel was connected to the hydrogenation manifold, evacuated and flushed with argon gas before being charged with hydrogen gas to the reported pressure. The reaction was stirred at the specified temperature for the reported period of time. The hydrogen gas was then vented, the catalyst removed via filtration through a Celite pad and the solvent evaporated under reduced pressure.

7.4.3 Asymmetric Hydrogenation Procedure[36,37,119]

In a dry box, a Fischer-Porter tube was charged with substrate, catalyst (substrate catalyst, 100:1) and dry deoxygenated solvent (4-10 mL). The reaction vessel was assembled and tightly sealed within the dry box. The apparatus was connected to the hydrogenation manifold and purged three times using a vacuum and argon flushing cycle before being pressurised with hydrogen gas to the reported pressure. The reaction was then stirred at the specified temperature for the reported period of time. The hydrogen gas was vented and the solvent was evaporated under reduced pressure. Purification was achieved by flash chromatography (silica, EtOAc).

Freeze-Pump-Thaw Procedure

For liquid substrates, a freeze-pump-thaw cycle was applied and the solution was transferred into a dry box and loaded into a Fischer-Porter tube as described above. The substrate was dissolved in MeOH or benzene in a Teflon-sealed vessel. The solution was frozen upon immersion in liquid nitrogen and opened to a vacuum source (high vacuum line ~0.05 mm) to remove gases. The vessel was re-sealed and the solution was allowed to thaw before being frozen with liquid nitrogen again. This cycle was repeated until gas evolution was no longer observed during the thaw cycle.

7.4.4 Wilkinson's Hydrogenation Procedure

In a dry box; a Fischer-Porter tube was charged with substrate, Wilkinson's catalyst (substrate:catalyst, 50:1) and dry deoxygenated solvent (4-10 mL). The apparatus was connected to the hydrogenation manifold and purged three times using a vacuum and argon flushing cycle before being pressurised with hydrogen gas to the reported pressure. The reaction was then stirred at ambient temperature for the reported reaction time. The hydrogen gas was vented and the solvent was evaporated under reduced pressure. Purification was achieved by flash chromatography (silica, EtOAc).

Hydrogenation experiments are described in the following format: substrate (mg), solvent (mL), catalyst, hydrogen pressure (psi), reaction temperature (° C.), reaction time (h), isolated yield (%), retention time ($t_R$, GC/HPLC conditions) and enantiomeric excess (e.e.).

7.5 Metathesis Procedures 7.5.1 Catalysts and Materials

Catalysts: Bis(tricyclohexylphosphine)(benzylidene)ruthenium(II) dichloride (Grubbs' catalyst), tricyclohexylphosphine[1,3-bis(2,4,6-trimethylphenyl)-4,5-dihydroimidazol-2-ylidene](benzylidene)ruthenium(II) dichloride (second generation Grubbs' catalyst) and 1,3-bis(2,4,6-trimethylphenyl)-2-(imidazolidinylidene)dichloro-(oiso-propoxyphenylmethylene)ruthenium(II) dichloride (second generation Hoveyda-Grubbs' second generation catalyst) were used as supplied by Aldrich and stored under nitrogen.

Volatile Olefins: Cis-2-butene (99%), cis+trans-2-butene (99%) 2-methylpropene (iso-butylene) and 2-methyl-2-butene were used as supplied by Aldrich. Ethylene was used as supplied by BOC gases.

Solvents: DCM and a solution of lithium chloride in DMF (0.4 M LiCl/DMF) used in metal-catalysed metathesis reactions were degassed with high purity argon prior to use.

Reaction vessels: Schlenk tubes and microwave reactor vessels fitted with stirrer beads were employed for ring closing and cross metathesis reactions involving the use of solid or liquid (non-volatile) reactants. Fischer-Porter shielded aerosol pressure reactors (100 mL) fitted with pressure gauge heads and stirrer beads were employed for cross metathesis reactions involving gaseous (ethylene, cis-2-butene, iso-butylene) or volatile (2-methyl-2-butene) reactants.

7.5.2 Conventional Ring Closing and Cross Metathesis Procedure[116,142,152]

A Schlenk tube was charged with substrate(s), catalyst (5-40 mol %) and deoxygenated solvent (~5 mL) under an inert (nitrogen or argon) atmosphere. The reaction mixture was stirred at 50° C. for the specified period of time. Metathesis reactions were terminated upon exposure to oxygen and volatile species were removed under reduced pressure. The crude product was purified by flash chromatography.

7.5.3 Microwave-Accelerated Ring Closing and Cross Metathesis Procedure

A high pressure quartz microwave vessel was loaded with resin-tethered peptide, catalyst (5-40 mol %) and deoxygenated solvent (~3-5 mL) under an inert (nitrogen and argon) atmosphere. The reaction mixture was irradiated with microwaves and stirred at 100° C. for the reported period of time. The mixtures were then filtered and washed with DMF (3 mL, 3×1 min), DCM (3 mL, 3×1 min), MeOH (3 mL, 3×1 min) and dried on the SPPS manifold for 1 h. A small aliquot of resin-peptide (~1 mg) was then subjected to the TFA-mediated cleavage procedure (Section 7.3.3). The isolated peptide was analysed by mass spectrometry.

7.5.4 Conventional Cross Metathesis Procedure (Gaseous Reactant)

In a dry box, a Fischer-Porter tube was charged with substrate, catalyst (5-50 mol %) and deoxygenated solvent (~5 mL). The reaction vessel was then evacuated and purged with ethylene, cis-2-butene or iso-butylene to the reported pressure. The reaction mixture was stirred at 50° C. for the specified period of time. Metathesis reactions were terminated upon exposure to oxygen and volatile species were removed under reduced pressure. The crude product was purified by flash chromatography.

7.5.5 Conventional Cross Metathesis Procedure (Volatile Reactant)

A Fischer-Porter tube was charged with substrate, catalyst (5 mol %), deoxygenated solvent (~5 mL) and 2-methyl-2-butene. The reaction mixture was stirred at 50° C. for the specified period of time. Metathesis reactions were terminated upon exposure to oxygen and volatile species were removed under reduced pressure. The crude product was purified by flash chromatography.

Metathesis experiments are described using the following format: substrate (mg), solvent (mL), catalyst (mg), reacting olefin (in the case of cross metathesis) reaction temperature (° C.), reaction time (h), percent conversion (%). Chromatographic purification conditions (isolated yield, %) are also listed.

Hydrogenation and metathesis experiments performed on-resin were subjected to the conditions described above. Resin-based metathesis reactions were quenched with ethyl vinyl ether (0.5 mL, 5 min). The mixtures were then filtered, washed with DCM (3 mL, 3×1 min), MeOH (3 mL, 3×1 min) and dried on the SPPS manifold for 1 h. A small aliquot of resin-peptide (~1 mg) was subjected to the TFA-mediated cleavage procedure (Section 7.33). The isolated peptide was analysed by mass spectrometry.

Experimental for Section 4

7.9 Synthesis of 5,5-Dimethylproline Precursors 7.9.1 N-Acetyl-2-hydroxyglycine 42

42

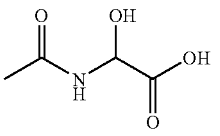

The titled compound 42 was prepared according to a procedure described by Williams et al.[195] A solution of acetamide 34 (6.10 g, 0.10 mol) and glyoxylic acid monohydrate 41 (10.60 g, 0.14 mol) in anhydrous acetone (150 mL) was heated at reflux for 18 h. The reaction mixture was evaporated under reduced pressure to afford the desired product 42 as a viscous yellow oil (13.75 g, 100%). Spectroscopic data indicated the crude product 42 did not require purification and was used directly in the subsequent reaction (Section 7.9.2). $\nu_{max}$ (neat): 3317 bs, 2974 w, 1732 s, 1668 s, 1538 s, 1379 m, 1234 w, 1112 w, 1048 m, 880 m $cm^{-1}$. $^1H$ n.m.r. (300 MHz, $D_6$-DMSO): δ 1.84 (s, 3H, $CH_3CO$), 5.39 (d, J=8.7 Hz, 1H, H2), (8.65, bd, J=8.4 Hz, 1H, NH), two exchangeable protons (OH) not observed. $^{13}C$ n.m.r. (75 MHz, $D_6$-DMSO): δ 22.5 ($CH_3CO$), 70.9 (C2), 169.4 (CONH), 171.5 (C1). Mass Spectrum ($ESI^+$, MeOH): m/z 134.2 $(M+H)^+$, $C_4H_8NO_4$ requires 134.1. Spectroscopic data were in agreement with those reported in the literature.[195]

7.6.2 Methyl N-Acetyl-2-methoxyglycinate 43

43

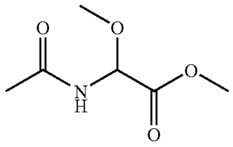

The methyl ester 43 was prepared according to a procedure described by Legall et al.[196] Concentrated $H_2SO_4$ (4.5 mL) was added to an ice-cooled solution of N-acetyl-2-hydroxyglycine 42 (13.69 g, 0.10 mol) in MeOH (150 mL). The solution was stirred for 2 days at room temperature then poured into an ice-cooled saturated $NaHCO_3$ solution (400 mL). The mixture was extracted with EtOAc (3×250 mL) and the combined organic extract was dried ($MgSO_4$) and evaporated under reduced pressure to yield the titled compound 43 as a yellow oil (9.57 g, 60%). Spectroscopic data indicated the crude product 43 did not require purification and was used directly in the subsequent reaction (Section 7.9.3). $\nu_{max}$ (neat): 3334 bm, 2955 w, 1753 s, 1671 s, 1528 m, 1439 m, 1375 m, 1221 m, 1088 m, 783 w $cm^{-1}$. H n.m.r. (300 MHz, $CDCl_3$): δ 2.10 (s, 3H, $CH_3CO$), 3.47 (s, 3H, $OCH_3$), 3.82 (s, 3H, $COOCH_3$), 5.55 (d, J=9.3 Hz, 1H, H2), 6.72 (bd, J=8.1 Hz, 1H, NH). $^{13}C$ n.m.r. (75 MHz, $CDCl_3$): δ 23.3 ($CH_3CO$), 53.0 ($OCH_3$), 56.8 ($COOCH_3$), 78.3 (C2), 168.7 (CONH), 170.8 (C1). Mass Spectrum ($ESI^+$, MeOH): m/z 184.1 $(M+Na)^+$, $C_6H_{11}NNaO_4$ requires 184.2. Spectroscopic data were in agreement with those reported in the literature.[196]

7.6.3 Methyl 2-N-Acetylamino-2-(dimethoxyphosphinyl) acetate 39

39

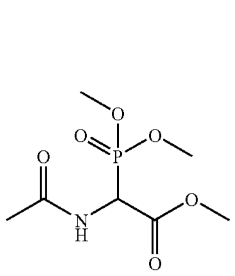

The phosphinyl compound 39 was prepared according to a procedure described by Schmidt et al.[197] Phosphorus (III) chloride (3.91 mL, 44.6 mmol) was added to a solution of methyl N-acetyl-2-methoxyglycinate 43 (7.19 g, 44.6 mmol) in toluene (100 mL) at 70° C. and the mixture was stirred at this temperature for 17 h. Trimethyl phosphite (5.27 mL, 44.7 mmol) was then added dropwise and the reaction mixture was left to stir for 2 h at 70° C. The mixture was evaporated under reduced pressure and the resultant oil was re-dissolved in DCM (100 mL) and washed with saturated $NaHCO_3$ solution (3×100 mL). The organic extract was dried ($MgSO_4$) and evaporated under reduced pressure to afford the product 39 as a colourless solid (1.46 g, 14%). The combined aqueous layers were extracted in a continuous extractor with DCM (150 mL) for 3 d. The organic layer was then evaporated under reduced pressure to give the product 39 as a colourless solid (3.21 g, 30%) (44% combined yield), m.p. 89-91° C. (lit.[197] 88-89° C.). Spectroscopic data indicated the crude product 39 did not require purification and was used directly in the subsequent reaction (Section 7.94). $\nu_{max}$(KBr): 3281 m, 3050 w, 2852 w, 1749 m, 1673 m, 1540 m, 1309 m, 1287 w, 1232 w, 1133 m, 1061 m, 1028 m $cm^{-1}$. $^1H$ n.m.r. (300MHz, $CDCl_3$): δ 2.08 (s, 3H, $CH_3CO$), 3.80-3.85 (m, 9H, $COOCH_3$, 2x P—$OCH_3$), 5.23 (dd, J=22.2, 8.9 Hz, 1H, H2), 6.42 (d, J=8.8 Hz, 1H, NH). $^{13}C$ n.m.r. (75 MHz, $CDCl_3$): δ 22.7 ($CH_3CO$), 50.0 (d, J=146.8 Hz, C2), 53.3 ($COOCH_3$), 54.1 (d, J=6.8 Hz, P—$OCH_3$), 54.2 (d, J=6.5 Hz, P—$OCH_3$), 167.0 (d, J=2.2 Hz, CONH), 169.0 (d, J=6.0 Hz, C1). Mass Spectrum ($ESI^+$, MeOH): m/z 262.1 $(M+Na)^+$, $C_6H_{11}NNaO_4$ requires 262.2.

7.7 Synthesis of Olefinic Substrates 7.7.1 (2Z)-Methyl 2-N-Acetylaminopenta-2,4-dienoate 57

57

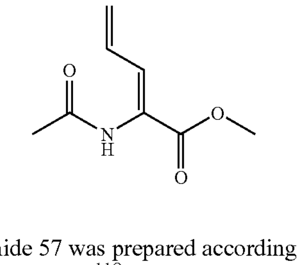

The dienamide 57 was prepared according to a procedure described by Teoh et al.[119] Tetramethylguanidine (3.22 mL, 25.7 mmol) and hydroquinone (10.0 mg) were added to a solution of methyl 2-N-acetylamino-2-(dimethoxyphosphinyl)acetate 39 (4.63 g, 19.4 mmol) in THF (60 mL) at −78° C. After 15 min, acrolein 58 (1.55 mL, 23.2 mmol) was added and the mixture was stirred at −78° C. for 2 h and then warmed to 25° C. and allowed to react an additional 2 h. The reaction mixture was diluted with DCM (100 mL) and washed with dilute HCl solution (1 M, 2×80 mL), $CuSO_4$ solution (1 M, 2×80 mL), saturated $NaHCO_3$ solution (2×80 mL) and saturated NaCl solution (1×80 mL). The organic layer was dried ($MgSO_4$) and evaporated under reduced pressure to give the desired dienamide 57 as an off-white solid (2.78 g, 85%), m.p. 60-62° C. (lit. I[9] 61-63° C.). Spectroscopic data indicated the crude product 57 did not require purification and was used directly in the subsequent reaction (Section 7.11.2). $\nu_{max}$ (KBr): 3277 m, 3011 m, 2955 m, 1733 s, 1655 s, 1594 m, 1518 s, 1438 m, 1377 w, 1350 w, 1250 w, 1113 s, 1016 m, 994 m, 950 s, 768 m $cm^{-1}$. $^1H$ n.m.r. (300 MHz, $CDCl_3$): δ 2.16 (s, 3H, $CH_3CO$), 3.81 (s, 3H, $OCH_3$), 5.49 (d, J=9.9 Hz, 1H, H5-E), 5.61 (d, J=17.1 Hz, 1H, H5-Z), 6.47 (m, 1H, H4), 7.05 (d, J=11.1 Hz, 1H, H3), 7.07 (bs, 1H, NH). $^{13}C$ n.m.r. (75 MHz, $CDCl_3$): δ 23.6 ($CH_3CO$), 52.7 ($OCH_3$), 123.7 (C2), 125.2 (C5), 132.0 (C4), 132.9 (C3), 165.5, 168.9 (C1, CONH). Mass Spectrum ($ESI^+$, MeOH): m/z 170.2 $(M+H)^+$, $C_8H_{12}NO_3$ requires 170.2. Spectroscopic data were in agreement with those reported in the literature.[119]

7.7.2 (2S)-Methyl 2-N-Acetylaminopent-4-enoate 21a

21a

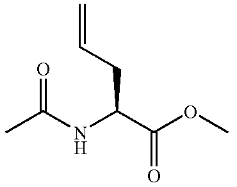

59

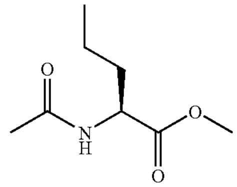

The dienamide 57 was subjected to the general asymmetric hydrogenation procedure (Section 7.4.3) under the following conditions: (2Z)-Methyl 2-N-acetylaminopenta-2,4-dienoate 57 (108 mg, 0.64 mmol), benzene (7 mL), Rh(I)-(S,S)-Et-DuPHOS, 30 psi, 22° C., 3 h. At the end of the reaction period, the solvent was evaporated under reduced pressure and the residue was purified by flash chromatography ($SiO_2$, EtOAc) to give a yellow oil (106 mg, 97%). $^1H$ n.m.r. spectroscopy confirmed formation of the desired product 21a and the fully saturated compound, (2S)-methyl 2-N-acetylaminopentanoate 59 (δ 0.93 (t, J=7.3 Hz, 3H, H5), 1.25-1.44 (m, 4H, H3, 4)), in a 97:3 ratio respectively. GC: (2S)-21a $t_R$=18.6 min (GC chiral column 50 CP2/XE60-SVALSAPEA, 100° C. for 1 min, 5° C. $min^{-1}$ to 280° C. for 9 min), 95% e.e. $[\alpha]_D^{22}$+45.0° (c=0.76, $CHCl_3$) containing 3% of 59 (lit.[208] for (S)-21a $[\alpha]_D^{22}$ +45.4° (c=3.57, $CHCl_3$)). $\nu_{max}$ (neat): 3278 s, 3079 w, 2955 w, 1744 s, 1657 s, 1546 m, 1438 m, 1375 m, 1275 w, 1226 w, 1151 m, 997 w, 924 w $cm^{-1}$. H n.m.r. (300 MHz, $CDCl_3$): δ 2.00 (s, 3H, $CH_3CO$), 2.43-2.62 (m, 2H, H3), 3.73 (s, 3H, $OCH_3$), 4.67 (dt, J=11.6, 5.8 Hz, 1H, H2), 5.08 (m, 1H, H5-E), 5.14 (m, 1H, H5-Z), 5.67 (m, 1H, H4), 6.06 (bs, 1H, NH). $^{13}C$ n.m.r. (100 MHz, $CDCl_3$): δ 23.1 ($CH_3CO$), 36.5 (C3), 51.8 (C2), 52.4 ($OCH_3$), 119.2 (C5), 132.3 (C4), 169.9, 172.4 (C1, CONH). Mass Spectrum ($ESI^+$, MeOH): m/z 194.1 $(M+Na)^+$, $C_8H_{13}NNaO_3$ requires 194.2. Spectroscopic data were in agreement with those reported in the literature.[119]

(2R)-Methyl 2-N-acetylaminopent-4-enoate 21a

21a

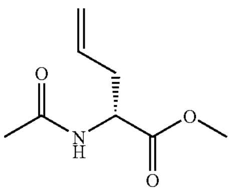

59

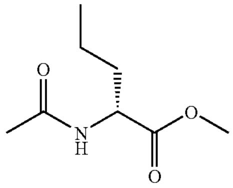

The dienamide 57 was subjected to the general asymmetric hydrogenation procedure (Section 7.4.3) under the following conditions: (2Z)-Methyl 2-N-acetylaminopenta-2,4-dienoate 57 (40.0 mg, 0.24 mmol), benzene (5 mL), Rh(I)-(R,R)Et-DuPHOS, 30 psi, 22° C., 3 h. At the end of the reaction period, the solvent was evaporated under reduced pressure and the residue was purified by flash chromatography ($SiO_2$, EtOAc) to give as a yellow oil (36.0 mg, 88%). $^1$H n.m.r. spectroscopy confirmed formation of the desired product 21a and the fully saturated compound, (2R)-methyl 2-N-acetylaminopentanoate 59 in a 95:5 ratio respectively GC: (2R)-21a $t_R$ 18.2 min (GC chiral column 50CP2/XE60-SVALSAPEA, 100° C. for 1 min, 5° C. $min^{-1}$ to 280° C. for 9 min), 95% e.e. $[\alpha]_D^{22}$ −43.0° (c=0.47, $CHCl_3$) containing 5% of 59. Spectroscopic data were in agreement with those previously reported for the (S)-enantiomer.

7.7.3 N-Benzoyl-2-hydroxyglycine 65

65

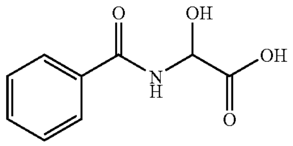

The titled compound 65 was prepared according to a procedure described by Zoller et al.[209] A mixture of benzamide 35 (5.00 g, 41.3 mmol) and glyoxylic acid monohydrate 41 (4.32 g, 46.9 mmol) in anhydrous acetone (70 mL) was heated at reflux for 19 h. The reaction mixture was evaporated under reduced pressure to afford the desired product 65 as a colourless solid (8.06 g, 100%), m.p. 198-200° C. (lit.[209] 200-201° C. (dec)) Spectroscopic data indicated the crude product 65 did not require purification and was used directly in the subsequent reaction (Section 7.11.4). $\nu_{max}$ (KBr): 3310 bs, 3058 w, 1728 s, 1646 s, 1602 w, 1582 w, 1535 s, 1491 w, 1452 w, 1315 m, 1292 w, 1254 m, 1161 m, 1097 s, 1040 m, 1002 w, 957 m, 805 w, 770 w, 728 m, 692 m, 654 m, 609 w, 515 m, 483 w $cm^{-1}$. $^1$H n.m.r. (300 MHz, $D_6$-DMSO): δ 5.60 (d, J=7.8 Hz, 1H, H2), 7.41-7.49 (m, 2H, H3', 5'), 7.55 (m, 1H, H4'), 7.86-7.92 (m, 2H, H2', 6'), 9.26 (d, J=7.8 Hz, 1H, NH), two exchangeable OH protons not observed. $^{13}$C n.m.r. (75 MHz, $D_6$-DMSO): δ 71.7 (C2), 127.6, 128.3, 131.7 (Arom CH), 133.7 (C1'), 166.0, 171.5 (C1, CONH). Mass Spectrum ($ESI^+$, MeOH): m/z 218.2 $(M+Na)^+$, $C_9H_9NNaO_4$ requires 218.2.

7.7.4 Methyl N-Benzoyl-2-methoxyglycinate 66

66

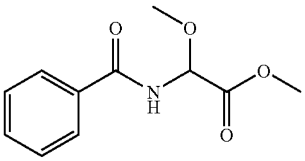

The methyl ester 66 was prepared according to a procedure described by Zoller et al.[209] Concentrated $H_2SO_4$ (2.0 mL) was added to an ice-cooled solution of N-benzoyl-2-hydroxyglycine 65 (8.05 g, 41.3 mmol) in MeOH (65 mL). The solution was stirred for 48 h at ambient temperature then poured into an ice-cooled saturated $NaHCO_3$ solution (100 mL). The mixture was extracted with EtOAc (3×100 mL) and the combined organic extract was dried ($MgSO_4$) and evaporated under reduced pressure to yield the titled compound 66 as a yellow oil (8.00 g, 87%). Spectroscopic data indicated the crude product 66 did not require purification and was used directly in the subsequent reaction (Section 7.11.5). $\nu_{max}$ (neat): 3310 bm, 2955 m, 2837 w, 1760 s, 1651 s, 1603 w, 1580 w, 1525 s, 1488 m, 1439 m, 1338 w, 1286 w, 1226 w, 1198 w, 1147 w, 1108 m, 1022 w, 924 m, 850 w, 803 m, 778 m, 692 m $cm^{-1}$. H n.m.r. (300 MHz, $CDCl_3$): δ 3.54 (s, 3H, $OCH_3$), 3.85 (s, 3H, $COOCH_3$), 5.78 (d, J=9.0 Hz, 1H, H2), 7.22 (bd, J=9.0 Hz, 1H, NH), 7.42-7.51 (m, 2H, H3', 5'), 7.56 (m, 1H, H4'), 7.80-7.88 (m, 2H, H2', 6'). $^{13}$C n.m.r. (75 MHz, $CDCl_3$): δ 53.2 ($OCH_3$), 57.0 ($COOCH_3$), 78.8 (C2), 127.4, 128.9, 132.5 (Arom CH), 133.2 (C1'), 167.6, 168.7 (C1, CONH). Mass Spectrum ($ESI^+$, MeOH): m/z 224.2 $(M+H)^+$, $C_{11}H_{14}NO_4$ requires 224.2; m/z 246.3 $(M+Na)^+$, $C_{11}H_{13}NNaO_4$ requires 246.2. Spectroscopic data were in agreement with those reported in the literature.[209]

7.7.5 Methyl 2-N-Benzoylamino-2-(dimethoxyphosphinyl)acetate 64

64

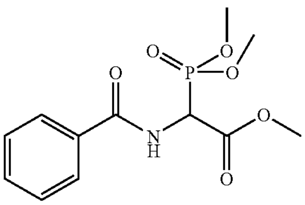

The phosphinyl compound 64 was prepared according to a procedure described by Teoh et al.[19] Phosphorus (III) chloride (3.15 mL, 36.0 mmol) was added to a solution of methyl N-benzoyl-2-methoxyglycinate 66 (8.00 g, 35.9 mmol) in toluene (70 mL) at 70° C. and the mixture was stirred at this temperature for 14 h. Trimethyl phosphite (4.25 mL, 36.0 mmol) was added dropwise and the reaction mixture was left to stir for 2 h at 70° C. At the end of the reaction period, the mixture was evaporated under reduced pressure and the resultant oil was re-dissolved in DCM (100 mL) and washed with saturated $NaHCO_3$ solution (3×70 mL). The organic extract was isolated, dried ($MgSO_4$) and evaporated under reduced pressure to afford the titled compound 64 as a colourless solid (8.21 g, 76%), m.p. 110-112° C. (lit.[210] 112-114°

C.). Spectroscopic data indicated the crude product 64 did not require purification and was used directly in the subsequent reaction (Section 7.11.6). $\nu_{max}$ (KBr): 3300 m, 3248 m, 3059 w, 2958 m, 2852 w, 1737 s, 1671 s, 1638 m, 1618 w, 1602 w, 1581 w, 1541 s, 1492 m, 1432 w, 1292 s, 1235 s, 1188 w, 1152 w, 1044 s, 915 m, 881 w, 832 m, 812 w, 791 w, 780 w, 758 m, 708 m, 616 w, 562 m $cm^{-1}$. H n.m.r. (300 MHz, $CDCl_3$): δ 3.82-3.90 (m, 9H, $COOCH_3$, 2×P—$OCH_3$), 5.47 (dd, J=21.9, 9.0 Hz, 1H, H2), 6.97 (bd, J=7.8 Hz, 1H, NH), 7.43-7.49 (m, 2H, H3', 5'), 7.56 (m, 1H, H4'), 7.82-7.87 (m, 2H, H2', 6'). $^{13}$C n.m.r. (75 MHz, $CDCl_3$): δ 50.6 (d, J=147.1 Hz, C2), 53.5 ($COOCH_3$), 54.2 (d, J=6.8 Hz, P—$OCH_3$), 127.4, 128.8, 132.3 (Arom CH), 133.1 (C1'), 166.9 (d, J=5.4 Hz, C1), 167.3 (d, J=2.0 Hz, CONH). Mass Spectrum (ESI$^+$, MeOH): m/z 302.2 $(M+H)^+$, $C_{12}H_{17}NO_6P$ requires 302.2; m/z 324.2 $(M+Na)^+$, $C_{12}H_{16}NNaO_6P$ requires 324.2.

7.7.6 (2Z)-Methyl 2-N-Benzoylaminopenta-2,4-dienoate 63

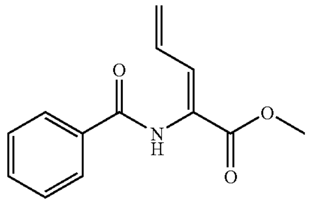
63

The dienamide 63 was prepared according to a procedure described by Teoh et al.[119]

Tetramethylguanidine (4.35 mL, 34.7 mmol) and hydroquinone (12.0 mg) were added to a solution of methyl 2-N-benzoylamino-2-(dimethoxyphosphinyl)acetate 64 (7.79 g, 25.9 mmol) in THF (120 mL) at −78° C. After 30 min, acrolein 58 (2.10 mL, 31.4 mmol) was added and the mixture was stirred at −78° C. for 2 h and then warmed to 25° C. and allowed to react an additional 2 h. The reaction mixture was diluted with DCM (150 mL) and washed with dilute HCl solution (1 M, 2×100 mL), $CuSO_4$ solution (1 M, 2×100 mL), saturated $NaHCO_3$ solution (2×100 mL) and saturated NaCl solution (1×100 mL). The organic extract was dried ($MgSO_4$) and evaporated under reduced pressure to give the crude product 63 as a waxy-brown solid. Purification by flash chromatography ($SiO_2$, light petroleum:EtOAc:DCM, 3:2:2) furnished the pure enamide 63 as colourless needles (4.78 g, 80%), m.p. 138-141° C. (dec). $\nu_{max}$ (KBr): 3288 bm, 2952 m, 2361 w, 1727 s, 1652 s, 1602 w, 1580 w, 1514 s, 1484 s, 1436 w, 1257 s, 1196 w, 1074 w, 1028 w, 991 w, 931 w, 800 w, 737 m, 710 m $cm^{-1}$. $^{1}$H n.m.r. (300 MHz, $CDCl_3$): δ 3.83 (s, 3H, $OCH_3$), 5.50 (dd, J=10.0, 1.7 Hz, 1H, H5-E), 5.64 (dd, J=16.8, 1.7 Hz, 1H, H5-Z), 6.56 (ddd, J=17.1, 11.4, 10.2 Hz, 1H, H4), 7.14 (d, J=11.2 Hz, 1H, H3), 7.45-7.51 (m, 2H, H3', 5'), 7.56 (m, 1H, H4'), 7.78 (bs, 1H, NH), 7.88-7.91 (m, 2H, H2', 6'). $^{3}$C n.m.r. (75 MHz, $CDCl_3$): δ 52.8 ($OCH_3$), 123.6 (C2), 125.2 (C5), 127.6 (C2', 6'), 128.9 (C3', 5'), 132.2, 132.2, 132.3 (C3, 4, 4'), 133.9 (C1'), 165.6, 165.8 (C1, CONH). Mass Spectrum (ESI$^+$, MeOH): m/z 232.1 $(M+H)^+$, $C_{13}H_{14}NO_3$ requires 232.3; m/z 254.2 $(M+Na)^+$, $C_{13}H_{13}NNaO_3$ requires 254.2. Spectroscopic data were in agreement with those reported in the literature.[211]

7.7.7 (2S)-Methyl 2-N-Benzoylaminopent-4-enoate 62

62

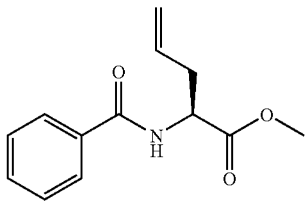

68

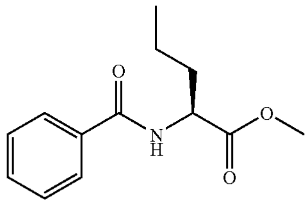

The dienamide 63 was subjected to the general asymmetric hydrogenation procedure (Section 7.4.3) under the following conditions: (2Z)-Methyl 2-N-benzoylaminopenta-2,4-dienoate 63 (100 mg, 0.43 mmol), benzene (8 mL), Rh(I)-(S, S)Et-DuPHOS, 30 psi, 22° C., 3 h. At the end of the reaction period, the solvent was evaporated under reduced pressure and the residue was purified by flash chromatography ($SiO_2$, EtOAc) to give a pale yellow oil (100 mg, 99%). $^{1}$H n.m.r. spectroscopy confirmed formation of the desired product 62 and the fully saturated compound, (2S)methyl 2-N-benzoylaminopentanoate 68 (δ 0.95 (t, J=7.3 Hz, 3H, H5), 1.36-1.50 (m, 2H, H4), 1.90-1.96 (m, 2H, H3)), in a 93:7 ratio respectively. GC: (2S)-62 $t_R$=27.0 min (GC chiral column 50 CP2/XE60-SVALSAPEA, 180° C. for 1 min, 2° C. $min^{-1}$ to 210° C. for 20 min), 100% e.e. $[\alpha]_D^{22}$ +49.3° (c=1.12, $CHCl_3$) containing 7% of 68. $\nu_{max}$ (neat): 3325 bw, 3062 w, 2955 w, 2360 w, 1743 s, 1644 s, 1603 w, 1580 w, 1538 m, 1489 m, 1438 w, 1360 w, 1268 w, 1225 w, 1159 w, 1075 w, 1028 w, 925 m, 802 w, 714 w, 668 w $cm^{-1}$. $^{1}$H n.m.r. (400 MHz, $CDCl_3$): δ 2.63-2.73 (m, 2H, H3), 3.79 (s, 3H, $OCH_3$), 4.91 (m, 1H, H2), 5.15 (m, 1H, H5-E), 5.18 (m, 1H, H5-Z), 5.75 (m, 1H, H4), 6.67 (bd, J=7.0 Hz, 1H, NH), 7.42-7.46 (m, 2H, H3', 5'), 7.52 (m, 1H, H4'), 7.78-7.81 (m, 2H, H2', 6'). $^{3}$C n.m.r. (100 MHz, $CDCl_3$): δ 36.8 (C3), 52.1 (C2), 52.6 ($OCH_3$), 119.5 (C5), 127.2 (C2', 6'), 128.8 (C3', 5'), 131.9 (C4), 132.4 (C4'), 134.1 (C1'), 167.0, 172.4 (C1, CONH). Mass Spectrum (ESI$^+$, MeOH): m/z 234.3 $(M+H)^+$, $C_{13}H_{16}NO_3$ requires 234.3; m/z 256.2 $(M+Na)^+$, $C_{13}H_{15}NNaO_3$ requires 256.3. Spectroscopic data were in agreement with those reported in the literature.[212]

(2R)-Methyl 2-N-benzoylaminopent-4-enoate 62

62

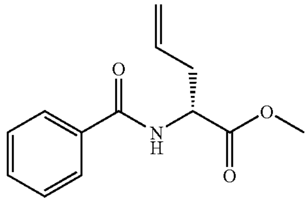

-continued

68

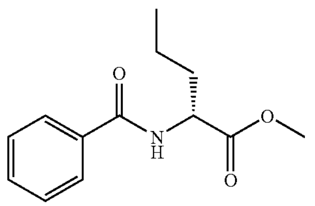

The dienamide 63 was subjected to the general asymmetric hydrogenation procedure (Section 7.4.3) under the following conditions: (2Z)-Methyl 2-N-benzoylaminopenta-2,4-dienoate 63 (100 mg, 0.43 mmol), benzene (8 mL), Rh(I)-(R, R)Et-DuPHOS, 30 psi, 22° C., 3 h. At the end of the reaction period, the solvent was evaporated under reduced pressure and the residue was purified by flash chromatography ($SiO_2$, EtOAc) to give a yellow oil (93.8 mg, 93%). $^1H$ n.m.r. spectroscopy confirmed formation of the desired product 62 and the fully saturated compound, (2R)-methyl 2-N-benzoylaminopentanoate 68, in a 91:9 ratio respectively. GC: (2R)-62 $t_R$=26.4 min (GC chiral column 50 CP2/XE60-SVALSA-PEA, 180° C. for 1 min, 2° C. $min^{-1}$ to 210° C. for 20 min), 100% e.e. $[\alpha]_D^{22}$ −49.7° (c=0.64, $CHCl_3$) containing 9% of 68. Spectroscopic data were in agreement with those previously reported for the (S)-enantiomer.

7.7.8 (2Z)-Methyl 2-N-Acetylamino-5-phenylpenta-2,4-dienoate 76

76

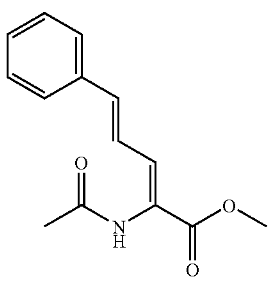

The dienamide 76 was prepared according to a procedure described by Burk et al[117]

Tetramethylguanidine (0.70 mL, 5.58 mmol) was added to a solution of methyl 2-N-acetylamino-2-(dimethoxyphosphinyl)acetate 64 (1.00 g, 4.18 mmol) in THF (50 mL) at −78° C. After 15 min, trans-cinnamaldehyde 78 (0.63 mL, 5.00 mmol) was added and the mixture was stirred at −78° C. for 2 h, warmed to 25° C. and allowed to react an additional 2 h. The reaction mixture was diluted with DCM (100 mL) and washed with dilute HCl solution (1 M, 2×75 mL), $CuSO_4$ solution (1 M, 2×75 mL), saturated $NaHCO_3$ solution (2×75 mL) and saturated NaCl solution (1×75 mL). The organic layer was dried ($MgSO_4$) and evaporated under reduced pressure to give the crude product 76 as a waxy solid (0.87 g). Purification by recrystallisation from a mixture of light petroleum, EtOAc and DCM furnished the pure dienamide 76 as an off-white solid (0.76 g, 74%), m.p. 180-181° C. (lit.[117] 179-180° C.). $\nu_{max}$(KBr): 3263 w, 1721 s, 1662 s, 1517 s, 1439 m, 1368 m, 1286 m, 1229 s, 1192 w, 1116 m, 993 m, 769 w, 752 m, 728 w, 692 m, 600 w $cm^{-1}$. $^1H$ n.m.r. (300 MHz, $CDCl_3$). δ 2.20 (s, 3H, $CH_3CO$), 3.82 (s, 3H, $OCH_3$), 6.89-6.91 (m, 2H, H3, 4), 7.01 (m, 1H, H5), 7.22 (bd, J obscured by residual $CHCl_3$ peak, 1H, NH), 7.29-7.37 (m, 3H, H3', 4', 5'), 7.45-7.48 (m, 2H, H2', 6'). $^{13}C$ n.m.r. (100 MHz, $CDCl_3$): δ 23.9, ($CH_3CO$), 52.7 ($OCH_3$), 123.0 (C2), 124.0, 127.5, 128.9, 129.2, 132.8, 140.2 (Arom CH, C3, 4, 5), 136.5 (C1'), 165.6, 168.7 (C1, CONH). Mass Spectrum ($ESI^+$, MeOH): m/z 246.2 $(M+H)^+$, $C_{14}H_{16}NO_3$ requires 246.3. Spectroscopic data were in agreement with those reported in the literature.[117]

7.7.9 (2S)-Methyl 2-N-Acetylamino-5-phenylpent-4-enoate 77

77

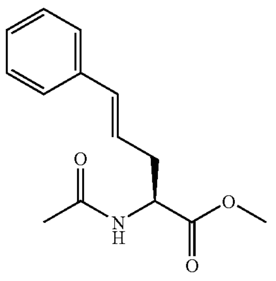

79

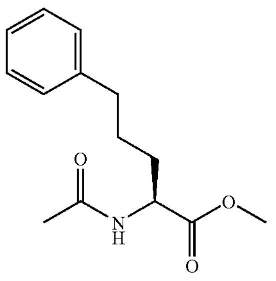

The dienamide 76 was subjected to the general asymmetric hydrogenation procedure (Section 7.4.3) under the following conditions: (2Z)-Methyl 2-N-acetylaminopenta-2,4-dienoate 76 (28.0 mg, 0.11 mmol), MeOH (7 mL), Rh(I)-(S,S)-Et-DuPHOS, 90 psi, 22° C., 2 h. At the end of the reaction period, the solvent was evaporated under reduced pressure and the residue was purified by flash chromatography ($SiO_2$, EtOAc) to give a yellow oil (27.2 mg, 96%). $^1H$ n.m.r. spectroscopy confirmed formation of the desired product 77 and the fully saturated compound, (2S)-methyl 2-N-acetylamino-5-phenylpentanoate 79 (δ 1.60-1.87 (m, 4H, H3, 4), 2.48-2.53 (m, 2H, H5), 3.72 (s, 3H, $OCH_3$), 4.65 (m, 1H, H2)), in a 91:9 ratio respectively. $[\alpha]_D^{22}$ +90.0° (c 0.64, $CHCl_3$) containing 9% of 79. $\nu_{max}$ (neat): 3280 bw, 3070 m, 2960 w, 2350 w, 1745 s, 1648 s, 1605 w, 1575 w, 1550 m, 1478 m, 1440 w, 1369 w, 1270 w, 1225 w, 1153 w, 1075 w, 1028 w, 925 m, 805 w, 720 w $cm^{-1}$. $^1H$ n.m.r. (400 MHz, $CDCl_3$): δ 2.02 (s, 3H, $CH_3CO$), 2.64-2.78 (m, 2H, H3), 3.76 (s, 3H, $OCH_3$), 4.77 (m, 1H, H2), 6.00-6.09 (m, 2H, H4, NH), 6.45 (d, J=15.8 Hz, 1H, H5), 7.20-7.34 (m, 5H, Arom CH). $^{13}C$ n.m.r. (100 MHz, $CDCl_3$): δ 23.3 ($CH_3CO$), 36.0 (C3), 52.1, 52.6 (C2, $OCH_3$), 123.6, 126.4, 127.8, 128.7, 134.3 (Arom CH, C4, 5), 136.9 (C1'), 171.5, 172.5 (C1, CONH). Mass Spectrum ($ESI^+$, MeOH): m/z 248.1 $(M+H)^+$, $C_{14}H_{18}NO_3$ requires 248.2. Spectroscopic data were in agreement with those reported in the literature.[117]

(2R)-Methyl 2-N-Acetylamino-5-phenylpent-4-enoate 77

77

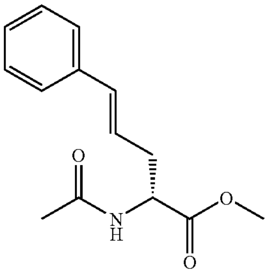

79

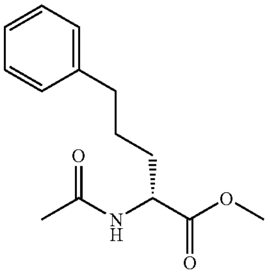

The dienamide 76 was subjected to the general asymmetric hydrogenation procedure (Section 7.4.3) under the following conditions: (2Z)-Methyl 2-N-acetylamino-5-phenylpenta-2,4-dienoate 76 (27.4 mg, 0.11 mmol), MeOH (5 mL), Rh(I)-(R,R)-Et-DuPHOS, 90 psi, 22° C., 2 h. At the end of the reaction period, the solvent was evaporated under reduced pressure and the residue was purified by flash chromatography ($SiO_2$, EtOAc) to give a yellow oil (25.7 mg, 93%). $^1H$ n.m.r. spectroscopy confirmed formation of the desired product 77 and the fully saturated compound, (2R)-methyl 2-N-acetylamino-5-phenylpentanoate 79 in a 87:13 ratio respectively. $[\alpha]_D^{22}$ $^-$89.8° (c=1.03, $CHCl_3$) containing 13% of 79. Spectroscopic data were in agreement with those previously reported for the (S)-enantiomer.

7.7.10 (2Z)-Methyl 2-N-Acetylamino-5-methylhexa-2,4-dienoate 20

20

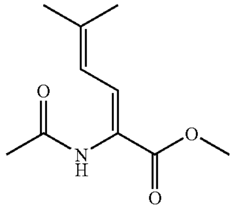

The preparation of (2Z)-methyl 2-N-acetylamino-5-methylhexa-2,4-dienoate 20 from the phosophonate 39 has been previously described (Section 7.9.4).

7.7.11 (2S)-Methyl 2-N-Acetylamino-5-methylhex-4-enoate 19

19

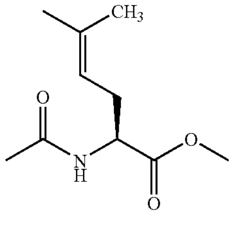

The preparation of (2S)-methyl 2-N-acetylamino-5-methylhex-4-enoate 19 via asymmetric hydrogenation of dienoate 20 has been previously described (Section 7.9.5).

Metathesis Reactions with Olefinic Substrates 7.8.1 (2S,7S)-Dimethyl 2,7-N,N'-Diacetylaminooct-4-enedioate 60

60

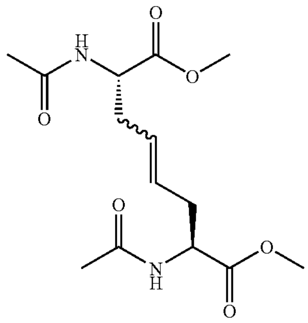

The dimer 60 was prepared via the conventional cross metathesis procedure (Section 7.5.2) under the following conditions: (2S)-Methyl 2-N-acetylaminopent-4-enoate 21a (95.0 mg, 0.56 mmol), DCM (4 mL), Grubbs' catalyst (91.0 mg, 0.11 mmol, 20 mol %), 50° C., 20 h, 100% conversion into 60. Purification by flash chromatography ($SiO_2$, DCM: light petroleum: EtOAc, 1:1:1→10% MeOH:DCM) furnished pure dimer 60 as a brown oil (76.7 mg, 88%). GC: $t_R$ (E/Z)=12.7 min, 12.8 min (GC column 30QC5/BPX5, 150° C. for 1 min, 10° C. $min^{-1}$ to 280° C. for 6 min). $[\alpha]_D^{22}$+92.0° (c=0.004, $CHCl_3$). $\nu_{max}$ (neat): 3286 bm, 2956 m, 2931 m, 2856 w, 1742 s, 1659 s, 1542 m, 1438 m, 1375 m, 1267 m, 1220 m, 1138 w, 1017 w $cm^{-1}$. $^1H$ n.m.r. (300 MHz, $CDCl_3$): δ 2.04 (s, 6H, $CH_3CO$), 2.40-2.50 (m, 4H, H3, 6), 3.74 (s, 6H, $OCH_3$), 4.64-4.70 (m, 2H, H2, 7), 5.36-5.40 (m, 2H, H4, 5), 6.34 (bd, J=7.2 Hz, 2H, NH). $^{13}C$ n.m.r. (100 MHz, $CDCl_3$): δ 23.1 ($CH_3CO$), 35.1 (C3, 6), 51.7 (C2, 7), 52.6 ($OCH_3$), 128.8 (C4, 5), 170.3, 172.6 (C1, 8, CONH). HRMS ($ESI^+$, MeOH): Found: m/z 337.1375 $(M+Na)^+$, $C_{14}H_{22}N_2NaO_6$ requires 337.1376. Spectroscopic data were in agreement with those reported in the literature.[264]

7.8.2 (2S,7S)-Dimethyl 2,7-N,N-Dibenzoylaminooct-4-enedioate 69

69

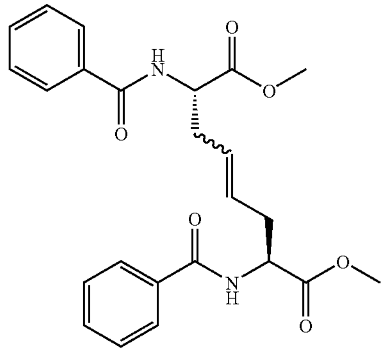

Method 1:

The dimer 69 was prepared via the conventional cross metathesis procedure (Section 7.5.2) under the following conditions: (2S)-Methyl 2-N-benzoylaminopent-4-enoate 62 (49.0 mg, 0.21 mmol), DCM (5 mL), Grubbs' catalyst (34.6 mg, 42.1 μmol, 20 mol %), 50° C., 18 h, 100% conversion into 69. Purification by flash chromatography ($SiO_2$, DCM:light petroleum:EtOAc, 1:1:1) gave pure dimer 69 as a pale brown solid (37.8 mg, 82%), m.p. 140-142° C. GC: $t_R$ (E/Z)=13.5, 13.9 min (GC column 30QC5/BPX5, 150° C. for 1 min, 10° C. $min^{-1}$ to 280° C. for 6 min). $[\alpha]_D^{22}$ +56.4° (c=0.27, $CHCl_3$). $\nu_{max}$ (KBr): 3322 bm, 2953 m, 2358 w, 1742 s, 1644 s, 1603 w, 1580 w, 1538 m, 1488 m, 1436 m, 1267 w, 1218 m, 1027 w, 973 w, 802 w, 736 m $cm^{-1}$. $^1H$ n.m.r. (300 MHz, $CDCl_3$): δ 2.57-2.69 (m, 4H, H3, 6), 3.67 (s, 6H, $OCH_3$), 4.85-4.98 (m, 2H, H2, 7), 5.49 (t, J=4.1 Hz, 2H, H4, 5), 6.86 (bd, J=7.4 Hz, 2H, NH), 7.40-7.44 (m, 4H, H3', 5'), 7.48-7.52 (m, 2H, H4'), 7.81-7.83 (m, 4H, H2', 6'). $^{13}C$ n.m.r. (100 MHz, $CDCl_3$): δ 35.2 (C3, 6), 52.5 (C2, 7), 52.6 ($OCH_3$), 127.2 (C2', 6'), 128.7 (C3', 5'), 128.8 (C4, 5), 131.9 (C4'), 133.9 (C1'), 167.1, 172.4 (C1, 8, CONH). HRMS ($ESI^+$, MeOH): Found: m/z 461.1695 $(M+Na)^+$, $C_{24}H_{26}N_2NaO_6$ requires 461.1689.

Method 2:

The dimer 69 was also prepared via the conventional cross metathesis procedure (Section 7.5.2) under the following conditions: (2S)-Methyl 2-N-benzoylaminopent-4-enoate 142, DCM (5 mL), Grubbs' catalyst (20 mol %), 50° C., 20 h, 100% conversion into 69.

7.8.3 Dimerisation of (2S)-Methyl 2-N-Benzoylaminopent-4-enoate 62 in the presence of (2S,7S)-Dimethyl 2,7-N,N'-Diacetylaniinooct-4-enedioate 60

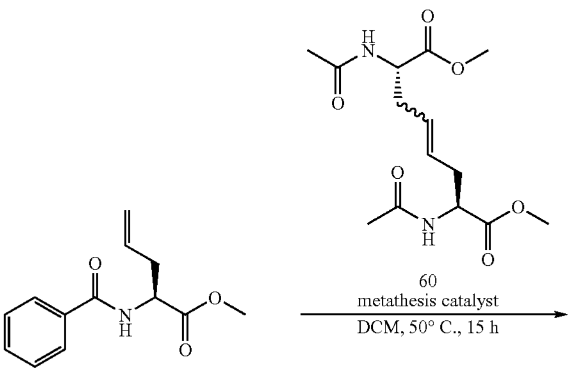

62

-continued

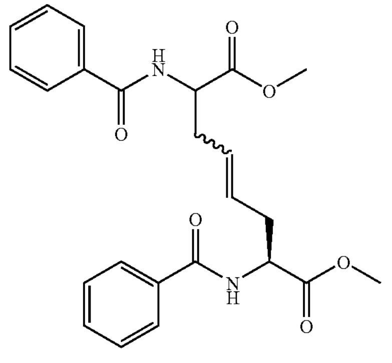

+ recovered 60

69

The olefinic mixture 62 and 60 was subjected to the conventional cross metathesis procedure (Section 7.5.2) under the following conditions:

Method A: (2S)-Methyl 2-N-benzoylaminopent-4-enoate 62 (37.0 mg, 0.16 mmol), (2S,7S)-dimethyl 2,7-N,N-diacetylaminooct-4-enedioate 60 (29.5 mg, 93.9 μmol), DCM (3 mL), 2nd generation Grubbs' catalyst (13.5 mg, 15.9 μmol, 10 mol %), 50° C., 15 h. Spectroscopic data indicated the presence of the starting acetyl-allylglycine dimer 60, the benzoyl-allylglycine dimer 69 and additional peaks which mass spectrometry indicated could be attributed to the "mixed" cross metathesis product, (2S,7S)-dimethyl 2-N-acetylamino-7-N-benzoylaminooct-4-enedioate 70. $^1H$ n.m.r. spectroscopic data for the homodimers 60 and 69 were in agreement with those previously reported (Section 7.12.1 and Section 7.12.2). The heterodimer 70 was detected by mass spectrometry. Mass spectrum ($ESI^+$, MeOH): m/z 337.2 $(M+Na)^+_{60}$, $C_{14}H_{22}N_2NaO_6$; m/z 399.3 $(M+Na)^+_{70}$, $C_{19}H_{24}N_2NaO_6$; m/z 461.2 $(M+Na)^+_{69}$, $C_{24}H_{26}N_2NaO_6$ requires 461.1689.

Method B: (2S)-Methyl 2-N-benzoylaminopent-4-enoate 62 (37.0 mg, 0.16 mmol), (2S,7S)-dimethyl 2,7-N,N'-diacetylaminooct-4-enedioate 60 (30.0 mg, 95.5 mol), DCM (4 mL), Grubbs' catalyst (26.1 mg, 31.7 μmol, 20 mol %), 50° C., 18 h, 100% conversion of 62 into dimer 69. Dimer 60 was recovered unchanged. Spectroscopic data for dimers 60 and 69 were in agreement with those previously reported (Section 7.12.1 and Section 7.12.2). No "mixed" cross metathesis product, heterodimer 70, was observed.

7.8.4 Attempted Dimerisation of (2Z)-Methyl 2-N-Acetylaminopenta-2,4-dienoate 57

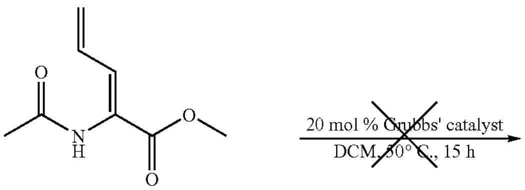

57

-continued

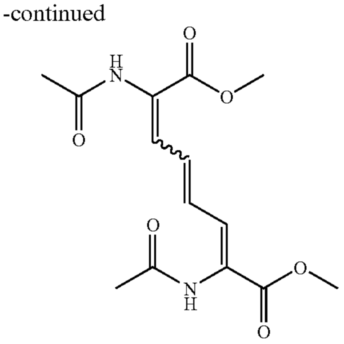

61

The dienamide 57 was subjected to the conventional cross metathesis procedure (Section 7.5.2) under the following conditions: (2Z)-Methyl 2-N-acetylaminopenta-2,4-dienoate 57 (33.0 mg, 0.20 mmol), DCM (3 mL), Grubbs' catalyst (34.0 mg, 41.3 μmol, 20 mol %), 50° C., 15 h, 0% conversion into dimer 61. The dienamide 57 did not react under these conditions. H n.m.r. spectroscopic data for the recovered dienamide 57 were in agreement with those previously reported (Section 7.11.1).

7.8.5 Attempted Dimerisation of (2S)-Methyl 2-N-Acetylaminopent-4-enoate 21a in the presence of (2Z)-Methyl 2-N-Acetylaminopenta-2,4-dienoate 57

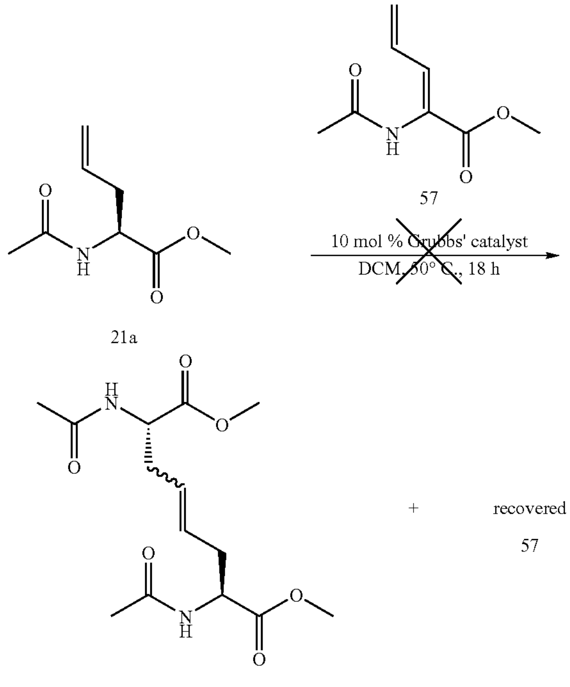

57

21a

60

The mixture of olefins 21a and 57 was subjected to the conventional cross metathesis procedure (Section 7.5.2) under the following conditions: (2S)-Methyl 2-N-acetylaminopent-4-enoate 21a (34.0 mg, 0.20 mmol), (2Z)-methyl 2-N-acetylaminopenta-2,4-dienoate 57 (33.6 mg, 0.20 mmol), DCM (4 mL), Grubbs' catalyst (16.3 mg, 19.8 μmol, 10 mol %), 50° C., 18 h. The $^1$H n.m.r. spectrum displayed peaks characteristic of the starting allylglycine derivative 21a and dienamide 57 but no peaks characteristic of expected dimer 60. The mass spectrum displayed peaks attributed to the allylglycine derivative 21a and the tricyclohexylphosphine-dienamide conjugate addition adduct, (2S)-methyl 2-N-acetylamino-5-tricyclohexylphosphinylpent-2-enoate 143. Mass Spectrum (ESI$^+$, DCM/MeOH): m/z 194.1 $(M+Na)^+$ $^{21}$a, $C_8H_{13}NNaO_3$; m/z 450.4 $(M^+)_{143}$, $C_{26}H_{45}NO_3P$

143

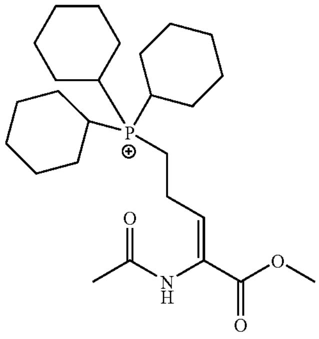

7.8.6 Attempted Dimerisation of (2S)-Methyl 2-N-Benzoylaminopent-4-enoate 62 in the presence of (2Z)-Methyl 2-N-Acetylaminopenta-2,4-dienoate 57

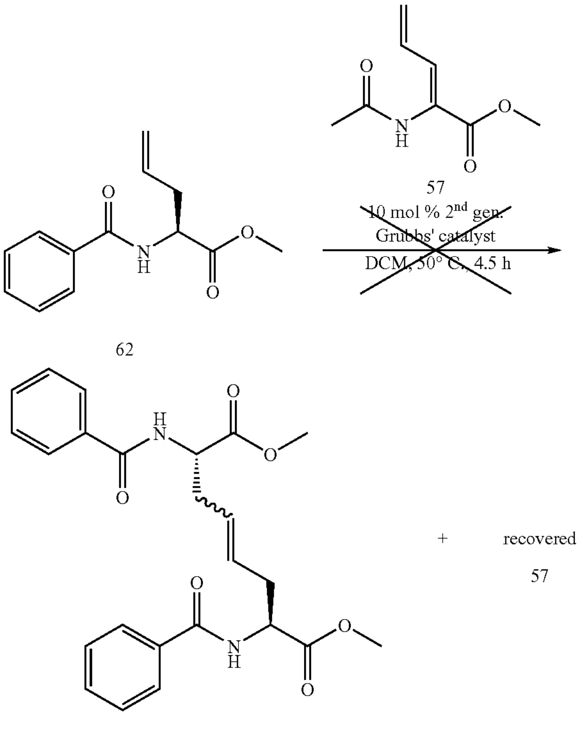

57

62

69

The mixture of olefins 57 and 62 was subjected to the conventional cross metathesis procedure (Section 7.5.2) under the following conditions: (2S)-Methyl 2-N-benzoylaminopent-4-enoate 62 (46.0 mg, 0.20 mmol), (2Z)-methyl 2-N-acetylaminopenta-2,4-dienoate 57 (33.4 mg, 0.20 mmol), DCM (4 mL), 2nd generation Grubbs' catalyst (16.8 mg, 19.8 μmol, 10 mol %), 50° C., 4.5 h. The reaction mixture was evaporated under reduced pressure to afford a dark brown oil (97.9 mg). The $^1H$ n.m.r. spectrum displayed peaks characteristic of the starting allylglycine derivative 62, dienamide 57, traces of the target allylglycine dimer 69 and additional peaks which were difficult to characterise. Mass spectrometry displayed peaks attributed to the allylglycine derivative 62, dienamide 57, allylglycine dimer 69, dienamide dimer (2S, 7S)-dimethyl 2,7-N,N'-diacetylaminooct-2,4,6-trienedioate 61, "mixed" dienamide-allylglycine dimer (2S,7S)-dimethyl 2-N-acetylamino-7-N-benzoyl-aminoocta-2,4-dienedioate 144 and the tricyclohexylphosphine-dienamide conjugate addition adduct 143.

144

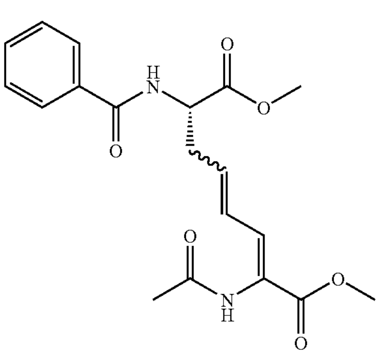

Mass Spectrum (ESI$^+$, DCM/MeOH): m/z 256.1 $(M+Na)^+_{62}$, $C_{13}H_{15}NNaO_3$; m/z 337.3 $(M+Na)^+_{61}$, $C_{14}H_{18}N_2NaO_6$; m/z 397.3 $(M+Na)^+_{144}$, $C_{19}H_{22}N_2NaO_6$; m/z 450.4 $(M)+_{143}$, $C_{26}H_{45}NO_3P^+$; m/z 461.3 $(M+Na)^+_{69}$, $C_{24}H_{26}N_2NaO_6$ requires 461.5.

7.8.7 NMR Study of Grubbs' Catalyst with Dienamide 57

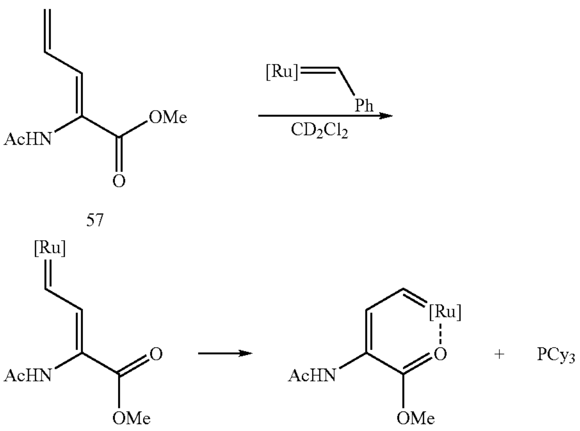

57

73 74 75

In a dry box, a Teflon-sealed n.m.r. tube was charged with (2S)-methyl 2-N-acetylaminopenta-2,4-dienoate 57 (10.8 mg, 63.9 μmol), Grubbs' catalyst (50.7 mg, 61.6 μmol) and degassed deuterated DCM ($CD_2Cl_2$, 0.8 mL) at room temperature. The n.m.r. tube was shaken gently and reaction progress was monitored by $^1H$ and $^{31}P$ n.m.r. spectroscopy. Compounds were identified by the following diagnostic resonances: $^1H$ n.m.r. (300 MHz, $CD_2Cl_2$): After 15 min: Grubbs' catalyst: δ 8.61 (d, J=7.6 Hz, 2H, ortho-Arom CH), 20.05 (s, 1H, [Ru]=CHPh); Ruthenium-dienamide complex 73: δ 7.96 (d, J=11.0 Hz, 1H, [Ru]=CH═CH), 20.11 (d, J=11.0 Hz, 1H, [Ru]=CH); Ruthenium-dienamide chelate 74 (trace): δ 15.20 (d, J=4.2 Hz, 1H, [Ru]=CH); Ratio of ruthenium complexes [Ru]=CHPh: 73:74=1.0:1.0:<0.1. After 60 min: Grubbs' catalyst: δ 8.45 (d, J=7.6 Hz, 2H, ortho-Arom CH), 20.04 (s, 1H, [Ru]=CHPh); Ruthenium-dienamide complex 73: δ 7.96 (d, J=11.0 Hz, 1H, [Ru]=CH═CH), 20.10 (d, J=11.0 Hz, 1H, [Ru]=CH); Ruthenium-dienamide chelate 74: δ 6.73 (d, J=3.0 Hz, 1H, [Ru]=CH═CH), 15.19 (d, J=4.2 Hz, 1H, [Ru]= CH); Ratio of ruthenium complexes [Ru]=CHPh: 73: 74 =3:1:1. After 120 min (no change after 18 h): Ruthenium-dienamide chelate 74: δ 6.71 (d, J=3.0 Hz, 1H, [Ru]= CH═CH), 15.19 (d, J=4.0 Hz, 1H, [Ru]=CH). $^{31}P$ n.m.r. (300 MHz, $CDCl_3$): δ Ruthenium-dienamide chelate 74: 35.0; Grubbs' catalyst: 37.0; Ruthenium-dienamide complex 73: 38.8; Tricyclohexylphosphine oxide: 46.5.

7.8.8 NMR Study of Grubbs' Catalyst with Dienamide 76

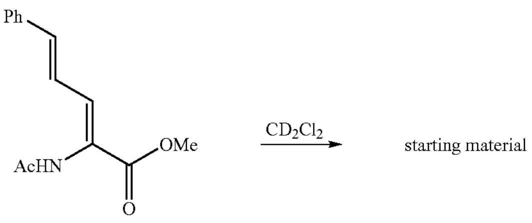

76

In a dry box, a Teflon-sealed n.m.r. tube was charged with (2S)-methyl 2-N-acetylamino-5-phenylpenta-2,4-dienoate 76 (10.0 mg, 40.8 μmol), Grubbs' catalyst (33.6 mg, 40.9 μmol) and degassed $CD_2Cl_2$ (0.8 mL) at room temperature. The n.m.r. tube was shaken gently and reaction progress was monitored by $^1H$ n.m.r. spectroscopy. After 4 h, ruthenium-vinylalkylidene formation was not observed and only peaks corresponding to Grubbs' catalyst and the starting dienamide 76 were present.

7.8.9 Dimerisation of (2S)-Methyl 2-N-Acetylamino-pent-4-enoate 21a in the presence of (2Z)-Methyl 2-N-Acetylamino-5-phenylpenta-2,4-dienoate 76

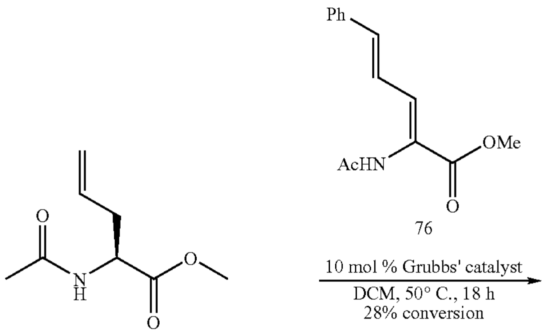

76

21a

-continued

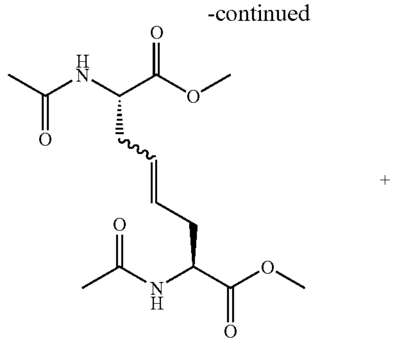

recovered

76

60

The mixture of olefins 21a and 76 was subjected to the conventional cross metathesis procedure (Section 7.5.2) under the following conditions: (2S)-Methyl 2-N-acetylaminopent-4-enoate 21a (18.1 mg, 0.11 mmol), (2Z)-methyl 2-N-acetylamino-5-phenylpenta-2,4-dienoate 76 (26.1 mg, 0.11 mmol), DCM (4.0 mL), Grubbs' catalyst (8.7 mg, 10.6 μmol, 10 mol %), 50° C., 18 h, 28% conversion of allylglycine 21a into 60. Dienamide 76 did not react under these conditions. $^{1}$H n.m.r. spectroscopic data for dienamide 76, dimer 60 and recovered allylglycine derivative 21a were in agreement with those previously reported (Section 7.11.8, Section 7.12.1 and Section 7.11.2 respectively).

7.8.10 Dimerisation of (2S)-Methyl 2-N-Acetylamino-5-phenylpent-4-enoate 77

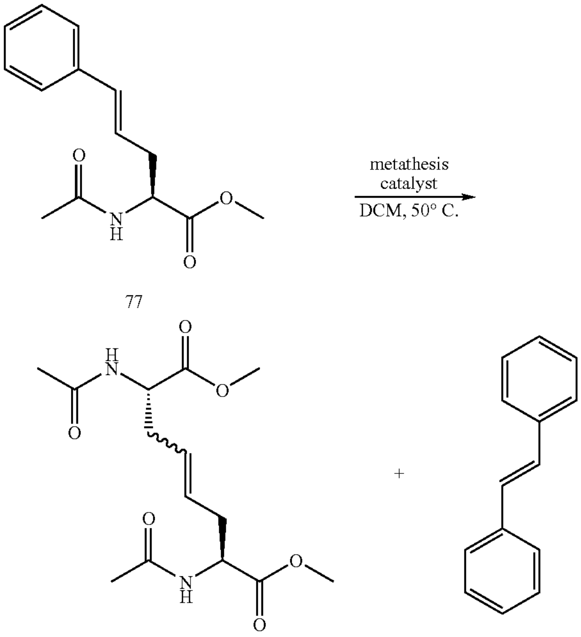

77

60

145

The enamide 77 was subjected to the conventional cross metathesis procedure (Section 7.5.2) under the following conditions.

Method A: (2S)-Methyl 2-N-acetylamino-5-phenylpent-4-enoate 77 (59.3 mg, 0.24 mmol), DCM (10 mL), Grubbs' catalyst (19.8 mg, 24.1 μmol, 10 mol %), 50° C., 13 h, 0% conversion into dimer 60. The starting enamide 77 was recovered. $^{1}$H n.m.r. spectroscopic data for olefin 77 were in agreement with those previously reported (Section 7.11.9).

Method B: (2S)-Methyl 2-N-acetylamino-5-phenylpent-4-enoate 77 (59.3 mg, 0.24 mmol), DCM (7 mL), 2$^{nd}$ generation Grubbs' catalyst (10.2 mg, 12.0 μmol, 5 mol %), 50° C., 20 h, 44% conversion into dimer 60. $^{1}$H n.m.r. spectroscopic data for dimer 60 were in agreement with those previously reported (Section 7.12.1). The stilbene byproduct 145 was observed in the $^{1}$H n.m.r. spectrum. $^{1}$H n.m.r. (300 MHz, $CDCl_3$): 7.15 (s, 2H, CH═), 7.40 (m, 4H, Arom CH), 7.55 (m, 4H, Arom CH), ortho-Arom CH peaks masked by starting olefin 77. $^{1}$H n.m.r. spectroscopic data for stilbene 145 were in agreement with those reported in the literature.[265]

7.8.11 Dimerisation of (2S)-Methyl 2-N-Acetylamino-pent-4-enoate 21a in the presence of (2S)-Methyl 2-N-Acetylamino-5-methylhex-4-enoate 19

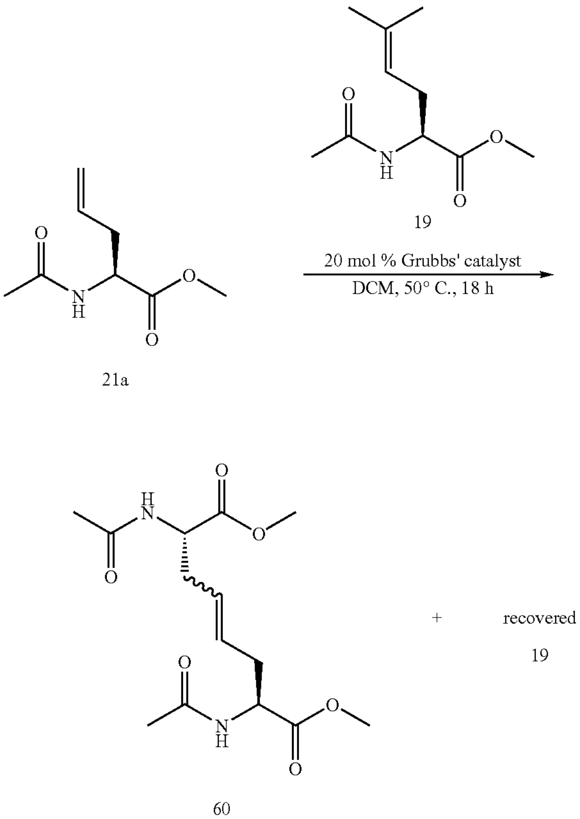

19

21a recovered

19

60

The mixture of olefins 21a and 19 was subjected to the conventional cross metathesis procedure (Section 7.5.2) under the following conditions: (2S)-Methyl 2-N-acetylaminopent-4-enoate 21a (12.7 mg, 74.2 μmol), (2S)-methyl 2-N-acetylamino-5-methylhex-4-enoate 19 (14.5 mg, 72.9 μmol), DCM (4 mL), Grubbs' catalyst (11.5 mg, 14.0 μmol, 20 mol %), 50° C., 18 h, 100% conversion of 21a into dimer 60. $^{1}$H n.m.r. spectroscopic data for dimer 60 were in agreement with those previously reported (Section 7.12.1). The prenylglycine derivative 19 was recovered unchanged.

7.8.12 Ethenolysis of (2S)-Methyl 2-N-Acetylamino-5-methylhex-4-enoate 19

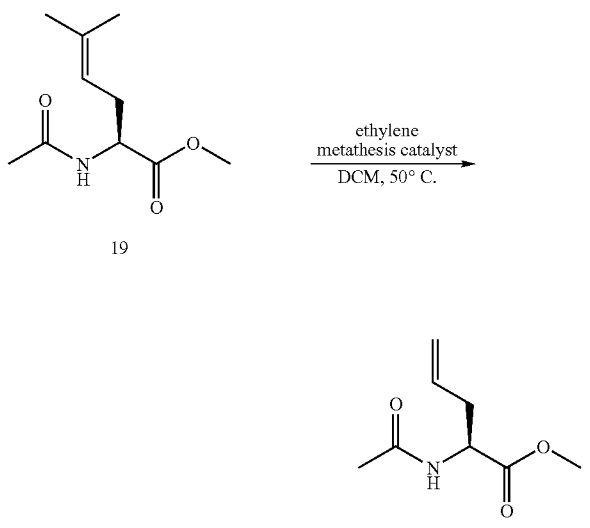

19

21a

The prenylglycine derivative 19 was subjected to the conventional cross metathesis procedure (Section 7.5.4) with ethylene under the following conditions:

Method A: (2S)-Methyl 2-N-acetylamino-5-methylhex-4-enoate 19 (11.0 mg, 55.2 μmol), ethylene (atmospheric pressure), Grubbs' catalyst (11.0 mg, 13.4 μmol, 20 mol %), DCM (4 mL), 22° C., 17 h, 0% conversion into 21a. $^{1}$H n.m.r. spectroscopy indicated the starting hex-4-enoate 19 was recovered.

Method B: (2S)-Methyl 2-N-acetylamino-5-methylhex-4-enoate 19 (10.8 mg, 54.2 μmol), ethylene (60 psi), 2$^{nd}$ generation Grubbs' catalyst (9.3 mg, 11 μmol, 20 mol %), DCM (4 mL), 22° C., 19 h, 9% conversion into 21a.

Method C: (2S)-Methyl 2-N-acetylamino-5-methylhex-4-enoate 19 (24.3 mg, 0.12 mmol), ethylene (60 psi), 2$^{nd}$ generation Grubbs' catalyst (31.1 mg, 36.6 μmol, 30 mol %), DCM (5 mL), 50° C., 38 h, 32% conversion into 21a. Spectroscopic data for 21a and the recovered prenylglycine derivative 19 were in agreement with those previously reported (Section 7.11.2 and Section 7.9.5 respectively).

7.8.13 Butenolysis of (2S)-Methyl 2-N-Acetylamino-5-methylhex-4-enoate 19

-continued

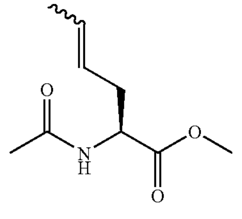

81

The prenylglycine derivative 19 was subjected to the conventional cross metathesis procedure (Section 7.5.4) with cis-2-butene under the following conditions: (2S)-Methyl 2-N-acetylamino-5-methylhex-4-enoate 19 (16.2 mg, 81.4 μmol), DCM (5 mL), 2nd generation Grubbs' catalyst (3.5 mg, 4.1 μmol, 5 mol %), cis-2-butene (5 psi), 50° C., 14 h, 100% conversion into 81. Purification by flash chromatography ($SiO_2$, light petroleum: DCM: EtOAc: MeOH, 1:2:1:0.2) gave (2S)-methyl 2-N-acetylaminohex-4-enoate 81 as a brown oil (12.6 mg, 84%). GC: $t_R$ (E/Z)=4.2 min, 4.4 min (GC column 30QC5/BPX5, 150° C. for 1 min, 110° C. min$^{-1}$ to 280° C. for 6 min). $\nu_{max}$ (neat): 3284 s, 2966 w, 2954 m, 2856 w, 1747 s, 1658 s, 1547 s, 1437 s, 1375 s, 1217 m, 1142 m, 1072 w, 1016 w, 968 m, 848 m cm$^{-1}$. $^{1}$H n.m.r. (300 MHz, $CDCl_3$): δ 1.60 (dd, J=6.3, 1.2 Hz, 3H, H6), 1.95 (s, 3H, $CH_3CO$), 2.36-2.44 (m, 2H, H3), 3.67 (s, 3H, $OCH_3$), 4.55 (dt, J=7.8 Hz, 5.9 Hz, 1H, H2), 5.24 (m, 1H, H5), 5.49 (m, 1H, H4), 6.17 (bd, J=6.4 Hz, 1H, NH). $^{13}$C n.m.r. (100 MHz, $CDCl_3$): δ 18.1 (C6), 23.3 ($CH_3CO$), 35.4 (C3), 52.1, 52.4 (C2, $OCH_3$), 124.6, 130.2 (C4, 5), 169.7, 172.6 (C1, CONH). Mass Spectrum (ESI$^+$, MeOH): m/z 208.1 $(M+Na)^+$, $C_9H_{15}NNaO_3$ requires 208.1. Spectroscopic data were in agreement with those reported in the literature.[117,119]

An analogous cross metathesis reaction was performed using a mixture of cis+trans-2-butene under the following conditions: (2S)-Methyl 2-N-acetylamino-5-methylhex-4-enoate 19 (12.8 mg, 64.3 μmol), DCM (5 mL), 2nd generation Grubbs' catalyst (2.8 mg, 3.3 μmol, 5 mol %), trans+cis-2-butene (10 psi), 50° C., 16 h, <10% conversion into crotylglycine 81.

7.8.14 Dimerisation of (2S)-Methyl 2-N-Acetylaminohex-4-enoate 81

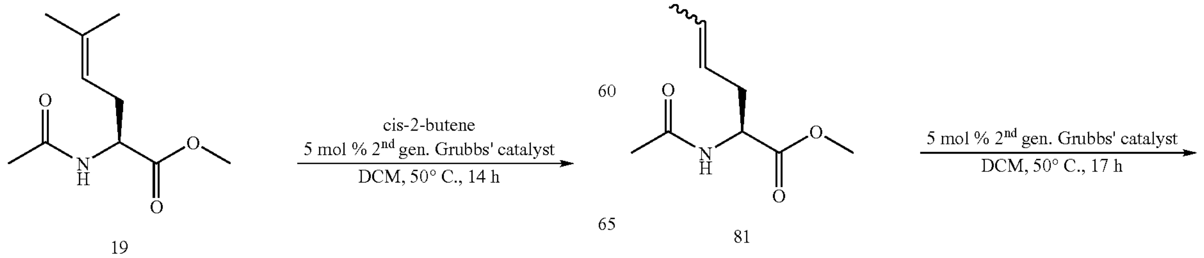

19

81

-continued

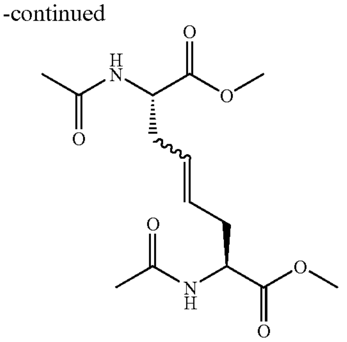

60

The crotylglycine derivative 81 was subjected to the conventional cross metathesis procedure (Section 7.5.2) under the following conditions: (2S)-Methyl 2-N-acetylaminohex-4-enoate 81 (17.0 mg, 91.9 μmol), DCM (4 mL), 2nd generation Grubbs' catalyst (4.2 mg, 5.0 μmol, 5 mol %), 50° C., 17 h, 100% conversion into dimer 60. The solvent was evaporated under reduced pressure to give the homodimer 60 as a brown oil (21.5 mg, 100% crude yield). Spectroscopic data for dimer 60 were in agreement with those previously reported (Section 7.12.1).

7.8.15 Activation of (2S)-Methyl 2-N-Benzoylamino-5-methylhex-4-enoate 87

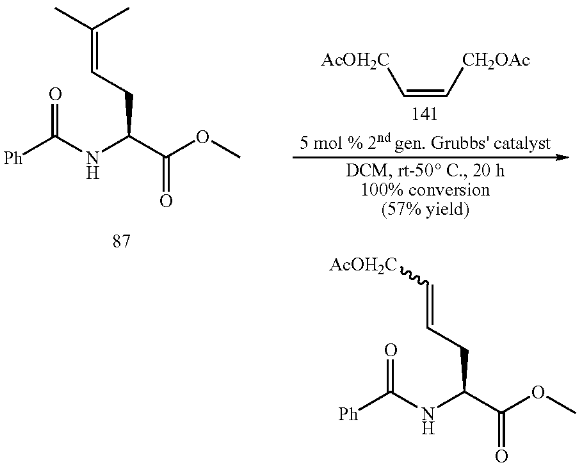

87 141 142

The prenylglycine derivative 87 was subjected to the conventional cross metathesis procedure (Section 7.5.5) with cis-1,4-diacetoxy-2-butene 141 under the following conditions: (25)-Methyl 2-N-benzoylamino-5-methylhex-4-enoate 87 (170 mg, 0.65 mmol), DCM (10 mL), 2nd generation Grubbs' catalyst (16.5 mg, 0.03 mmol, 5 mol %), cis-1,4-diacetoxy-2-butene (5 psi), 50° C., 20 h, 100% conversion into 142. Purification by flash chromatography ($SiO_2$, light petroleum:EtOAc, 1:1) gave (2S)-6-Acetoxy-2-benzoylamino-4-hexenoic acid methyl ester 142 as a dark brown oil (113 mg, 57%). $\nu_{max}$ (neat): 3333.3 s; 3056.4 w; 3015.4 w; 2943.6 s; 1738.5 s; 1661.5 m; 1641.0 s; 1605.1 m; 1574.4 m; 1533.3 s; 1487.2 m; 1435.9 m; 1364.1,m; 1235.9,s; 1153.8,w; 1071.6,w; 1025.6,m; 969.2,m; 800.8,w; 717.9, m; 692.3,w $cm^{-1}$. $^1H$ NMR (400 MHz, $CDCl_3$): δ 2.00, s, 3H, $CH_3$; 2.67, m, 2H, H3; 3.77, s, 3H, $OCH_3$; 4.49, d, J=4.7 Hz, 2H, H6; 4.89, q, J=5.8 Hz, 1H, H2; 5.68, t, J=5.2 Hz, 2H, H4, 5; 6.75, d, J=7.4 Hz, 2H, H4, 5; 7.42, t, J=7.2 Hz, 2H, H4', 6'; 7.50, t, J=6.4 Hz, 1H, H5'; 7.78, d, J=7.1 Hz, 2H, H3', 7'. $^{13}C$ NMR (125 MHz, $CDCl_3$): δ 20.92, $CH_3$; 35.22, C3; 52.09, $OCH_3$; 52.65, C2; 64.52, C6; 127.17, C3', 7'; 128.70, C4', 6'; 128.93, C5; 129.14, C4; 131.93, C5'; 133.93, C2'; 167.07, C1'; 170.80, C1"; 172.27, C1. Mass Spectrum ($ESI^+$, $CH_3CN$): m/z 328.1 ($M+Na^+$) $C_{16}H_{19}NO_5Na$.

7.8.16 Synthesis of (2S,7S)-dimethyl 2-N-acetylamino-7-N-benzoylaminoocta-4-enedioate 143

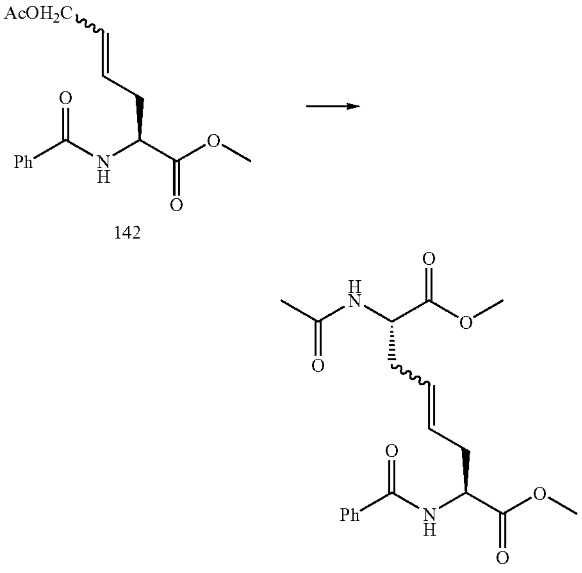

142 143

2-Acetylamino-7-benzoylamino-oct-4-enedioic acid dimethyl ester 143 was synthesised using standard solution-phase metathesis conditions (refer to Section 7.5.2): 6-Acetoxy-2-benzoylamino-4-hexenoic acid methyl ester 142 (50 mg, 0.16 mmol), dichloromethane (10 mL), second generation Grubbs' catalyst (5 mol %, 7 mg, 8 μmol), methyl-2-acetylamino-4-pentenoate 21a (168 mg, 0.98 mmol), 50° C., 18 h. The desired compound was obtained as a brown oil and purified via column chromatography ($SiO_2$; EtOAc:hexane; 2:1). $^1H$ NMR (500 MHz, $CDCl_3$, mixture of isomers (1:1.2)): δ 1.95, s (major isomer) and 1.97, s (minor isomer), 3H, $CH_3$; 2.42-2.70, m, 4H, H3, 6; 3.62, s (minor isomer), 3.64, s (major isomer), 3.78, s (minor isomer) and 3.79, s (major isomer), 6H, $2\times OCH_3$; 4.63-4.66, m, 1H, H2; 4.85-4.91, m, 1H, H7; 5.35-5.49, m, 2H, H4, 5; 6.20, d, J=7.7 Hz (major isomer) and 6.34, d, J=7.5 Hz, 1H, NH (minor isomer); 6.87, t, J=7.55 Hz, 1H, NH; 7.44, t, J=7.1 Hz, 2H, H4', 6'; 7.50, t, J=6.9 Hz, 1H, H5'; 7.84, t, J=7.9 Hz, 2H, H3', 7'. $^{13}C$ NMR (75 MHz, $CDCl_3$, mixture of isomers (1:1.2)): δ 22.83, $CH_3$; 34.84, 35.05, 35.38 and 35.73, C3, 6; 51.51 and 51.55, C2; 52.35, 52.46, 52.53, 52.60 and 52.66, C7, $2\times OCH_3$; 127.18 and 127.22, C3', 7'; 128.57 and 128.62, C4', 6'; 128.88 and 129.00, C4, 5; 131.86 and 131.91, C5'; 133.71, C2'; 167.06, COPh; 170.03 and 170.11, COMe; 172.20, 172.21, 172.24 and 172.43, $2\times COOMe$. Mass Spectrum ($ESI^+$, $CH_3OH$): m/z 399.2 ($M+Na^+$) $C_{19}H_{24}N_2O_6Na$.

7.9 Wilkinson's Hydrogenation of Olefinic Substrates 7.9.1 (2S,7S)-Dimethyl 2,7-N,N'-Diacetylaminooctanedioate 71

71

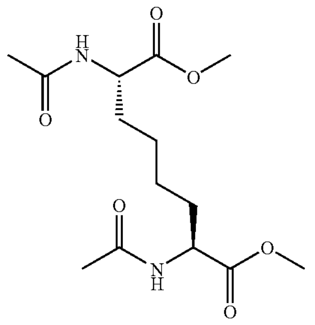

(2S,7S)-Dimethyl 2,7-N,N'-diacetylaminooct-4-enedioate 60 was subjected to the general Wilkinson's hydrogenation procedure (Section 7.4.4) under the following conditions: Dimer 60 (25.0 mg, 79.6 μmol), benzene (5 mL), Wilkinson's catalyst, 60 psi, 22° C., 4 h. At the end of the reaction period, the solvent was evaporated under reduced pressure and the resulting oil was purified by flash chromatography ($SiO_2$, EtOAc) to afford the saturated product 71 as a brown oil (25.0 mg, 99%). GC: $t_R$=14.4 min (GC column 30QC5/BPX5, 150° C. for 1 min, 10° C. $min^{-1}$ to 280° C. for 6 min). $\nu_{max}$ (neat): 3426 bm, 3055 w, 2932 m, 2857 w, 2360 w, 1741 s, 1666 s, 1543 w, 1438 m, 1375 w, 1266 s, 1177 w, 1120 w, 896 w, 738 w, 702 w $cm^{-1}$. $^1H$ n.m.r. (400 MHz, $CDCl_3$): δ 1.30-1.40 (m, 4H, H4, 5), 1.82-1.90 (m, 4H, H3, 6), 2.02 (s, 6H, $CH_3CO$), 3.74 (s, 6H, $OCH_3$), 4.56-4.63 (m, 2H, H2, 7), 6.16 (bd, J=7.5 Hz, 2H, NH). $^{13}C$ n.m.r. (100 MHz, $CDCl_3$): δ 23.3 ($CH_3CO$), 24.7 (C4, 5), 32.3 (C3, 6), 52.0 (C2, 7), 52.5 ($OCH_3$), 170.0, 173.1 (C1, 8, CONH). HRMS ($ESI^+$, MeOH): Found: m/z 339.1531 $(M+Na)^+$, $C_{14}H_{24}N_2NaO_6$ requires 339.1532.

7.9.2 (2S,7S)-Dimethyl 2,7-N,N'-Dibenzoylaminooctanedioate 72

72

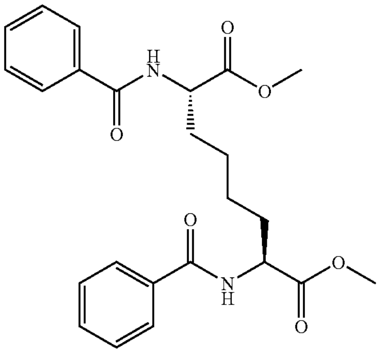

(2S,7S)-Dimethyl 2,7-N,N'-dibenzoylaminoocta-4-enedioate 69 was subjected to the general Wilkinson's hydrogenation procedure (Section 7.4.4) under the following conditions: Dimer 69 (20.0 mg, 45.7 μmol), benzene (5 mL), Wilkinson's catalyst, 60 psi, 22° C., 4 h. At the end of the reaction period, the solvent was evaporated under reduced pressure and the resulting oil was purified by flash chromatography ($SiO_2$, EtOAc) to afford the saturated product 72 as a brown oil (20.0 mg, 100%). GC: $t_R$=17.2 min (GC column 30QC5/BPX5, 150° C. for 1 min, 10° C. $min^{-1}$ to 280° C. for 6 min). $\nu_{max}$ (neat): 3055 m, 2986 w, 2955 w, 1741 s, 1662 s, 1603 w, 1580 w, 1518 m, 1486 m, 1438 s, 1359 w, 1286 s, 1182 m, 1120 m, 1028 w, 896 m $cm^{-1}$. $^1H$ n.m.r. (400 MHz, $CDCl_3$): δ 1.35-1.53 (m, 4H, H4, 5), 1.80-2.02 (m, 4H, H3, 6), 3.78 (s, 6H, $OCH_3$), 4.82 (dt, J=7.3, 5.4 Hz, 2H, H2, 7), 6.73 (bd, J=7.4 Hz, 2H, NH), 7.40-7.49 (m, 6H, H3', 4', 5'), 7.78-7.82 (m, 4H, H2', 6'). $^{13}C$ n.m.r. (100 MHz, $CDCl_3$): δ 24.9 (C4, 5), 32.6 (C3, 6), 52.5, 52.7 (C2, $OCH_3$), 127.2 (C2', 6'), 128.6 (C3', 5'), 131.9 (C4'), 134.1 (C1'), 167.2, 173.2 (C1, 8, CONH). HRMS ($ESI^+$, MeOH): Found: m/z 463.1842 $(M+Na)^+$, $C_{24}H_{28}N_2NaO_6$ requires 463.1845.

7.9.3 Wilkinson's Hydrogenation of (2Z)-Methyl 2-N-Acetylamino-5-phenylpenta-2,4-dienoate 76

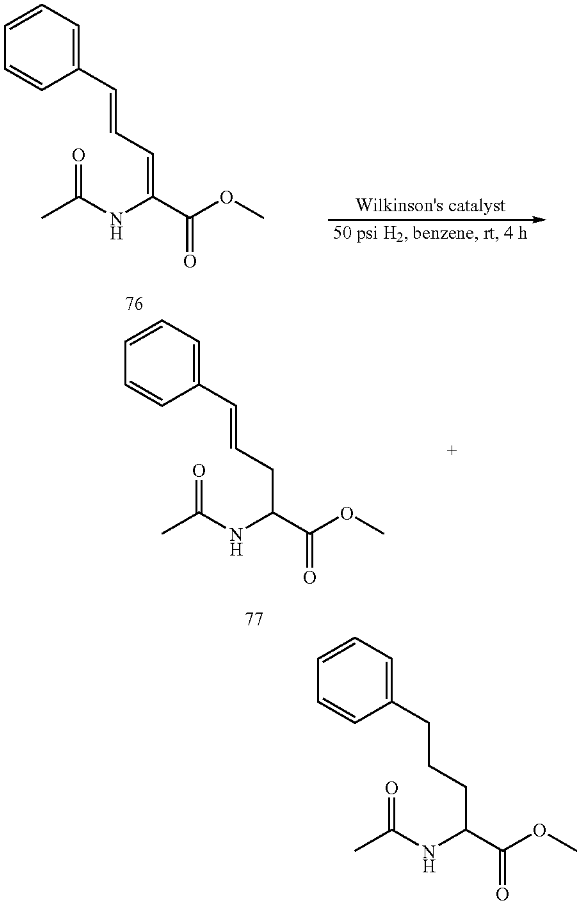

76

77

+

79

The dienamide 76 was subjected to the general Wilkinson's hydrogenation procedure (Section 7.4.4) under the following conditions: (2Z)-Methyl 2-N-acetylamino-5-phenylpenta-2,4-dienoate 76 (11.5 mg, 46.9 μmol), benzene (5 mL), Wilkinson's catalyst, 50 psi $H_2$, 22° C., 4 h, 99% yield (mass recovery) of a 1:4 mixture of 77:79 as a brown oil. GC: $t_R$=10.8 min 79, 13.9 min 77 (GC column 30QC5/BPX5, 150° C. for 1 min, 10° C. $min^{-1}$ to 280° C. for 6 min). $^1H$ n.m.r. spectroscopic data for olefin 77 were in agreement with those previously reported (Section 7.11.9). Hydrogenation of the mixture using identical conditions led to 100% conversion into 79 (41.2 mg, 100% crude yield). $\nu_{max}$ (neat): 3262 w, 3054 m, 2956 m, 1736 s, 1676 s, 1509 m, 1438 s, 1372 w, 1265 s, 1174 w, 1120 m, 1028 w, 738 s, 700 w $cm^{-1}$. H n.m.r. (300 MHz, $CDCl_3$): δ 1.53-1.65 (m, 4H, H3, 4), 1.94 (s, 3H, $CH_3CO$), 2.52-2.59 (m, 2H, H5), 3.65 (s, 3H, $OCH_3$), 4.59 (m, 1H, H2), 5.90 (bd, J=7.2 Hz, 1H, NH), 7.07-7.29 (m, 5H, Arom CH). $^{13}C$ n.m.r. (75 MHz, $CDCl_3$): δ 23.3 ($CH_3CO$), 27.2 (C4), 32.3 (C3), 35.5 (C5), 52.1, 52.5 (C2, $OCH_3$), 126.1, 128.5, 132.2 (Arom CH), 141.7, (Arom C), 169.9, 173.2 (C1, CONH). Mass Spectrum ($ESI^+$, MeOH): m/z 272.2 $(M+Na)^+$, $C_{14}H_{19}NNaO_3$ requires 272.1.

7.9.4 Wilkinson's Hydrogenation of (2S)-Methyl 2-N-Acetylamino-5-methylhex-4-enoate 19

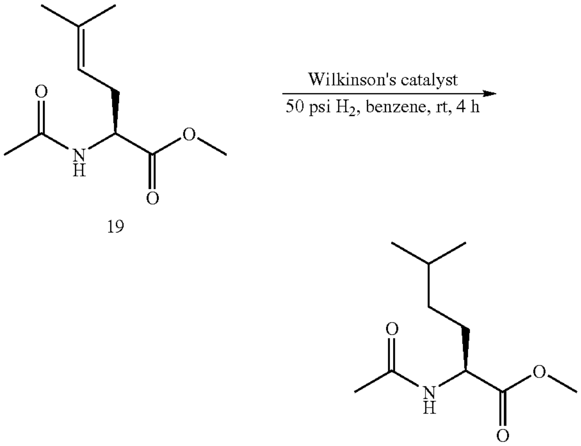

19

80

(2S)-Methyl 2-N-acetylamino-5-methylhex-4-enoate 19 was subjected to the general Wilkinson's hydrogenation procedure (Section 7.4.4) under the following conditions: Hex-4-enoate derivative 19 (11.3 mg, 56.8 μmol), benzene (4 mL), Wilkinson's catalyst, 50 psi, 22° C., 4 h. At the end of the reaction period, the solvent was evaporated under reduced pressure to afford a brown oil (12.5 mg). $^1H$ n.m.r. spectroscopy indicated the reaction gave only 6% conversion into the saturated product 80; 94% of the starting prenylglycine derivative 19 was recovered. $^1H$ n.m.r. (300 MHz, $CDCl_3$): Hexanoate 80: δ 0.87 (d, J=6.6 Hz, 6H, H6), 1.09-1.28 (m, 2H, H4), 1.54 (h, J=6.7 Hz, 1H, H5), 1.61-1.71 (m, 2H, H3), 2.03 (s, 3H, $CH_3CO$), 3.75 (s, 3H, $OCH_3$), 4.60 (dt, J=7.8 Hz, 5.5 Hz, 1H, H2), 5.96 (bd, J=7.8 Hz, 1H, NH).

Experimental for Chapter 5

7.10 Synthesis of Olefinic Substrates 7.10.1 (2S)-Methyl 2-N-(p-Nitrobenzoyl)aminopent-4-enoate 83

83

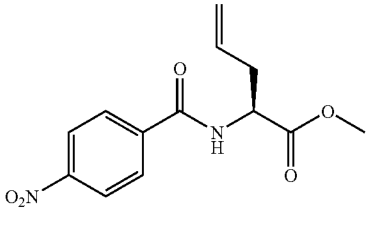

A solution of p-nitrobenzoyl chloride 89 (1.21 g, 6.54 mmol) in a mixture of DCM:$Et_2O$ (2:1, 15 mL) was added dropwise to a stirred solution of methyl 2-aminopent-4-enoate hydrochloride 51 (0.98 g, 5.94 mmol) and $Et_3N$ (1.80 mL, 13.0 mmol) in a mixture of DCM:$Et_2O$ (2:1, 15 mL) at 0° C. The reaction mixture was allowed to warm to room temperature and stirred for 20 h. The mixture was acidified with dilute HCl solution (1 M, pH 2) and extracted with DCM (3×20 mL). The combined organic extract was washed with distilled water (20 mL), dried ($MgSO_4$) and evaporated under reduced pressure to afford the titled compound 83 as an off-white solid (1.63 g, 99%), m.p. 99-100° C. Spectroscopic data indicated the crude product 83 did not require purification and was used directly in the subsequent reaction (Section 7.15.1). GC: $t_R$=12.20 min (GC column 30QC5/BPX5, 150° C. for 1 min, 10° C. $min^{-1}$ to 280° C. for 6 min). $[\alpha]_D^{22}$ +29.9° (c=0.37, $CHCl_3$). $\nu_{max}$ (neat): 3293 w, 2954 m, 2839 m, 1725 s, 1641 m, 1602 w, 1538 w, 1529 w, 1456 s, 1377 s, 1256 m, 1160 m, 1118 w, 1066 w, 998 m, 972 m, 941 w, 841 m $cm^{-1}$. $^1H$ n.m.r. (300 MHz, $CDCl_3$): δ 2.65-2.76 (m, 2H, H3), 3.82 (s, 3H, $OCH_3$), 4.90 (dt, J=5.6, 7.5 Hz, 1H, H2), 5.14-5.30 (m, 2H, H5), 5.75 (m, 1H, H4), 6.73 (bd, J=6.6 Hz, 1H, NH), 7.95 (d, J=7.7 Hz, 2H, H2', 6'), 8.30 (d, J=7.6 Hz, 2H, H3', 5'). $^{13}C$ n.m.r. (75 MHz, $CDCl_3$): δ 36.6 (C3), 52.4, 52.9 (C2, $OCH_3$), 119.9 (C5), 124.0 (C3', 5'), 128.4 (C2', 6'), 132.0 (C4), 139.6 (C1'), 150.0 (C4'), 165.1 (C1), 172.1 (CONH). HRMS ($ESI^+$, MeOH): Found: m/z 279.0977 $(M+H)^+$, $C_{13}H_{15}N_2O_5$ requires 279.0981; m/z 301.0798 $(M+Na)^+$, $C_{13}H_{14}N_2NaO_5$ requires 301.0800.

7.10.2 (2S)-Methyl 2-N-Acetylamino-5-methylhex-4-enoate 19

19

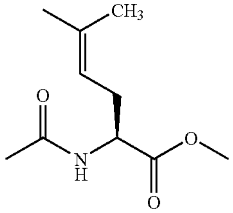

The preparation of (2S)-methyl 2-N-acetylamino-5-methylhex-4-enoate 19 via asymmetric hydrogenation of the dienoate 20 has been previously described (Section 7.9.5).

7.10.3 (2Z)-Methyl 2-N-Benzoylamino-5-methylhexa-2,4-dienoate 82

82

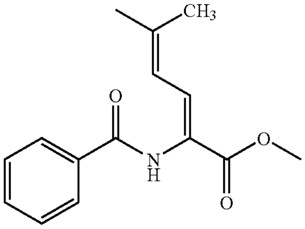

The dienamide 82 was prepared according to a procedure described by Teoh et al.[118,119] Tetramethylguanidine (3.40 mL, 27.1 mmol) and hydroquinone (3.0 mg) were added to a solution of methyl 2-N-benzoylamino-2-(dimethoxyphosphinyl)-acetate 64 (6.10 g, 20.3 mmol) in THF (120 mL) at −78° C. After 30 min, 3-methyl-2-butenal 40 (2.40 mL, 24.9 mmol) was added and the mixture was stirred at −78° C. for 2 h, warmed to 25° C. and allowed to react an additional 16 h. The mixture was diluted with DCM (150 mL) and washed with dilute HCl solution (1 M, 2×70 mL), $CuSO_4$ solution (1

M, 2×70 mL), saturated $NaHCO_3$ solution (2×70 mL) and saturated NaCl solution (1×70 mL). 4 The organic extract was dried ($MgSO_4$) and evaporated under reduced pressure to give the crude product 82 as a yellow oil (5.37 g). Purification by flash chromatography ($SiO_2$, light petroleum:EtOAc, 2:1) furnished the pure dienamide 82 as an off-white solid (3.84 g, 73%), m.p. 98-99° C. GC: $t_R$=11.00 min (GC column 30QC5/BPX5, 150° C. for 1 min, 10° C. $min^{-1}$ to 280° C. for 6 min). $\nu_{max}$ (KBr): 3286 m, 2991 w, 2948 w, 1716 s, 1649 s, 1601 w, 1579 w, 1524 s, 1489 s, 1436 m, 1389 w, 1331 m, 1286 m, 1254 s, 1207 m, 1190 w, 1162 w, 1135 w, 1087 s, 1048 w, 996 w, 977 w, 931 w, 864 m, 802 m, 760 m, 739 m, 710 s, 688 w, 677 w, 630 w, 614 w, 585 w $cm^{-1}$. $^1H$ n.m.r. (400 MHz, $CDCl_3$): δ 1.87 (s, 3H, H6), 1.91 (d, J=0.7 Hz, 3H, $CH_3C$=), 3.78 (s, 3H, $OCH_3$), 6.03 (d with fine splitting, J=11.9 Hz, 1H, H4), 7.41 (d, J=11.8 Hz, 1H, H3), 7.43-7.47 (m, 2H, H3', 5'), 7.53 (m, 1H, H4'), 7.63 (bs, 1H, NH), 7.89-7.90 (m, 2H, H2', 6'). $^3C$ n.m.r. (100 MHz, $CDCl_3$): δ 19.3 ($CH_3C$=), 27.1 (C6), 52.5 ($OCH_3$), 121.0 (C4), 121.2 (C5), 127.6 (C2', 6'), 128.9 (C3', 5'), 129.9 (C3), 132.0 (C4'), 134.1 (C2), 147.2 (C1'), 166.0, 166.1 (C1, CONH). HRMS ($ESI^+$, MeOH): Found: m/z 260.1282 $(M+H)^+$, $C_{15}H_{18}NO_3$ requires 260.1287; m/z 282.1099 $(M+Na)^+$, $C_{15}H_{17}NNaO_3$ requires 282.1106.

7.11 Metathesis Reactions with Olefinic Substrates 7.11.1 (2S,7S)-Dimethyl 2,7-N,N'-Di[(p-nitrobenzoyl)amino]oct-4-enedioate 90

90

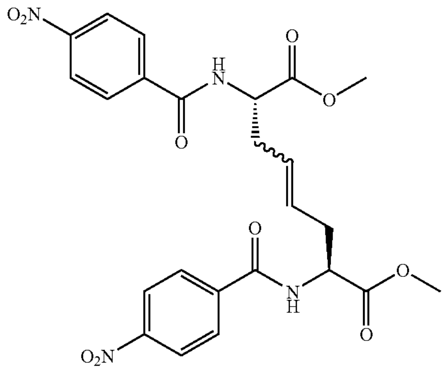

Method A: The dimer 90 was prepared via the conventional cross metathesis procedure (Section 7.5.2) under the following conditions: (2S)-Methyl 2-N-(p-nitrobenzoyl)aminopent-4-enoate 83 (43.5 mg, 0.16 mmol), DCM (3 mL), Grubbs' catalyst (26.0 mg, 31.6 μmol, 20 mol %), 50° C., 14 h, 100% conversion into dimer 90. The reaction mixture was evaporated under reduced pressure to give the homodimer 90 as a brown oil (69.7 mg, 100% crude yield).

Method B: The dimer 90 was also prepared and purified from an analogous reaction using $2^{nd}$ generation Grubbs' catalyst under the following conditions: (2S)Methyl 2-N-(p-nitrobenzoyl)aminopent-4-enoate 83 (86.3 mg, 0.31 mmol), DCM (4 mL), 2nd generation Grubbs' catalyst (13.6 mg, 16.0 μmol, 5 mol %), 50° C., 12 h, 100% conversion into dimer 90. Purification by flash chromatography ($SiO_2$, light petroleum: EtOAc: DCM, 4:2:1) gave the pure dimer 90 as a pale brown solid (74.0 mg, 90%), m.p. 90-92° C. GC: $t_R$ (E/Z)=16.1 min, 16.2 min (GC column 30QC5/BPX5, 150° C. for 1 min, 10° C. $min^{-1}$ to 280° C. for 6 min). $[\alpha]_D^{22}$ +20.0° (c=0.21, $CHCl_3$). $\nu_{max}$ (neat): 3365 m, 3057 w, 2957 w, 2854 w, 1728 s, 1667 s, 1602 m, 1525 s, 1487 m, 1437 m, 1348 s, 1267 m, 1227 m, 1174 w, 1157 w, 1110 w, 1014 m, 974 m, 869 m, 874 m, 737 s, 718 s $cm^{-1}$. $^1H$ n.m.r. (400 MHz, $CDCl_3$): δ2.60-2.64 (m, 4H, H3, 6), 3.70 (s, 6H, $OCH_3$), 4.88 (apparent q, J=5.9 Hz, 2H, H2, 7), 5.49-5.53 (m, 2H, H4, 5), 7.11 (bd, J=7.4 Hz, 2H, NH), 8.02 (d, J=8.7 Hz, 4H, H2', 6'), 8.21-8.29 (m, 4H, H3', 5'). $^{13}C$ n.m.r. (100 MHz, $CDCl_3$): δ 35.0 (C3, 6), 52.8, 52.8 (C2, 7, $OCH_3$), 123.8 (C3', 5'), 128.8, 128.9 (C2', 6', C4, 5), 139.2 (C1'), 149.9 (C4'), 165.2 (C1, 8), 172.1 (CONH). HRMS ($ESI^+$, MeOH): Found: m/z 529.1560 $(M+H)^+$, $C_{24}H_{25}N_4O_{10}$ requires 529.1571; m/z 551.1379 $(M+Na)^+$, $C_{24}H_{24}N_4NaO_{10}$ requires 551.1390.

7.11.2 Attempted Dimerisation of (2Z)-Methyl 2-N-Benzoylamino-5-methylhexa-2,4-dienoate 82

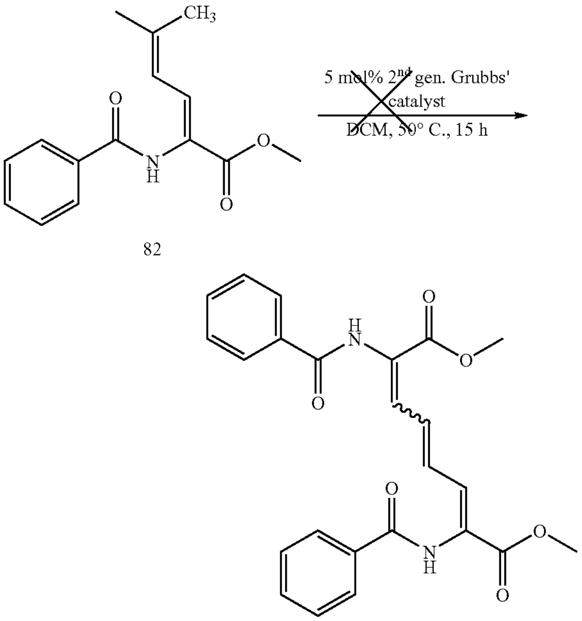

82

84

The dienamide 82 was subjected to the conventional cross metathesis procedure (Section 7.5.2) under the following conditions: (2Z)-Methyl 2-N-benzoylamino-5-methylhexa-2,4-dienoate 82 (30.7 mg, 0.12 mmol), DCM (5 mL), $2^{nd}$ generation Grubbs' catalyst (5.1 mg, 6.0 μmol, 5 mol %), 50° C., 15 h, 0% conversion into dimer 84. The dienamide 82 was recovered unchanged. $^1H$ n.m.r. spectroscopic data for the recovered dienamide 82 were in agreement with those previously reported (Section 7.14.3).

7.11.3 Attempted Butenolysis of (2Z)-Methyl 2-N-Benzoylamino-5-methylhexa-2,4-dienoate 82

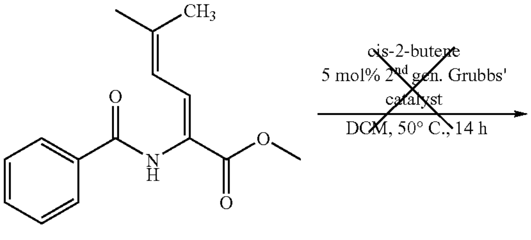

82

-continued

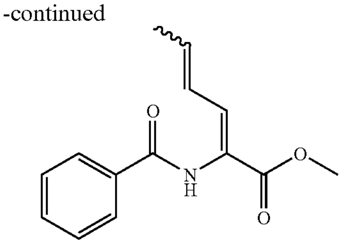

86

The dienamide 82 was subjected to the conventional cross metathesis procedure (Section 7.5.4) with cis-2-butene under the following conditions: (2Z)-Methyl 2-N-benzoylamino-5-methylhexa-2,4-dienoate 82 (39.3 mg, 0.15 mmol), DCM (5 mL), cis-2-butene (15 psi), 2nd generation Grubbs' catalyst (6.6 mg, 7.8 μmol, 5 mol %), 50° C., 14 h, 0% conversion into 86. The dienamide 82 was recovered unchanged. [1]H n.m.r. spectroscopic data for the recovered dienamide 82 were in agreement with those previously reported (Section 7.14.3).

7.12 Activation of Dormant Olefins 7.12.1 Butenolysis of (2Z)-Methyl 2-N-Acetylamino-5-methylhex-4-enoate 19

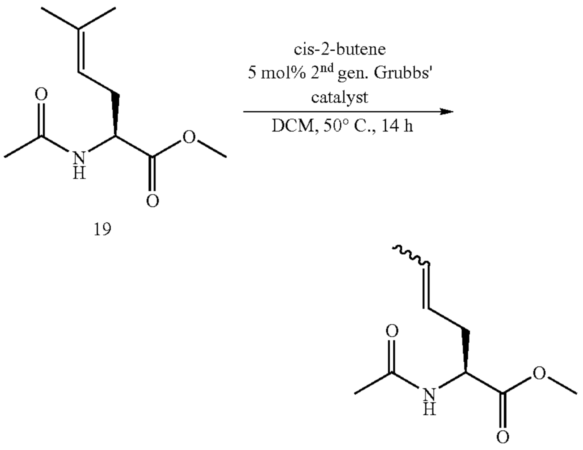

19

81

The activation of prenylglycine 19 via butenolysis (Section 7.5.4) to give the crotylglycine derivative 81 has been previously described (Section 7.12.13).

7.12.2 (2S)-Methyl 2-N-Benzoylamino-5-methylhex-4-enoate 87

87

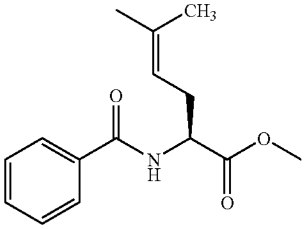

The dienamide 82 was subjected to the general asymmetric hydrogenation procedure (Section 7.4.3) under the following conditions: (2Z)-Methyl 2-N-benzoylamino-5-methylhexa-2,4-dienoate 82 (26.1 mg, 0.10 mmol), MeOH (5 mL), Rh(I)-(S,S)-Et-DuPHOS, 75 psi, 22° C., 3 h,. At the end of the reaction period, the solvent was evaporated under reduced pressure and the residue was purified by flash chromatography ($SiO_2$, EtOAc) to give the prenylglycine derivative 87 as a pale yellow oil (23.9 mg, 91%). HPLC: $t_R$=6.20 min (Chiralcel OJ column, 1.0 mL $min^{-1}$, detection at 254 nm, 5% EtOH:95% hexane). $[\alpha]_D^{22}$ +53.0° (c=1.19, $CHCl_3$). $\nu_{max}$ (neat): 3334 m, 2953 w, 1744 s, 1645 s, 1603 w, 1580 w, 1538 s, 1489 m, 1437 m, 1353 w, 1274 w, 1211 w, 1175 w, 1095 w, 1031 w, 736 w, 714 w, 693 w $cm^{-1}$. [1]H n.m.r. (300 MHz, $CDCl_3$): δ 1.61 (d, J=0.5 Hz, 3H, $CH_3C$=), 1.71 (d, J=1.0 Hz, 3H, H6), 2.52-2.76 (m, 2H, H3), 3.77 (s, 3H, $OCH_3$), 4.85 (dt, J=7.7, 5.5 Hz, 1H. H2), 5.08 (m, 1H, H4), 6.65 (bd, J=6.9 Hz, 1H NH), 7.41-7.47 (m, 2H, H3', 5'), 7.51 (m, 1H, H4'), 7.76-7.79 (m, 2H, H2', 6'). [13]C n.m.r. (75 MHz, $CDCl_3$): δ 18.0 ($CH_3C$=), 26.0 (C6), 30.9 (C3), 52.5, 52.6 (C2, $OCH_3$), 117.6 (C4), 127.2 (C2', 6'), 128.7 (C3', 5'), 131.8 (C4'), 134.3 (C5), 136.8 (C1'), 167.0, 172.8 (C1, CONH). HRMS ($ESI^+$, MeOH): Found: m/z 262.1441 $(M+H)^+$, $C_{15}H_{20}NO_3$ requires 262.1443; m/z 284.1256 $(M+Na)^+$, $C_{15}H_{19}NNaO_3$ requires 284.1263.

(2R)-Methyl 2-N-benzoylamino-5-methylhex-4-enoate 87

87

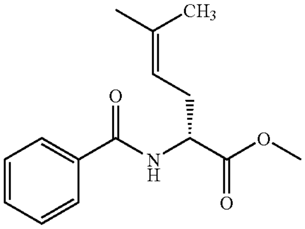

The dienamide 82 was subjected to the general asymmetric hydrogenation procedure (Section 7.4.3) under the following conditions: (2Z)-Methyl 2-N-benzoylamino-5-methylhexa-2,4-dienoate 82 (80.1 mg, 0.31 mmol), MeOH (7 mL), Rh(I)-(R,R)-Et-DuPHOS, 75 psi, 22° C., 3 h. At the end of the reaction period, the solvent was evaporated under reduced pressure and the residue was purified by flash chromatography ($SiO_2$, EtOAc) to give the prenylglycine derivative 87 as a yellow oil (78.2 mg, 97%). HPLC: $t_R$=5.90 min (Chiralcel OJ column, 1.0 mL $min^{-1}$, detection at 254 nm, 5% EtOH: 95% hexane). $[\alpha]_D^{22}$ −53.4° (c=0.98, $CHCl_3$). Spectroscopic data were in agreement with those previously reported for the (S)-enantiomer.

7.12.3 (2S)-Methyl 2-N-Benzoylaminohex-4-enoate 88

88

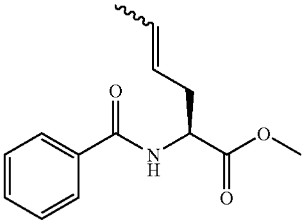

The enamide 87 was subjected to the conventional cross metathesis procedure (Section 7.5.5) with cis-2-butene under the following conditions: (2S)-Methyl 2-N-benzoylamino-5-methylhex-4-enoate 87 (90.0 mg, 0.35 mmol), DCM (5 mL), cis-2-butene (15 psi), $2^{nd}$ generation Grubbs' catalyst (14.6 mg, 17.2 mmol, 5 mol %), 50° C., 12 h, 100% conversion into 88. The reaction mixture was evaporated under reduced pressure to give the crotylglycine derivative 88 as a brown oil (101 mg, 100% crude yield). GC: $t_R$ (E/Z)=9.68 min, 9.93 min (GC Column 30QC5/BPX5, 150° C. for 1 min, 10° C. $min^{-1}$ to 280° C. for 6 min). $v_{max}$ (neat): 3337 bm, 3057 w, 2954 m, 2856 w, 1743 s, 1652 s, 1603 w, 1580 w, 1532 s, 1488 m, 1438 m, 1360 w, 1266 s, 1217 w, 1180 w, 1116 w, 1031 m, 969 w, 896 w, 801 w, 738 s, 638 w $cm^{-1}$. $^1H$ n.m.r. (300 MHz, $CDCl_3$): δ 1.66 (dd, J=6.4, 1.4 Hz, 3H, H6), 2.52-2.66 (m, 2H, H3), 3.77 (s, 3H, $OCH_3$), 4.82 (apparent dd, J=7.6, 5.7 Hz, 1H, H2), 5.33 (m, 1H, H5), 5.63 (m, 1H, H4), 6.66 (bd, J=7.0 Hz, 1H, NH), 7.43 (t, J=7.0 Hz, 2H, H3', 5'), 7.50 (m, 1H, H4'), 7.78 (d, J=7.1 Hz, 2H, H2', 6'). $^{13}C$ n.m.r. (100 MHz, $CDCl_3$): δ 18.0 (C6), 35.4 (C3), 52.4, 52.5 (C2, $OCH_3$), 124.5 (C5), 127.1 (C2', 6'), 128.6 (C3', 5'), 130.2 (C4), 131.7 (C4'), 134.1 (C1'), 166.9, 172.5 (C1, CONH). HRMS ($ESI^+$, MeOH): Found: m/z 248.1284 $(M+H)^+$, $C_{14}H_{18}NO_3$ requires 248.1287; m/z 270.1098 $(M+Na)^+$, $C_{14}H_{17}NNaO_3$ requires 270.1106.

7.12.4 Dimerisation of (2S)-Methyl 2-N-Acetylaminohex-4-enoate 81

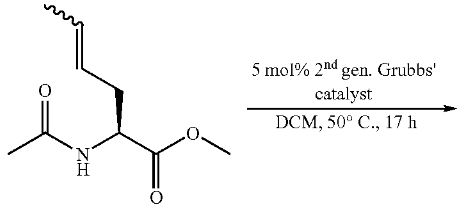

81

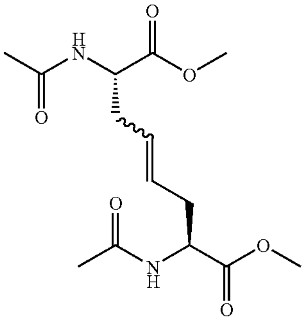

60

The dimerisation of crotylglycine 81 using the conventional cross metathesis procedure has been previously described (Section 7.12.14).

7.12.5 Dimerisation of (2S)-Methyl 2-N-Benzoylamino-hex-4-enoate 88

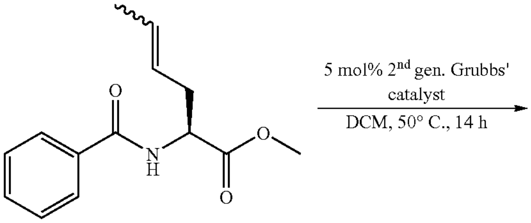

88

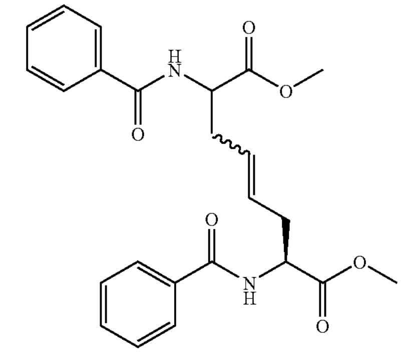

69

The enamide 88 was subjected to the conventional cross metathesis procedure under the following conditions: (2S)-Methyl 2-N-benzoylaminohex-4-enoate 88 (89.6 mg, 0.36 mmol), DCM (5 mL), $2^{nd}$ generation Grubbs' catalyst (15.3 mg, 18.0 μmol, 5 mol %), 50° C., 17 h, 100% conversion into dimer 69. The reaction mixture was evaporated under reduced pressure to afford the homodimer 69 as a brown oil (106 mg, 100% crude yield). Spectroscopic data for dimer 69 were in agreement with those previously reported (Section 7.12.2).

7.13 Wilkinson's Hydrogenation Reactions 7.13.1 Wilkinson's Hydrogenation of (2Z)-Methyl 2-N-Benzoylamino-5-methylhexa-2,4-dienoate 82

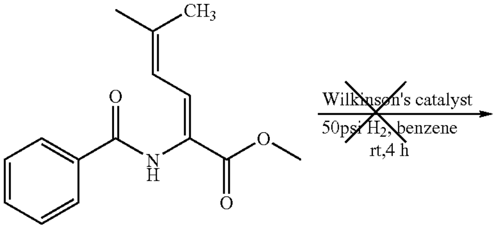

82

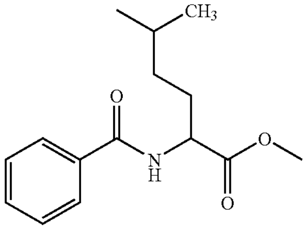

85

Method A: The dienamide 82 was subjected to the general Wilkinson's hydrogenation procedure (Section 7.4.4) under the following conditions: (2Z)-Methyl 2-N-benzoylamino-5-methylhexa-2,4-dienoate 82 (47.0 mg, 0.18 mmol), benzene (5 mL), Wilkinson's catalyst, 50 psi, 22° C., 4 h. The dienamide 82 was recovered unchanged. $^{1}H$ n.m.r. spectroscopic data for the recovered dienamide 83 were in agreement with those previously reported (Section 7.14.3).

7.13.2 (2S,7S)-Dimethyl 2,7-N,N'-Di(p-nitrobenzoyl) aminooctanedioate 91

91

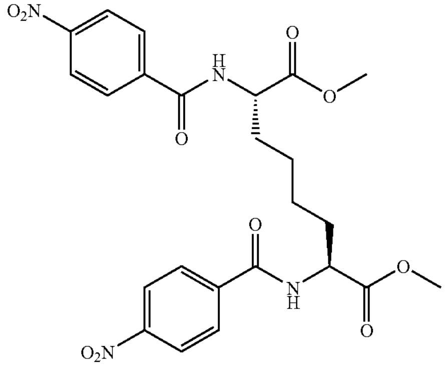

(2S,7S)-Dimethyl 2,7-N,N'-di(p-nitrobenzoyl)aminoocta-4-enedioate 90 was subjected to the general Wilkinson's hydrogenation procedure (Section 7.4.4) under the following conditions: Dimer 90 (20.6 mg, 0.04 mmol), THF: $^{t}$BuOH (1:1, 5 mL), Wilkinson's catalyst, 15 psi $H_2$, 22° C., 14 h. At the end of the reaction period, the solvent was evaporated under reduced pressure to afford the product 91 as a brown oil. Purification by flash chromatography ($SiO_2$, light petroleum:EtOAc:DCM, 1:1:1) gave the pure dimer 91 as an off-white solid (13.8 mg, 67%), m.p. 117-119° C. GC: $t_R$=16.8 min (GC column 30QC5/BPX5, 150° C. for 1 min, 10° C. $min^{-1}$ to 280° C. for 6 min). $\nu_{max}$ (neat): 3304 w, 2932 w, 1740 s, 1637 s, 1603 m, 1528 s, 1438 w, 1348 m, 1265 s, 1109 w $cm^{-1}$. $^{1}H$ n.m.r. (400 MHz, $CDCl_3$): δ 1.39-1.54 (m, 4H, H4, 5), 1.74-2.04 (m, 4H, H3, 6), 3.81 (s, 6H, $OCH_3$), 4.82 (dt, J=7.3, 5.4 Hz, 2H, H2, 7), 6.85 (bd, J=7.4 Hz, 2H, NH), 7.96 (d, J=8.8 Hz, 4H, H2', 6'), 8.28 (d, J=8.7 Hz, 4H, H3', 5'). $^{13}C$ n.m.r. (100 MHz, $CDCl_3$): δ 24.7 (C4, 5), 32.4 (C3, 6), 52.7, 52.9 (C2, $OCH_3$), 124.0 (C2', 6'), 128.5 (C3', 5'), 139.5 (C1'), 150.0 (C4'), 165.3, 172.8 (C1, 8, CONH). HRMS (ESI$^+$, MeOH): Found: m/z 553.1550 $(M+Na)^+$, $C_{24}H_{26}N_4NaO_{10}$ requires 553.1547.

Experimental for Section 6

7.14 Synthesis of Non-Proteinaceous Fmoc-Amino Acids

Peptide sequences are represented by structural diagrams and three-letter codes of constituent amino acids. Synthetic amino acids allylglycine, crotylglycine and prenylglycine are represented by Hag, Crt and Pre respectively. Procedures for the preparation of the Fmoc-protected olefinic amino acids: (2S)-2-N-Fluorenylmethoxycarbonylaminopent-4-enoic acid (Fmoc-L-Hag-OH) 96, (2S)-2-N-fluorenylmethoxycarbonylaminohex-4-enoic acid (Fmoc-L-Crt-OH) 100 and (2S)-2-N-fluorenylmethoxycarbonylamino-5-methylhex-4-enoic acid (Fmoc-L-Pre-OH) 92, are detailed below.

7.14.1 2-N-Fluorenylmethoxycarbonylaminopent-4-enoic acid 96 (Fmoc-Hag-OH)

96

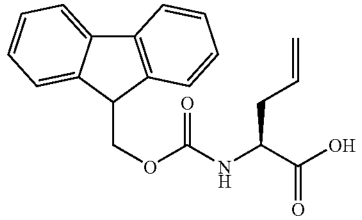

The allylglycine derivative 96 was prepared according to the procedure described by Paquet.[230] Fmoc-OSu (14.60 g, 43.3 mmol) was added to stirred solution of L-allylglycine (5.00 g, 43.5 mmol) and $NaHCO_3$ (18.20 g, 0.22 mol) in a mixture of acetone:water (200 mL). The resultant white suspension was stirred at room temperature and after 20 h, t.l.c. analysis ($SiO_2$, light petroleum:EtOAc; 1:1) showed the absence of starting material. The reaction mixture was acidified with concentrated HCl (pH 2) and the acetone was removed under reduced pressure. The resultant suspension was extracted into DCM (3×75 mL) and the combined organic extract was washed with dilute HCl solution (1 M, 2×50 mL), water (2×50 mL), dried ($MgSO_4$) and evaporated under reduced pressure to afford the titled Fmoc-amino acid 96 as a colourless solid (14.01 g, 96%), m.p. 137-138° C. (lit.[266] 134-136° C.). $\nu_{max}$ (KBr): 3484 s, 3198 bs, 3085 m, 2967 m, 2923 m, 1723 s, 1644 m, 1525 s, 1478 w, 1449 s, 1396 m, 1340 m, 1233 s, 1189 s, 1099 m, 1048 s, 998 w, 966 w, 943 m, 924 w, 850 m, 781 m, 761 s, 740 m, 648 w, 623 m, 582 m, 560 w, 540 m, 424 w $cm^{-1}$. $^{1}H$ n.m.r. (400 MHz, $CDCl_3$): δ 2.52-2.70 (2.34-2.49) (m, 2H, H3), 4.23 (t, J=6.9 Hz, 1H, H9'), 4.42 (4.30) (d, J=6.9 Hz, 2H, $CH_2O$), 4.52 (m, 1H, H2), 5.13-5.23 (m, 2H, H5), 5.31 (5.87) (bd, J=7.8 Hz, 1H, NH), 5.75 (m, 1H, H4), 6.63 (bs, 1H, OH), 7.31 (td, J=7.4, 0.8 Hz, 2H, H2', 7'), 7.38 (t, J=7.4 Hz, 2H, H3', 6'), 7.52-7.63 (m, 2H, H1', 8'), 7.76 (d, J=7.5 Hz, 2H, H4', 5'), one exchangeable proton (OH) not observed. $^{13}C$ n.m.r. (100 MHz, $CDCl_3$): δ 36.7 (C3), 47.5 (C9'), 53.4 (C2), 68.1 ($CH_2O$), 122.0 (C5), 120.1 (C2', 7'), 125.4 (C3', 6'), 127.9 (C1', 8'), 128.0 (C4', 5'), 131.1 (C4), 141.7 (C8'a, 9'a), 144.0 (C4'a, 4'b), 156.3 (OCONH), 176.4 (C1). Mass Spectrum (ESI$^+$, MeOH): m/z 338.4 $(M+H)^+$, $C_{20}H_{20}NO_4$ requires 338.1; 360.3 $(M+Na)^+$, $C_{20}H_{19}NNaO_4$ requires 360.1. Spectroscopic data were in agreement with those reported in the literature.[266]

7.14.2 2-N-Fluorenylmethoxycarbonylaminohex-4-enoic acid 100 (Fmoc-Crt-OH)

100

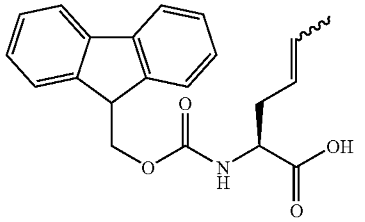

A solution of(2S)-methyl 2-N-acetylaminohex-4-enoate 81(1.30 g, 7.05 mmol) in dilute HCl (1 M, 8 mL) was heated at reflux for 21 h. The reaction mixture was evaporated under reduced pressure to give 2-aminohex-4-enoic acid hydrochloride salt (L-crotylglycine·HCl) 101 as a pale brown solid (1.17 g, 100%), m.p. 212-214° C. $\nu_{max}$ (KBr): 3500 bs, 2965 m, 2358 s, 1731 s, 1651 m, 1455 m, 901 m $cm^{-1}$. $^{1}H$ n.m.r. (300 MHz, $CD_3OD$): δ 1.69 (d, J=5.3 Hz, 3H, H6), 2.51-2.74 (m, 2H, H3), 3.99 (m, 1H, H2), 5.42 (m, 1H, H5), 5.73 (m, 1H, H4), exchangeable protons (NH and OH) not observed. $^{13}C$ n.m.r. (75 MHz, $CD_3OD$): δ 18.7 (C6), 35.1 (C3), 48.7 (C2), 124.6 (C5), 133.6 (C4), 174.3 (C1). Mass Spectrum ($ESI^+$, MeOH): m/z 130.1 $(M+H)^+$, $C_6H_{12}NO_2$ requires 130.1.

2-N-Fluorenylmethoxycarbonylaminohex-4-enoic acid 100 was prepared according to the procedure described by Paquet.[230] Fmoc-OSu (2.36 g, 7.00 mmol) was added to a stirred suspension of L-crotylglycine HCl 101 (1.16 g, 7.03 mmol) and $NaHCO_3$ (2.95 g, 35.0 mmol) in a mixture of acetone:water (1:1, 30 mL). The resultant suspension was stirred at room temperature for 15 h. The reaction mixture was then acidified with concentrated HCl (pH 2) and the acetone was removed under reduced pressure. The resultant suspension was extracted into DCM (3×25 mL) and the combined organic extract was washed with dilute HCl solution (1 M, 2×25 mL), water (2×25 mL), dried ($MgSO_4$) and evaporated under reduced pressure to afford the titled Fmoc-amino acid 100 as colourless solid (1.91 g, 78%), m.p. 119-121° C. $\nu_{max}$ (KBr): 3390 bm, 3033 m, 2961 s, 2357 w, 1730 s, 1651 w, 1505 w, 1450 w, 1395 w, 850 w $cm^{-1}$. $^{1}H$ n.m.r. (300 MHz, $CDCl_3$): δ 1.67 (d, J=6.2 Hz, 3H, H6), 2.37-2.69 (m, 2H, H3), 4.23 (t, J=6.8 Hz, 1H, H9'), 4.42-4.48 (m, 3H, $CH_2O$, H2), 5.30-5,37 (m, 2H, H5, NH), 5.61 (m, 1H, H4), 7.31 (td, J=7.2, 1.3 Hz, 2H, H2', 7'), 7.34 (td, J=7.4, 1.5 Hz, 2H, H3', 6'), 7.60 (d, J=7.3 Hz, 2H, H1', 8'), 7.74 (d, J=7.0 Hz, 2H, H4', 5'), one exchangeable proton (OH) not observed. $^{13}C$ n.m.r. (75 MHz, $CDCl_3$): δ 16.7 (C6), 34.1 (C3), 46.2 (C9'), 52.3 (C2), 66.2 ($CH_2O$), 118.9 (C5), 123.0 (C2', 7'), 124.6 (C3', 6'), 125.2 (C1', 8'), 127.5 (C4', 5'), 129.7 (C4), 140.3 (C8'a, 9'a), 142.7 (C4'a, 4'b), 154.9 (OCONH), 175.0 (C1). Mass Spectrum ($ESI^+$, MeOH): m/z 352.1 $(M+H)^+$, $C_{21}H_{22}NO_4$ requires 352.2. Spectroscopic data were in agreement with those reported in the literature.[146]

7.12.3 2-N-Fluorenylmethoxycarbonylamino-5-methylhex-4-enoic acid 92 (Fmoc-Pre-OH)

92

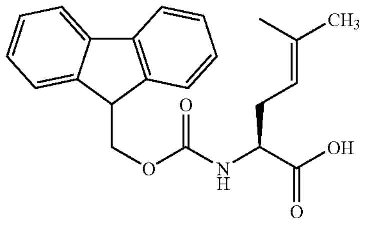

The allylglycine derivative 96 was subjected to the conventional cross metathesis procedure with 2-methyl-2-butene (Section 0) under the following conditions: 2-N-Fluorenylmethoxycarbonylaminopent-4-enoic acid 96 (200 mg, 0.59 mmol), DCM (7 mL), 2nd generation Grubbs' catalyst (26.0 mg, 30.6 μmol, 5 mol %), 2-methyl-2-butene (1 mL, 10 psi), 50° C., 12 h, 100% conversion into 92. The reaction mixture was evaporated under reduced pressure to give the prenylglycine derivative 92 as a brown oil (245 mg, 100% crude yield). $\nu_{max}$ (neat): 3426 w, 3324 w, 3066 w, 2932 m, 1716 s, 1514 m, 1478 w, 1450 m, 1378 w, 1338 m, 1265 m, 1220 w, 1106 w, 1057 m, 910 m, 855 w, 759 w, 738 s, 704 w, 648 w, 621 w $cm^{-1}$. H n.m.r. (400 MHz, $CDCl_3$): δ 1.63 (s, 3H, H6), 1.73 (s, 3H, $CH_3$), 2.49-2.65 (m, 2H, H3), 4.23 (t, J=6.7 Hz, 1H, H9'), 4.40 (d, J=6.7 Hz, 2H, $CH_2O$), 5.11 (m, 1H, H4), 5.41 (bd, J=7.5 Hz, 1H, NH), 7.31 (t, J=7.3 Hz, 2H, H2', 7'), 7.40 (t, J=7.3 Hz, 2H, H3', 6'), 7.58-7.66 (m, 2H, H1', 8'), 7.76 (d, J=7.4 Hz, 2H, H4', 5'), 9.22 (bs, 1H, OH). $^{13}C$ n.m.r. (100 MHz, $CDCl_3$): δ 18.1 (C6), 26.0 ($CH_3C$=), 30.8 (C3), 47.3 (C9'), 53.8 (C2), 67.2 ($CH_2O$), 117.5 (C4), 120.1 (C2', 7'), 125.2 (C3', 6'), 127.2 (C1', 8'), 127.8 (C4', 5'), 136.9 (C5), 141.4, 143.9 (Arom C), 156.1 (CONH), 176.2 (C1). HRMS ($ESI^+$, MeOH): Found: m/z 388.1522 $(M+Na)^+$, $C_{22}H_{23}NNaO_4$ requires 388.1525. The product later crystallised on standing to give a pale brown solid, m.p. 109-111° C.

7.15 Pentapeptide Transformations 7.15.1 Linear: Fmoc-Hag-Ala-Trp-Arg-Hag-$NH_2$ 94

94

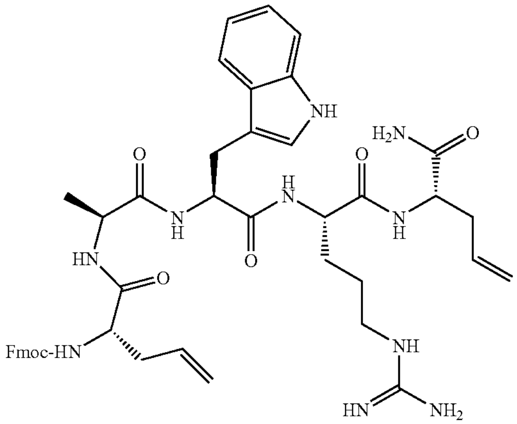

The procedure described in Section 7.3.2.2 was used for the attachment of the first amino acid, Fmoc-L-Hag-OH 96, to Rink amide resin. Quantities of the resin and coupling reagents HATU and NMM are presented in Table 7.1. The first coupling reaction was shaken for 14 h.

TABLE 7.1

Quantities of Reagents used in the Synthesis of Peptide 94

| Reagent | Mass (mg) or Volume (μl) | Mole (mmol) |
|---|---|---|
| Rink Amide Resin | 155 mg | 0.11 |
| Fmoc-L-Hag-OH | 110 mg | 0.33 |
| HATU | 83.0 mg | 0.22 |
| NMM | 71.8 μl | 0.65 |

The procedure outlined in Section 7.3.2.2 was also utilised for subsequent coupling reactions in the synthesis of the pentapeptide 94. Quantities of the coupling agents HATU and NMM remained constant throughout the synthesis. The quantities of successive amino acids and their reaction durations are detailed in Table 7.2.

TABLE 7.2

Quantities of Amino Acids used in the Synthesis of Peptide 94

| Amino Acid | Mass (mg) | Mole (mmol) | Reaction Time (h)* |
|---|---|---|---|
| Fmoc-L-Arg(Pbf)-OH | 211 | 0.33 | 5 |
| Fmoc-L-Trp(Boc)-OH | 171 | 0.32 | 3 |
| Fmoc-L-Ala-OH | 102 | 0.33 | 4.5 |
| Fmoc-L-Hag-OH | 110 | 0.33 | 20 |

*Note: Reaction times have not been optimised.

After the final amino acid coupling, a small aliquot of peptidyl-resin was subjected to the TFA-mediated cleavage procedure (Section 7.3.3). Mass spectral analysis of the isolated residue confirmed formation of the pentapeptide 94. Mass spectrum ($ESI^+$, $MeCN/H_2O$): m/z 847.1 $(M+H)^+$, $C_{45}H_{55}N_{10}O_7$ requires 847.4.

7.15.2 Linear: Fmoc-Crt-Ala-Trp-Arg-Crt-$NH_2$ 99

99

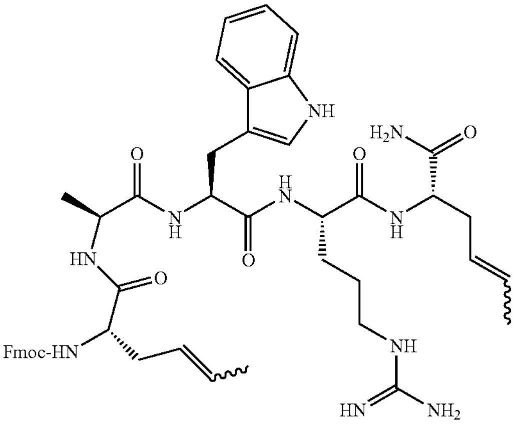

The procedure described in Section 7.3.2.2 was used for the attachment of the first amino acid, Fmoc-L-Crt-OH 100, to Rink amide resin. Quantities of the resin and coupling reagents HATU and NMM are presented in Table 7.3. The first coupling reaction was shaken for 3 h.

TABLE 7.3

Quantities of Reagents used in the Synthesis of Peptide 99

| Reagent | Mass (mg) or Volume (μl) | Mole (mmol) |
|---|---|---|
| Rink Amide Resin | 110 mg | 0.08 |
| Fmoc-L-Crt-OH | 81.5 mg | 0.23 |
| HATU | 58.6 mg | 0.15 |
| NMM | 51.0 μl | 0.46 |

The procedure outlined in Section 7.3.2.2 was also utilised for subsequent coupling reactions in the synthesis of the pentapeptide 99. Quantities of the coupling agents HATU and NMM remained constant throughout the synthesis. The quantities of successive amino acids and their reaction durations are detailed in Table 7.4.

TABLE 7.4

Quantities of Amino Acids used in the Synthesis of Peptide 99

| Amino Acid | Mass (mg) | Mole (mmol) | Reaction Time (h)* |
|---|---|---|---|
| Fmoc-L-Arg(Pbf)-OH | 150 | 0.23 | 20 |
| Fmoc-L-Trp(Boc)-OH | 122 | 0.23 | 4 |
| Fmoc-L-Ala-OH | 72.0 | 0.23 | 2 |
| Fmoc-L-Crt-OH | 81.5 | 0.23 | 12 |

*Note: Reaction times have not been optimised.

After the final amino acid coupling, a small aliquot of peptidyl-resin was subjected to the TFA-mediated cleavage procedure (Section 7.3.3). Mass spectral analysis of the isolated residue confirmed formation of the pentapeptide 99. Mass spectrum ($ESI^+$, $MeCN/H_2O$): m/z 875.2 $(M+H)^+$, $C_{47}H_{59}N_{10}O_7$ requires 875.4.

7.15.3 Linear: Fmoc-Hag-Pro-Trp-Arg-Hag-$NH_2$ 97

97

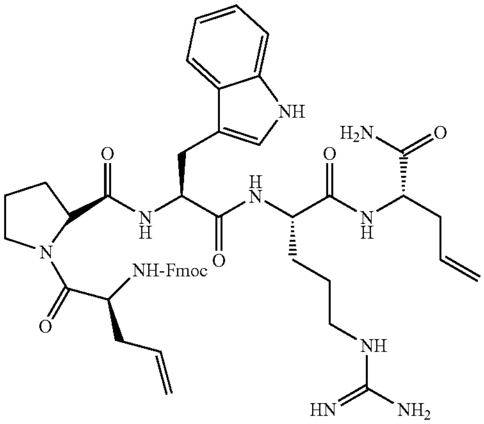

The procedure described in Section 7.3.2.2 was used for the attachment of the first amino acid, Fmoc-L-Hag-OH 96, to Rink amide resin. Quantities of the resin and coupling reagents HATU and NMM are presented in Table 7.5. The first coupling reaction was shaken for 14 h.

TABLE 7.5

Quantities of Reagents used in the Synthesis of Peptide 97

| Reagent | Mass (mg) or Volume (μl) | Mole (mmol) |
|---|---|---|
| Rink Amide Resin | 154 mg | 0.11 |
| Fmoc-L-Hag-OH | 109 mg | 0.32 |
| HATU | 82 mg | 0.22 |
| NMM | 71.4 μl | 0.65 |

The procedure outlined in Section 7.3.2.2 was also utilised for subsequent coupling reactions in the synthesis of the pentapeptide 97. Quantities of the coupling agents HATU and NMM remained constant throughout the synthesis. The quantities of successive amino acids and their reaction durations are detailed in Table 7.6

TABLE 7.6

Quantities of Amino Acids used in the Synthesis of Peptide 97

| Amino Acid | Mass (mg) | Mole (mmol) | Reaction Time (h)* |
|---|---|---|---|
| Fmoc-L-Arg(Pbf)-OH | 210 | 0.32 | 5 |
| Fmoc-L-Trp(Boc)-OH | 170 | 0.32 | 3 |
| Fmoc-L-Pro-OH | 110 | 0.33 | 4.5 |
| Fmoc-L-Hag-OH | 109 | 0.32 | 22 |

*Note: Reaction times have not been optimised.

After the final amino acid coupling, a small aliquot of peptidyl-resin was subjected to the TFA-mediated cleavage procedure (Section 7.3.3). Mass spectral analysis of the isolated residue confirmed formation of the pentapeptide 97. Mass spectrum ($ESI^+$, $MeCN/H_2O$): m/z 873.2 $(M+H)^+$, $C_{47}H_{57}N_{10}O_7$ requires 873.4; 895.1 $(M+Na)^+$, $C_{47}H_{56}N_{10}NaO_7$ requires 895.4.

7.15.4 Unsaturated Cyclic: Fmoc-c[Hag-Ala-Trp-Arg-Hag]-$NH_2$ 95

95

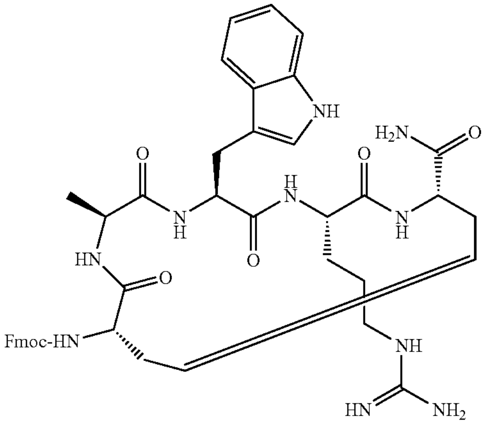

Method A: The resin-bound peptide 94a was subjected to the conventional RCM procedure (Section 7.5.2) under the following conditions: Resin-peptide 94a (20.0 mg, 14.0 μmol), DCM (3 mL), LiCl/DMF (0.4 M, 0.3 mL), Grubbs' catalyst (2.3 mg, 2.8 μmol, 20 mol %), 50° C., 41 h. At the end of the reaction period, a small aliquot of peptidyl-resin was subjected to the TFA-mediated cleavage procedure (Section 7.3.3). Mass spectral analysis of the isolated residue indicated recovery of the starting linear peptide 94. Mass spectrum ($ESI^+$, $MeCN/H_2O$): m/z 847.2 $(M+H)^+_{linear}$, $C_{45}H_{55}N_{10}O_7$.

Method B: The resin-bound peptide 94a was subjected to the conventional RCM procedure (Section 7.5.2) under the following conditions: Resin-peptide 94a (37.0 mg, 25.9 μmol), DCM (3 mL), LiCl/DMF (0.4 M, 0.3 mL), $2^{nd}$ generation Grubbs' catalyst (4.4 mg, 5.2 μmol, 20 mol %), 50° C., 41 h. At the end of the reaction period, a small aliquot of peptidyl-resin was subjected to the TFA-mediated cleavage procedure (Section 0). Mass spectral analysis of the isolated residue confirmed the presence of both cyclic 95 and linear 94 peptides. Mass spectrum ($ESI^+$, $MeCN/H_2O$): m/z 819.2 $(M+H)^+_{cyclic}$, $C_{43}H_{51}N_{10}O_7$ requires 819.4; m/z 847.2 $(M+H)^+_{linear}$, $C_{45}H_{55}N_{10}O_7$.

Method C: The resin-bound peptide 99a was subjected to the conventional RCM procedure (Section 7.5.2) under the following conditions: Resin-peptide 99a (32.8 mg, 23.0 μmol), DCM (5 mL), LiCl/DMF (0.4 M, 0.5 mL), $2^{nd}$ generation Grubbs' catalyst (4.0 mg, 4.7 μmol, 20 mol %), 50° C., 41 h, 100% conversion into 95. At the end of the reaction period, a small aliquot of peptidyl-resin was subjected to the TFA-mediated cleavage procedure (Section 7.3.3). Mass spectral analysis of the isolated residue confirmed formation of the cyclic peptide 95.† Mass spectrum ($ESI^+$, $MeCN/H_2O$): m/z 819.2 $(M+H)^+$ cyclic, $C_{43}H_{51}N_{10}O_7$ requires 819.4.

† RCM of the crotylglycine-containing peptide 99 leads to the same unsaturated carbocycle 95 resulting from cyclisation of the allylglycine-containing sequence 94, i.e. Fmoc-c[Hag-Ala-Trp-Arg-Hag]-OH is identical to Fmoc-c [Crt-Ala-Trp-Arg-Crt]-OH.

7.15.5 Unsaturated Cyclic: Fmoc-c[Hag-Pro-Trp-Arg-Hag]-$NH_2$ 98

98

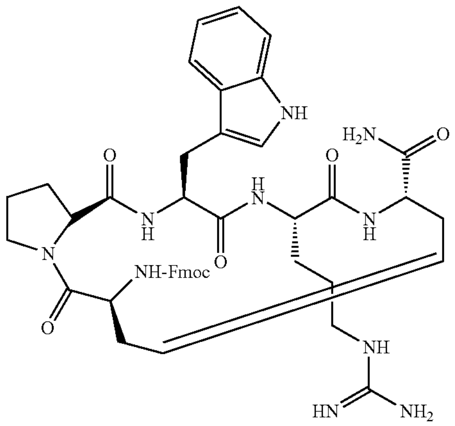

Method A: The resin-bound peptide 97a was subjected to the conventional RCM procedure (Section 7.5.2) under the following conditions: Resin-peptide 97a (26.4 mg, 18.5 μmol), DCM (5 mL), LiCl/DMF (0.4 M, 0.5 mL), Grubbs' catalyst (6.1 mg, 7.4 μmol, 20 mol %), 50° C., 41 h. At the end of the reaction period, a small aliquot of peptidyl-resin was subjected to the TFA-mediated cleavage procedure (Section 7.3.3). Mass spectral analysis of the isolated residue indicated recovery of the starting linear peptide 97. Mass spectrum ($ESI^+$, $MeCN/H_2O$): m/z 873.2 $(M+H)^+_{linear}$, $C_{47}H_{57}N_{10}O_7$.

Method B: The resin-bound peptide 97a was subjected to the conventional RCM procedure (Section 7.5.2) under the following conditions: Resin-peptide 97a (36.0 mg, 25.2 μmol), DCM (3 mL), LiCl/DMF (0.4 M, 0.3 mL), $2^{nd}$ generation Grubbs' catalyst (4.4 mg, 5.2 μmol, 20 mol %), 50° C., 41 h, 100% conversion into 98. At the end of the reaction period, a small aliquot of peptidyl-resin was subjected to the TFA-mediated cleavage procedure (Section 7.3.3). Mass spectral analysis of the isolated residue confirmed formation of the cyclic peptide 98. Mass spectrum ($ESI^+$, $MeCN/H_2O$): m/z 845.1 $(M+H)^+$, $C_{45}H_{53}N_{10}O_7$ requires 845.4; 867.1 $(M+Na)^+$, $C_{45}H_{52}N_{10}NaO_7$ requires 867.4.

7.15.6 Linear: Fmoc-Hag-Pro-Pre-Arg-Hag-OH 102

102

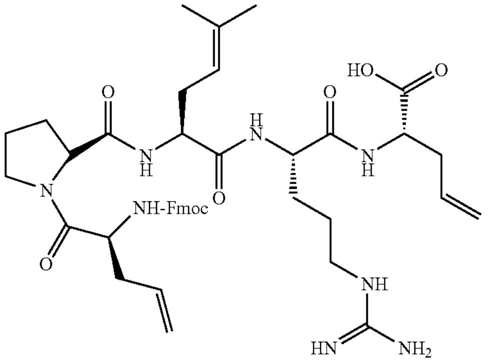

The procedure outlined in Section 7.3.2.1 was used for the attachment of the first amino acid, Fmoc-Hag-OH 96, to Wang resin. Quantities of the resin and coupling reagents are presented in Table 7.7. The first coupling reaction was shaken for 14 h.

TABLE 7.7

| Quantities of Reagents used in the Synthesis of Peptide 102 | | |
|---|---|---|
| Reagent | Mass (mg) or Volume (μl) | Mole (mmol) |
| Wang Resin | 212 mg | 0.19 |
| Fmoc-L-Hag-OH | 195 mg | 0.58 |
| DIC | 90.6 μl | 0.58 |
| DMAP | 7.1 mg | 0.06 |

The procedure outlined in Section 7.3.2.1 was also utilised for subsequent coupling reactions in the synthesis of the pentapeptide 102. Quantities of the coupling reagents HATU and NMM are tabulated (Table 7.8) and remained constant throughout the synthesis. The quantities of successive amino acids and their reaction durations are detailed in Table 7.9.

TABLE 7.8

| Quantities of Coupling Reagents used in the Synthesis of Peptide 102 | | |
|---|---|---|
| Coupling Reagent | Mass (mg) or Volume (mL) | Mole (mmol) |
| HATU | 147 mg | 0.39 |
| NMM | 128 μl | 1.16 |

TABLE 7.9

| Quantities of Amino Acids used in the Synthesis of Peptide 102 | | | |
|---|---|---|---|
| Amino Acid | Mass (mg) | Mole (mmol) | Reaction Time (h)* |
| Fmoc-L-Arg(Pbf)-OH | 376 | 0.58 | 2 |
| Fmoc-L-Pre-OH | 211 | 0.58 | 3 |
| Fmoc-L-Pro-OH | 196 | 0.58 | 6 |
| Fmoc-L-Hag-OH | 195 | 0.58 | 2 (1) |

*Note: Reaction times have not been optimised.

After the final amino acid coupling, a small aliquot of peptidyl-resin was subjected to the TFA-mediated cleavage procedure (Section 7.3.3). Mass spectral analysis of the isolated residue confirmed formation of the pentapeptide 102. Mass spectrum (ESI$^+$, MeCN/$H_2O$): m/z 813.6 $(M+H)^+$, $C_{43}H_{57}N_8O_8$ requires 813.4; m/z 831.5 $(M+H_2O+H)+_{103}$, $C_{43}H_{59}N_8O_9$ requires 831.4; m/z 927.6 $(M+TFA+H)^+$, $C_{45}H_{58}F_3N_{10}O_{10}$ requires 927.4.

The pentapeptide 102 was also synthesised on Wang resin (590 mg) with reduced loading (0.3 mmol $g^{-1}$) using the procedured described above. The relative quantities of the Fmoc-amino acids and coupling agents remained constant throughout the synthesis: Wang resin: DIC: DMAP: Fmoc-amino acid: HATU: NMM, 1:3:0.3:3:2:6 equiv.

7.15.7 Unsaturated Cyclic: Fmoc-c[Hag-Pro-Pre-Arg-Hag]-OH 104

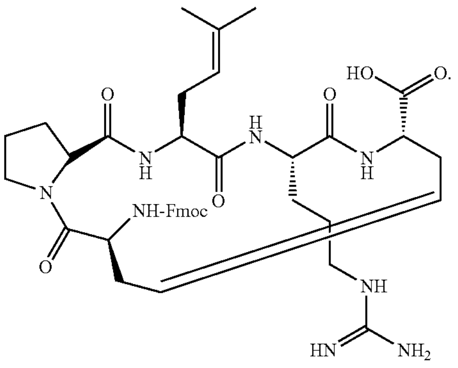

104

The resin-bound peptide 102a was subjected to the conventional RCM procedure (Section 7.5.2) under the following conditions: Resin-peptide 102a (70.0 mg, 63.7 μmol), DCM (5 mL), LiCl/DMF (0.4 M, 0.5 mL), 2$^{nd}$ generation Grubbs' catalyst (21.6 mg, 25.4 μmol, 40 mol %), 50° C., 42 h, 100% conversion into 104. At the end of the reaction period, a small aliquot of peptidyl-resin was subjected to the TFA-mediated cleavage procedure (Section 7.3.3). Mass spectral analysis of the isolated residue confirmed formation of the cyclic peptide 104. Mass spectrum (ESI$^+$, MeCN/$H_2O$): m/z 785.4 $(M+H)^+$, $C_{41}H_{53}N_8O_8$ requires 785.4; m/z 803.3 $(M+H_2O+H)^+$, $C_{41}H_{55}N_8O_9$ requires 803.4; m/z 899.4 $(M+TFA+H)^+$, $C_{43}H_{54}F_3N_8O_{10}$ requires 899.4.

The resin-bound peptide 102a (synthesised on reduced loading Wang resin) was subjected to the conventional RCM procedure (Section 7.5.2) under the following conditions: Resin-peptide 102a (97.0 mg, 29.1 μmol), DCM (5 mL), LiCl/DMF (0.4 M, 0.5 mL), 2$^{nd}$ generation Grubbs' catalyst (2.5 mg, 2.9 μmol, 10 mol %), 50° C., 42 h, 100% conversion into 104. Mass spectral data of the isolated residue confirmed formation of the cyclic peptide 104 and were in agreement with those reported above.

7.15.8 Saturated Cyclic: Fmoc-c[Hag-Pro-Pre-Arg-Hag]-OH 105

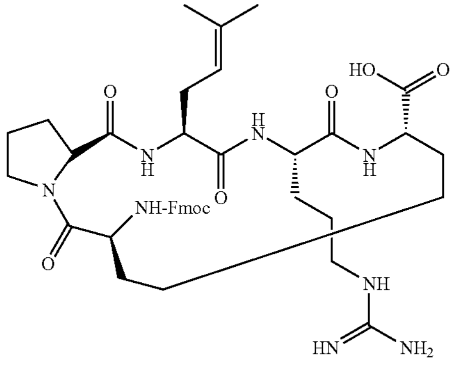

105

The resin-bound peptide 104a was subjected to the general Wilkinson's hydrogenation procedure (Section 7.4.4) under the following conditions: Resin-peptide 104a (350 mg, 0.32 mmol), DCM:MeOH (9:1, 8 mL), Wilkinson's catalyst, 80 psi $H_2$, 22° C., 22 h, 100% conversion into 105. At the end of the reaction period, a small aliquot of peptidyl-resin was subjected to the TFA-mediated cleavage procedure (Section 7.3.3). Mass spectral analysis of the isolated residue confirmed formation of the saturated cyclic pentapeptide 105. Mass spectrum ($ESI^+$, $MeCN/H_2O$): m/z 787.2 $(M+H)^+$, $C_{41}H_{55}N_8O_8$ requires 787.4; m/z 805.2 $(M+H_2O+H)^+$, $C_{41}H_{57}N_8O_9$ requires 803.4; m/z 901.3 $(M+TFA+H)^+$, $C_{43}H_{56}F_3N_8O_{10}$ requires 901.4.

7.15.9 Olefin Activation: Saturated Cyclic: Fmoc-c[Hag-Pro-Crt-Arg-Hag]-OH 106

106

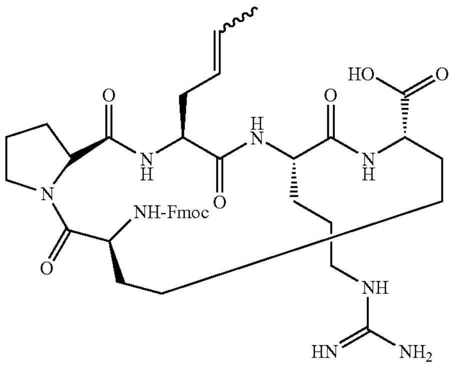

The resin-bound peptide 105a was subjected to the general cross metathesis procedure (Section 7.5.4) with cis-2-butene under the following conditions: Resin-peptide 105a (212 mg, 0.19 mmol), DCM (8 mL), $2^{nd}$ generation Grubbs' catalyst (82 mg, 9.7 μmol, 50 mol %), cis-2-butene (15 psi), 50° C., 42 h. At the end of the reaction period, a small aliquot of peptidyl-resin was subjected to the TFA-mediated cleavage procedure (Section 7.3.3). Mass spectral analysis of the isolated residue indicated the presence of the starting peptide 105 and the desired butenolysis product 106. The recovered resin-peptide was subjected to the same butenolysis conditions in order to drive the reaction to completion. After 42 h, a small aliquot of peptidyl-resin was subjected to the TFA-mediated cleavage procedure (Section 7.3.3). Mass spectral analysis of the isolated residue confirmed quantitative conversion to the activated peptide 106. Mass spectrum ($ESI^+$, $MeCN/H_2O$): m/z 773.2 $(M+H)^+$, $C_{40}H_{53}N_8O_8$ requires 773.4.

7.15.10 Cross Metathesis of Activated Olefin: Saturated CyclicFmoc-c[Hag-Pro-Sub-Arg-Hag]-OH 107

107

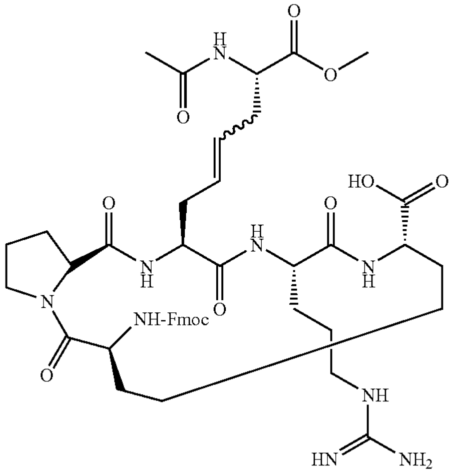

The resin-bound peptide 106a was subjected to the general microwave-accelerated cross metathesis procedure (Section 7.5.3) under the following conditions: Resin-peptide 106a (20.0 mg, 18.0 μmol), DCM (4 mL), LiCl/DMF (0.4 M, 0.4 mL), $2^{nd}$ generation Grubbs' catalyst (6.2 mg, 7.3 μmol, 40 mol %), (2S)-methyl 2-N-acetylaminohex-4-enoate 81 (70.0 mg, 0.38 mmol), 100° C., 2 h. At the end of the reaction period, a small aliquot of peptidyl-resin was subjected to the TFA-mediated cleavage procedure (Section 7.3.3). Mass spectral analysis of the isolated residue confirmed formation of the cross metathesis product 107. Mass spectrum ($ESI^+$, $MeCN/H_2O$): m/z 902.4 $(M+H)^+$, $C_{45}H_{60}N_9O_{11}$ requires 902.4.

7.15.11 Wilkinson's Hydrogenation of Saturated Cyclic 107:

Fmoc-c[Hag-Pro-sat(Sub)-Arg-Hag]-OH 108

108

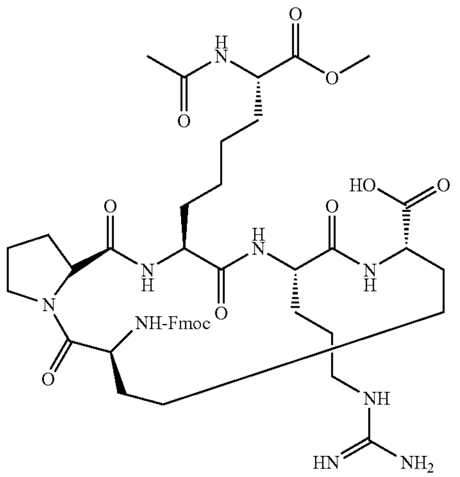

The resin-bound peptide 107a was subjected to the general Wilkinson's hydrogenation procedure (Section 7.4.4) under the following conditions: Resin-peptide 107a (15.0 mg, 13.5 μmol), DCM:MeOH (9:1, 5 mL), Wilkinson's catalyst, 80 psi $H_2$, 22° C., 22 h. At the end of the reaction period, a small aliquot of peptidyl-resin was subjected to the TFA-mediated cleavage procedure (Section 7.3.3). Mass spectral analysis of the isolated residue confirmed formation of the reduced cyclic pentapeptide 108. Mass spectrum ($ESI^+$, $MeCN/H_2O$): m/z 904.4 $(M+H)^+$, $C_{45}H_{62}N_9O_{11}$ requires 904.5.

7.15.12 Olefin Activation: Synthesis of Fmoc-Gly($CH_2CH{=}CHCH_2OAc$)-Phe-OH 145

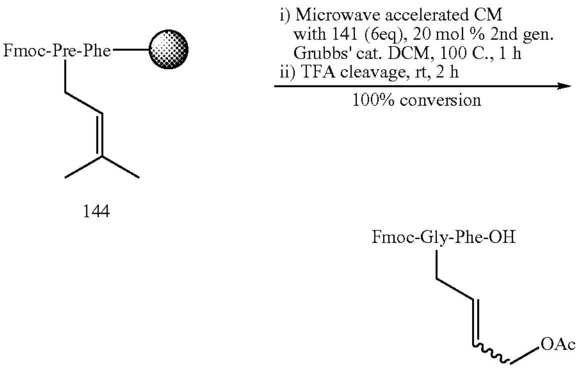

144

145

The resin-bound peptide Fmoc-Pre-Phe-Wang 144 was subjected to the microwave-assisted cross metathesis procedure (Section 7.5.3) with cis-1,4-diacetoxy-2-butene 141 under the following conditions: Resin (Wang)-peptide 144 (180 mg, 0.09 mmol), DCM (10 mL), $2^{nd}$ generation Grubbs' catalyst (16 mg, 20 mol %), cis-1,4-diacetoxy-2-butene (96 mg, 0.56 mmol, 15 psi), 100° C., 1 h. At the end of the reaction period, the peptidyl-resin was subjected to the TFA-mediated cleavage procedure (Section 7.3.3). Mass spectral analysis of the isolated residue indicated the presence of the desired dipeptide product 145 and no starting material. Mass spectral analysis of the isolated residue confirmed quantitative conversion to the activated peptide 145. Mass spectrum ($ESI^+$, $CH_3OH$): m/z 579.0 ($M+Na^+$) $C_{32}H_{32}N_2O_7Na$.

7.16 [2,8]-Dicarba-[3,12]-Cystino Conotoxin Transformations 7.16.1 Linear [2,8]-Hag-[3,12]-Cys Conotoxin ImI:

112

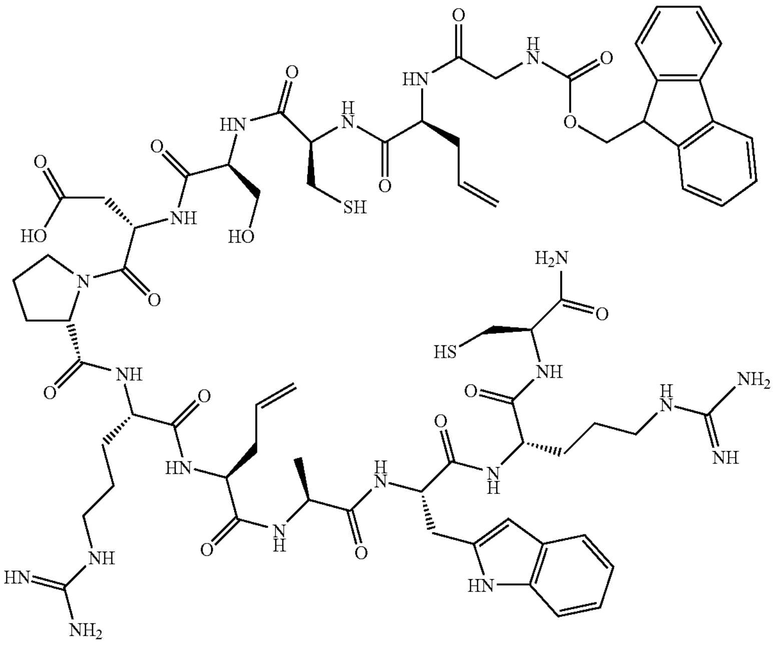

The procedure described in Section 7.3.2 was used for the attachment of the first amino acid, Fmoc-L-Cys(Trt)-OH, to Rink amide resin. Quantities of the resin and coupling reagents HATU and NMM are presented in Table 7.10. The first coupling reaction was shaken for 14 h.

TABLE 7.10

Quantities of Reagents used in the Synthesis of Peptide 112

| Reagent | Mass (mg) or Volume (μl) | Mole (mmol) |
|---|---|---|
| Rink Amide Resin | 740 mg | 0.39 |
| Fmoc-L-Cys(Trt)-OH | 676 mg | 1.15 |
| HATU | 293 mg | 0.77 |
| NMM | 255 μl | 2.31 |

The procedure outlined in Section 7.3.2.2 was also utilised for subsequent coupling reactions in the synthesis of the dodecapeptide 112. Quantities of the coupling agents HATU and NMM remained constant throughout the synthesis. The quantities of successive amino acids and their reaction durations are detailed in Table 7.11.

TABLE 7.11

Quantities of Amino Acids used in the Synthesis of Peptide 112

| Amino Acid | Mass (mg) | Mole (mmol) | Reaction Time (h)* |
|---|---|---|---|
| Fmoc-L-Arg(Pbf)-OH | 749 | 1.15 | 2.5 |
| Fmoc-L-Trp(Boc)-OH | 608 | 1.15 | 2.5 |
| Fmoc-L-Ala-OH | 360 | 1.16 | 14 |
| Fmoc-L-Hag-OH | 390 | 1.16 | 2.5 |
| Fmoc-L-Arg(Pbf)-OH | 750 | 1.16 | 2.5 |
| Fmoc-L-Pro-OH | 390 | 1.16 | 1 |
| Fmoc-L-Asp($^{t}$Bu)-OH | 475 | 1.15 | 14 |
| Fmoc-L-Ser($^{t}$Bu)-OH | 443 | 1.16 | 2.5 |
| Fmoc-L-Cys(Trt)-OH | 676 | 1.15 | 2.5 |

TABLE 7.11-continued

Quantities of Amino Acids used in the Synthesis of Peptide 112

| Amino Acid | Mass (mg) | Mole (mmol) | Reaction Time (h)* |
|---|---|---|---|
| Fmoc-L-Hag-OH | 390 | 1.16 | 2.5 |
| Fmoc-L-Gly-OH | 343 | 1.15 | 14 |

*Note: Reaction times have not been optimised.

After the final amino acid coupling, a small aliquot of peptidyl-resin was subjected to the TFA-mediated cleavage procedure (Section 7.3.3). Mass spectral analysis of the isolated residue confirmed formation of the dodecapeptide 112. Mass spectrum ($ESI^+$, $MeCN/H_2O$): m/z 783.5 $[½(M+2H)]^+$, $½(C_{71}H_{98}N_{20}O_{17}S_2)$ requires 783.3; m/z 1565.7 $(M+H)^+$, $C_{71}H_{97}N_{20}O_{17}S_2$ requires 1565.7. LC-MS (Luna C8 RP-column, 10-60% MeOH, 0.1% formic acid): $t_R$=8.86 min.

7.16.2 [2,8]-Dicarba-[3,12]-Cys Conotoxin ImI:

114

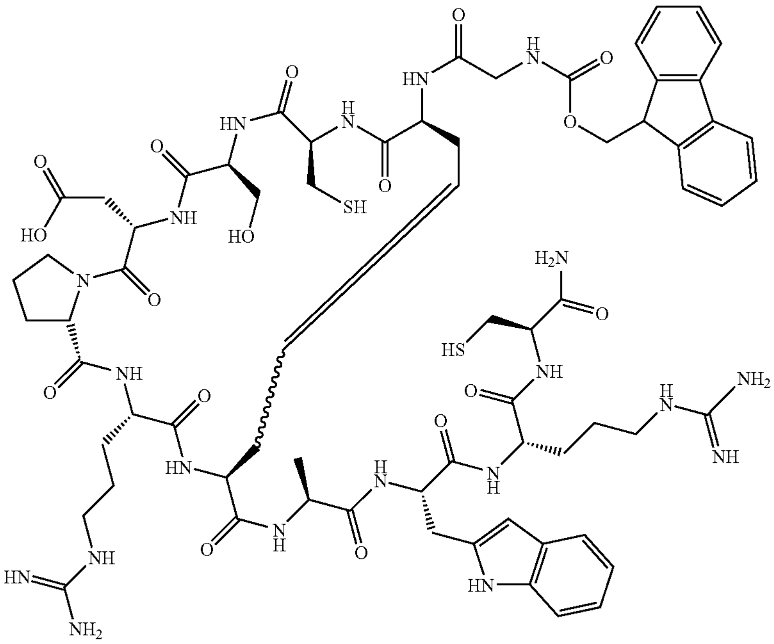

The resin-bound peptide was subjected to the general microwave-accelerated RCM procedure (Section 7.5.3) under the following conditions: Resin-peptide 112a (158 mg, 82.2 μmol), DCM (3 mL), LiCl/DMF (0.4 M, 0.3 mL), 2$^{nd}$ generation Grubbs' catalyst (7.0 mg, 8.2 μmol, 10 mol %), 100° C., 1 h, 100% conversion into 114. At the end of the reaction period, a small aliquot of peptidyl-resin was subjected to the TFA-mediated cleavage procedure (Section 7.3.3). Mass spectral analysis of the isolated residue confirmed formation of the cyclic peptide 114. Mass spectrum ($ESI^+$, $MeCN/H_2O$): m/z 769.4 $[½(M+2H)]^+$, $½(C_{69}H_{94}N_{20}O_{17}S_2)$ requires 769.3; m/z 1537.7 $(M+H)^+$, $C_{69}H_{93}N_{20}O_{17}S_2$ requires 1537.6. LC-MS (Luna C8 RP-column, 10-60% MeOH, 0.1% formic acid): $t_R$=8.59 min.

An analogous microwave-accelerated RCM reaction using 5 mol % 2$^{nd}$ generation Grubbs' catalyst was performed: Resin-peptide 112a (80.2 mg, 42 μmol), DCM (3 mL), LiCl/DMF (0.4 M, 0.3 mL), 2$^{nd}$ generation Grubbs' catalyst (7.0 mg, 2.1 μmol, 5 mol %), 100° C., 2 h, 100% conversion into 114. Mass spectral data were in agreement with those reported above.

7.16.3 [2,8]-Dicarba-[3,12]-Cystino Conotoxin ImI:

118

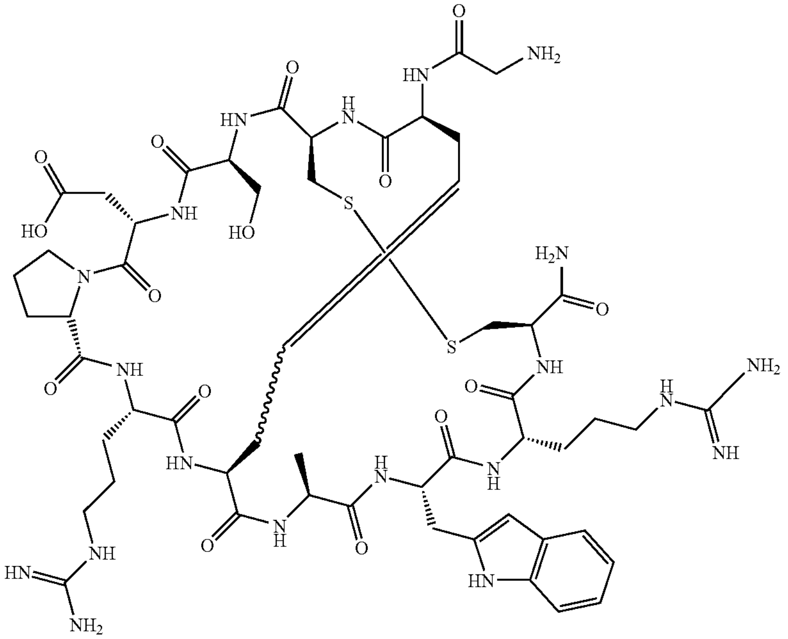

The Rink-amide bound peptide 114a (100 mg, 52.0 μmol) was swollen with DCM (3×1 min, 1×30 min) and DMF (3×1 min, 1×30 min) and deprotected with 20% piperidine/DMF (1×1 min, 2×20 min). The resin was then washed with DMF (5×1 min), DCM (3×1 min), MeOH (3×1 min) and dried on the SPPS manifold for 1 h. The Fmoc-deprotected peptidyl-resin (47.0 mg, 24.4 μmol) was subjected to the TFA-mediated cleavage procedure (Section 0). The residue was then lyophilised for 18 h to give the fully deprotected carbocyclic peptide 116 as a colourless solid (20.0 mg, 15.2 μmol). Mass spectrum (ESI$^+$, MeCN/$H_2O$): m/z 658.4 [½(M+2H)]$^+$, ½($C_{54}H_{84}N_{20}O_{15}S_2$) requires 658.3; m/z 1315.6 (M+H)$^+$, $C_{54}H_{83}N_{20}O_{15}S_2$ requires 1315.6. LC-MS (Luna C8 RP-column, 10-60% MeOH, 0.1% formic acid): $t_R$=5.63 min

116

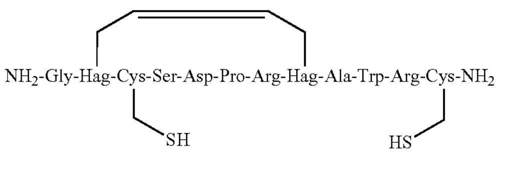

A sample of lyophilised peptide (10.1 mg, 7.7 μmol) was dissolved in an aqueous solution of $(NH_4)_2CO_3$ (0.1 M, 80 mL) containing 5% DMSO (4 mL). The reaction was stirred at room temperature and monitored by the Ellman's test (Section 7.3.4). After 3 d, the reaction mixture was lyophilised and mass spectral analysis of the isolated residue confirmed formation of the cysteine-oxidised peptide 118. The peptide was purified by RP-HPLC (Luna C8 RP-column, 10-60% MeOH, 0.1% formic acid) and the unsaturated [2,8]-dicarba-[3,12]-cystino conotoxin hybrid 118 was isolated as a colourless solid (1.8 mg, 5%) in >99% purity. Mass spectrum (ESI$^+$, MeCN/$H_2O$): m/z 657.4 [½(M+2H)]$^+$, ½($C_{54}H_{82}N_{20}O_{15}S_2$) requires 657.3; m/z 668.3 [½(M+H+ Na)]$^+$, ½($C_{54}H_{81}N_{20}NaO_{15}S_2$) requires 668.3; m/z 1313.5 (M+H)$^+$, $C_{54}H_{81}N_{20}O_{15}S_2$ requires 1313.6. LC-MS (Luna C8 RP-column, 10-60% MeOH, 0.1% formic acid): $t_R$=5.50 min.

7.16.4 [2,8]-Saturated Dicarba-[3,12]-Cystino Conotoxin ImI:

122

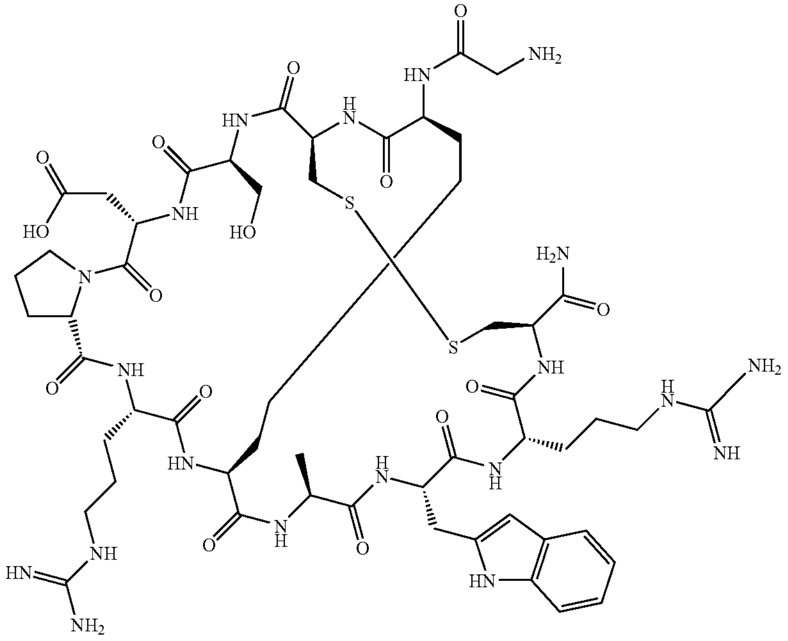

The resin-bound peptide 114a was subjected to the general Wilkinson's hydrogenation procedure (Section 7.4.4) under the following conditions: Resin-peptide 114a (285 mg, 0.15 mmol), DCM:MeOH (9:1, 5 mL), Wilkinson's catalyst, 80 psi $H_2$, 22° C., 22 h. At the end of the reaction period, a small aliquot of peptidyl-resin was Fmoc-deprotected (20% piperidine/DMF, 1×1 min, 2×10 min) and washed with DMF (5×1 min), DCM (5×1 min), MeOH (5×1 min) and dried on the SPPS manifold for 1 h. The Fmoc-deprotected peptidyl-resin was then subjected to the TFA-mediated cleavage procedure (Section 7.3.3). Mass spectral analysis of the isolated residue indicated the presence of a mixture of the cysteine-oxidised 122 and reduced 120 form of the saturated product. Mass spectrum (ESI$^+$, MeCN/$H_2O$): m/z 658.6 [½(M+2H)]$^+_{oxidised}$, ½($C_{54}H_{84}N_{20}O_{15}S_2$) requires 658.3; m/z 1315.7 (M+H)$^+_{oxidised}$, $C_{54}H_{83}N_{20}O_{15}S_2$ requires 1315.6; m/z 659.4 [½(M+2H)]$^+_{reduced}$, ½($C_{54}H_{86}N_{20}O_{15}S_2$) requires 659.3; m/z 1317.8 (M+H)$^+$ reduced, $C_{54}H_{85}N_{20}O_{15}S_2$ requires 1317.6. LC-MS (Luna C8 RP-column, 10-60% MeOH, 0.1% formic acid): $t_R$ (122)=6.01 min.

7.17 [3,12]-Dicarba-[2,8]-Cystino Conotoxin Transformations 7.17.1 Linear [2,8]-Cys-[3,12]-Hag Conotoxin IMI:

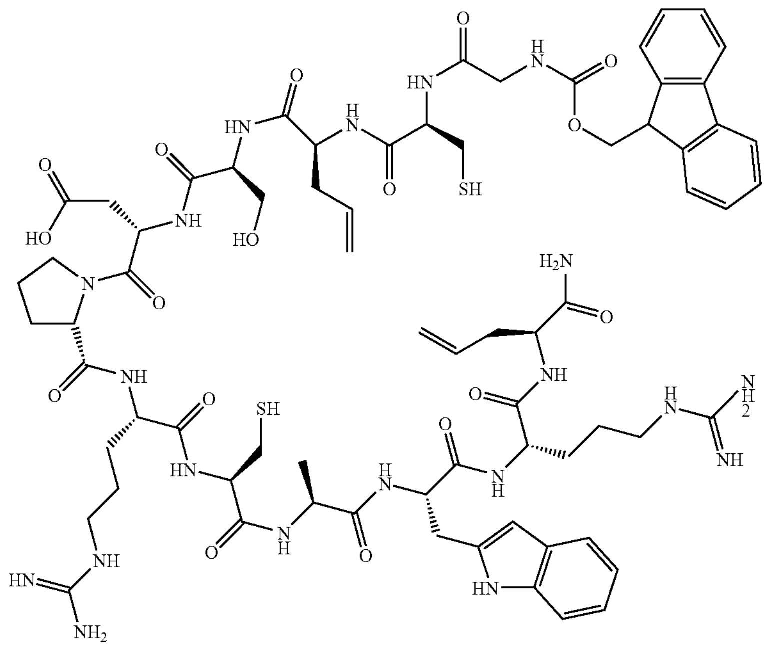

113

The procedure described in Section 7.3.2.2 was used for the attachment of the first amino acid, Fmoc-L-Hag-OH 96, to Rink amide resin. Quantities of the resin and coupling reagents HATU and NMM are presented in Table 7.12. The first coupling reaction was shaken for 14 h.

TABLE 7.12

Quantities of Reagents used in the Synthesis of Peptide 113

| Reagent | Mass (mg) or Volume (μl) | Mole (mmol) |
|---|---|---|
| Rink Amide Resin | 730 mg | 0.38 |
| Fmoc-L-Hag-OH | 384 mg | 1.14 |
| HATU | 289 mg | 0.76 |
| NMM | 250 μl | 2.27 |

The procedure outlined in Section 7.3.2.2 was also utilised for subsequent coupling reactions in the synthesis of the dodecapeptide 113. Quantities of the coupling agents HATU and NMM remained constant throughout the synthesis. The quantities of successive amino acids and their reaction durations are detailed in Table 7.13.

TABLE 7.13

Quantities of Amino Acids used in the Synthesis of Peptide 113

| Amino Acid | Mass (mg) | Mole (mmol) | Reaction Time (h)* |
|---|---|---|---|
| Fmoc-L-Arg(Pbf)-OH | 739 | 1.14 | 2.5 |
| Fmoc-L-Trp(Boc)-OH | 600 | 1.14 | 2.5 |
| Fmoc-L-Ala-OH | 355 | 1.14 | 14 |
| Fmoc-L-Cys(Trt)-OH | 667 | 1.14 | 2.5 |
| Fmoc-L-Arg(Pbf)-OH | 740 | 1.14 | 2.5 |
| Fmoc-L-Pro-OH | 385 | 1.14 | 1 |
| Fmoc-L-Asp($^t$Bu)-OH | 470 | 1.14 | 14 |
| Fmoc-L-Ser($^t$Bu)-OH | 437 | 1.14 | 2.5 |
| Fmoc-L-Hag-OH | 385 | 1.14 | 2.5 |
| Fmoc-L-Cys(Trt)-OH | 667 | 1.14 | 2.5 |
| Fmoc-L-Gly-OH | 340 | 1.14 | 14 |

*Note: Reaction times have not been optimised.

After the final amino acid coupling, a small aliquot of peptidyl-resin was subjected to the TFA-mediated cleavage procedure (Section 7.3.3). Mass spectral analysis of the isolated residue confirmed formation of the dodecapeptide 113. Mass spectrum (ESI$^+$, MeCN/$H_2O$): m/z 783.5 [½(M+2H)]$^+$, ½($C_{71}H_{98}N_{20}O_{17}S_2$) requires 783.3; m/z 1565.7 (M+H)$^+$, $C_{71}H_{97}N_{20}O_{17}S_2$ requires 1565.7. LC-MS (Luna C8 RP-column, 10-60% MeOH, 0.1% formic acid): $t_R$=9.13 min.

7.17.2[2,8]-Cys-[3,12]-Dicarba Conotoxin ImI:

115

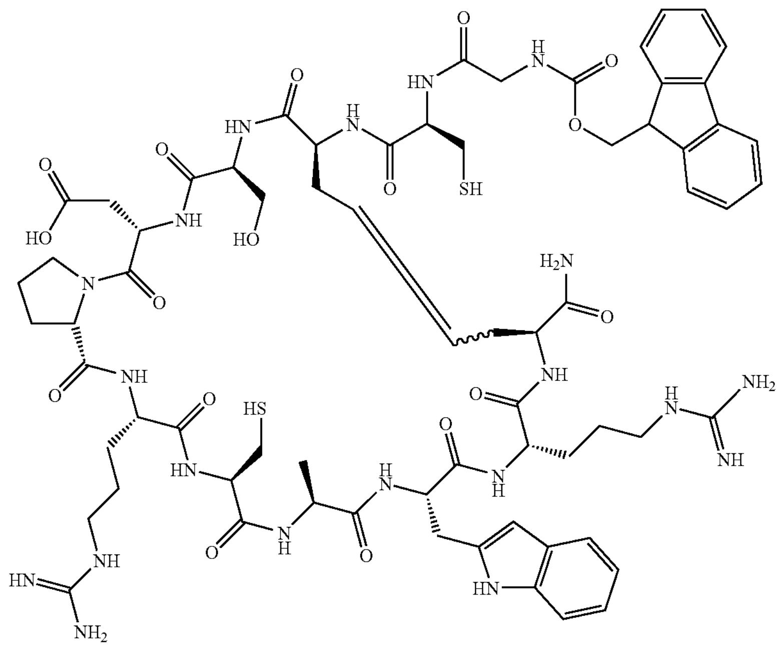

The resin-bound peptide 113a was subjected to the general microwave-accelerated RCM procedure (Section 7.5.3) under the following conditions: Resin-peptide 113a (840 mg, 0.44 mmol), DCM (5 mL), LiCl/DMF (0.4 M, 0.5 mL), 2nd generation Grubbs' catalyst (74.3 mg, 87,5 μmol, 20 mol %), 100° C., 1 h, 100% conversion into 115. At the end of the reaction period, a small aliquot of peptidyl-resin was subjected to the TFA-mediated cleavage procedure (Section 7.3.3). Mass spectral analysis of the isolated residue confirmed formation of the cyclic peptide 115. Mass spectrum (ESI$^+$, MeCN/$H_2O$): m/z 769.4 [½(M+2H)]$^+$, ½($C_{69}H_{94}N_{20}O_{17}S_2$) requires 769.3; m/z 1537.7 (M+H)$^+$, $C_{69}H_{93}N_{20}O_{17}S_2$ requires 1537.6. LC-MS (Luna C8 RP-column, 10-60% MeOH, 0.1% formic acid): $t_R$=8.99 min.

7.17.3 [2,8]-Cystino-[3,12]-Dicarba Conotoxin ImI:

119

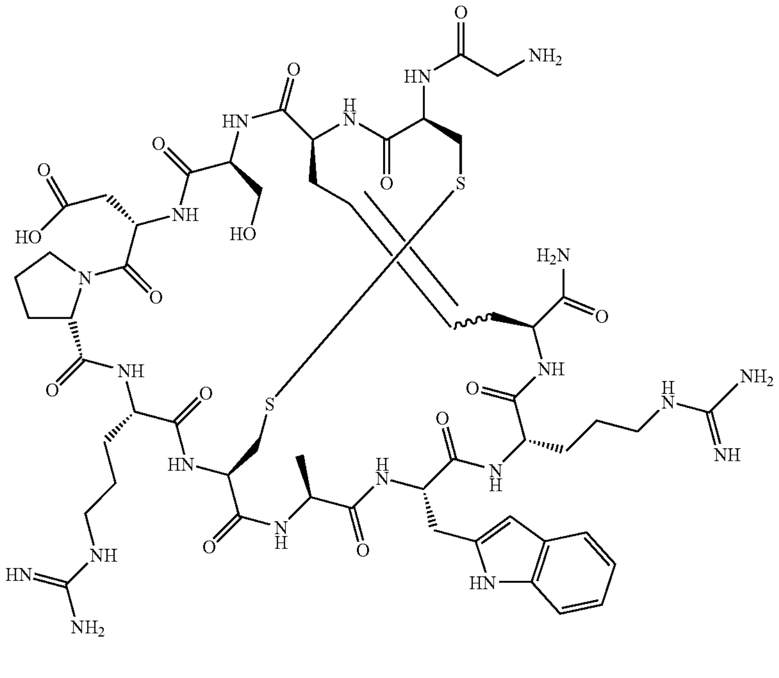

The resin-bound peptide 115a (100 mg, 52.0 μmol) was swollen with DCM (3×1 min, 1×30 min) and DMF (3×1 min, 1×30 min) and deprotected with 20% piperidine/DMF (1×1 min, 2×20 min). The resin was then washed with DMF (5×1 min), DCM (3×1 min), MeOH (3×1 min) and dried on the SPPS manifold for 1 h. The Fmoc-deprotected peptidyl-resin (61.7 mg, 32.1 μmol) was subjected to the TFA-mediated cleavage procedure (Section 7.3.3). The residue was then lyophilised for 18 h to give the fully deprotected carbocyclic peptide 117 as a colourless solid (15.1 mg, 11.5 μmol). Mass spectrum ($ESI^+$, $MeCN/H_2O$): m/z 658.4 $[½(M+2H)]^+$, ½($C_{54}H_{84}N_{20}O_{15}S_2$) requires 658.3; m/z 669.4 $[½(M+H+Na)]^+$, ½($C_{54}H_{84}N_{20}O_{15}S_2$) requires 669.4; m/z 1315.6 $(M+H)^+$, $C_{54}H_{83}N_{20}O_{15}S_2$ requires 1315.6. LC-MS (Luna C8 RP-column, 10-60% MeOH, 0.1% formic acid): $t_R$=6.62 min.

117

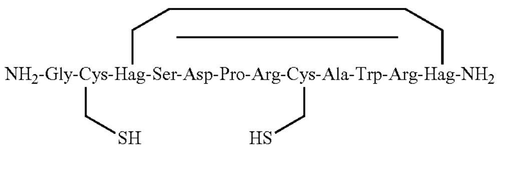

A sample of lyophilised peptide (11.2 mg, 8.5 μmol) was dissolved in an aqueous solution of $(NH_4)_2CO_3$ (0.1 M, 80 mL) containing 5% DMSO (4 mL). The reaction was stirred at room temperature and monitored by the Ellman's test. After 3 d, the reaction mixture was lyophilised and mass spectral analysis of the isolated residue confirmed formation of the cysteine-oxidised peptide 119. The peptide was purified by RP-HPLC (Luna C8 RP-column, 10-60% MeOH, 0.1% formic acid) and the unsaturated [2,8]-cystino-[3,12]-dicarba conotoxin hybrid 119 was isolated as a colourless solid (2.3 mg, 5%) in >99% purity. Mass spectrum ($ESI^+$, $MeCN/H_2O$): m/z 657.3 $[½(M+2H)]^+$, ½($C_{54}H_{82}N_{20}O_{15}S_2$) requires 657.3; m/z 668.3 $[½(M+H+Na)]^+$, ½($C_{54}H_{81}N_{20}NaO_{15}S_2$) requires 668.3; m/z 1313.6 $(M+H)^+$, $C_{54}H_{81}N_{20}O_{15}S_2$ requires 1313.6. LC-MS (Luna C8 RP-column, 10-60% MeOH, 0.1% formic acid): $t_R$=4.46 min.

7.17.4 [2,8]-Cystino-[3,12]-Saturated Dicarba Conotoxin ImI:

123

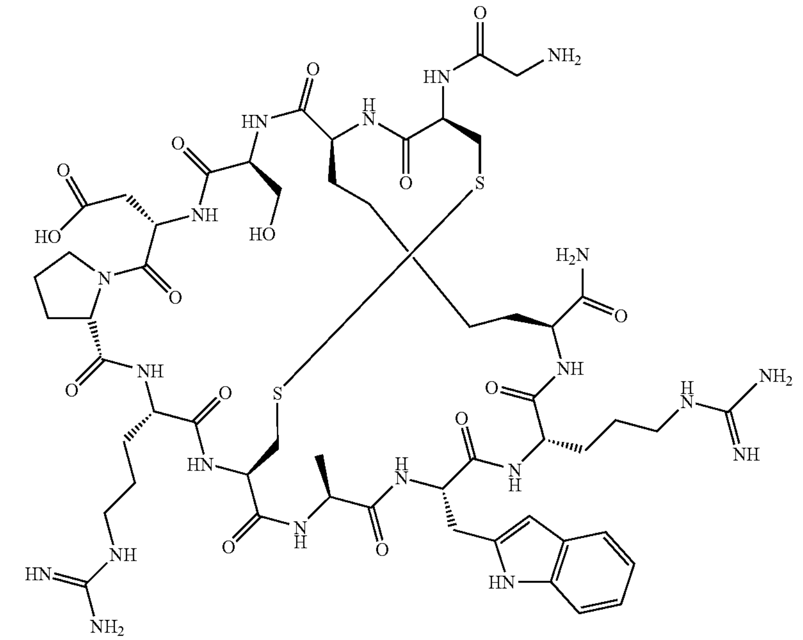

The resin-bound peptide 119a was subjected to the general Wilkinson's hydrogenation procedure (Section 7.4.4) under the following conditions: Resin-peptide 119a (320 mg, 0.17 mmol), DCM:MeOH (9:1, 5 mL), Wilkinson's catalyst, 80 psi $H_2$, 22° C., 22 h. At the end of the reaction period, a small aliquot of peptidyl-resin was Fmoc-deprotected (20% piperidine/DMF, 1×1 min, 2×10 min) and washed with DMF (5×1 min), DCM (5×1 min), MeOH (5×1 min) and dried on the SPPS manifold for 1 h. The Fmoc-deprotected peptidyl-resin was then subjected to the TFA-mediated cleavage procedure (Section 7.3.3). Mass spectral analysis of the isolated residue indicated the presence of a mixture of the cysteine-oxidised 123 and reduced 121 form of the saturated product. Mass spectrum ($ESI^+$, $MeCN/H_2O$): m/z 658.5 $[½(M+2H)]^+_{oxidised}$, ½($C_{54}H_{84}N_{20}O_{15}S_2$) requires 658.3; m/z 1315.7 $(M+H)^+$ oxidised, $C_{54}H_{83}N_{20}O_{15}S_2$ requires 1315.6; m/z 659.3 $[½(M+2H)]^+_{reduced}$, ½($C_{54}H_{86}N_{20}O_{15}S_2$) requires 659.3; m/z 1317.6 $(M+H)^+$ reduced, $C_{54}H_{85}N_{20}O_{15}S_2$ requires 1317.6. LC-MS (Luna C8 RP-column, 10-60% MeOH, 0.1% formic acid): $t_R$ (123)=7.02 min.

7.18 [2,8]-[3,12]-Dicarba Conotoxin Transformations 7.18.1 Linear [2,8]-Hag-[3,12]-Pre Conotoxin ImI:

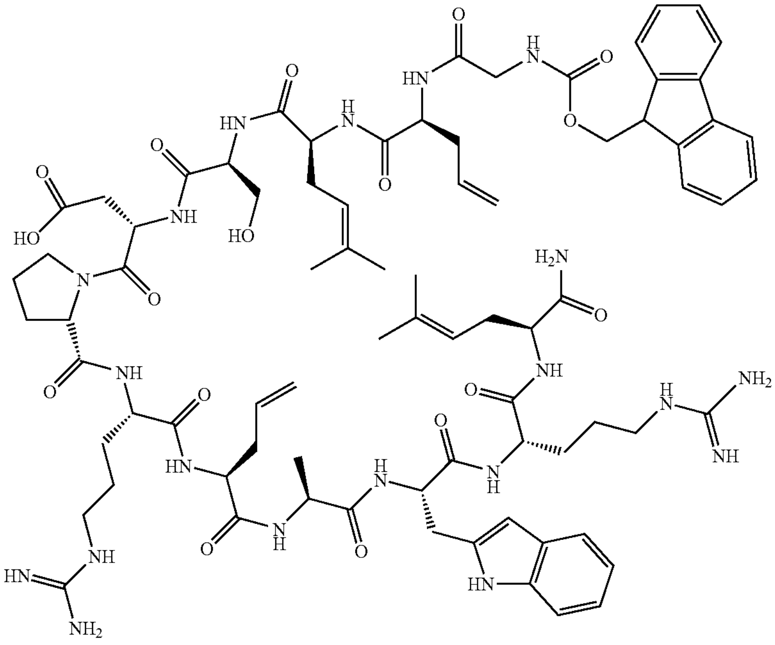

127

The procedure described in Section 7.3.2.2 was used for the attachment of the first amino acid, Fmoc-L-Pre-OH 92, to Rink amide resin. Quantities of the resin and coupling reagents HATU and NMM are presented in Table 7.14. The first coupling reaction was shaken for 4 h.

TABLE 7.14

Quantities of Reagents used in the Synthesis of Peptide 127

| Reagent | Mass (mg) or Volume (μl) | Mole (mmol) |
|---|---|---|
| Rink Amide Resin | 610 mg | 0.32 |
| Fmoc-L-Pre-OH | 350 | 0.96 |
| HATU | 241 mg | 0.63 |
| NMM | 210 μl | 1.91 |

The procedure outlined in Section 7.3.2.2 was also utilised for subsequent coupling reactions in the synthesis of the dodecapeptide 127. The quantities of successive amino acids and their reaction durations are detailed in Table 7.15.

TABLE 7.15

Quantities of Amino Acids used in the Synthesis of Peptide 127

| Amino Acid | Mass (mg) | Mole (mmol) | Reaction Time (h)* |
|---|---|---|---|
| Fmoc-L-Arg(Pbf)-OH | 617 | 0.95 | 12 |
| Fmoc-L-Trp(Boc)-OH | 502 | 0.95 | 2.5 |
| Fmoc-L-Ala-OH | 297 | 0.95 | 2.5 |

TABLE 7.15-continued

Quantities of Amino Acids used in the Synthesis of Peptide 127

| Amino Acid | Mass (mg) | Mole (mmol) | Reaction Time (h)* |
|---|---|---|---|
| Fmoc-L-Hag-OH | 321 | 0.95 | 2.5 |
| Fmoc-L-Arg(Pbf)-OH | 617 | 0.95 | 14 |
| Fmoc-L-Pro-OH | 321 | 0.95 | 4 |
| Fmoc-L-Asp($^t$Bu)-OH | 392 | 0.95 | 2.5 |
| Fmoc-L-Ser($^t$Bu)-OH | 365 | 0.95 | 2.5 |
| Fmoc-L-Pre-OH | 350 | 0.96 | 12 |
| Fmoc-L-Hag-OH | 322 | 0.95 | 2.5 |
| Fmoc-L-Gly-OH | 285 | 0.96 | 2.5 (1) |

*Note: Reaction times have not been optimised.

After the final amino acid coupling, a small aliquot of peptidyl-resin was subjected to the TFA-mediated cleavage procedure (Section 7.3.3). Mass spectral analysis of the isolated residue confirmed formation of the dodecapeptide 127. Mass spectrum ($ESI^+$, $MeCN/H_2O$): m/z 805.6 [½(M+2H)]$^+$, ½($C_{79}H_{110}N_{20}O_{17}$) requires 805.4; m/z 814.6 [½(M+$H_2O$+2H)]$^+$, ½($C_{79}H_{112}N_{20}O_{18}$) requires 814.4.

7.18.2 [2,8]-Dicarba-[3,12]-Pre Conotoxin ImI:

129

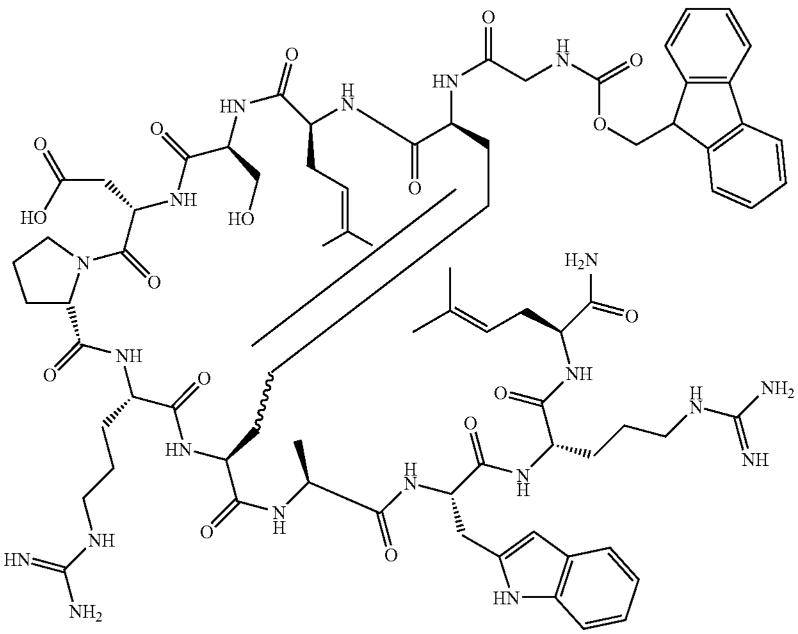

Method A: The Rink amide-bound peptide 127a was subjected to the conventional RCM procedure (Section 7.5.2) under the following conditions: Resin-peptide 127a (165 mg, 0.12 mmol), DCM (5 mL), LiCl/DMF (0.4 M, 0.5 mL), $2^{nd}$ generation Grubbs' catalyst (39.9 mg, 47.0 µmol, 40 mol %), 50° C., 40 h, 100% conversion into 129. At the end of the reaction period, a small aliquot of peptidyl-resin was subjected to the TFA-mediated cleavage procedure (Section 7.3.3). Mass spectral analysis of the isolated residue confirmed formation of the cyclic peptide 129. Mass spectrum ($ESI^+$, $MeCN/H_2O$): m/z 791.4 [½(M+2H)]$^+$, ½($C_{77}H_{106}N_{20}O_{17}$) requires 791.4. m/z 800.5 [½(M+$H_2O$+2H)]$^+$, ½($C_{77}H_{108}N_{20}O_{18}$) requires 800.4.

Method B: The Rink amide-bound peptide 127a was subjected to the general microwave-accelerated RCM procedure (Section 7.5.3) under the following conditions: Resin-peptide 127a (127 mg, 66.0 µmol), DCM (5 mL), LiCl/DMF (0.4 M, 0.5 mL), $2^{nd}$ generation Grubbs' catalyst (5.6 mg, 6.6 mmol, 10 mol %), 100° C., 1 h, 100% conversion into 129. At the end of the reaction period, a small aliquot of peptidyl-resin was subjected to the TFA-mediated cleavage procedure (Section 7.3.3). Mass spectral analysis of the isolated residue confirmed formation of the cyclic peptide 129. Mass spectrum ($ESI^+$, $MeCN/H_2O$): m/z 791.5 [½(M+2H)]$^+$, ½($C_{77}H_{106}N_{20}O_{17}$) requires 791.4.

7.18.3 [2,8]-Saturated Dicarba-[3,12]-Pre Conotoxin ImI:

133

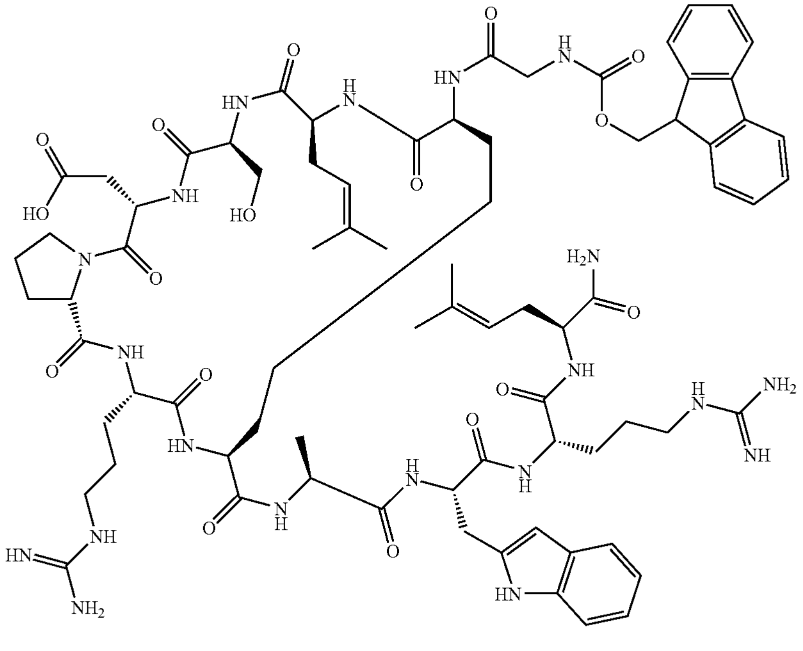

The resin-bound peptide 129a was subjected to the general Wilkinson's hydrogenation procedure (Section 7.4.4) under the following conditions: Resin-peptide 129a (130 mg, 91.0 μmol), DCM:MeOH (9:1, 6.5 mL), Wilkinson's catalyst, 80 psi $H_2$, 22° C., 24 h. At the end of the reaction period, a small aliquot of peptidyl-resin was subjected to the TFA-mediated cleavage procedure (Section 7.3.3). Mass spectral analysis of the isolated residue confirmed formation of the selectively hydrogenated cyclic dodecapeptide 133. Mass spectrum ($ESI^+$, MeCN/$H_2O$): m/z 792.5 $[½(M+2H)]^+$, $½(C_{77}H_{108}N_{20}O_{17})$ requires 792.4; m/z 801.4 $[½(M+H_2O+2H)]^+$, $½(C_{77}H_{10}N_{20}O_{18})$ requires 801.4.

7.18.4 Olefin Activation: [2,8]-Saturated Dicarba-[3,12]-Act† Conotoxin ImI:

† Act=Activated sidechain, i.e. crotylglycine (Crt) or allylglycine (Hag).

desired butenolysis product 135. No starting material was evident, however, low intensity doubly charged higher homologue species separated by m/z+7 units were observed.

Mass spectrum ($ESI^+$, MeCN/$H_2O$): m/z 778.4 $[½(M+2H)]^+_{product}$, $½(C_{75}H_{104}N_{20}O_{17})$ requires 778.4. Low intensity higher homologue species at m/z 785.4, 793.5, 800.4; Very low intensity peaks at m/z 807.8, 814.3, 821.3, 828.1, 835.7, 842.6, 849.8, 856.1, 863.6.

Method B: Resin-peptide 133a (20.0 mg, 10.4 μmol), DCM (3 mL), LiCl/DMF (0.3 mL), 2d generation Grubbs' catalyst (1.0 mg, 1.2 μmol, 10 mol %), cis-2-butene (20 psi), 50° C., 62 h. At the end of the reaction period, a small aliquot of peptidyl-resin was subjected to the TFA-mediated cleavage procedure (Section 7.3.3). Mass spectral analysis of the isolated residue indicated the presence of the desired product

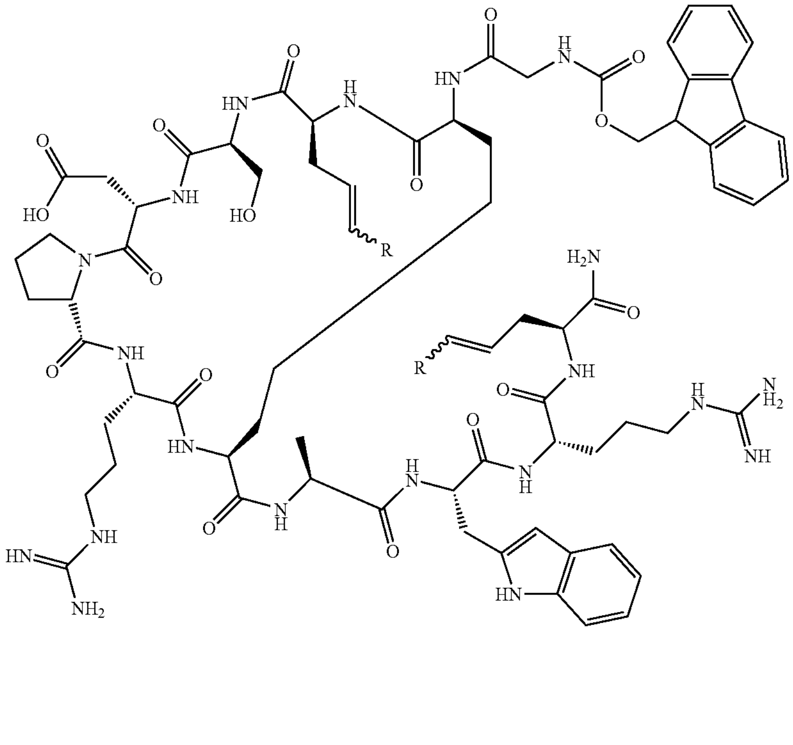

135 R = Me
145 R = H

The resin-bound peptide 133a was subjected to the general cross metathesis procedure with cis-2-butene (Section 7.5.4) under the following conditions:

Method A: Resin-peptide 133a (76.0 mg, 55.5 μmol), DCM (5 mL), $2^{nd}$ generation Grubbs' catalyst (24.0 mg, 28.3 μmol, 50 mol %), cis-2-butene (15 psi), benzoquinone (6.2 mg, 57.4 μmol), 50° C., 38 h. At the end of the reaction period, a small aliquot of peptidyl-resin was subjected to the TFA-mediated cleavage procedure (Section 7.3.3). Mass spectral analysis of the isolated residue indicated the presence of the 135, a partially metathesised peptide (mono-crotylglycine containing peptide) 136 and the starting peptide 133. Mass spectrum ($ESI^+$, MeCN/$H_2O$): m/z 778.4 $[½(M+2H)]^+_{product}$, $½(C_{75}H_{104}N_{20}O_{17})$ requires 778.4. m/z 785.5 $[½(M+2H)]^+_{136}$, $½(C_{76}H_{106}N_{20}O_{17})$; m/z 792.4 $[½(M+2H)]^+_{133}$, $½(C_{77}H_{108}N_{20}O_{17})$; m/z 801.4 $[½(M+H_2O+2H)]^{+\,133}$, $½(C_{77}H_{110}N_{20}O_{18})$.

Method C: Resin-peptide 133a (35.0 mg, 18 μmol), DCM (5 mL), LiCl/DMF (0.5 mL), $2^{nd}$ generation Grubbs' catalyst (6.2 mg, 7.3 μmol, 40 mol %), cis-2-butene (20 psi), 50° C., 24 h. At the end of the reaction period, a small aliquot of peptidyl-resin was subjected to the TFA-mediated cleavage procedure (Section 7.3.3). Mass spectral analysis of the isolated residue indicated the presence of the desired product 135, a partially metathesised peptide (mono-crotylglycine containing peptide) 136 and the starting peptide 133. Mass spectral data were consistent with those reported above (Method B).

An analogous reaction was performed for 62 h under the following conditions: Resin-peptide 133a (30.2 mg, 15.7 μmol), DCM (5 mL), LiCl/DMF (0.5 mL), 2$^{nd}$ generation Grubbs' catalyst (6.2 mg, 7.3 μmol, 40 mol %), cis-2-butene (20 psi), 50° C., 62 h. At the end of the reaction period, a small aliquot of peptidyl-resin was subjected to the TFA-mediated cleavage procedure (Section 7.3.3). Mass spectral analysis of the isolated residue indicated the presence of the desired product 135, a partially metathesised peptide 136 and the starting peptide 133. Mass spectral data were consistent with those previously reported (Method B).

The resin-bound peptide 133a was subjected to the general cross metathesis procedure with ethylene (Section 7.5.4) under the following conditions:

Method D: Resin-peptide 133a (42.0 mg, 21.8 μmol), DCM (5 mL), LiCl/DMF (0.5 mL), 2$^{nd}$ generation Grubbs' catalyst (7.5 mg, 8.8 μmol, 40 mol %), ethylene (60 psi), 50° C., 62 h. At the end of the reaction period, a small aliquot of peptidyl-resin was subjected to the TFA-mediated cleavage procedure (Section 7.3.3). Mass spectral analysis of the isolated residue indicated the presence of the starting peptide 133 and a partially metathesised peptide (mono-allylglycine containing peptide) 137. Mass spectrum (ESI$^+$, MeCN/$H_2O$): m/z 778.4 [½(M+2H)]$^+_{137}$, ½($C_{75}H_{104}N_{20}O_{17}$); m/z 792.4 [½(M+2H)]$^+_{133}$.

An analogous reaction was performed in the absence of the chaotropic salt (LiCl) under the following conditions: Resin-peptide 133a (68.0 mg, 35.4 μmol), DCM (5 mL), 2$^{nd}$ generation Grubbs' catalyst (12.0 mg, 14.1 μmol, 40 mol %), ethylene (60 psi), 50° C., 62 h. At the end of the reaction period, a small aliquot of peptidyl-resin was subjected to the TFA-mediated cleavage procedure (Section 7.3.3). Mass spectral analysis of the isolated residue indicated the presence of the starting peptide 133 and a partially metathesised peptide (mono-allylglycine containing peptide) 137. Mass spectral data were consistent with those reported above.

7.18.5 [2,8]-Saturated Dicarba-[3,12]-Dicarba Conotoxin ImI:

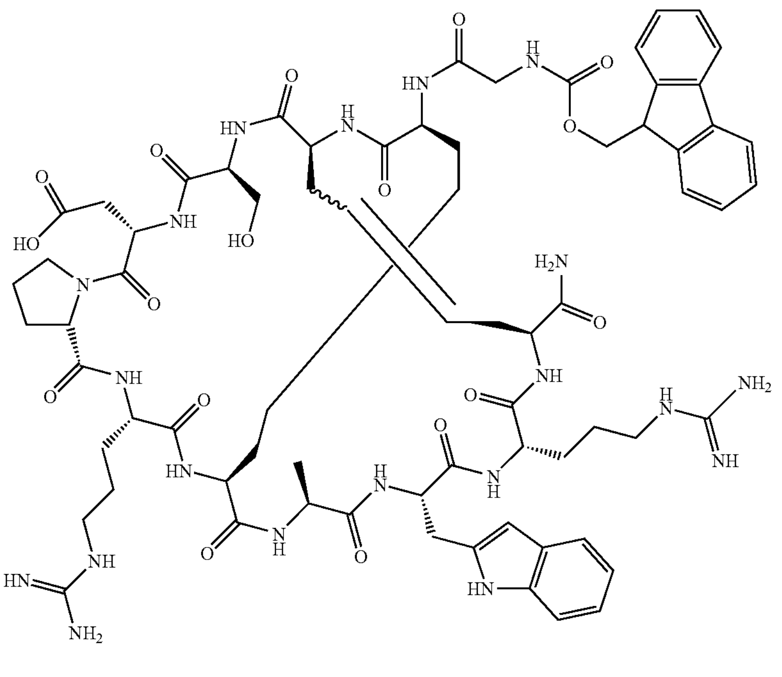

140

The Rink amide-bound peptide 135a was subjected to the general microwave-accelerated RCM procedure (Section 7.5.3) under the following conditions: Resin-peptide 135a (20.0 mg, 14.0 μmol), DCM (5 mL), LiCl/DMF (0.4 M, 0.5 mL), 2$^{nd}$ generation Grubbs' catalyst (2.4 mg, 2.8 μmol, 20 mol %), 100° C., 1 h. At the end of the reaction period, a small aliquot of peptidyl-resin was subjected to the TFA-mediated cleavage procedure (Section 7.3.3). LC-MS analysis of the isolated residue supported formation of the bicyclic peptide 140. LC-MS (Luna C8 RP-column, 10-60% MeOH, 0.1% formic acid): $t_R$=9.18 min, m/z 750.4 [½(M+2H)]$^+$, ½($C_{71}H_{94}N_{20}O_{17}$) requires 750.4.

7.18.6 Attempted Synthesis of [2,8]-[3,12]-Saturated Bis-Dicarba Conotoxin

126

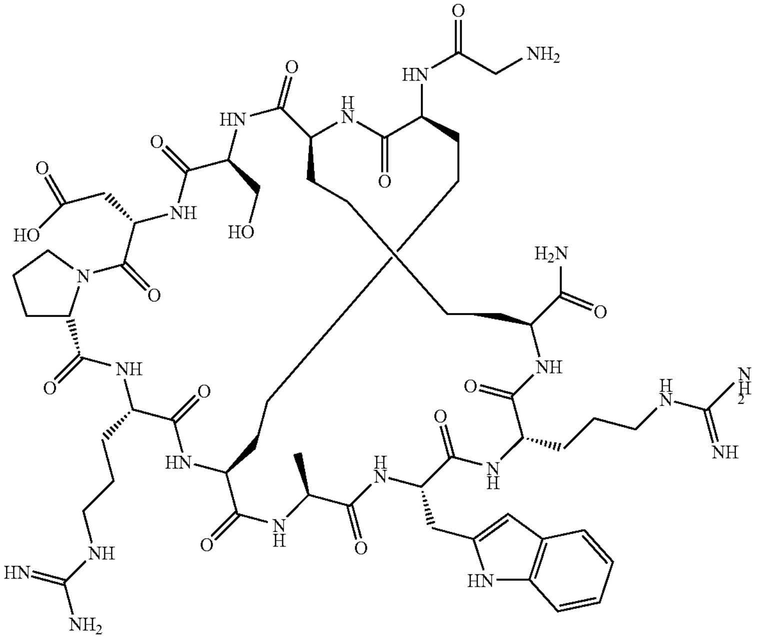

The resin-bound peptide 140a was subjected to the general Wilkinson's hydrogenation procedure (Section 7.4.4) under the following conditions: Resin-peptide 140a (12.2 mg, 8.5 μmol), DCM:MeOH (9:1, 6.5 mL), Wilkinson's catalyst, 80 psi $H_2$, 22° C., 24 h. At the end of the reaction period, a small aliquot of peptidyl-resin was Fmoc-deprotected with 20% piperidine/DMF (1×1 min, 2×20 min). The resin was then washed with DMF (5×1 min), DCM (3×1 min), MeOH (3×1 min) and dried on the SPPS manifold for 1 h. The Fmoc-deprotected peptidyl-resin was then subjected to the TFA-mediated cleavage procedure (Section 7.3.3). Mass spectral and LC-MS data of the isolated residue were inconclusive. The mass spectrum and LC-traces did not display peaks due to the fully deprotected starting peptide 125 and the target saturated bicycle 126. Lack of material and time constraints did not allow us to investigate this chemistry further.

7.19 [2,8]-[3,12]-Dicarba Conotoxin Transformations 7.19.1 Linear [2,8]-Pre-[3,12]-Hag Conotoxin ImI:

128

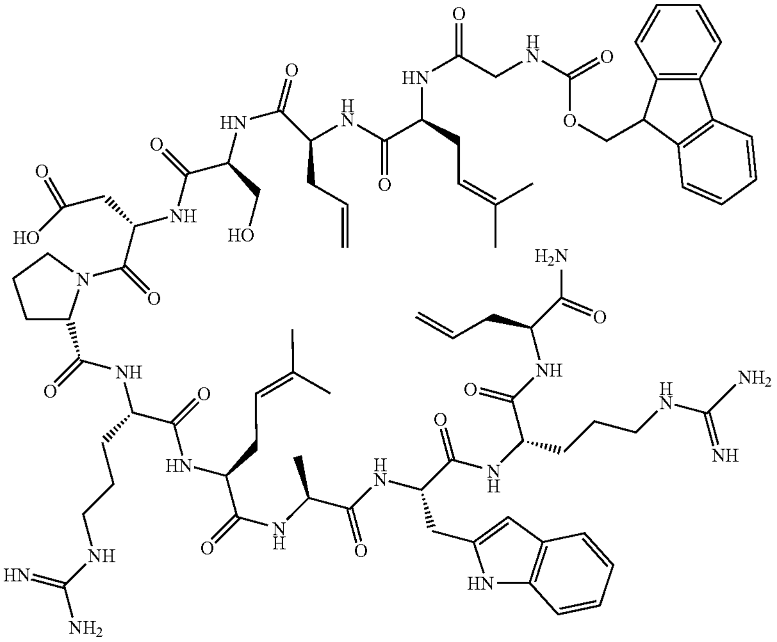

The procedure described in Section 7.3.2.2 was used for the attachment of the first amino acid, Fmoc-L-Hag-OH 96, to Rink amide resin. Quantities of the resin and coupling reagents HATU and NMM are presented in Table 7.16. The first coupling reaction was shaken for 12 h.

TABLE 7.16

Quantities of Reagents used in the Synthesis of Peptide 128

| Reagent | Mass (mg) or Volume (μl) | Mole (mmol) |
|---|---|---|
| Rink Amide Resin | 705 mg | 0.37 |
| Fmoc-L-Hag-OH | 371 mg | 1.10 |
| HATU | 280 mg | 0.74 |
| NMM | 245 μl | 2.22 |

TABLE 7.17-continued

Quantities of Amino Acids used in the Synthesis of Peptide 128

| Amino Acid | Mass (mg) | Mole (mmol) | Reaction Time (h)* |
|---|---|---|---|
| Fmoc-L-Pre-OH | 402 | 1.10 | 2.5 |
| Fmoc-L-Gly-OH | 328 | 1.10 | 2 (12) |

*Note: Reaction times have not been optimised.

After the final amino acid coupling, a small aliquot of peptidyl-resin was subjected to the TFA-mediated cleavage procedure (Section 7.3.3). Mass spectra analysis of the isolated residue confirmed formation of the dodecapeptide 128. Mass spectrum (ESI$^+$, MeCN/$H_2O$): m/z 805.6 [½(M+2H)]$^+$, ½($C_{79}H_{10}N_{20}O_{17}$) requires 805.4; m/z 816.6 [½(M+Na$^+$H)]$^+$, ½($C_{79}H_{110}N_{20}NaO_{18}$) requires 816.4.

7.19.2 [2,8]-Pre-[3,12]-Dicarba Conotoxin ImI:

132

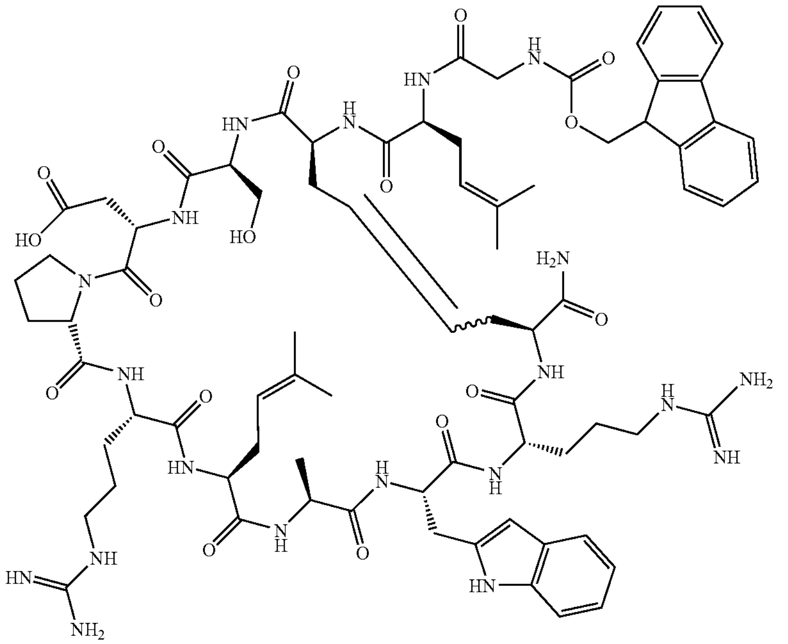

The procedure outlined in Section 7.3.2.2 was also utilised for subsequent coupling reactions in the synthesis of the dodecapeptide 128. The quantities of successive amino acids and their reaction durations are detailed in Table 7.17.

TABLE 7.17

Quantities of Amino Acids used in the Synthesis of Peptide 128

| Amino Acid | Mass (mg) | Mole (mmol) | Reaction Time (h)* |
|---|---|---|---|
| Fmoc-L-Arg(Pbf)-OH | 715 | 1.10 | 2.5 |
| Fmoc-L-Trp(Boc)-OH | 580 | 1.10 | 2.5 |
| Fmoc-L-Ala-OH | 343 | 1.10 | 2.5 |
| Fmoc-L-Pre-OH | 402 | 1.10 | 12 |
| Fmoc-L-Arg(Pbf)-OH | 715 | 1.10 | 2.5 |
| Fmoc-L-Pro-OH | 371 | 1.10 | 2.5 |
| Fmoc-L-Asp($^t$Bu)-OH | 453 | 1.10 | 2.5 |
| Fmoc-L-Ser($^t$Bu)-OH | 422 | 1.10 | 12 |
| Fmoc-L-Hag-OH | 371 | 1.10 | 2.5 |

Method A: The resin-bound peptide 128a was subjected to the conventional RCM procedure (Section 7.5.2) under the following conditions: Resin-peptide 128a (19.7 mg, 10.2 μmol), DCM (3 mL), LiCl/DMF (0.4 M, 0.3 mL), 2$^{nd}$ generation Grubbs' catalyst (3.5 mg, 4.1 mol, 40 mol %), 50° C., 40 h. At the end of the reaction period, a small aliquot of peptidyl-resin was subjected to the TFA-mediated cleavage procedure (Section 7.3.3). Mass spectral analysis of the isolated residue indicated recovery of the linear peptide 132. Mass spectrum (ESI$^+$, MeCN/$H_2O$): m/z 805.6 [½(M+2H)]$^+_{linear}$, ½($C_{79}H_{110}N_{20}O_{17}$).

Method B: The resin-bound peptide 128a was subjected to the general microwave-accelerated RCM procedure (Section 7.5.3) under the following conditions: Resin-peptide 128a (550 mg, 0.29 mmol), DCM (5 mL), LiCl/DMF (0.4 M, 0.5 mL), 2$^{nd}$ generation Grubbs' catalyst (49.0 mg, 57.7 μmol, 20 mol %), 100° C., 1 h, 100% conversion into 132. At the end of the reaction period, a small aliquot of peptidyl-resin was subjected to the TFA-mediated cleavage procedure (Section 7.3.3). Mass spectral analysis of the isolated residue confirmed formation of the cyclic peptide 132. Mass spectrum ($ESI^+$, $MeCN/H_2O$): m/z 791.4 $[\frac{1}{2}(M+2H)]^+$, $\frac{1}{2}(C_{77}H_{106}N_{20}O_{17})$ requires 791.4.

9.3 [3,12]-Pre-[2,8]-Saturated Dicarba Conotoxin:

aliquot of peptidyl-resin was subjected to the TFA-mediated cleavage procedure (Section 7.3.3). Mass spectral analysis of the isolated residue confirmed formation of the selectively hydrogenated cyclic peptide 134. Mass spectrum ($ESI^+$,

134

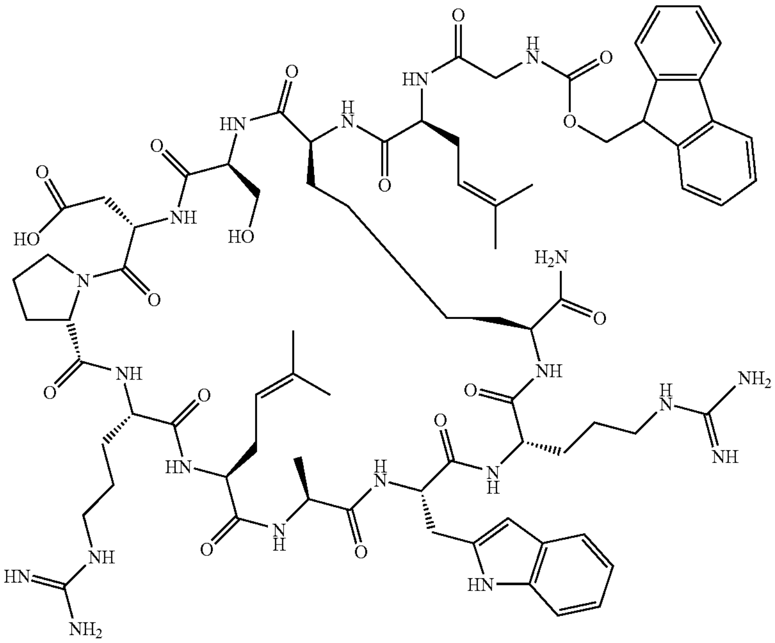

The resin-bound peptide 132a was subjected to the general Wilkinson's hydrogenation procedure (Section 7.4.4) under the following conditions: Resin-peptide 132a (365 mg, 0.19 mmol), DCM:MeOH (9:1, 5 mL), Wilkinson's catalyst, 80 psi $H_2$, 22° C., 19 h. At the end of the reaction period, a small $MeCN/H_2O$): m/z 792.5 $[\frac{1}{2}(M+2H)]^+$, $\frac{1}{2}(C_{77}H_{108}N_{20}O_{17})$ requires 792.4; m/z 801.4 $[\frac{1}{2}(M+H_2O+2H)]^+$, $\frac{1}{2}(C_{77}H_{110}N_{20}O_{18})$ requires 801.4.

7.19.4 Attempted Synthesis of Fmoc-Gly-Crt-c[Hag-Ser-Asp-Pro-Arg-Crt-Ala-Trp-Arg-Hag]-$NH_2$ 138

138

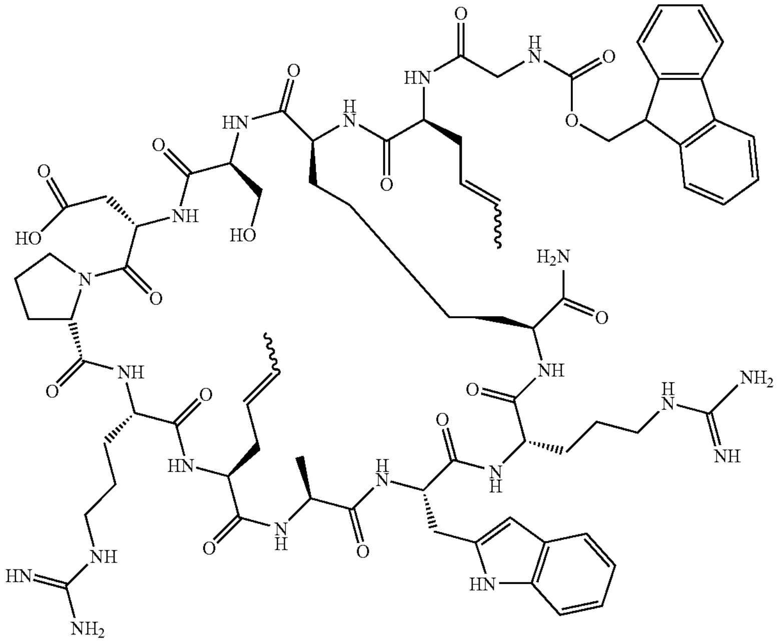

The resin-bound peptide 134a was subjected to the conventional cross metathesis procedure with cis-2-butene (Section 7.5.4) under the following conditions:

Method A: Resin-peptide 134a (78.5 mg, 41 μmol), DCM (5 mL), 2$^{nd}$ generation Grubbs' catalyst (13.9 mg, 16 μmol, 40 mol %), cis-2-butene (15 psi), 50° C., 62 h. At the end of the reaction period, a small aliquot of peptidyl-resin was subjected to the TFA-mediated cleavage procedure (Section 7.3.3). Mass spectral analysis of the isolated residue indicated the presence of a mixture of peptides: the starting peptide 134, the desired product 138 and a partially metathesised peptide (mono-butenolysis product) 139. Mass spectrum (ESI$^+$, MeCN/$H_2O$): m/z 778.5 [½(M+2H)]$^+$ $_{product}$, ½($C_{75}H_{104}N_{20}O_{17}$) requires 778.4; m/z 785.5 [½(M+2H)]$^+_{139}$, ½($C_{76}H_{106}N_{20}O_{17}$); m/z 792.5 [½(M+2H)]$^+_{134}$, ½($C_{77}H_{108}N_{20}O_{17}$).

An analogous reaction in the presence of a chaotropic salt (LiCl) was performed under the following conditions: Resin-peptide 134a (60.1 mg, 31,mol), DCM (5 mL), LiCl/DMF (0.4 M, 0.5 mL), 2$^{nd}$ generation Grubbs' catalyst (10.6 mg, 12 μmol, 40 mol %), cis-2-butene (15 psi), 50° C., 62 h. At the end of the reaction period, a small aliquot of peptidyl-resin was subjected to the TFA-mediated cleavage procedure (Section 7.3.3). Mass spectral analysis of the isolated residue indicated the presence of a mixture of peptides: the starting peptide 134a, the desired product 138 and a partially metathesised peptide 139. Mass spectral data were consistent with those reported above.

7.19.5 Linear [2,8]-Pre-[3,12]-Hag Conotoxin 1 ml (Ala9→Pro9 Replacement):

130

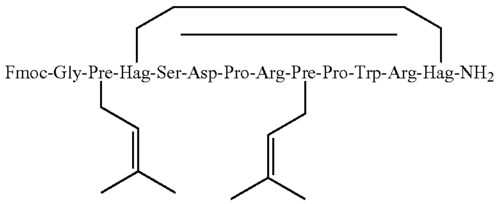

The procedure described in Section 7.3.2.2 was used for the attachment of the first amino acid, Fmoc-L-Hag-OH 96, to Rink amide resin. Quantities of the resin and coupling reagents HATU and NMM are presented in Table 7.18. The first coupling reaction was shaken for 5 h.

TABLE 7.18

Quantities of Reagents used in the Synthesis of Peptide 130

| Reagent | Mass (mg) or Volume (μl) | Mole (mmol) |
|---|---|---|
| Rink Amide Resin | 400 mg | 0.29 |
| Fmoc-L-Hag-OH | 295 mg | 0.88 |
| HATU | 223 mg | 0.59 |
| NMM | 193 μl | 1.75 |

The procedure outlined in Section 7.3.2.2 was also utilised for subsequent coupling reactions in the synthesis of the dodecapeptide 130. The quantities of successive amino acids and their reaction durations are detailed in Table 7.19.

TABLE 7.19

Quantities of Amino Acids used in the Synthesis of Peptide 130

| Amino Acid | Mass (mg) | Mole (mmol) | Reaction Time (h)* |
|---|---|---|---|
| Fmoc-L-Arg(Pbf)-OH | 570 | 0.88 | 12 |
| Fmoc-L-Trp(Boc)-OH | 462 | 0.88 | 2 (1) |
| Fmoc-L-Pro-OH | 296 | 0.88 | 1 (12) |
| Fmoc-L-Pre-OH | 328 | 0.90 | 4 |
| Fmoc-L-Arg(Pbf)-OH | 570 | 0.88 | 2 (12) |
| Fmoc-L-Pro-OH | 296 | 0.88 | 2 (2) |
| Fmoc-L-Asp($^t$Bu)-OH | 361 | 0.88 | 2 (2) |
| Fmoc-L-Ser($^t$Bu)-OH | 336 | 0.88 | 2 (12) |
| Fmoc-L-Hag-OH | 296 | 0.88 | 4 |
| Fmoc-L-Pre-OH | 330 | 0.90 | 1 (2) |
| Fmoc-L-Gly-OH | 262 | 0.88 | 2 (1) |

*Note: Reaction times have not been optimised.

After the final amino acid coupling, a small aliquot of peptidyl-resin was subjected to the TFA-mediated cleavage procedure (Section 7.3.3). Mass spectral analysis of the isolated residue confirmed formation of the dodecapeptide 130. Mass spectrum (ESI$^+$, MeCN/$H_2O$): m/z 818.6 [½(M+2H)]$^+$, ½($C_{81}H_{112}N_{20}O_{17}$) requires 818.4; m/z 827.6 [½(M+$H_2O$+2H)]$^+$, ½($C_{81}H_{114}N_{20}O_{18}$) requires 827.4.

7.19.6 [2,8]-Pre-[3,12]-Dicarba Conotoxin ImI (Ala9→Pro9 replacement):

131

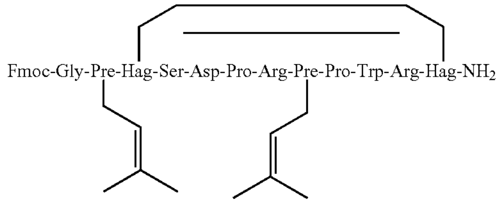

The resin-bound peptide 130a was subjected to the conventional RCM procedure (Section 7.5.2) under the following conditions: Resin-peptide 130a (97.0 mg, 70.8 μmol), DCM (5 mL), LiCl/DMF (0.4 M, 0.5 mL), 2$^{nd}$ generation Grubbs' catalyst (24.1 mg, 28.4 μmol, 40 mol %), 50° C., 40 h. At the end of the reaction period, a small aliquot of peptidyl-resin was subjected to the TFA-mediated cleavage procedure (Section 7.3.3). Mass spectral analysis of the isolated residue confirmed the presence of both cyclic 131 and linear 130 peptides. Mass spectrum (ESI$^+$, MeCN/$H_2O$): m/z 804.5 [½(M+2H)]$^+$ $_{cyclic}$, ½($C_{79}H_{108}N_{20}O_{17}$) requires 804.4; m/z 813.8 [½(M+$H_2O$+2H)]$^+$ $_{cyclic}$, ½($C_{79}H_{110}N_{20}O_{18}$) requires 813.4; m/z 818.7 [½(M+2H)]$^+$ $_{linear}$, ½($C_{81}H_{112}N_{20}O_{17}$); m/z 827.3 [½(M+$H_2O$+2H)]$^+$ $_{linear}$, ½($C_{81}H_{114}N_{20}O_{18}$).

8.0 Biological Testing

Bovine adrenal chromaffin cells can be used to test for the activity of α-CTX ImI at neuronal-type nicotinic receptors. These cells are of two types, adrenaline- and noradrenaline-containing, and possess the neuronal-type nicotinic receptor subtypes α3β4 and α7. When stimulated with nicotine, these cells release adrenaline and noradrenaline which can be measured. Native α-CTX ImI peptides inhibit the nicotine-stimulated release of these neurotransmitters by interacting with the α3β4-receptor subtype.

Dicarba-conotoxins 118 and 119 were assayed in quadruplicate in multiwells (6×4) containing monolayer cultures of bovine adrenal chromaffin cells as described by Broxton et al. (Loughnan, M., Bond, T., Atkins, A., Cuevas, J., Adams, D. J., Broxton, N.M., Livett, B. G., Down, J. G., Jones, A., Alewood, P. F., Lewis, R. J. *J. Biol. Chem.,* 1998, 273 (25), $_{15667}$-15674.)$^{X}$ The response of the cells to these peptides was tested at two peptide concentrations 1 uM and 5 uM. The cells were stimulated with nicotine (4 uM) for 5 min at room temp (23C) and the amount of catecholamine release (noradrenaline and adrenaline) was measured over a 5 period and expressed as a % of the initial cellular content of these amines. This was performed in the presence and absence (control) of dicarba-conotoxin peptides. The chromaffin cells also leak small amounts of catecholamine over the measurement period, so a 'basal release' (no nicotine added) measurement is also recorded.

Figure 4:
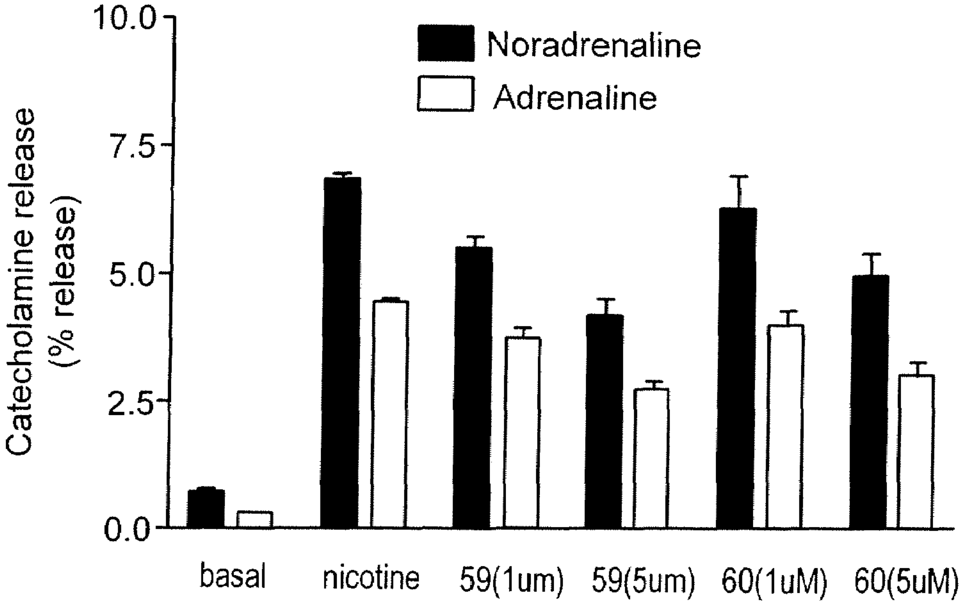
FIG. 4 is a bar graph showing the results of studies of catecholamine release from dicarba-conotoxins 118 and 119.

FIG. 4 shows catecholamine release from dicarba-conotoxins 118 and 119. Basal release was measured at 0.72% (and is subtracted from other measurements). Nicotine stimulation alone released (6.85-0.72)=6.13% of the noradrenaline in the cells, but only (4.15-0.72)=3.43% in the presence of 5 uM of [2,8]-cystino-[3,12]-dicarba conotoxin 119. This represents 55.97% of the release produced by nicotine alone, or a 44% inhibition of release (see Table). The % inhibition of release of adrenaline (41%) was similar to that for noradrenaline (44%). This inhibition was found to be concentration related: A 1 uM sample of dicarba-conotoxin 119 produced only a 21.6% inhibition of noradrenaline release and a 16.5% inhibition of release of adrenaline.

Data for [2,8]-dicarba-[3,12]-cystino conotoxin 118 is also shown in FIG. 4 and Table 8.1. This data shows that these dicarba-analogues are biologically active and possess activity profiles analogous to the native conotoxin sequences.

TABLE 8.1

Catecholamine release for dicarba-conotoxins 118 and 119

| | 1st | 2nd | 3rd | 4th | mean | SEM | n | % control | % inhibition |
|---|---|---|---|---|---|---|---|---|---|
| Noradrenaline Release | | | | | | | | | |
| BASE | 0.68 | 0.61 | 0.66 | 0.93 | 0.72 | 0.07 | 4 | | |
| NICOTINE (4 uM) | 6.62 | 6.89 | 6.99 | 6.89 | 6.85 | 0.08 | 4 | 100.000 | |
| 119 (1 uM) | 4.89 | 5.75 | 5.73 | 5.73 | 5.52 | 0.21 | 4 | 78.400 | 21.600 |
| 119 (5 uM) | 3.22 | 4.58 | 3.99 | 4.81 | 4.15 | 0.35 | 4 | 55.971 | 44.029 |
| 118 (1 uM) | 4.52 | 6.29 | 7.00 | 7.34 | 6.29 | 0.63 | 4 | 90.859 | 9.141 |
| 118 (5 uM) | 4.19 | 5.86 | 4.32 | 5.51 | 4.97 | 0.42 | 4 | 69.384 | 30.616 |
| Adrenaline Release | | | | | | | | | |
| BASE | 0.38 | 0.28 | 0.31 | 0.34 | 0.33 | 0.02 | 4 | | |
| NICOTINE (4 uM) | 4.31 | 4.52 | 4.52 | 4.48 | 4.46 | 0.05 | 4 | 100.000 | |
| 119 (1 uM) | 3.31 | 3.67 | 4.14 | 3.98 | 3.77 | 0.18 | 4 | 83.420 | 16.580 |
| 119 (5 uM) | 2.32 | 2.95 | 2.76 | 3.02 | 2.76 | 0.16 | 4 | 58.888 | 41.112 |
| 118 (1 uM) | 2.94 | 4.40 | 4.46 | 4.09 | 3.97 | 0.35 | 4 | 88.260 | 11.740 |
| 118 (5 uM) | 2.55 | 3.63 | 2.62 | 3.31 | 3.03 | 0.26 | 4 | 65.306 | 34.694 |

9.0 Stability

9.1 Thiol Stability

Peptides samples (0.25 mM) were dissolved in a solution containing either 0.25 mM reduced glutathione, 12.3 μM reduced thioredoxin (Promega, Madison, Wis.) or 0.5 mM human serum albumin (Sigma, Madison, Wis.) in 100 mM phosphate buffer+1 mM EDTA, pH 7.4 (300 μL) and incubated at 37C. Thioredoxin was reduced by treating the oxidised form with 0.9 equivalents of dithiothreitol for 15 minutes immediately prior to use. Aliquots (30 μL) were taken at various time intervals, quenched with extraction buffer consisting of 50% aqueous acetonitrile, 100 mM NaCl, and 1% TFA (30 μL) and analysed by reverse-phase-HPLC. The ratio of the degradation product to the tested peptide sample was determined by measuring the peak height, and compared against the peak height results for the HPLC of the corresponding natural or native peptide. The product was considered to have improved stability if the comparative HPLC test results showed less degradation product after 6 hours of contact with one of the agents (reduced glutathione, reduced thioredoxin or human serum albumin).

9.2 Human Blood Plasma Stability

Whole human blood containing 1% EDTA was centrifuged at 14,000 rpm for 30 minutes. The supernatant was then transferred to an Eppendorf tube and centrifuged for an additional 30 min at 14,000 rpm. Peptide samples were dissolved in plasma (200 μL) to an initial peptide concentration of approximately 0.25 mM. Aliquots (30 PL) were removed at various time intervals and quenched with extraction buffer (30 μL). The aliquot was then vortexed, diluted with additional water (60 μL) and chilled in an ice bath for 5 minutes prior to centrifuging at 14,000 rpm for 15 minutes. The supernatant was then analysed by RP-HPLC. The stability of the peptide sample was assessed by comparing the ratio of the peak heights representing the tested peptide, and the degradation products, against a sample of the corresponding natural or native peptide not containing the dicarba bridge or bridges. The product was considered to have improved stability in human blood plasma if the comparative HPLC test results showed less degradation product after 6 hours of contact.

It will be understood to persons skilled in the art of the invention that many modifications may be made without departing from the spirit and scope of the invention.

REFERENCES

1. Maggon, K. *Drug Discovery Today* 2005, 10, 739-742.
2. Giannis, A.; Kolter, T. *Angew. Chem., Int. Ed. Engl.* 1993, 32, 1244-1267.
3. Olson, G. L.; Bolin, D. R.; Bonner, M. P.; Bös, M.; Cook, C. M.; Fry, D. C.; Graves, B. J.; Hatada, M.; Hill, D. E.;

Kahn, M.; Madison, V. S.; Rusiecki, V. K.; Sarabu, R.; Sepinwall, J.; Vincent, G. P.; Voss, M. E. *J. Med. Chem.* 1993, 36, 3039-3049
4. Fix, J. A. *Pharm. Res.* 1996, 13, 1760-1764.
5. Fletcher, M. D.; Campbell, M. M. *Chem. Rev.* 1998, 98, 763-795.
6. Steer, D. L.; Lew, R. A.; Perlmutter, P.; Smith, A. I.; Aguilar, M. *Curr. Med. Chem.* 2002, 9, 811-822.
7. Seebach, D.; Overhand, M.; Kuhlne, F. N. M.; Martinoni, B.; Oberer, L.; Hommel, U.; Widmer, H. *Helv. Chim. Acta* 1996, 79, 913-941.
8. Seebach, D.; Ciceri, P. E.; Overhand, M.; Jaun, B.; Rigo, D.; Oberer, L.; Hommel, U.; Amstutz, R.; Widmer, H. *Helv. Chim. Acta* 1996, 79, 2043-2065.
9. Appella, D. H.; Christianson, L. A.; Karle, I. L.; Powell, D. R.; Gellman, S. H. *J. Am. Chem. Soc.* 1996, 118, 13071-13072.
10. Appella, D. H.; Christianson, L. A.; Klein, D. A.; Powell, D. R.; Xialolin, H.; Barchi, J. J.; Gellman, S. H. *Nature* 1997, 387, 381-384.
11. Iverson, B. *Nature* 1997, 385, 113-115.
12. Kimmerlin, T.; Seebach, D. *J. Pept. Res.* 2005, 65, 229-260.
13. Seebach, D.; Beck, A. K.; Bierbaum, D. J. *Chem. Biodivers.* 2004, 1, 1211-1239.
14. Arvidsson, P. I.; Ryder, N. S.; Weiss, H. M.; Hook, D. F.; Escalante, J.; Seebach, D. *Chem. Biodivers.* 2005, 2, 401-420.
15. Baldauf, C.; Hofmann, H.-J.; Günther, R. *Helv. Chim. Acta* 2003, 86, 2573-2588.
16. Li, P.; Roller, P. P. *Curr. Top. Med. Chem.* 2002, 2, 325-341.
17. Garzone, P. D.; Colburn, W. A.; Mokotoff, M. E. *Pharmacokinet. Pharmacodyn.* 1991, 3, 116-127.
18. Gorske, B. C.; Jewell, S. A.; Guerard, E. J.; Blackwell, H. E. *Org. Lett.* 2005, 7, 1521-1524.
19. Isabel, M.; Perez-Paya, E.; Messeguer, A. *Comb. Chem. High Throughput Screen.* 2005, 8, 235-239.
20. Nielsen, P. E.; Egholm, M.; Berg, R. H.; Buchardt, O. *Science* 1991, 254, 1497-1500.
21. Hyrup, B.; Nielsen, P. E. *Bioorg. Med. Chem.* 1996, 4, 5-23.
22. Uhlmann, E.; Peyman, A.; Breipohl, G.; Will, D. W. *Angew. Chem. Int. Ed.* 1998, 37, 2796-2823.
23. *Peptide Nucleic Acids;* Egholm, M.; Nielsen, P. E., Eds.; Horizon Scientific Press: England, 1999.
24. Dean, D. A. *Adv. Drug Delivery Rev.* 2000, 44, 81-95.
25. Romanelli, A.; Saviano, M.; Pedone, C. *Recent Res. Dev. Org. Chem.* 2004, 8, 237-254.
26. Kumar, V. A.; Ganesh, K. N. *Acc. Chem. Res.* 2005, 38, 404-412.
27. Guichard, G.; Benkirane, N.; Zeder-Lutz, G.; Van Regenmortel, M. H. V.; Briand, J. P.; Muller, S. *Proc. Natl. Acad. Sci. USA* 1994, 91, 9765-9769.
28. Chorev, M. *Biopolymers* 2005, 80, 67-84.
29. An, S. S. A.; Lester, C. C.; Peng, J.-L.; Li, Y.-J.; Rothwarf, D. M.; Welker, E.; Thannhauser, T. W.; Zhang, L. S.; Tam, J. P.; Scheraga, H. A. *J. Am. Chem. Soc.* 1999, 121, 11558-11566.
30. Arnold, U.; Hinderaker, M. P.; Köditz, J.; Golbik, R.; Ulbrich-Hoffmann, R.; Raines, R. T. *J. Am. Chem. Soc.* 2003, 125, 7500-7501.
31. Tang, W.; Zhang, X. *Chem. Rev.* 2003, 103, 3029-3069.
32. Zsigmond, A.; Balatoni, I.; Notheisz, F.; Hegednes, C.; Bakos, J. *Catalysis Lett.* 2005, 101, 195-199.
33. Burk, M. J.; Feaster, J. E.; Nugent, W. A.; Harlow, R. L. *J. Am. Chem. Soc.* 1993, 115, 10125-10138.
34. Burk, M. J. *J. Am. Chem. Soc.* 1991, 113, 8518-8519.
35. Burk, M. J.; Feaster, J. E. *J. Am. Chem. Soc.* 1992, 114, 6266-6267.
36. Robinson, A. J.; Lim, C. Y.; Li, H.-Y.; He, L.; Ma, P. *J. Org. Chem.* 2001, 66, 4141-4147.
37. Robinson, A. J.; Stanislawski, P.; Mulholland, D. *J. Org. Chem.* 2001, 66, 4148-4152.
38. Juaristi, E. *Enantioselective Synthesis off* β-*Amino Acids*; Wiley-VCH: New York, 1997.
39. *The Organic Chemistry of* β-*Lactams*; Georg, G. I., Ed.; Verlag Chemie: New York, 1993.
40. Juaristi, E.; Quintana, D.; Escalante, J. *Aldrichim. Acta* 1994, 27, 3-11.
41. Ondetti, M. A.; Engel, S. L. *J. Med. Chem.* 1975, 18, 761-763.
42. Abele, S.; Seebach, D. *Eur. J. Org. Chem.* 2000, 1-15.
43. Borman, S. *Chem. Eng. News* 1997, 75, 32-35.
44. Gellman, S. H. *Acc. Chem. Res.* 1998, 31, 173-180.
45. Seebach, D.; Matthews, J. L. *Chem. Commun.* 1997, 2015-2022.
46. Seebach, D.; Gademann, K.; Schreiber, J. V.; Matthews, J. L.; Hintermann, T.; Jaun, B. *Helv. Chim. Acta* 1997, 80, 2033-2038.
47. Seebach, D.; Abele, S.; Gademann, K.; Guichard, G.; Hintermann, T.; Jaun, B.; Matthews, J. L.; Schreiber, J. V. *Helv. Chim. Acta* 1998, 81, 932-982.
48. Appella, D. H.; Christianson, L. A.; Klein, D. A.; Richards, M. R.; Powell, D. R.; Gellman, S. H. *J. Am. Chem. Soc.* 1999, 121, 7574-7581.
49. Claridge, T. D. W.; Goodman, J. M.; Moreno, A.; Angus, D.; Barker, S. F.; Taillefiumier, C.; Watterson, M. P.; Fleet, G. W. *J. Tetrahedron Lett.* 2001, 42, 4251-4255.
50. Rueping, M.; Schreiber, J. V.; Lelais, G.; Jaun, B.; Seebach, D. *Helv. Chim. Acta* 2002, 85, 2577-2593.
51. Matthews, J. L.; Overhand, M.; Kühnle, F. N. M.; Ciceri, P. E.; Seebach, D. *Liebigs Ann.* 1997, 1371-1379.
52. Chung, Y. J.; Christianson, L. A.; Stanger, H. E.; Powell, D. R.; Gellman, S. H. *J. Am. Chem. Soc.* 1998, 120, 10555-10556.
53. Krauthäuser, S.; Christianson, L. A.; Powell, D. R.; Gellman, S. H. *J. Am. Chem. Soc.* 1997, 119, 11719-11720.
54. Seebach, D.; Abele, S.; Gademann, K.; Jaun, B. *Angew. Chem. Int. Ed.* 1999, 38, 1595-1597.
55. Langenhan, J. M.; Guzei, I. A.; Gellman, S. H. *Angew. Chem. Int. Ed.* 2003, 42, 2402-2405.
56. Syud, F. A.; Stanger, H. E.; Mortell, H. S.; Espinosa, J. F.; Fisk, J. D.; Fry, C. G.; Gellman, S. H. *J. Mol. Biol.* 2003, 326, 553-568.
57. Seebach, D.; Matthews, J. L.; Meden, A.; Wessels, T.; Baerlocher, C.; McCusker, L. B. Helv. Chim. Acta 1997, 80, 173-182.
58. Hintermann, T.; Seebach, D. *Chimia* 1997, 51, 244-247.
59. Seebach, D.; Abele, S.; Schreiber, J. V.; Martinoni, B.; Nussbaum, A. K.; Schild, H.; Schulz, H.; Hennecke, H.; Woessner, R.; Bitsch, F. *Chimia* 1998, 52, 734-739.
60. Frackenpohl, J.; Arvidsson, P. I.; Schreiber, J. V.; Seebach, D. *ChemBioChem* 2001, 2, 445-455.
61. Schreiber, J. V.; Frackenpohl, J.; Moser, F.; Fleischmann, T.; Kohler, H.—P. E.; Seebach, D. *ChemBioChem* 2002, 3, 424-432.
62. Wiegand, H.; Wirz, B.; Schweitzer, A.; Camenisch, G. P.; Perez, M. I. R.; Gross, G.; Woessner, R.; Voges, R.; Arvidsson, P. I.; Frackenpohl, J.; Seebach, D. *Biopharm. Drug Dispos.* 2002, 23, 251-262.
63. Gademann, K.; Ernst, M.; Hoyer, D.; Seebach, D. *Angew. Chem. Int. Ed.* 1999, 38, 1223-1226.

64. Gademann, K.; Kimmerlin, T.; Hoyer, D.; Seebach, D. *J. Med. Chem.* 2001, 44, 2460-2468.

65. Nunn, C.; Rueping, M.; Langenegger, D.; Schuepbach, E.; Kimmerlin, T.; Micuch, P.; Hurth, K.; Seebach, D.; Hoyer, D. *Naunyn-Schmiedeberg's Arch Pharmacol* 2003, 367, 95-103.

66. Takashiro, E.; Hayakawa, I.; Nitta, T.; Kasuya, A.; Miyamoto, S.; Ozawa, Y.; Yagi, R.; Yamamoto, I.; T., S.; Nakagawa, A.; Yabe, Y. *Bioorg. Med. Chem.* 1999, 7, 2063-2072.

67. Arvidsson, P. I.; Ryder, N. S.; Weiss, H. M.; Gross, G.; Kretz, O.; Woessner, R.; Seebach, D. *ChemBioChem* 2003, 4, 1345-1347.

68. White, J. D.; Hong, J.; Robarge, L. A. *J. Org. Chem.* 1999, 64, 6206-6216.

69. Arndt, F.; Eistert, B.; Partale, W. *Ber. Dtsch. Chem. Ges.* 1927, 60, 1364-1370.

70. Leggio, A.; Liguori, A.; Procopio, A.; Sindona, G. *J. Chem. Soc., Perkin Trans. I* 1997, 1969-1971.

71. Marti, R. E.; Bleicher, K. H.; Bair, K. W. *Tetrahedron Lett.* 1997, 38, 6145-6148.

72. Guichard, G.; Abele, S.; Seebach, D. *Helv. Chim. Acta* 1998, 81, 187-206.

73. *Named Organic Reactions*; Laue, T.; Plagens, A., Eds.; Wiley: Chichester, 2000.

74. Yang, H.; Foster, K.; Stephenson, C. R. J.; Brown, W.; Roberts, E. *Org. Lett.* 2000, 2, 2177-2179.

75. Lubell, W. D.; Kitamura, M.; Noyori, R. *Tetrahedron: Asymmetry* 1991, 2, 543-554.

76. Zhu, G.; Chen, Z.; Zhang, X. *J. Org. Chem.* 1999, 64, 6907-6910.

77. Heller, D.; Holz, J.; Drexler, H.-J.; Lang, J.; Drauz, K.; Krimmer, H.-P.; Börner, A. *J. Org. Chem.* 2001, 66, 6816-6817.

78. Holz, J.; Stürmer, R.; Schmidt, U.; Drexler, H.-J.; Heller, D.; Krimmer, H.-P.; Börner, A. *Eur. J. Org. Chem.* 2001, 4615-4624.

79. Yasutake, M.; Gridnev, I. D.; Higashi, N.; Imamoto, T. *Org. Lett.* 2001, 3, 1701-1704.

80. Heller, D.; Holz, J.; Komarov, I. V.; Drexler, H.-J.; You, J.; Drauz, K.; Börner, A. *Tetrahedron: Asymmetry* 2002, 13, 2735-2741.

81. Heller, D.; Drexler, H.-J.; You, J.; Baumann, W.; Drauz, K.; Krimmer, H.—P.; Börner, A. *Chem. Eur. J.* 2002, 8, 5196-5203.

82. Lee, S.; Zhang, Y. J. *Org. Lett.* 2002, 4, 2429-2431.

83. Peña, D.; Minnaard, A. J.; de Vries, J. G.; Feringa, B. L. *J. Am. Chem. Soc.* 2002, 124, 14552-14553.

84. Tang, W.; Zhang, X. *Org. Lett.* 2002, 4, 4159-4161.

85. Zhou, Y.-G.; Tang, W.; Wang, W.-B.; Li, W.; Zhang, X. *J. Am. Chem. Soc.* 2002, 124, 4952-4953.

86. Holz, J.; Monsees, A.; Jiao, H.; You, J.; Komarov, I. V.; Fischer, C.; Drauz, K.; Börner, A. *J. Org. Chem.* 2003, 68, 1701-1707.

87. Jerphagnon, T.; Renaud, J.-L.; Demonchaux, P.; Ferreira, A.; Bruneau, C. *Tetrahedron: Asymmetry* 2003, 14, 1973-1977.

88. Tang, W.; Wang, W.; Chi, Y.; Zhang, X. *Angew. Chem. Int. Ed.* 2003, 42, 3509-3511.

89. Wu, J.; Chen, X.; Guo, R.; Yeung, C.-H.; Chan, A. S.C. *J. Org. Chem.* 2003, 68, 2490-2493.

90. Lee, H.; Park, J.; Kim, B. Y.; Gellman, S. H. *J. Org. Chem.* 2003, 68, 1575-1578.

91. Beddow, J. E.; Davies, S. G.; Smith, A. D.; Russel, A. *J. Chem. Commun.* 2004, 2778-2779.

92. Seebach, D.; Schaeffer, L.; Gessier, F.; Bindschadler, P.; Jager, C.; Josien, D.; Kopp, S.; Lelais, G.; Mahajan, Y. R.; Micuch, P.; Sebesta, R.; Schweizer, B. W. *Helv. Chim. Acta* 2003, 86, 1852-1861.

93. Davies, H. M. L.; Venkataramani, C. *Angew. Chem. Int. Ed.* 2002, 41, 2197-2199.

94. Sammis, G. M.; Jacobsen, E. N. *J. Am. Chem. Soc.* 2003, 125, 4442-4443.

95. Bower, J. F.; Jumnah, R.; Williams, A. C.; Williams, J. M. J. *J. Chem. Soc., Perkin Trans. I* 1997, 1411-1420.

96. Duursma, A.; Minnaard, A. J.; Feringa, B. L. *J. Am. Chem. Soc.* 2003, 125, 3700-3701.

97. Elaridi, J.; Thaqi, A.; Prosser, A.; Jackson, W. R.; Robinson, A. J. *Tetrahedron: Asymmetry* 2005, 16, 1309-1319.

98. Tang, W.; Wu, S.; Zhang, X. *J. Am. Chem. Soc.* 2003, 125, 9570-9571.

99. Lefort, L.; Boogers, J. A. F.; de Vries, A. H. M.; de Vries, J. G. *Org. Lett.* 2004, 6, 1733-1735.

100. Stewart, D. E.; Sarkar, A.; Wampler, J. E. *J. Mol. Biol.* 1990, 214, 253-260.

101. Hinderaker, M. P.; Raines, R. T. *Protein Science* 2003, 12, 1188-1194.

102. Weiss, M. S.; Jabs, A.; Hilgenfield, R. *Nat. Struct. Biol.* 1998, 5, 676.

103. Jabs, A.; Weiss, M. S.; Hilgenfield, R. *J. Mol. Biol.* 1999, 286, 291-304.

104. MacArthur, M. W.; Thornton, J. M. *J. Mol. Biol.* 1991, 218, 397-412.

105. Wöhr, T.; Wahl, F.; Nefzi, A.; Rohwedder, B.; Sato, T.; Sun, X.; Mutter, M. *J. Am. Chem. Soc.* 1996, 118, 9218-9227.

106. Haack, T.; Mutter, M. *Tetrahedron Lett.* 1992, 33, 1589-1592.

107. Sampson, W. R.; Patsiouras, H.; Ede, N. J. *J. Peptide Sci.* 1999, 5, 403-409.

108. Wittelsberger, A.; Keller, M.; Scarpellino, L.; Patiny, L.; Acha-Orbea, H.; Mutter, M. *Angew. Chem. Int. Ed.* 2000, 39, 1111-1115.

109. Keller, M.; Miller, A. D. *Bioorg. Med. Chem. Lett.* 2001, 11, 857-859.

110. von Eggelkraut-Gottanka, R.; Machova, Z.; Grouzmann, E.; BeckSickinger, A. G. *ChemBioChem* 2003, 4, 425-433.

111. White, P.; Keyte, J. W.; Bailey, K.; Bloomberg, G. *J. Peptide Sci.* 2004, 10, 18-26.

112. Magaard, V. W.; Sanchez, R. M.; Bean, J. W.; Moore, M. L. *Tetrahedron Lett.* 1993, 34, 381-384.

113. Bonnett, R.; Clark, V. M.; Giddey, A.; Todd, S. A. *J. Chem. Soc.* 1959, 2087-2093.

114. Aldous, D. J.; Drew, M. G. B.; Hamelin, E. M.-N.; Harwood, L. M.; Jahans, A. B.; Thurairatnam, *S. Synlett* 2001, 12, 1836-1840.

115. Xia, Q.; Ganem, B. *Tetrahedron Lett.* 2002, 43, 1597-1598.

116. Elaridi, J.; Jackson, W. R.; Robinson, A. *J. Tetrahedron: Asymmetry* 2005, 16, 2025-2029.

117. Burk, M. J.; Allen, J. G.; Kiesman, W. F. *J. Am. Chem. Soc.* 1998, 120, 657-663.

118. Teoh, E.; Campi, E. M.; Jackson, W. R.; Robinson, A. J. *Chem. Commun.* 2002, 978-979.

119. Teoh, E.; Campi, E. M.; Jackson, W. R.; Robinson, A. J. *New J. Chem.* 2003, 27, 387-394.

120. Schwab, P.; France, M. B.; Ziller, J. W.; Grubbs, R. H. *Angew. Chem., Int. Ed. Engl.* 1995, 34, 2039-2041.

121. Scholl, M.; Ding, S.; Lee, C. W.; Grubbs, R. H. *Org. Lett.* 1999, 1, 953-956.

122. Gessler, S.; Randl, S.; Blechert, S. *Tetrahedron Lett.* 2000, 41, 9973-9976.

123. Garber, S. B.; Kingsbury, J. S.; Gray, B. L.; Hoveyda, A. H. *J. Am. Chem. Soc.* 2000, 122, 8168-8179.

124. Grubbs, R. H.; Pine, S. H. *Comprehensive Organic Synthesis*; Pergamon: New York, 1991; Vol. 5.

125. Ivin, K. J.; Moi, J. C. *Olefin Metathesis and Metathesis Polymerisation*; Academic Press: San Diego, 1997.

126. Fürstner, A. *Alkene Metathesis in Organic Synthesis*; Springer-Verlag: New York, 1998.

127. Grubbs, R. H. *Handbook of Metathesis*; Wiley-VCH: Weinheim, 2003; Vol. 2.

128. Trnka, T. M.; Grubbs, R. H. *Acc. Chem. Res.* 2001, 34, 18-29.

129. Connon, S. J.; Blechert, S. *Angew. Chem. Int. Ed.* 2003, 42, 1900-1923.

130. Chatterjee, A. K.; Choi, T.-L.; Sanders, D. P.; Grubbs, R. H. *J. Am. Chem. Soc.* 2003, 125, 11360-11370.

131. Jones, R. M.; Bulaj, G. *Curr. Opin. Drug Discovery Dev.* 2000, 3, 141-154.

132. Pons, M.; Albericio, F. R.; Royo, M. *Synlett* 2000, 2, 172-181.

133. Wouters, M. A.; Lau, K. K.; Hog, P. J. Bioessays 2003, 26, 73-79.

134. Frisch, M. J.; Trucks, G. W.; Schlegel, H. B.; Scuseria, G. E.; Robb, M. A.; Cheeseman, J. R.; Montgomery, J. A.; Vreven, T.; Kudin, K. N.; Burant, J. C.; Millam, J. M.; Iyengar, S. S.; Tomasi, J.; Barone, V.; Mennucci, B.; Cossi, M.; Scalmani, G.; Rega, N.; Petersson, G. A.; Nakatsuji, H.; Hada, M.; Ehara, M.; Toyota, K.; Fukuda, R.; Hasegawa, J.; Ishida, M.; Nakajima, T.; Honda, Y.; Kitao, O.; Nakai, H.; Klene, M.; Li, X.; Knox, J. E.; Hratchian, H. P.; Cross, J. B.; Bakken, V.; Adamo, C.; Jaramillo, J.; Gomperts, R.; Stratmann, R. E.; Yazyev, O.; Austin, A. J.; Cammi, R.; Pomelli, C.; Ochterski, J. W.; Ayala, P. Y.; Morokuma, K.; Voth, G. A.; Salvador, P.; Dannenberg, J. J.; Zakrzewski, V. G.; Dapprich, S.; Daniels, A. D.; Strain, M. C.; Farkas, O.; Malick, D. K.; Rabuck, A. D.; Raghavachari, K.; Foresman, J. B.; Ortiz, J. V.; Cui, Q.; Baboul, A. G.; Clifford, S.; Cioslowski, J.; Stefanov, B. B.; Liu, G.; Liashenko, A.; Piskorz, P.; Komaromi, I.; Martin, R. L.; Fox, D. J.; Keith, T.; Al-Laham, M. A.; Peng, C. Y.; Nanayakkara, A.; Challacombe, M.; Gill, P. M. W.; Johnson, B.; Chen, W.; Wong, M. W. G., C.; Pople, J. A.; Gaussian Inc.: Wallingford Conn., 2004.

135. Walker, R.; Yamanaka, T.; Sakakibara, S. *Proc. Natl. Acad. Sci. USA* 1974, 71, 1901-1905.

136. Nutt, R. F.; Verber, D. F.; Saperstein, R. *J. Am. Chem. Soc.* 1980, 102, 6539-6545.

137. Collier, P. N.; Campbell, A. D.; Patel, I.; Raynham, T. M.; Taylor, R. J. K. *J. Org. Chem.* 2002, 67, 1802-1815.

138. Lange, M.; Fischer, P. M. Helv. Chim. Acta 1998, 81, 2053-2061.

139. Hase, S.; Morikawa, T.; Sakakibara, S. *Experientia* 1969, 25, 1239-1240.

140. Kambayashi, Y.; Nakajima, S.; Ueda, M.; Inouye, K. *FEBS Letters* 1989, 248, 28-34.

141. Whelan, A.; Elaridi, J.; Harte, M.; Smith, S.; Jackson, W. R.; Robinson, A. *J. Tetrahedron Lett.* 2004, 45, 9545-9547.

142. Whelan, A.; Elaridi, J.; Mulder, R.; Jackson, W. R.; Robinson, A. J. *Can. J. Chem.* 2005, 83, 875-881.

143. Carotenuto, A.; D'Addona; D.; Rivalta, E.; Chelli, M.; Papini, A. M.; Rovero, P.; Ginanneschi, M. *Lett. Org. Chem.* 2005, 2, 274-279.

144. Jost, K.; Sorm, F. *Coll. Czech. Chem. Commun.* 1971, 36, 234-245.

145. Stymiest, J. L.; Mitchell, B. F.; Wong, S.; Vederas, J. C. *Org. Lett.* 2003, 5, 47-49.

146. Stymiest, J. L.; Mitchell, B. F.; Wong, S.; Vederas, J. C. *J. Org. Chem.* 2005, 70, 7799-7809.

147. Cerovsky, V.; Wunsch, E.; Brass, J. Eur. *J. Biochem.* 1997, 247, 231-237.

148. Lange, M.; Cuthbertson, A. S.; Towart, R.; Fischer, P. M. *J. Peptide Sci.* 1998, 4, 289-293.

149. Bhatnagar, P. K.; Agner, E. K.; Alberts, D.; Arbo, B. E.; Callahan, J. F.; Cuthbertson, A. S.; Angelsen, S. J.; Fjerdingstad, H.; Hartmann, M.; Heerding, D.; Hiebl, J.; Huffman, W. F.; Hysben, M.; King, A. G.; Kremminger, P.; Kwon, C.; LoCastro, S.; Lovhaug, D.; Pelus, L. M.; Petteway, S.; Takata, J. S. *J. Med. Chem.* 1996, 39, 3814-3819.

150. Hiebl, J.; Blanka, M.; Guttman, A.; Hollman, H.; Leitner, K.; Mayrhofer, G.; Rovenszky, F.; Winkler, K. *Tetrahedron* 1998, 54, 2059-2074.

151. Williams, R. M.; Yuan, C. *J. Org. Chem.* 1992, 57, 6519-6527.

152. Miller, S. J.; Blackwell, H. E.; Grubbs, R. H. *J. Am. Chem. Soc.* 1996, 118, 9606-9614.

153. Gao, Y.; Lane-Bell, P.; Vederas, J. C. *J. Org. Chem.* 1998, 63, 2133-2143.

154. Williams, R. M.; Lui, J. *J. Org. Chem.* 1998, 63, 2130-2132.

155. Aguilera, B.; Wolf, L. B.; Nieczypor, P.; Rutjes, F. P. J. T.; Overkleeft, H. S.; van Hest, J. C. M.; Schoemaker, H. E.; Wang, B.; Mol, J. C.; Furstner, A.; Overland, M.; van der Marel, G. A.; van Boom, J. H. *J. Org. Chem.* 2001, 66, 3584-3589.

156. Creighton, C. J.; Reitz, A. B. *Org. Lett.* 2001, 3, 893-895.

157. Ghalit, N.; Rijkers, D. T. S.; Kemmink, J.; Versluis, C.; Liskamp, R. M. *J. Chem. Commun.* 2005, 192-194.

158. Miller, S. J.; Blackwell, H. E.; Grubbs, R. H. *J. Am. Chem. Soc.* 1995, 117, 5855-5856.

159. Blackwell, H. E.; Sadowsky, J. D.; Howard, R. J.; Sampson, J. N.; Chao, J. A.; Steinmetz, W. E.; O'Leary, D. J.; Grubbs, R. H. *J. Org. Chem.* 2001, 66, 5291-5302.

160. Clark, T. D.; Ghadiri, M. R. *J. Am. Chem. Soc.* 1995, 117, 12364-12365.

161. Chaleix, V.; Sol, V.; Guilloton, M.; Granet, R.; Krausz, P. *Tetrahedron Lett.* 2004, 45, 5295-5299.

162. Pemerstorfer, J.; Schuster, M.; Blechert, S. *Chem. Commun.* 1997, 1949-1950.

163. Piscopio, A. D.; Miller, J. F.; Koch, K. *Tetrahedron Lett.* 1997, 38, 7143-7146.

164. Piscopio, A. D.; Miller, J. F.; Koch, K. *Tetrahedron Lett.* 1998, 39, 2667-2670.

165. Jarvo, E. R.; Copeland, G. T.; Papaioannou, N.; Bonitatebus, P. J.; Miller, S. J. *J. Am. Chem. Soc.* 1999, 121, 11638-11643.

166. Piscopio, A. D.; Miller, J. F.; Koch, K. *Tetrahedron* 1999, 55, 8189-8198.

167. Schmiedeberg, N.; Kessler, H. *Org. Lett.* 2002, 4, 59-62.

168. Kazmaier, U.; Hebach, C.; Watzke, A.; Maier, S.; Mues, H.; Huch, V. *Org. Biomol. Chem.* 2005, 3, 136-145.

169. Hsieh, H.; Wu, Y.; Chen, S.; Wang, K. *Bioorg. Med. Chem.* 1999, 7, 1797-1803.

170. Suetake, T.; Aizawa, T.; Koganesawa, N.; Osaki, T.; Kobashigawa, Y.; Demura, M.; Kawabata, S.; Kawano, K.; Tsuda, S.; Nitta, K. *PEDS* 2002, 15, 763-769.

171. Adams, D. J.; Alewood, P. F.; Craik, D. J.; Drinkwater, R. D.; Lewis, R. J. *Drug Dev. Res.* 1999, 46, 219-234.

172. Hu, Y.-L.; Huang, F.; Jiang, H.; Fan, C.-X.; Chen, C.-Y.; Chen, J.-S. *Wuli Huaxue Xuebao* 2005, 21, 474-478.

173. Rogers, J. P.; Luginbühl, P.; Shen, G. S.; McCabe, R. T.; Stevens, R. C.; Wemmer, D. E. *Biochemistry* 1999, 38.

174. Maslennikova, I. V.; Shenkareva, Z. O.; Zhmaka, M. N.; Ivanova, V. T.; Methfesselb, C.; Tsetlina, V. I.; Arseniev, A. S. *FEBS Letters* 1999, 444, 275-280.

175. Craik, D. J.; Daly, N. L.; Bond, T.; Waine, C. *J. Mol. Biol.* 1999, 294, 1327-1336.

176. Rosengren, K. J.; Daly, N. L.; Plan, M. R.; Waine, C.; Craik, D. J. *J. Biol. Chem.* 2003, 278, 8606-8616.

177. Hill, C. P.; Yee, J.; Selsted, M. E.; Eisenberg, D. *Science* 1991, 251, 1481-1485.

178. Cornet, B.; Bonmatin, J. M.; Hetru, C.; Hoffmann, J. A.; Ptak, M.; Vovelle, F. *Structure* 1995, 3, 435-448.

179. Aumelas, A.; Mangoni, M.; Roumestand, C.; Chiche, L.; Despaux, E.; Grassy, G.; Calas, B.; Chavanieu, A. Eur. *J. Biochem.* 1996, 237, 575-583.

180. Fahrner, R. L.; Dieckmann, T.; Harwig, S. S.; Lehrer, R. I.; Eisenberg, D.; Feigon, *J. Chem. Biol.* 1996, 3, 543-550.

181. Rodighiero, C.; Lencer, W. I. *Microbial Pathogenesis and the Intestinal Epithelial Cell* 2003, 385-401.

182. Chatterjee, A. K.; Sanders, D. P.; Grubbs, R. H. *Org. Lett.* 2002, 4, 1939-1942.

183. Marx, J. N.; Argyle, J. C.; Norman, L. R. *J. Am. Chem. Soc.* 1974, 96, 2121-2129.

184. Klioze, S. S.; Darmory, F. P. *J. Org. Chem.* 1975, 40, 1588-1592.

185. Folkers, K.; Adkins, H. *J. Am. Chem. Soc.* 1931, 53, 1416-1419.

186. Burk, M. J.; Kalberg, C. S.; Pizzaro, A. *J. Am. Chem. Soc.* 1998, 120, 4345-4353.

187. Noyori, R. *Asymmetric Catalysis in Organic Synthesis*; John Wiley and Sons Inc.: USA, 1994.

188. Imamoto, T.; Watanabe, J.; Wada, Y.; Masuda, H.; Yamada, H.; Tsuruta, H.; Matsukawa, S.; Yamaguchi, K. *J. Am. Chem. Soc.* 1998, 120, 1635-1636.

189. Yamanoi, Y.; Imamoto, T. *J. Org. Chem.* 1999, 64, 2988-2989.

190. Gridnev, I. D.; Yamanoi, Y.; Higashi, N.; Tsuruta, H.; Yasutake, M.; Imamoto, T. *Adv. Synth. Catal.* 2001, 343, 118-136.

191. Armstrong, S. K.; Brown, J. M.; Burk, M. *J. Tetrahedron Lett.* 1993, 34, 879-882.

192. Landis, C. R.; Feldgus, S. *Angew. Chem. Int. Ed.* 2000, 39, 2863-2866.

193. Feldgus, S.; Landis, C. R. *J. Am. Chem. Soc.* 2000, 122, 12714-12727.

194. Feldgus, S.; Landis, C. R. *Organometallics* 2001, 20, 2374-2386.

195. Williams, R. M.; Aldous, D. J.; Aldous, S. C. *J. Org. Chem.* 1990, 55, 4657-4663.

196. Legall, P.; Sawhney, K. N.; Conley, J. D.; Kohn, H. *Int. J. Peptide Protein Res.* 1988, 32, 279-291.

197. Schmidt, U.; Lieberknecht, A.; Wild, J. *Synthesis* 1984, 53-60.

198. Burk, M. J.; Gross, M. F.; Harper, T. G. P.; Kalberg, C. S.; Lee, J. R.; Martinez, J. P. *Pure Appl. Chem.* 1996, 68, 37-44.

199. Burk, M. J.; Wang, Y. M.; Lee, J. R. *J. Am. Chem. Soc.* 1996, 118, 5142-5143.

200. Chatterjee, A. K.; Grubbs, R. H. *Org. Lett.* 1999, 1, 1751-1753.

201. Letham, D. S.; Young, H. *Phytochemistry* 1971, 10, 23-28.

202. Schwab, P.; Grubbs, R. H.; Ziller, J. W. *J. Am. Chem. Soc.* 1998, 118, 100-110.

203. Adlhart, C.; Chen, P. J. *J. Am. Chem. Soc.* 2004, 126, 3496-3510.

204. Hong, S. H.; Day, M. W.; Grubbs, R. H. *J. Am. Chem. Soc.* 2004, 126, 7414-7415.

205. Schlummer, B.; Hartwig, J. F. *Org. Lett.* 2002, 4, 1471-1474.

206. Eliel, E. L.; Wilen, S. H.; Mander, L. N. *Stereochemistry of Organic Compounds*; John Wiley & Sons, Inc.: New York, 1994.

207. Eliel, E. L.; Wilen, S. H.; Mander, L. N. *Stereochemistry of Organic Compounds*; John Wiley & Sons, Inc.: New York, 1994.

208. Cox, R. J.; Sherwin, W. A.; Lister, K. P. L.; Vederas, J. C. *J. Am. Chem. Soc.* 1996, 118, 7449-7460.

209. Zoller, U.; Ben-Ishai, D. *Tetrahedron* 1975, 31, 863-866.

210. Mauldin, S.C.; Hornback, W. J.; Munroe, J. E. *J. Chem. Soc., Perkin Trans. I* 2001, 1554-1558.

211. Easton, C. J.; Roselt, P. D.; Tiekink, E. R. *T. Tetrahedron* 1995, 51, 7809-7822.

212. Tanaka, K.; Ahn, M.; Watanabe, Y.; Fuji, K. *Tetrahedron. Asymmetry* 1996, 7, 1771-1782.

213. Furstner, A.; Thiel, O. R.; Lehmann, C. W. *Organometallics* 2002, 21, 331-335.

214. Louie, J.; Grubbs, R. H. *Organometallics* 2002, 21, 2153-2164.

215. Osborn, J. A.; Jardine, F. H.; Young, J. F.; Wilkinson, G. *J. Chem. Soc. A* 1966, 1711-1736.

216. Jardine, J. H.; Osborn, J. A.; Wilkinson, G. *J. Chem. Soc. A* 1967, 1574-1580.

217. Burdett, K. A.; Harris, L. D.; Margl, P.; Maughon, B. R.; Mokhtar-Zadeh, T.; Saucier, P. C.; Wasserman, E. P. *Organometallics* 2004, 23, 2027-2047.

218. Patel, J.; Elaridi, J.; Jackson, W. R.; Robinson, A. J.; Serelis, A. K.; Such, C. *Chem. Commun.* 2005, 44, 5546-5547.

219. Schwab, P.; Grubbs, R. H.; Ziller, J. W. *J. Am. Chem. Soc.* 1996, 118, 100-110.

220. Jourdant, A.; Gonzalez-Zamora, E.; Zhu, J. *J. Org. Chem.* 2002, 67, 3163-3164.

221. *Fmoc Solid Phase Peptide Synthesis. A Practical Approach*; Chan, W. C.; White, P. D., Eds.; Oxford University Press: England, 2000.

222. Illesinghe, J.; Campi, E. M.; Jackson, W. R.; Robinson, A. J. Aust. *J. Chem.* 2004, 57, 531-536.

223. Barrett, A. G. M.; Hennessy, A. J.; Vézouët, R. L.; Procopiou, P. A.; Seale, P. W.; Stefaniak, S.; Upton, R. J.; White, A. J. P.; Williams, D. J. *J. Org. Chem.* 2004, 69, 1028-1037.

224. Schafiniester, C. E.; Po, J.; Verdine, G. L. *J. Am. Chem. Soc.* 2000, 122, 5891-5892.

225. Jones, R. M.; Bulaj, G. *Curr. Pharm. Design* 2000, 6, 1249-1285.

226. McIntosh, J. M.; Yoshikami, D.; Mahe, E.; Nielsen, D. B.; Rivier, J. E.; Gray, W. R.; Olivera, B. M. *J. Biol. Chem.* 1994, 269, 16733-16739.

227. Skropeta, D.; Jolliffe, K. A.; Turner, P. *J. Org. Chem.* 2004, 69, 8804-8809.

228. Jolliffe, K. A. *Supramolecular Chem.* 2005, 17, 81-86.

229. Nima, S.; Skropeta, D.; Jolliffe, K. A. *Org. Lett.* 2005, 7, 5497-5499.

230. Paquet, A. *Can. J. Chem.* 1982, 60, 976-980.

231. Kubo, S.; Chino, N.; Kimura, T.; Sakakibara, S. *Biopolymers* 1996, 38, 733-744.

232. Schuster, M.; Blechert, S. *Angew. Chem., Int. Ed. Engl.* 1997, 36, 2036-2056.

233. Moroder, L.; Musiol, H.-J.; Gotz, M.; Renner, C. *Biopolymers* 2005, 80, 85-97.

234. Alewood, P.; Hopping, G.; Armishaw, C. *Aust. J. Chem.* 2003, 56, 769-774.

235. Fazlic, S. Honours Thesis, Monash University, 2004.

236. Mayo, K. G.; Nearhoof, E. H.; Kiddle, J. *J. Org. Lett.* 2002, 4, 1567-1570.

237. Yang, C.; Murray, W. V.; Wilson, L. J. *Tetrahedron Lett.* 2003, 44.

238. Grigg, R.; Martin, W.; Morris, J.; Sridharan, V. *Tetrahedron Lett.* 2003, 44, 4899-4901.

239. Efskind, J.; Undheim, K. *Tetrahedron Lett.* 2003, 44, 2837-2839.

240. Balan, D.; Adolfsson, H. *Tetrahedron Lett.* 2004, 45, 3089-3092.

241. Aitken, S. G.; Abell, A. D. *Aust. J. Chem.* 2005, 58, 3-13.

242. Appukkuttan, P.; Dehaen, W.; Van der Eycken, E. *Org. Lett.* 2005, 7, 2723-2726.

243. Poulsen, S.; Bornaghi, L. F. *Tetrahedron Lett.* 2005, 46, 7389-7392.

244. Nosse, B.; Schall, A.; Jeong, W. B.; Reiser, O. *Adv. Synth. Catal.* 2005, 347, 1869-1874.

245. Varray, S.; Gauzy, C.; Lamaty, F.; Lazaro, R.; Martinez, J. *J. Org. Chem.* 2000, 65, 6787-6790.

246. Organ, M. G.; Mayer, S.; Lepifre, F.; N'Zemba, B.; Khatri, J. *Molecular Diversity* 2003, 7, 211-227.

247. Personal communication with Professor Paul Alewood, University of Queensland (Australia).

248. Rigby, A. C.; Lucas-Meunier, E.; Kalume, D. E.; Czerwiec, E.; Hambe, B.; Dahlqvist, I.; Fossier, P.; Baux, G.; Roepstorff, P.; Baleja, J. D.; Furie, B. C.; Furie, B.; Stenflo, J. *Proc Natl Acad Sci USA.* 1999, 96, 5758-5763.

249. Bulaj, G.; Buczek, O.; Goodsell, I.; Jimenez, E. C.; Kranski, J.; Nielsen, J. S.; Garrett, J. E.; Olivera, B. M. *Proc Natl Acad Sci USA.* 2003, 100, 14562-14568.

250. Buczek, O.; Olivera, B. M.; Bulaj, G. *Biochemistry* 2004, 43, 1093-1101.

251. Dela, C. R.; Whitby, F.; Buczek, O.; Bulaj, G. *J. Pept. Res.* 2003, 61, 202-212.

252. Collaboration with Professor Paul Alewood, University of Queensland (Australia).

253. Erdélyi, M.; Gogoll, A. *Synthesis* 2002, 11, 1592-1596.

254. Frost & Sullivan *Research Report: Strategic Analysis of the Therapeutic Peptides Market in Europe*, October 2004.

255. Kaiser, E.; Colescott, R. L.; Bossinger, C. D.; Cook, P. I. *Anal. Biochem.* 1970, 34, 595-598.

256. Fontenot, J. D.; Ball, J. M.; Miller, M. A.; Montelaro, R. C. *Pep. Res.* 1991, 4, 19-25.

257. Ellman, G. L. *Arch. Biochem. Biophys.* 1959, 82, 70-77.

258. Davies, S. J.; Ayscough, A. P.; Beckett, R. P.; Bragg, R. A.; Clements, J. M.; Doel, S.; Grew, C.; Launchbury, S. B.; Perkins, G. M.; Pratt, L. M.; Smith, H. K.; Spavold, Z. M.; Thomas, S. W.; Todd, R. S.; Whittaker, M. *Bioorg. Med. Chem. Lett.* 2003, 13, 2709-2713.

259. Berney, D. *Helv. Chim. Acta* 1982, 65, 1694-1699.

260. Saylik, D.; Campi, E. M.; Donohue, A. C.; Jackson, W. R.; Robinson, A. J. *Tetrahedron. Asymmetry* 2001, 12, 657-667.

261. Testa, E.; Cignarella, G.; Pifferi, G.; Furesz, S.; Timbal, M. T.; Schiatti, P.; Maffi, G. *Farmaco Ed. Sci.* 1964, 19, 895-912.

262. Papageorgiou, C.; Borer, X.; French, R. R. *Bioorg. Med. Chem. Lett.* 1994, 4, 267-272.

263. Williams, R. M.; Im, M.-N. *Tetrahedron Lett.* 1988, 29, 6075-6078.

264. Bremner, J. B.; Keller, P. A.; Pyne, S. G.; Robertson, A. D.; Skelton, B. W.; White, A. H.; Witchard, H. M. *Aust. J. Chem.* 2000, 53, 535-540.

265. Arvela, R. K.; Leadbeater, N. E.; Sangi, M. S.; Williams, V. A.; Granados, P.; Singer, R. D. *J. Org. Chem.* 2005, 70, 161-168.

266. Spetzler, J. C.; Hoeg-Jensen, T. *J. Peptide Sci.* 2001, 7, 537-551.

The Amino Acids

The Amino Acids

| Amino acid | One letter code | Three letter code | Structure |
|---|---|---|---|
| Alanine | A | Ala | 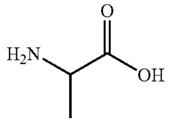 |
| Allylglycine* | — | Hag | 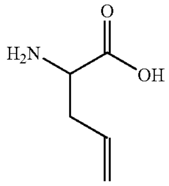 |
| Arginine | R | Arg | 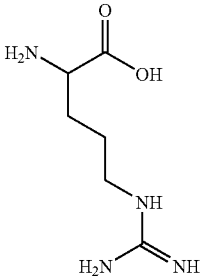 |
| Asparagine | N | Asn | 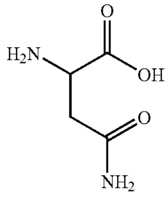 |
| Aspartic acid | D | Asp | 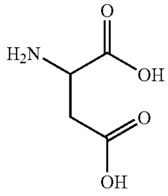 |
| Crotylglycine | — | Crt | 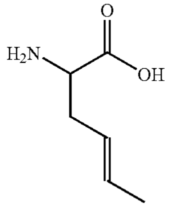 |
| Cysteine | C | Cys | 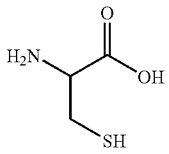 |

-continued
The Amino Acids
| Amino acid | One letter code | Three letter code | Structure |
|---|---|---|---|
| 5,5-Dimethylproline* | — | dmP | 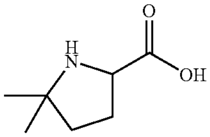 |
| Glutamic acid | E | Glu | 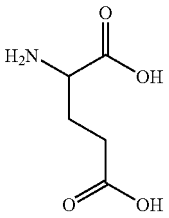 |
| Glutamine | Q | Gln | 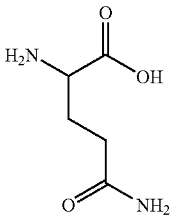 |
| Glycine | G | Gly | 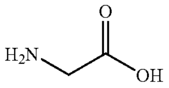 |
| Histidine | H | His | 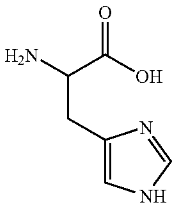 |
| Isoleucine | I | Ile | 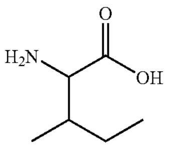 |
| Leucine | L | Leu | 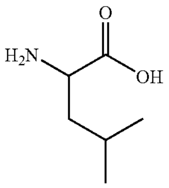 |
| Lysine | K | Lys | 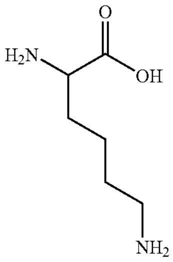 |
| Methionine | M | Met | 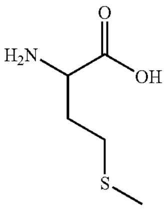 |
| Phenylalanine | F | Phe | 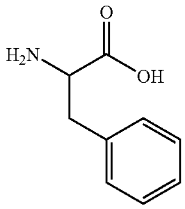 |
| Prenylglycine* | — | Pre | 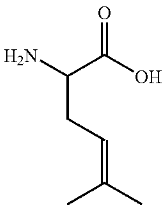 |
| Proline | P | Pro | 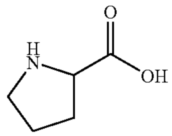 |
| Serine | S | Ser | 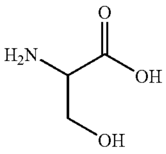 |
| Threonine | T | Thr | 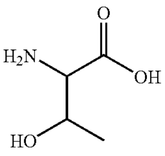 |

-continued

| The Amino Acids | | | |
|---|---|---|---|
| Amino acid | One letter code | Three letter code | Structure |
| Tryptophan | W | Trp | 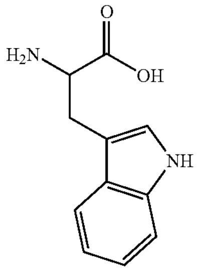 |
| Tyrosine | Y | Tyr | 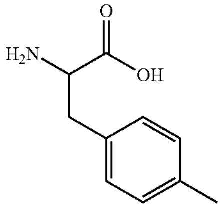 |
| Valine | V | Val | 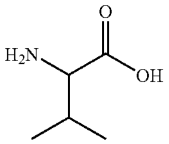 |

*Synthetic amino acids.

What is claimed is:

1. A method for the synthesis of a peptide with two intramolecular dicarba bridges, the method comprising:

(a) providing a first peptide comprising a series of amino acids attached to a solid support, wherein two amino acids comprise sidechains with a first pair of complementary metathesisable groups and two amino acids comprise sidechains with a second pair of blocked complementary metathesisable groups;

(b) subjecting the peptide to cross-metathesis to form a peptide with an unsaturated dicarba bridge between the amino acids bearing the first pair of complementary metathesisable groups;

(c) unblocking the second pair of complementary metathesisable groups; and (d) subjecting the peptide to cross-metathesis to form a peptide with an unsaturated dicarba bridge between the amino acids bearing the second pair of complementary metathesisable groups, to form a dicarba bridge between the amino acids that bore the second metathesisable groups.

2. The method of claim 1, wherein two amino acids in the peptide are protected cysteine residues, and the method comprises deprotecting the cysteine residues and oxidising the cysteine residues to form a disulfide bridge.

3. The method of claim 1, wherein one or both of the cross-metathesis steps is followed by a hydrogenation to form a saturated dicarba bridge between the amino acids that bore the complementary metathesisable groups.

4. The method of claim 1, wherein the amino acids that bear the first pair of complementary metathesisable groups are selected from allyl glycine and crotyl glycine, or a combination thereof.

5. The method of claim 1, wherein the amino acids bearing the blocked complementary metathesisable groups of the second pair of complementary metathesisable groups are prenyl glycine or protected prenyl glycine, and the reaction to unblock the blocked metathesisable groups of the second pair of complementary metathesisable groups comprises cross-metathesis with a disposable olefin.

6. The method of claim 5, wherein the cross-metathesis with a disposable olefin comprises cross-metathesis with a mono-substituted ethylene or a 1,2-disbstituted ethylene.

7. The method of claim 6, wherein the cross-metathesis with a disposable olefin comprises cross-metathesis with disposable olefin comprising a polar functional group.

8. The method of claim 1, wherein the cross-metathesis of the first and/or the second complementary metathesisable groups is conducted under microwave radiation conditions.

9. The method of claim 1, wherein the cross-metathesis is performed using a cross-metathesis catalyst, and the cross-metathesis is performed in a solvent combination of a resin-swelling solvent, with a coordinating solvent for the catalyst.

10. The method of claim 9, wherein the cross-metathesis is performed in a solvent combination of a resin-swelling solvent, with a coordinating solvent for the catalyst which is an alcohol.

11. The method of claim 9, wherein the cross-metathesis is performed in a solvent combination containing about 1-30% of the coordinating solvent by volume, with respect to the total solvent combination.

12. The method of claim 1, wherein the peptide is attached to a solid support during the cross-metathesis of the complementary metathesisable groups and the loading of peptide on the solid support is at least 0.2 mmol/g.

13. A method for the synthesis of a peptide with two intramolecular dicarba bridges, and a disulfide bridge, the method comprising:

(a) providing a first peptide comprising a series of amino acids attached to a solid support, wherein two amino acids comprise sidechains with a first pair of complementary metathesisable groups and two amino acids comprise sidechains with a second pair of blocked complementary metathesisable groups, and two amino acids in the peptide are protected cysteine residues;

(b) subjecting the peptide to cross-metathesis to form a peptide with an unsaturated dicarba bridge between the amino acids bearing the first pair of complementary metathesisable groups;

(c) unblocking the second pair of complementary metathesisable groups, (d) subjecting the peptide to cross-metathesis to form a peptide with an unsaturated dicarba bridge between the amino acids bearing the second pair of complementary metathesisable groups, to form a dicarba bridge between the amino acids that bore the second metathesisable groups, and (e) deprotecting the cysteine residues and oxidising the cysteine residues to form a disulfide bridge.

14. The method of claim 13, wherein one or both of the cross-metathesis steps is followed by a hydrogenation to form a saturated dicarba bridge between the amino acids that bore the complementary metathesisable groups.

15. The method of claim 13, wherein the amino acids that bear the first pair of complementary metathesisable groups are selected from allyl glycine and crotyl glycine, or a combination thereof.

16. The method of claim 13, wherein the amino acids bearing the blocked complementary metathesisable groups of the second pair of complementary metathesisable groups are prenyl glycine or protected prenyl glycine, and the reaction to unblock the blocked metathesisable groups of the second pair of complementary metathesisable groups comprises cross-metathesis with a disposable olefin.

17. The method of claim 16, wherein the cross-metathesis with a disposable olefin comprises cross-metathesis with a mono-substituted ethylene or a 1,2-disibstituted ethylene.

18. The method of claim 17, wherein the cross-metathesis with a disposable olefin comprises cross-metathesis with disposable olefin comprising a polar functional group.

19. The method of claim 13, wherein the cross-metathesis of the first and/or the second complementary metathesisable groups is conducted under microwave radiation conditions.

20. The method of claim 13, wherein the cross-metathesis is performed using a cross-metathesis catalyst, and the cross-metathesis is performed in a solvent combination of a resin-swelling solvent, with a coordinating solvent for the catalyst.

21. The method of claim 20, wherein the cross-metathesis is performed in a solvent combination of a resin-swelling solvent, with a coordinating solvent for the catalyst which is an alcohol.

22. The method of claim 20, wherein the cross-metathesis is performed in a solvent combination containing about 1-30% of the coordinating solvent by volume, with respect to the total solvent combination.

23. The method of claim 13, wherein the loading of peptide on the solid support is at least 0.2 mmol/g.

24. A method for the synthesis of a peptide with one intramolecular dicarba bridge, and a second dicarba bridge which is an intermolecular, the method comprising:
  (a) providing a first peptide comprising a series of amino acids attached to a solid support, wherein two amino acids comprise sidechains with a first pair of complementary metathesisable groups which may be blocked or unblocked, and one amino acid comprises a sidechain with a second metathesisable group which may be blocked or unblocked, with the proviso that the metathesisable groups out of at least one of the first or the second metathesisable groups are blocked;
  (b) unblocking the first pair of complementary metathesisable groups, if said groups are blocked and subjecting the peptide to cross-metathesis to form a peptide with an unsaturated dicarba bridge between the amino acids bearing the first pair of complementary metathesisable groups, to form a peptide with an intramolecular dicarba bridge, and
  (c) contacting the first peptide with a second peptide comprising one amino acid with a metathesisable group complementary to the second metathesisable group on the first peptide; (d) unblocking the second complementary metathesisable groups, if the second metathesisable groups are blocked; and (e) subjecting the peptide to cross-metathesis to form a peptide with an unsaturated dicarba bridge between the amino acids bearing the second pair of complementary metathesisable groups, to form a dicarba bridge between the amino acids that bore the second metathesisable groups,
  wherein steps (b) and (c) are performed in either order, so as to form a peptide with an intermolecular bridge and an intramolecular bridge.

25. The method of claim 24, wherein the first peptide, or the combination of the first peptide and the second peptide, comprises a pair of protected cysteines, and the process further comprises deprotecting the cysteine residues and oxidising the cysteine residues to form a disulfide bridge.

26. The method of claim 24, wherein one or both of the cross-metathesis steps is followed by a hydrogenation to form a saturated dicarba bridge between the amino acids that bore the complementary metathesisable groups.

27. The method of claim 24, wherein the amino acids that bear the first pair of complementary metathesisable groups are selected from allyl glycine and crotyl glycine, or a combination thereof.

28. The method of claim 24, wherein the amino acids bearing the blocked complementary metathesisable groups of the second pair of complementary metathesisable groups are prenyl glycine or protected prenyl glycine, and the reaction to unblock the blocked metathesisable groups of the second pair of complementary metathesisable groups comprises cross-metathesis with a disposable olefin.

29. The method of claim 28, wherein the cross-metathesis with a disposable olefin comprises cross-metathesis with a mono-substituted ethylene or a 1,2-disibstituted ethylene.

30. The method of claim 28, wherein the cross-metathesis with a disposable olefin comprises cross-metathesis with disposable olefin comprising a polar functional group.

31. The method of claim 24, wherein the cross-metathesis of the first and/or the second complementary metathesisable groups is conducted under microwave radiation conditions.

32. The method of claim 24, wherein the cross-metathesis is performed using a cross-metathesis catalyst, and the cross-metathesis is performed in a solvent combination of a resin-swelling solvent, with a coordinating solvent for the catalyst.

33. The method of claim 32, wherein the cross-metathesis is performed in a solvent combination of a resin-swelling solvent, with a coordinating solvent for the catalyst which is an alcohol.

34. The method of claim 32, wherein the cross-metathesis is performed in a solvent combination containing about 1-30% of the coordinating solvent by volume, with respect to the total solvent combination.

35. The method of claim 24, wherein the loading of peptide on the solid support is at least 0.2 mmol/g.

36. The method of claim 1, further comprising:
  providing a third pair of complementary metathesisable groups in the first peptide, or one in the first peptide and one in a second or in a third peptide to be coupled to the first peptide through an intermolecular bridge;
  unblocking the third pair of complementary metathesisable groups, if the metathesisable groups are blocked; and
  subjecting the third pairs of complementary metathesisable groups to cross metathesis.

37. A method for the synthesis of a peptide with one intramolecular dicarba bridge, an intermolecular dicarba bridge, and a disulfide bridge, the method comprising:
  (a) providing a first peptide comprising a series of amino acids attached to a solid support, wherein two amino acids comprise sidechains with a first pair of complementary metathesisable groups which may be blocked or unblocked, and one amino acid comprises a sidechain with a second metathesisable group which may be blocked or unblocked, with the proviso that the metathesisable groups out of at least one of the first or the second metathesisable groups are blocked;
  (b) unblocking the first pair of complementary metathesisable groups, if said groups are blocked and subjecting the peptide to cross-metathesis to form a peptide with an unsaturated dicarba bridge between the amino acids bearing the first pair of complementary metathesisable groups, to form a peptide with an intramolecular dicarba bridge;

(c) contacting the first peptide with a second peptide comprising one amino acid with a metathesisable group complementary to the second metathesisable group on the first peptide;

(d) unblocking the second complementary metathesisable groups, if the second metathesisable groups are blocked; and (e) subjecting the peptide to cross-metathesis to form a peptide with an unsaturated dicarba bridge between the amino acids bearing the second pair of complementary metathesisable groups, to form a dicarba bridge between the amino acids that bore the second metathesisable groups, wherein steps (b) and (c) are performed in either order, so as to form a peptide with an intermolecular bridge and an intramolecular bridge, and wherein the first peptide, or the combination of the first peptide and the second peptide, comprises a pair of protected cysteines, and the process further comprises deprotecting the cysteine residues and oxidising the cysteine residues to form a disulfide bridge.

38. The method of claim 37, wherein one or both of the cross-metathesis steps is followed by a hydrogenation to form a saturated dicarba bridge between the amino acids that bore the complementary metathesisable groups.

39. The method of claim 37, wherein the amino acids that bear the first pair of complementary metathesisable groups are selected from allyl glycine and crotyl glycine, or a combination thereof.

40. The method of claim 37, wherein the amino acids bearing the blocked complementary metathesisable groups of the second pair of complementary metathesisable groups are prenyl glycine or protected prenyl glycine, and the reaction to unblock the blocked metathesisable groups of the second pair of complementary metathesisable groups comprises cross-metathesis with a disposable olefin.

41. The method of claim 40, wherein the cross-metathesis with a disposable olefin comprises cross-metathesis with a mono-substituted ethylene or a 1,2-disibstituted ethylene.

42. The method of claim 40, wherein the cross-metathesis with a disposable olefin comprises cross-metathesis with disposable olefin comprising a polar functional group.

43. The method of claim 37, wherein the cross-metathesis of the first and/or the second complementary metathesisable groups is conducted under microwave radiation conditions.

44. The method of claim 37, wherein the cross-metathesis is performed using a cross-metathesis catalyst, and the cross-metathesis is performed in a solvent combination of a resin-swelling solvent, with a coordinating solvent for the catalyst.

45. The method of claim 44, wherein the cross-metathesis is performed in a solvent combination of a resin-swelling solvent, with a coordinating solvent for the catalyst which is an alcohol.

46. The method of claim 44, wherein the cross-metathesis is performed in a solvent combination containing about 1-30% of the coordinating solvent by volume, with respect to the total solvent combination.

47. The method of claim 37, wherein the loading of peptide on the solid support is at least 0.2 mmol/g.

48. The method of claim 37, further comprising:

providing a third pair of complementary metathesisable groups in the first peptide, or one in the first peptide and one in a second or in a third peptide to be coupled to the first peptide through an intermolecular bridge;

unblocking the third pair of complementary metathesisable groups, if the metathesisable groups are blocked; and subjecting the third pairs of complementary metathesisable groups to cross metathesis.

49. A method for the synthesis of a peptide with three intramolecular bridges, the method comprising:

(a) providing a first peptide comprising a series of amino acids attached to a solid support, wherein two amino acids comprise sidechains with a first pair of complementary metathesisable groups, two amino acids comprise sidechains with a second pair of blocked complementary metathesisable groups and two amino acids comprise sidechains with a third pair of blocked complementary metathesisable groups;

(b) subjecting the peptide to cross-metathesis under microwave radiation conditions to form a peptide with an unsaturated dicarba bridge between the amino acids bearing the first pair of complementary metathesisable groups;

(c) optionally subjecting the unsaturated dicarba bridge to hydrogenation (suitably homogeneous hydrogenation);

(d) unblocking the second pair of complementary metathesisable groups;

(e) subjecting the peptide to cross-metathesis to form a peptide with an unsaturated dicarba bridge between the amino acids that bore the second pair of complementary metathesisable groups;

(f) optionally subjecting the unsaturated dicarba bridge to hydrogenation (suitably homogeneous hydrogenation);

(g) unblocking the third pair of complementary metathesisable groups;

(h) subjecting the peptide to cross-metathesis to form a peptide with an unsaturated dicarba bridge between the amino acids that bore the third pair of complementary metathesisable groups; and (i) optionally subjecting the unsaturated dicarba bridge to hydrogenation (suitably homogeneous hydrogenation).

* * * * *